(12) United States Patent
Wyatt et al.

(10) Patent No.: US 10,058,604 B2
(45) Date of Patent: Aug. 28, 2018

(54) SOLUBLE HIV-1 ENVELOPE GLYCOPROTEIN TRIMERS

(71) Applicants: International AIDS Vaccine Initiative, New York, NY (US); The Scripps Research Institute, La Jolla, CA (US)

(72) Inventors: Richard Wyatt, New York, NY (US); Andrew Ward, La Jolla, CA (US); Karen Tran, New York, NY (US); Shailendra Kumar, New York, NY (US); Jidnyasa Ingale, La Jolla, CA (US); Javier Guenaga, New York, NY (US); Yu Feng, New York, NY (US); Viktoriya Dubrovskaya, La Jolla, CA (US); Natalia de Val Alda, La Jolla, CA (US)

(73) Assignees: International AIDS Vaccine Initiative, New York, NY (US); The Scripps Research Institute, La Jolla, CA (US)

(*) Notice: Subject to any disclaimer, the term of this patent is extended or adjusted under 35 U.S.C. 154(b) by 0 days.

(21) Appl. No.: 14/508,369

(22) Filed: Oct. 7, 2014

(65) Prior Publication Data

US 2017/0035877 A1 Feb. 9, 2017

Related U.S. Application Data

(60) Provisional application No. 62/054,727, filed on Sep. 24, 2014, provisional application No. 62/032,507, filed on Aug. 1, 2014, provisional application No. 61/941,101, filed on Feb. 18, 2014, provisional application No. 61/887,618, filed on Oct. 7, 2013.

(51) Int. Cl.
| | | |
|---|---|---|
| *C07K 14/005* | (2006.01) | |
| *A61K 39/12* | (2006.01) | |
| *C12N 7/00* | (2006.01) | |
| *A61K 39/21* | (2006.01) | |
| *A61K 39/00* | (2006.01) | |
| *C07K 14/16* | (2006.01) | |

(52) U.S. Cl.
CPC ............ *A61K 39/21* (2013.01); *A61K 39/12* (2013.01); *C07K 14/005* (2013.01); *C07K 14/162* (2013.01); *C12N 7/00* (2013.01); *A61K 2039/55505* (2013.01); *A61K 2039/55555* (2013.01); *A61K 2039/645* (2013.01); *C12N 2740/16022* (2013.01); *C12N 2740/16034* (2013.01); *C12N 2740/16122* (2013.01); *C12N 2740/16134* (2013.01)

(58) Field of Classification Search
CPC ............ A61K 39/12; A61K 39/21; C12N 2740/16122; C12N 2740/16134; C07K 14/005

See application file for complete search history.

(56) References Cited

U.S. PATENT DOCUMENTS

| 8,981,057 B2 | 3/2015 | Sanders |
| 2005/0106160 A1 | 5/2005 | Dimitrov et al. |
| 2008/0274134 A1 | 11/2008 | Schulke et al. |
| 2013/0139274 A1 | 5/2013 | Sanders |

FOREIGN PATENT DOCUMENTS

| WO | 03/077838 | 9/2003 |
| WO | 2006/002079 | 1/2006 |
| WO | 2011/108937 | 9/2011 |

OTHER PUBLICATIONS

Harris et al., Trimeric HIV-1 glycoprotein gp140 immunogens and native HIV-1 envelope glycoproteins display the same closed and open quaternary molecular architectures, PNAS, 2011, 108(28):11440-11445.*
Partial European Search Report dated Apr. 7, 2015, which issued during prosecution of European Application No. 14003443.0.
Ilja Bontjer, et al. "Comparative Immunogenicity of Evolved V1V2-Deleted HIV-1 Envelope Glycoprotein Trimers" PLOS One 8(6):e67484, Jun. 2013.
Antu K. Dey, et al. "Specific amino acids in the N-terminus of the gp41 ectodomain contribute to the stabilization of a soluble, cleaved gp140 envelope glycoprotein from human immunodeficiency virus type 1" Virology 360(1):199-208, Feb. 2007.
Youdong Mao, et al. "Subunit organization of the membrane-bound HIV-1 envelope glycoprotein trimer" Nature Structural & Molecular Biology 19(9):893-899, Aug. 2012.
Tommy Tong, et al. "HIV-1 Virus-Like Particles Bearing Pure Env Trimers Expose Neutralizing Epitopes but Occlude Nonneutralizing Epitopes" Journal of Virology 86(7):3574-3587, Apr. 2012.
Per Johan Klasse, et al. "Influences on Trimerization and Aggregation of Soluble, Cleaved HIV-1 SOSIP envelope Glycoprotein" Journal of Virology 87(149873-9885, Jul. 2013.
Richard Wyatt, et al. "Immunogenicity and structure of the HIV-1 envelope glycoprotein spike" Meeting of the CFAR Immunity Scientific Focus Group, pp. 1-26, San Diego, Apr. 3, 2014.
Javier Guenaga, et al. "Well-Ordered Trimeric HIV-1 Subtype B and C Soluble Spike Mimetics Generated by Negative Selection Display Native-like Properties" PLOS Pathogens 11(1):e1004570, Jan. 2015.
European communication pursuant to Article 94(3) EPC dated Jun. 29, 2016 which issued during prosecution of European Application No. 14 003 443.
European Search Report dated Aug. 11, 2015, which issued during prosecution of European Application No. 14003443.0.
Melchers, et al. "Targeting HIV-1 Envelope Glycoprotein Trimers to B Cells by Using APRIL Improves Antibody Responses" Journal of Virology, Mar. 2012, 86(5):2488-2500.

* cited by examiner

*Primary Examiner* — Barry A Chestnut
(74) *Attorney, Agent, or Firm* — Duane Morris LLP; Thomas J. Kowalski; Deborah L. Lu

(57) ABSTRACT

The present application relates to novel HIV-1 envelope glycoproteins which may be utilized as an HIV-1 vaccine immunogens, antigens for crystallization and for the identification of broad neutralizing antibodies. The present invention encompasses the preparation and purification of immunogenic compositions which are formulated into the vaccines of the present invention.

17 Claims, 85 Drawing Sheets
(65 of 85 Drawing Sheet(s) Filed in Color)
Specification includes a Sequence Listing.

JRFL-SOSIP+PGT128 Template stack

JRFL-SOSIP+PGV04 Template stack

| JRFL V1 | V3 | | | | | | | | |
|---|---|---|---|---|---|---|---|---|---|
| | S306 | I307 | H308 | R315 | A316 | F317 | Y318 | T319 | T320 |
| V135 | | | | | | | | | |
| N136 | | | | | | | | | |
| A137 | | | | | | | | | |
| T138 | | | | | | | | | |
| F159 | | | | | | | | | |
| N160 | | | | | | | | | |
| I161 | | | | | | | | | |
| T162 | | | | | | | | | |
| T163 | | | | | | | | | |
| S164 | | | | | | | | | |
| I165 | | | | | | | | | |

FIG. 4A

| BG505 V1 | V3 | | | | | | | | |
|---|---|---|---|---|---|---|---|---|---|
| | S306 | I307 | R308 | Q315 | A316 | F317 | Y318 | A319 | T320 |
| V135 | | | | | | | | | |
| T136 | | | | | | | | | |
| N137 | | | | | | | | | |
| N138 | | | | | | | | | |
| F159 | | | | | | | | | |
| N160 | | | | | | | | | |
| M161 | | | | | | | | | |
| T162 | | | | | | | | | |
| T163 | | | | | | | | | |
| E164 | | | | | | | | | |
| L165 | | | | | | | | | |

FIG. 4B

JRFL SOSIP E168K dMPER

MPMGSLQPLATLYLLGMLVASVLAVEKLWVTVYYGVPVWKEATTTLFCASDAKAYDT
EVHNVWATHACVPTDPNPQEVVLENVTEHFNMWKNNMVEQMQEDIISLWDQSLKPCV
KLTPLCVTLNCKDVNATNTTNDSEGTMERGEIKNCSFNITTSIRDKVQKEYALFYKLDV
VPIDNNNTSYRLISCDTSVITQACPKISFEPIPIHYCAPAGFAILKCNDKTFNGKGPCKNVS
TVQCTHGIRPVVSTQLLLNGSLAEEEVVIRSDNFTNNAKTIIVQLKESVEINCTRPNNNTR
KSIHIGPGRAFYTTGEIIGDIRQAHCNISRAKWNDTLKQIVIKLREQFENKTIVFNHSSGGD
PEIVMHSFNCGGEFFYCNSTQLFNSTWNNNTEGSNNTEGNTITLPCRIKQIINMWQEVGK
AMYAPPIRGQIRCSSNITGLLLTRDGGINENGTEIFRPGGGDMRDNWRSELYKYKVVKIE
PLGVAPTKCKRRVRRRKKRAVGIGAVFLGFLGAAGSTMGAASMTLTVQARLLLSGIVQ
QQNNLLRAPEAQQRMLQLTVWGIKQLQARVLAVERYLGDQQLLGIWGCSGKLICCTA
VPWNASWSNKSLDRIWNNMTWMEWEREIDNYTSEIYTLIEESQNQQEKNEQELLELGG
GGHHHHHH.

FIG. 5

JRFL MIF gp120 V1-V3 Cys-Cys linkage

MPMGSLQPLATLYLLGMLVASVLAEATTTLFCASDAKAYDTEVHNVWATHACVPTDP
NPQEVVLENVTEHFNMWKNNMVEQMQEDIISLWDQSLKPCVKLTPLCVTLNCKD▓▓▓
▓NTTNDSEGTMERGEIKNCS▓▓▓▓▓▓RDKVQKEYALFYKLDVVPIDNNNTSYRLISCDT
SVITQACPKISFEPIPIHYCAPAGFAILKCNDKTFNGKGPCKNVSTVQCTHGIRPVVSTQLL
LNGSLAEEEVVIRSDNFTNNAKTIIVQLKESVEINCTRPNNNTRK▓▓▓IGPG▓▓▓▓▓▓GEII
GDIRQAHCNISRAKWNDTLKQIVIKLREQFENKTIVFNHSSGGDPEIVMHSFNCGGEFFY
CNSTQLFNSTWNNNTEGSNNTEGNTITLPCRIKQIINMWQEVGKAMYAPPIRGQIRCSSN
ITGLLLTRDGGINENGTEIFRPGGGDMRDNWRSELYKYKVVKIEPLGVAPVTIMFIVNTN
VPRASVPDGFLSELTQQLAQATGKPPQYIAVHVVPDQLMAFGGSSEPCALCSLHSIGKIG
GAQNRSYSKLLCGLLAERLRISPDRVYINYYDMNAASVGWNGGAKFVAAWTLKAAAG
GHHHHHHH.

| | V3 | | | | | | | | |
|---|---|---|---|---|---|---|---|---|---|
| | S306 | I307 | H308 | R315 | A316 | F317 | Y318 | T319 | T320 |
| V135 | | | | | | | | | |
| N136 | | | | | | | | | |
| A137 | | | | | | | | | |
| T138 | | | | | | | | | |
| F159 | | | | | | | | | |
| N160 | | | | | | | | | |
| I161 | | | | | | | | | |
| T162 | | | | | | | | | |
| T163 | | | | | | | | | |
| S164 | | | | | | | | | |
| I165 | | | | | | | | | |

FIG. 6

JRFL HPTM gp145

MPMGSLQPLATLYLLGMLVASVLAVEKLWVTVYYGVPVWKEATTTLFCASDAKAYDT
EVHNVWATHACVPTDPNPQEVVLENVTEHFNMWKNNMVEQMQEDIISLWDQSLKPCV
KLTPLCVTLNCKDVNATNTTNDSEGTMERGEIKNCSFNITTSIRDKVQKEYALFYKLDV
VPIDNNNTSYRLISCDTSVITQACPKISFEPIPIHYCAPAGFAILKCNDKTFNGKGPCKNVS
TVQCTHGIRPVVSTQLLLNGSLAEEEVVIRSDNFTNNAKTIIVQLKESVEINCTRPNNNTR
KSIHIGPGRAFYTTGEIIGDIRQAHCNISRAKWNDTLKQIVIKLREQFENKTIVFNHSSGGD
PEIVMHSFNCGGEFFYCNSTQLFNSTWNNNTEGSNNTEGNTITLPCRIKQIINMWQEVGK
AMYAPPIRGQIRCSSNITGLLLTRDGGINENGTEIFRPGGGDMRDNWRSELYKYKVVKIE
PLGVAPTKAKRRV▓▓▓▓▓▓AVGIGAVFLGFLGAAGSTMGAASMTLTVQARLLLSGIVQ
QQNNLLRAIEAQQRMLQLTVWGIKQLQARVLAVERYLGDQQLLGIWGCSGKLICTTAV
PWNASWSNKSLDRIWNNMTWMEWEREIDNYTSEIYTLIEESQNQQEKNEQELLELDKW
ASLWNWFDITKWLWYIK▓▓▓▓▓▓▓▓▓▓▓▓▓▓▓▓▓▓▓▓▓▓▓▓GGHHHHHH.

FIG. 7

HPTM2

MPMGSLQPLATLYLLGMLVASVLAVEKLWVTVYYGVPVWKEATTTLFCASDAKAYDT
EVHNVWATHACVPTDPNPQEVVLENVTEHFNMWKNNMVEQMQEDIISLWDQSLKPCV
KLTPLCVTLNCKDVNATNTTNDSEGTMERGEIKNCSFNITTSIRDKVQKEYALFYKLDV
VPIDNNNTSYRLISCDTSVITQACPKISFEPIPIHYCAPAGFAILKCNDKTFNGKGPCKNVS
TVQCTHGIRPVVSTQLLLNGSLAEEEVVIRSDNFTNNAKTIIVQLKESVEINCTRPNNNTR
KSIHIGPGRAFYTTGEIIGDIRQAHCNISRAKWNDTLKQIVIKLREQFENKTIVFNHSSGGD
PEIVMHSFNCGGEFFYCNSTQLFNSTWNNNTEGSNNTEGNTITLPCRIKQIINMWQEVGK
AMYAPPIRGQIRCSSNITGLLLTRDGGINENGTEIFRPGGGDMRDNWRSELYKYKVVKIE
PLGVAPTKAKRRVVQSLKSAVGIGAVFLGFLGAAGSTMGAASMTLTVQARLLLSGIVQ
QQNNLLRAIEAQQRMLQLTVWGIKQLQARVLAVERYLGDQQLLGIWGCSGKLICTTAV
PWNASWSNKSLDRIWNNMTWMEWEREIDNYTSEIYTLIEESQNQQEKNEQELLELDKW
ASLWNWFDITKWLWYIK▓▓▓▓▓▓▓▓▓▓▓▓▓▓▓▓▓▓▓▓▓▓▓▓GGHHHHHH.

HPTM2s

MPMGSLQPLATLYLLGMLVASVLAVEKLWVTVYYGVPVWKEATTTLFCASDAKAYDT
EVHNVWATHACVPTDPNPQEVVLENVTEHFNMWKNNMVEQMQEDIISLWDQSLKPCV
KLTPLCVTLNCKDVNATNTTNDSEGTMERGEIKNCSFNITTSIRDKVQKEYALFYKLDV
VPIDNNNTSYRLISCDTSVITQACPKISFEPIPIHYCAPAGFAILKCNDKTFNGKGPCKNVS
TVQCTHGIRPVVSTQLLLNGSLAEEEVVIRSDNFTNNAKTIIVQLKESVEINCTRPNNNTR
KSIHIGPGRAFYTTGEIIGDIRQAHCNISRAKWNDTLKQIVIKLREQFENKTIVFNHSSGGD
PEIVMHSFNCGGEFFYCNSTQLFNSTWNNNTEGSNNTEGNTITLPCRIKQIINMWQEVGK
AMYAPPIRGQIRCSSNITGLLLTRDGGINENGTEIFRPGGGDMRDNWRSELYKYKVVKIE
PLGVAPTKAKRRVVQSLKSAVGIGAVFLGFLGAAGSTMGAASMTLTVQARLLLSGIVQ
QQNNLLRAIEAQQRMLQLTVWGIKQLQARVLAVERYLGDQQLLGIWGCSGKLICTTAV
PWNASWSNKSLDRIWNNMTWMEWEREIDNYTSEIYTLIEESQNQQEKNEQELLELDKW
ASLWNWFDITKWLWYIK▓▓▓▓GGHHHHHH.

HPTM2s N666 N674 N685

MPMGSLQPLATLYLLGMLVASVLAVEKLWVTVYYGVPVWKEATTTLFCASDAKAYDT
EVHNVWATHACVPTDPNPQEVVLENVTEHFNMWKNNMVEQMQEDIISLWDQSLKPCV
KLTPLCVTLNCKDVNATNTTNDSEGTMERGEIKNCSFNITTSIRDKVQKEYALFYKLDV
VPIDNNNTSYRLISCDTSVITQACPKISFEPIPIHYCAPAGFAILKCNDKTFNGKGPCKNVS
TVQCTHGIRPVVSTQLLLNGSLAEEEVVIRSDNFTNNAKTIIVQLKESVEINCTRPNNNTR
KSIHIGPGRAFYTTGEIIGDIRQAHCNISRAKWNDTLKQIVIKLREQFENKTIVFNHSSGGD
PEIVMHSFNCGGEFFYCNSTQLFNSTWNNNTEGSNNTEGNTITLPCRIKQIINMWQEVGK
AMYAPPIRGQIRCSSNITGLLLTRDGGINENGTEIFRPGGGDMRDNWRSELYKYKVVKIE
PLGVAPTKAKRRVVQSLKSAVGIGAVFLGFLGAAGSTMGAASMTLTVQARLLLSGIVQ
QQNNLLRAIEAQQRMLQLTVWGIKQLQARVLAVERYLGDQQLLGIWGCSGKLICTTAV
PWNASWSNKSLDRIWNNMTWMEWEREIDNYTSEIYTLIEESQNQQEKNEQELLELDK▓
A▓LWNWF▓▓KWLWYIK▓▓IVGGHHHHHH.

FIG. 8

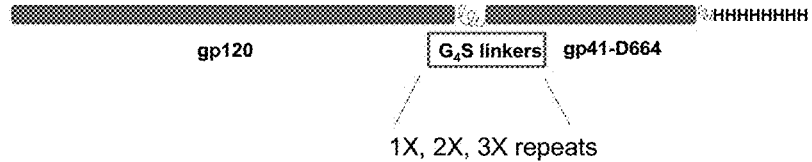

FIG. 9

JR-FL gp140-NFL1P construct

MPMGSLQPLATLYLLGMLVASVLAVEKLWVTVYYGVPVWKEATTTLFCASDAKAYDTEVH
NVWATHACVPTDPNPQEVVLENVTEHFNMWKNNMVEQMQEDIISLWDQSLKPCVKLTPLC
VTLNCKDVNATNTTNDSEGTMERGEIKNCSFNITTSIRDKVQKEYALFYKLDVVPIDNNN
TSYRLISCDTSVITQACPKISFEPIPIHYCAPAGFAILKCNDKTFNGKGPCKNVSTVQCT
HGIRPVVSTQLLLNGSLAEEEVVIRSDNFTNNAKTIIVQLKESVEINCTRPNNNTRKSIH
IGPGRAFYTTGEIIGDIRQAHCNISRAKWNDTLKQIVIKLREQFENKTIVFNHSSGGDPE
IVMHSFNCGGEFFYCNSTQLFNSTWNNNTEGSNNTEGNTITLPCRIKQIINMWQEVGKAM
YAPPIRGQIRCSSNITGLLLTRDGGINENGTEIFRPGGGDMRDNWRSELYKYKVVKIEPL
GVAPTKAKRRVVQ░░░░AVGIGAVFLGFLGAAGSTMGAASMTLTVQARLLLSGI
VQQQNNLLRAPEAQQRMLQLTVWGIKQLQARVLAVERYLGDQQLLGIWGCSGKLICTTAV
PWNASWSNKSLDRIWNNMTWMEWEREIDNYTSEIYTLIEESQNQQEKNEQELLEL[664]░░░░
░HHHHHHHH*

FIG. 10

JR-FL gp140-NFL2P construct

MPMGSLQPLATLYLLGMLVASVLAVEKLWVTVYYGVPVWKEATTTLFCASDAKAYDTEVH
NVWATHACVPTDPNPQEVVLENVTEHFNMWKNNMVEQMQEDIISLWDQSLKPCVKLTPLC
VTLNCKDVNATNTTNDSEGTMERGEIKNCSFNITTSIRDKVQKEYALFYKLDVVPIDNNN
TSYRLISCDTSVITQACPKISFEPIPIHYCAPAGFAILKCNDKTFNGKGPCKNVSTVQCT
HGIRPVVSTQLLLNGSLAEEEVVIRSDNFTNNAKTIIVQLKESVEINCTRPNNNTRKSIH
IGPGRAFYTTGEIIGDIRQAHCNISRAKWNDTLKQIVIKLREQFENKTIVFNHSSGGDPE
IVMHSFNCGGEFFYCNSTQLFNSTWNNNTEGSNNTEGNTITLPCRIKQIINMWQEVGKAM
YAPPIRGQIRCSSNITGLLLTRDGGINENGTEIFRPGGGDMRDNWRSELYKYKVVKIEPL
GVAPTKAKRRVVQ░░░░░░░AVGIGAVFLGFLGAAGSTMGAASMTLTVQARLLLSGI
VQQQNNLLRAPEAQQRMLQLTVWGIKQLQARVLAVERYLGDQQLLGIWGCSGKLICTTAV
PWNASWSNKSLDRIWNNMTWMEWEREIDNYTSEIYTLIEESQNQQEKNEQELLEL[664]░░░░
░HHHHHHHH*

FIG. 11

JR-FL gp140-NFL3P construct

MPMGSLQPLATLYLLGMLVASVLAVEKLWVTVYYGVPVWKEATTTLFCASDAKAYDTEVH
NVWATHACVPTDPNPQEVVLENVTEHFNMWKNNMVEQMQEDIISLWDQSLKPCVKLTPLC
VTLNCKDVNATNTTNDSEGTMERGEIKNCSFNITTSIRDKVQKEYALFYKLDVVPIDNNN
TSYRLISCDTSVITQACPKISFEPIPIHYCAPAGFAILKCNDKTFNGKGPCKNVSTVQCT
HGIRPVVSTQLLLNGSLAEEEVVIRSDNFTNNAKTIIVQLKESVEINCTRPNNNTRKSIH
IGPGRAFYTTGEIIGDIRQAHCNISRAKWNDTLKQIVIKLREQFENKTIVFNHSSGGDPE
IVMHSFNCGGEFFYCNSTQLFNSTWNNNTEGSNNTEGNTITLPCRIKQIINMWQEVGKAM
YAPPIRGQIRCSSNITGLLLTRDGGINENGTEIFRPGGGDMRDNWRSELYKYKVVKIEPL
GVAPTKAKRRVVQ░░░░░░░░░░░░░AVGIGAVFLGFLGAAGSTMGAASMTLTVQARLLLSGI
VQQQNNLLRA░EAQQRMLQLTVWGIKQLQARVLAVERYLGDQQLLGIWGCSGKLICTTAV
PWNASWSNKSLDRIWNNMTWMEWEREIDNYTSEIYTLIEESQNQQEKNEQELLEL$^{664}$░░░░
░HHHHHHHH*

FIG. 12

Clade C 16055 gp140-NFL2P construct

16055 gp140-NFL2P: It has I559P mutation (highlighted in green and underlined)
MPMGSLQPLATLYLLGMLVASVLAGNLWVTVYYGVPVWKEAKTTLFCASDAKAYEK
EVHNVWATHACVPTDPNPQEMVLENVTENFNMWKNDMVEQMHEDVISLWDQSLKPC
VKLTPLCVTLECRQVNTTNATSSVNVTNGEEIKNCSFNATTEIRDKKQKVYALFYRLDIV
PLEEERKGNSSKYRLINCNTSAITQACPKVTFDPIPIHYCAPAGYAILKCNNKTFNGTGPC
NNVSTVQCTHGIKPVVSTQLLLNGSLAEGEIIIRSENLTNNVKTIIVHLNESVEIVCTRPNN
NTRKSIRIGPGQTFYATGDIIGNIRQAYCNIKKDDWIRTLQRVGKKLAEHFPRRIINFTSPA
GGDLEITTHSFNCRGEFFYCNTSSLFNSTYNPNDTNSNSSSSNSSLDITIPCRIKQIINMWQ
EVGRAMYAPPIEGNITCKSNITGLLLVRDGGVESNETEIFRPGGGDMRNNWRSELYKYK
VVEIKPLGIAPTAAKRRVVE░░░░░░░░░░░AVGLGAVIFGFLGAAGSTMGAASITLTVQ
ARQLLSGIVQQQSNLLKA░EAQQHLLQLTVWGIKQLQTRVLAIERYLKDQQLLGIWGCS
GKLICTTAVPWNSSWSNKSHDEIWGNMTWMQWDREISNYTNTIYRLLEDSQNQQEQNE
KDLLALD ░░░░░░░░░░░░░░--

FIG. 13

Clade A BG505 gp140-NFL2P construct

BG505 gp140-NFL2P: It has T332N and I559P mutation (highlighted in green and underlined)

MPMGSLQPLATLYLLGMLVASVLAAENLWVTVYYGVPVWKDAETTLFCASDAKAYET
EKHNVWATHACVPTDPNPQEIHLENVTEEFNMWKNNMVEQMHTDIISLWDQSLKPCV
KLTPLCVTLQCTNVTNNITDDMRGELKNCSFNMTTELRDKKQKVYSLFYRLDVVQINE
NQGNRSNNSNKEYRLINCNTSAITQACPKVSFEPIPIHYCAPAGFAILKCKDKKFNGTGPC
PSVSTVQCTHGIKPVVSTQLLLNGSLAEEEVMIRSENITNNAKNILVQFNTPVQINCTRPN
NNTRKSIRIGPGQAFYATGDIIGDIRQAHCNVSKATWNETLGKVVKQLRKHFGNNTIIRF
ANSSGGDLEVTTHSFNCGGEFFYCNTSGLFNSTWISNTSVQGSNSTGSNDSITLPCRIKQII
NMWQRIGQAMYAPPIQGVIRCVSNITGLILTRDGGSTNSTTETFRPGGGDMRDNWRSEL
YKYKVVKIEPLGVAPTRAKRRVVGGGGGSGGGGSAVGIGAVFLGFLGAAGSTMGAAS
MTLTVQARNLLSGIVQQQSNLLRAPEAQQHLLKLTVWGIKQLQARVLAVERYLRDQQL
LGIWGCSGKLICTTNVPWNSSWSNRNLSEIWDNMTWLQWDKEISNYTQIIYGLLEESQN
QQEKNEQDLLALDGGGGSHHHHHHHH

FIG. 14

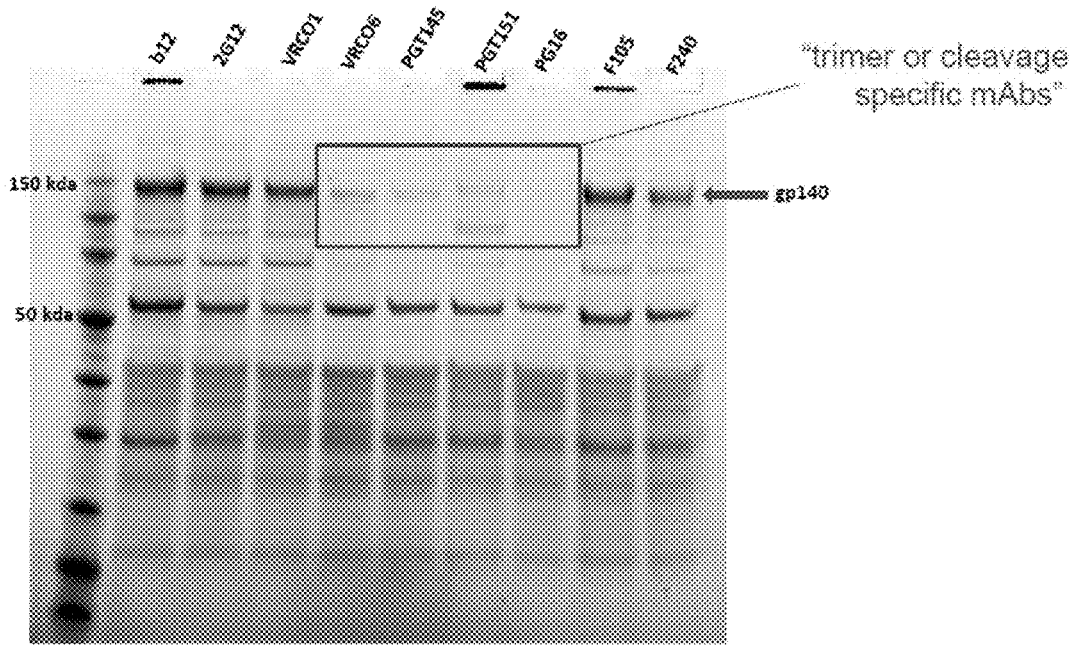

FIG. 15

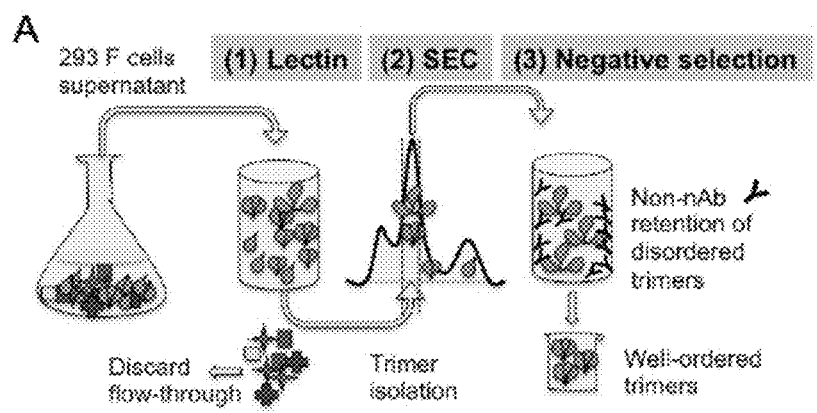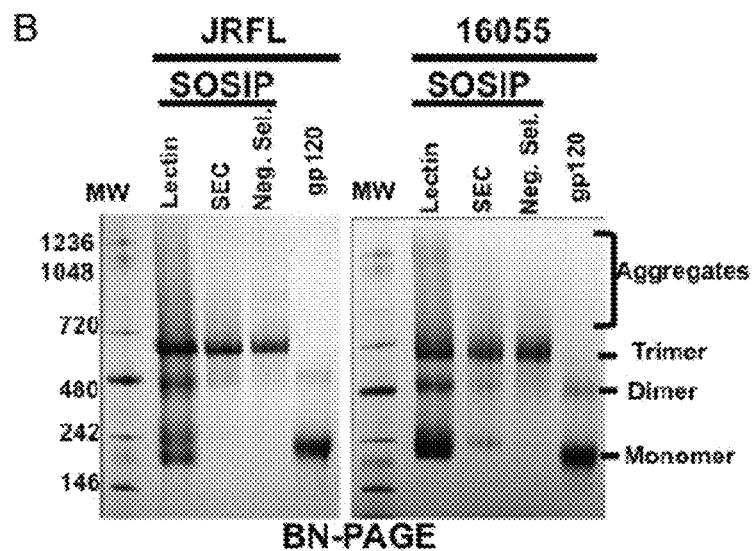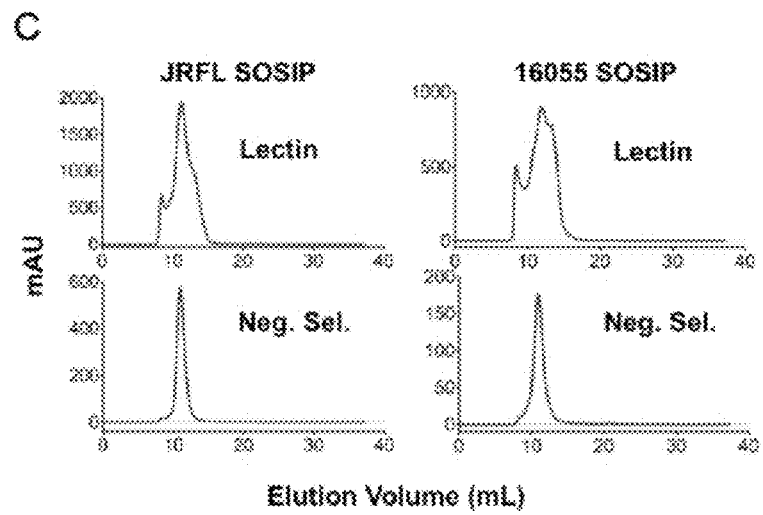
FIGS. 28A-C

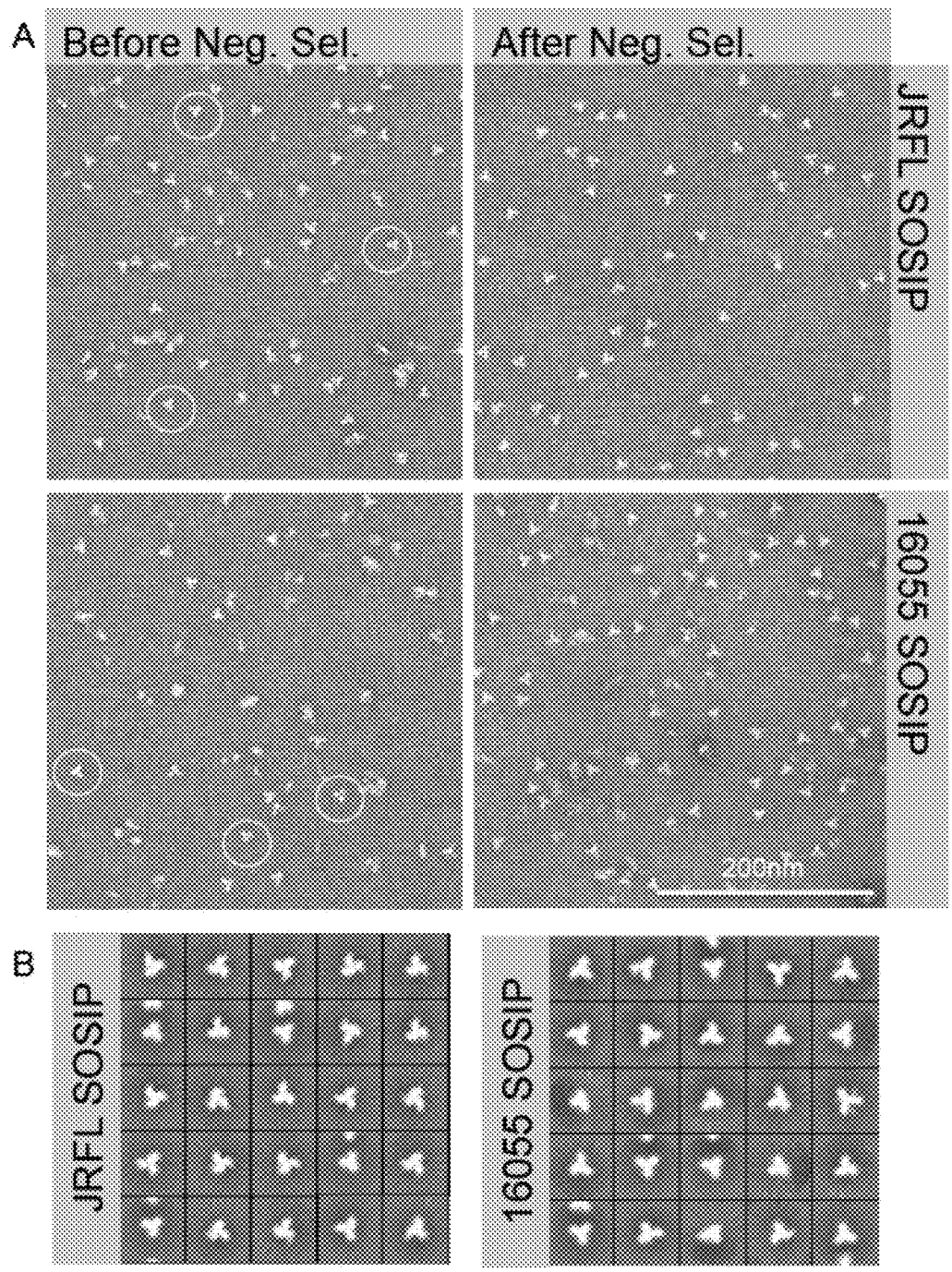
FIGS. 29A-B

FIGS. 31A-B

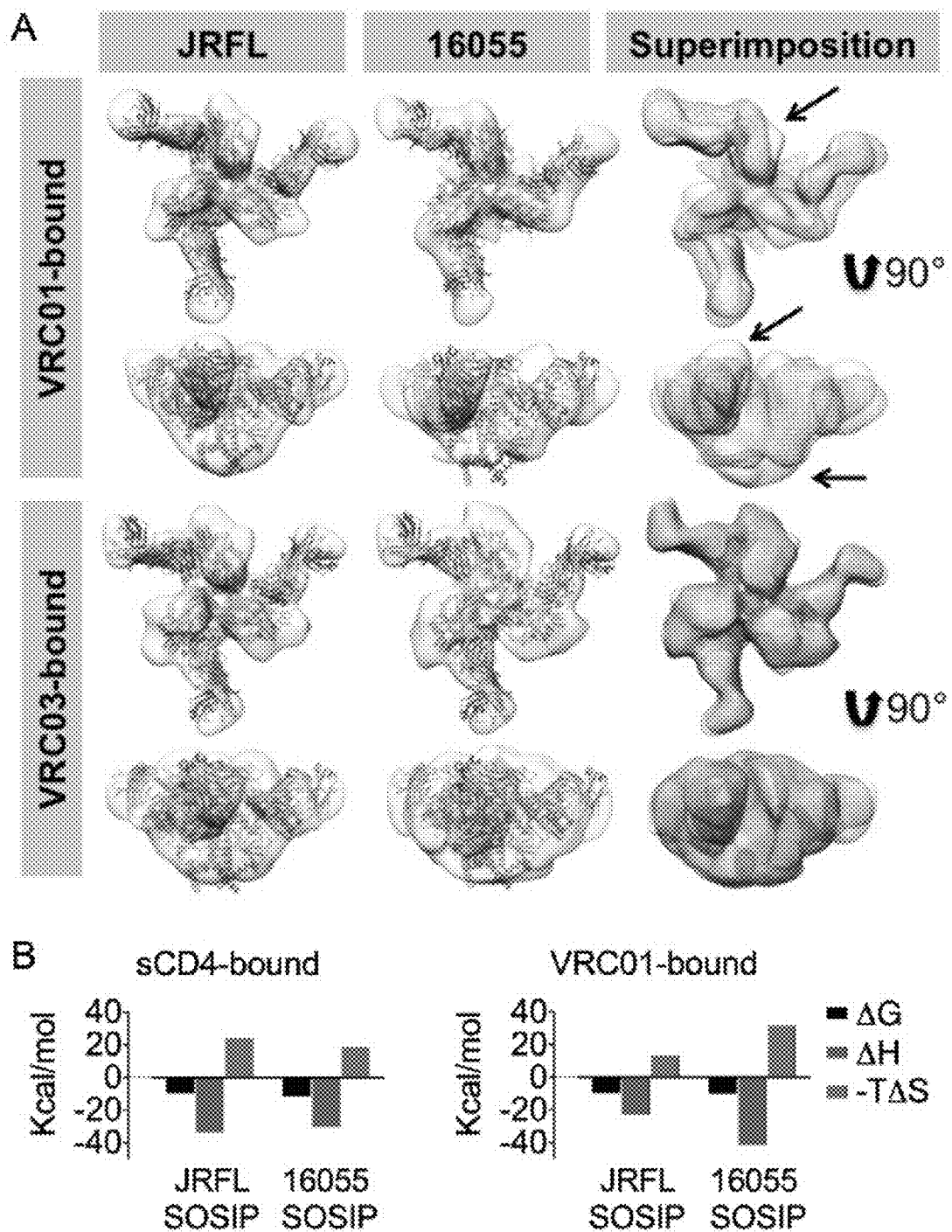
FIGS. 33A-B

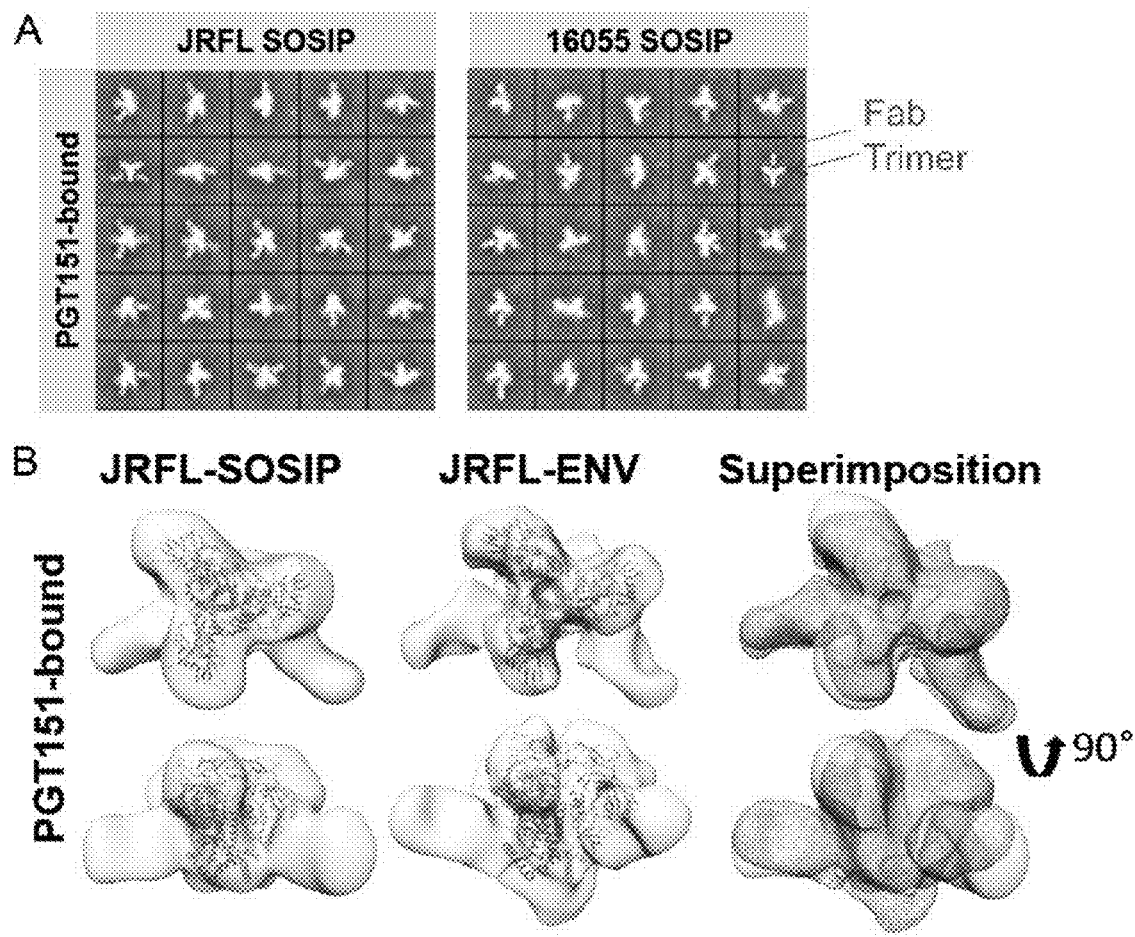
FIGS. 34A-B

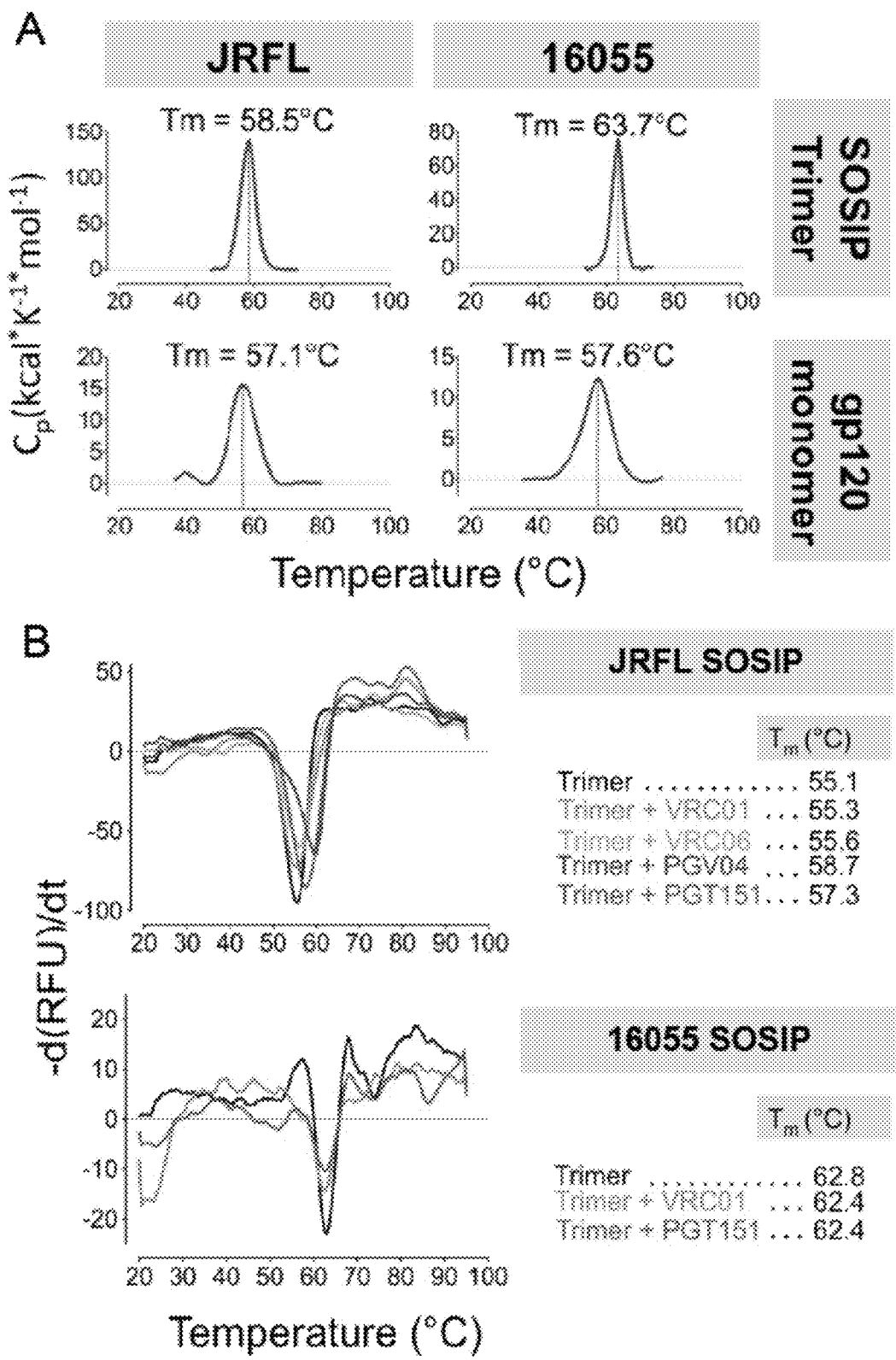
FIGS. 35A-B

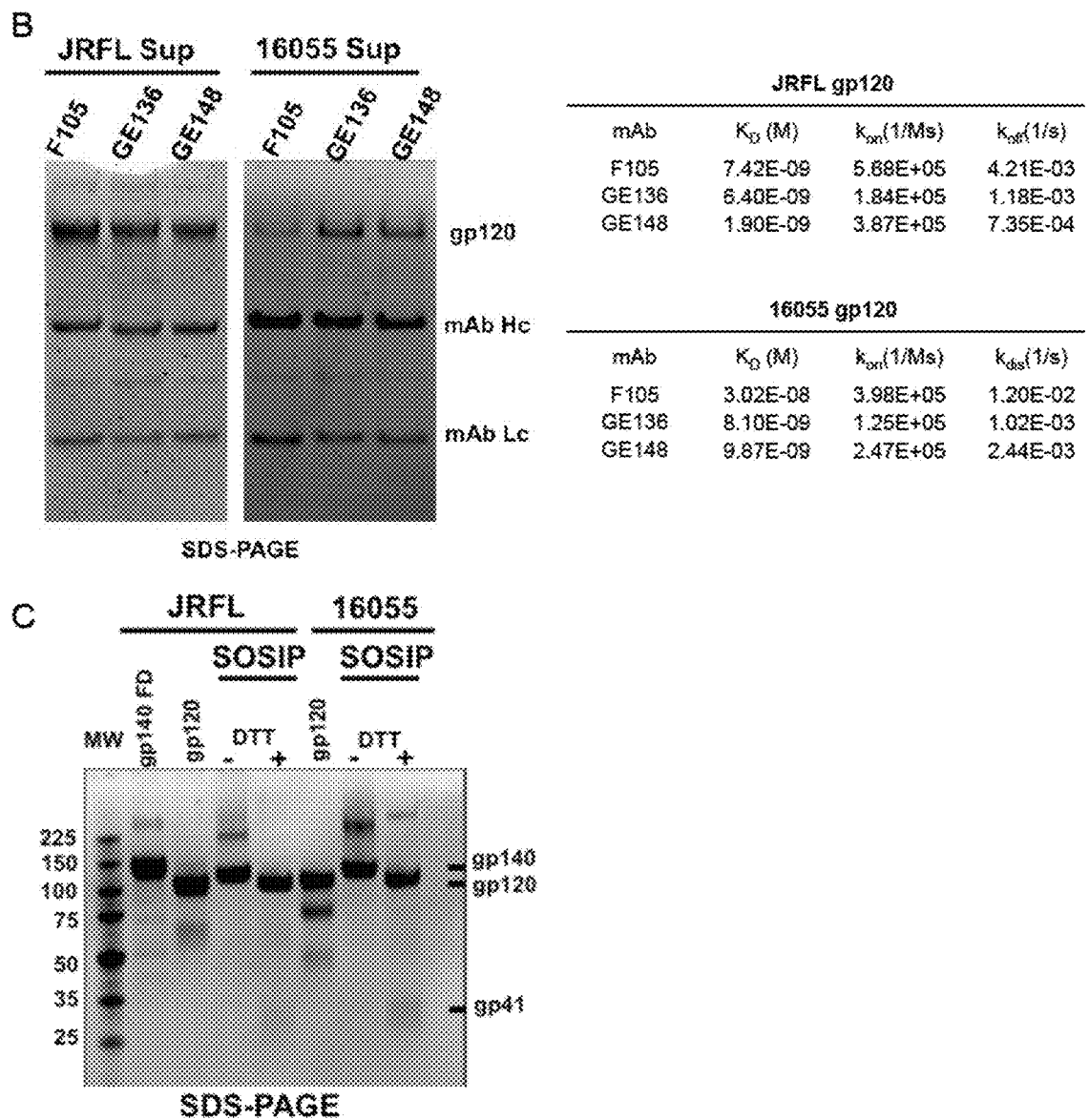
FIGS. 36B-C

| | 2G12 | VRC06 | PGT145 | PGT151 | F105 | 19b |
|---|---|---|---|---|---|---|
| BG505_I535P | +++ | ++ | ++ | ++ | + | + |
| BG505_L539P | +++ | ++ | ++ | ++ | + | + |
| BG505_A558P | +++ | + | + | + | + | + |
| BG505_I559P | +++ | +++ | ++ | ++ | + | + |
| BG505_L568P | +++ | ++ | ++ | ++ | + | + |
| BG505_T569P | +++ | + | + | + | + | + |
| BG505_I573P | +++ | - | - | - | + | ++ |
| BG505_M535P | +++ | - | - | - | + | ++ |
| BG505_L571P | +++ | - | - | - | + | ++ |
| BG505_Q571P | ++ | - | - | - | + | + |
| BG505_I574P | ++ | - | - | - | + | ++ |
| BG505_L576P | + | - | - | - | + | n.d. |
| BG505_I577P | +++ | - | - | - | + | ++ |
| BG505_Q578P | + | - | - | - | + | n.d. |
| BG505_V580P | + | - | - | - | + | n.d. |

+++ : strong binding  
++ : moderate binding  
+ : weak binding  
- : no binding

FIG. 47

10 µM liposome recipe:

60% DGPC
39% cholesterol
1% DOGS-NTA-Nickel

Number of lipid molecules per liposome $$N_{tot} = \frac{\left[4\pi\left(\frac{d}{2}\right)^2 + 4\pi\left(\frac{d}{2} - h\right)^2\right]}{a}$$

d = diameter
h = thickness of the monolayer
a = area of lipid head group $$N_{tot} = 17.69 \times \left[\left(\frac{d}{2}\right)^2 + \left(\frac{d}{2} - 5\right)^2\right]$$

800 Ni sites per liposome

Number of liposomes per ml of solution (7×10¹⁰ liposomes per ml PBS)

$$N_{lipo} = \frac{M_{lipid} \times N_A}{N_{tot} \times 1000}$$

$N_A$ = Avagadro number
$M_{lipid}$ = molar concentration of lipid
$N_{tot}$ = total number of lipid molecules per liposome

| % Ni lipid | No. of Ni sites/liposome | Amt of protein for conjugation/ml liposomes |
|---|---|---|
| 4 | 3200 | 4400 µg |
| 2 | 1600 | 2200 µg |
| 1 | 800 | 1100 µg |
| 0.5 | 400 | 550 µg |
| 0.25 | 200 | 275 µg |

FIG. 50

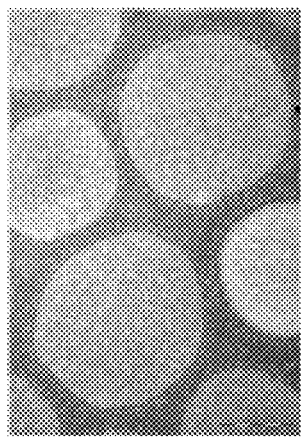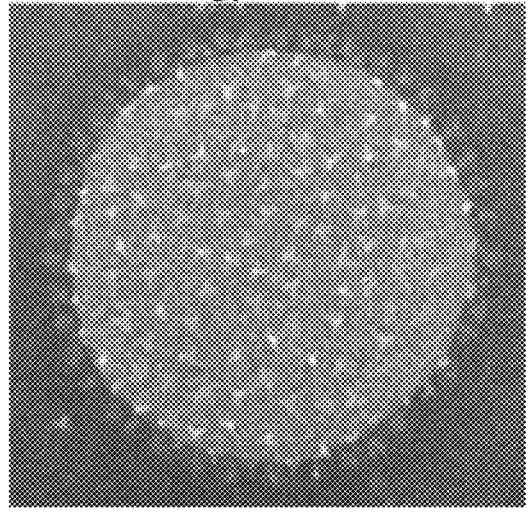
FIG. 55

FIG. 59

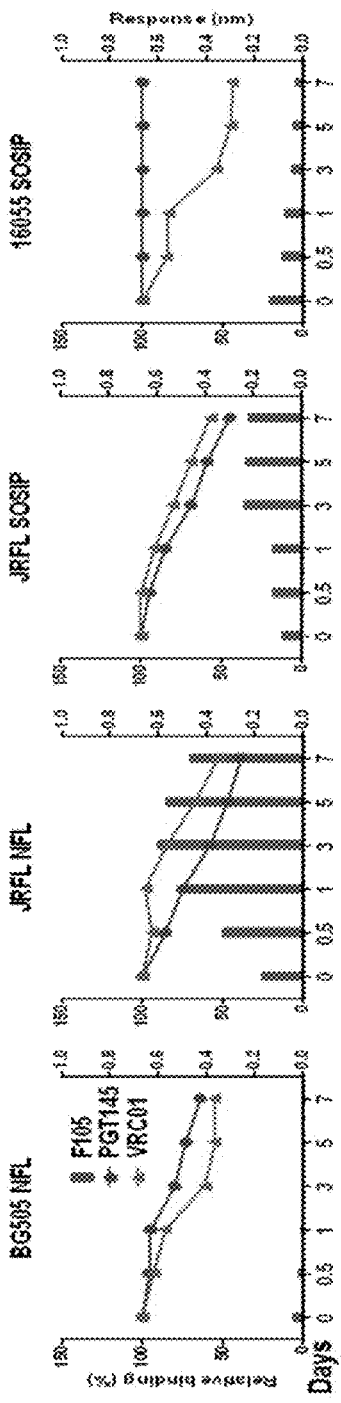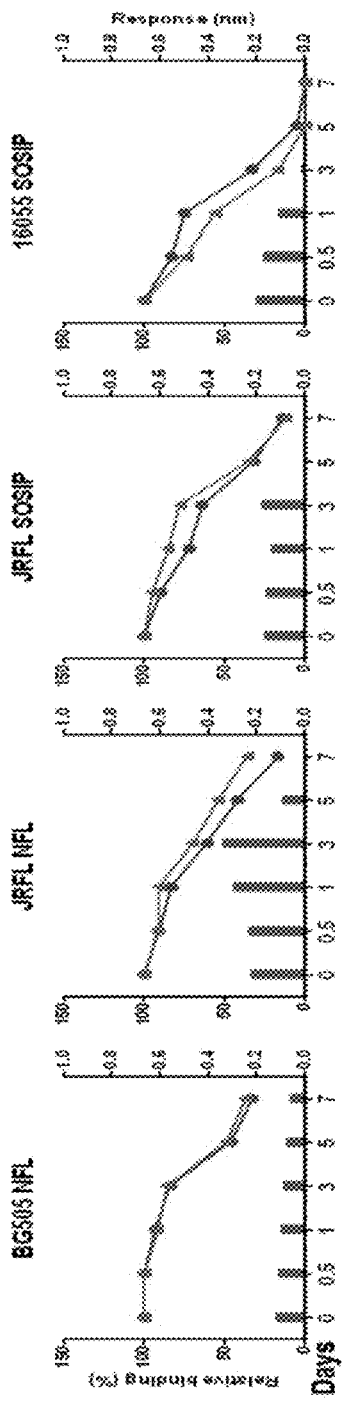
FIG. 62

JRFL NFL fixation:
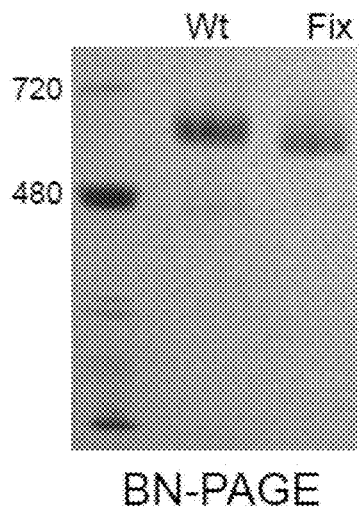
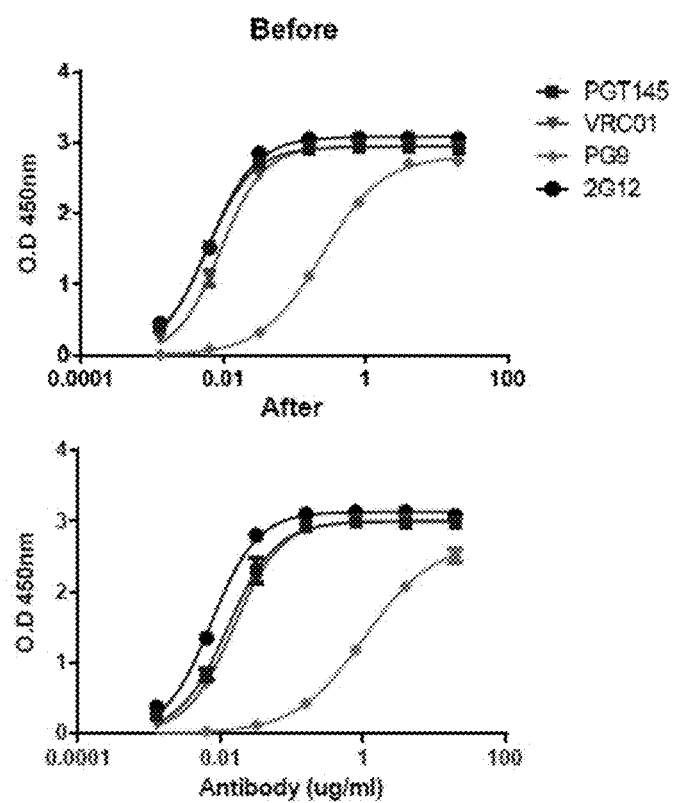
FIG. 63

BG505NFL2P_C
ATGCCTATGGGATCACTGCAGCCTCTGGCAACTCTGTATCTGCTGGGGATGCTGGTCGCAAGCGTCCTGGCCGCC
GAAAATCTGTGGGTGACCGTCTACTATGGCGTGCCTGTCTGGAAGGACGCCGAAACCACACTGTTCTGCGCCAGC
GATGCTAAGGCATACGAAACAGAGAAACACAATGTGTGGGCAACTCATGCCTGTGTCCCAACCGACCCAAACCCC
CAGGAAATCCACCTGGAGAATGTGACTGAGGAGTTCAACATGTGGAAGAACAATATGGTGGAGCAGATGCATACC
GACATCATTTCCCTGTGGGATCAGTCTCTGAAGCCTTGCGTGAAACTGACTCCACTGTGCGTCACCCTGCAGTGT
ACCAACGTGACAAACAATATCACCGACGATATGAGGGGAGAACTGAAGAATTGTTCATTCAACATGACTACCGAG
CTGCGAGACAAGAAACAGAAAGTGTACAGCCTGTTTTATCGGCTGGATGTGGTCCAGATCAATGAAAACCAGGGC
AATCGCAGTAACAATTCAAACAAGGAGTACCGACTGATCAATTGCAACACTAGCGCTATTACCCAGGCATGTCCA
AAAGTGTCCTTCGAGCCTATCCCAATTCATTATTGCGCCCCCGCTGGCTTCGCCATCCTGAAGTGTAAAGATAAG
AAGTTCAACGGGACAGGACCCTGCCCTTCAGTGAGCACAGTCCAGTGTACTCACGGGATTAAGCCAGTGGTCAGT
ACTCAGCTGCTGCTGAATGGATCACTGGCCGAGGAAGAAGTGATGATCCGGTCTGAGAACATCACAAACAACGCT
AAGAACATCCTGGTGCAGTTCAACACTCCCGTCCAGATTAATTGCACAAGACCTAACAATAACACTCGAAAATCC
ATCCGGATTGGCCCTGGCCAGGCTTTTTATGCAACCGGGGACATCATTGGCGACATCCGCCAGGCACACTGCAAT
GTGTCTAAGGCTACCTGGAACGAGACACTGGGAAAGGTGGTCAAACAGCTGCGGAAACATTTCGGCAATAACACC
ATCATTAGATTTGCCAATAGCTCCGGCGGGGACCTGGAAGTGACAACTCACTCCTTCAACTGCGGAGGCGAGTTC
TTTTACTGTAACACAAGTGGCCTGTTTAATTCAACATGGATCAGCAACACTTCCGTGCAGGGCTCCAATTCTACT
GGGTCTAACGATAGTATCACCCTGCCCTGCAGGATTAAGCAGATCATTAATATGTGGCAGCGCATTGGACAGGCC
ATGTATGCTCCCCCTATCCAGGGCGTGATTAGATGTGTCAGTAATATCACCGGGCTGATTCTGACAAGGGACGGG
GGATCAACCAACAGCACCACAGAGACCTTCCGGCCCGGCGGAGGAGACATGAGAGATAACTGGAGGAGCGAACTG
TACAAGTATAAAGTGGTCAAGATCGAGCCACTGGGAGTGGCACCAACCCGCGCTAAACGAAGAGTGGTCGGAGGA
GGAGGAGGGAGCGGAGGAGGAGGCAGCGCTGTGGGAATTGGCGCAGTCTTCCTGGGGTTTCTGGGAGCCGCTGGC
TCAACAATGGGCGCAGCCAGCATGACACTGACTGTCCAGGCCCGCAATCTGCTGTCCGGGATCGTGCAGCAGCAG
TCTAACCTGCTGCGAGCA▒▒▒GAAGCCCAGCAGCACCTGCTGAAGCTGACCGTGTGGGGGATCAAACAGCTGCAG
GCACGGGTGCTGGCCGTCGAGAGATACCTGCGCGATCAGCAGCTGCTGGGGATCTGGGGATGCAGCGGCAAGCTG
ATTTGTACTACCAATGTGCCTTGGAACTCTAGTTGGTCTAATAGAAACCTGAGTGAAATCTGGGACAATATGACC
TGGCTGCAGTGGGATAAGGAGATTTCTAACTACACACAGATCATCTACGGCCTGCTGGAAGAGAGTCAGAATCAG
CAGGAGAAGAACGAGCAGGACCTGCTGGCCCTGGATGGCGGAGGAGGCTCCCACCATCATCACCACCATCACCAT
TGCTGA

BG505NFL2P_GSG_C
ATGCCTATGGGATCACTGCAGCCTCTGGCAACTCTGTATCTGCTGGGGATGCTGGTCGCAAGCGTCCTGGCCGCC
GAAAATCTGTGGGTGACCGTCTACTATGGCGTGCCTGTCTGGAAGGACGCCGAAACCACACTGTTCTGCGCCAGC
GATGCTAAGGCATACGAAACAGAGAAACACAATGTGTGGGCAACTCATGCCTGTGTCCCAACCGACCCAAACCCC
CAGGAAATCCACCTGGAGAATGTGACTGAGGAGTTCAACATGTGGAAGAACAATATGGTGGAGCAGATGCATACC
GACATCATTTCCCTGTGGGATCAGTCTCTGAAGCCTTGCGTGAAACTGACTCCACTGTGCGTCACCCTGCAGTGT
ACCAACGTGACAAACAATATCACCGACGATATGAGGGGAGAACTGAAGAATTGTTCATTCAACATGACTACCGAG
CTGCGAGACAAGAAACAGAAAGTGTACAGCCTGTTTTATCGGCTGGATGTGGTCCAGATCAATGAAAACCAGGGC
AATCGCAGTAACAATTCAAACAAGGAGTACCGACTGATCAATTGCAACACTAGCGCTATTACCCAGGCATGTCCA
AAAGTGTCCTTCGAGCCTATCCCAATTCATTATTGCGCCCCCGCTGGCTTCGCCATCCTGAAGTGTAAAGATAAG
AAGTTCAACGGGACAGGACCCTGCCCTTCAGTGAGCACAGTCCAGTGTACTCACGGGATTAAGCCAGTGGTCAGT
ACTCAGCTGCTGCTGAATGGATCACTGGCCGAGGAAGAAGTGATGATCCGGTCTGAGAACATCACAAACAACGCT
AAGAACATCCTGGTGCAGTTCAACACTCCCGTCCAGATTAATTGCACAAGACCTAACAATAACACTCGAAAATCC
ATCCGGATTGGCCCTGGCCAGGCTTTTTATGCAACCGGGGACATCATTGGCGACATCCGCCAGGCACACTGCAAT
GTGTCTAAGGCTACCTGGAACGAGACACTGGGAAAGGTGGTCAAACAGCTGCGGAAACATTTCGGCAATAACACC
ATCATTAGATTTGCCAATAGCTCCGGCGGGGACCTGGAAGTGACAACTCACTCCTTCAACTGCGGAGGCGAGTTC
TTTTACTGTAACACAAGTGGCCTGTTTAATTCAACATGGATCAGCAACACTTCCGTGCAGGGCTCCAATTCTACT
GGGTCTAACGATAGTATCACCCTGCCCTGCAGGATTAAGCAGATCATTAATATGTGGCAGCGCATTGGACAGGCC
ATGTATGCTCCCCCTATCCAGGGCGTGATTAGATGTGTCAGTAATATCACCGGGCTGATTCTGACAAGGGACGGG
GGATCAACCAACAGCACCACAGAGACCTTCCGGCCCGGCGGAGGAGACATGAGAGATAACTGGAGGAGCGAACTG
TACAAGTATAAAGTGGTCAAGATCGAGCCACTGGGAGTGGCACCAACCCGCGCTAAACGAAGAGTGGTCGGAGGA
GGAGGAGGGAGCGGAGGAGGAGGCAGCGCTGTGGGAATTGGCGCAGTCTTCCTGGGGTTTCTGGGAGCCGCTGGC
TCAACAATGGGCGCAGCCAGCATGACACTGACTGTCCAGGCCCGCAATCTGCTGTCCGGGATCGTGCAGCAGCAG
TCTAACCTGCTGCGAGCA▒▒▒GAAGCCCAGCAGCACCTGCTGAAGCTGACCGTGTGGGGGATCAAACAGCTGCAG
GCACGGGTGCTGGCCGTCGAGAGATACCTGCGCGATCAGCAGCTGCTGGGGATCTGGGGATGCAGCGGCAAGCTG
ATTTGTACTACCAATGTGCCTTGGAACTCTAGTTGGTCTAATAGAAACCTGAGTGAAATCTGGGACAATATGACC
TGGCTGCAGTGGGATAAGGAGATTTCTAACTACACACAGATCATCTACGGCCTGCTGGAAGAGAGTCAGAATCAG
CAGGACAAGAACCAGCAGGACCTGCTGGCCCTGGATGGCGGAGGAGGCTCCCACCATCATCACCACCATCACCAT
GGATCCGGCTGCTGA

FIG. 69

HM623558-NFL2
```
ATGCCCATGGGCTCCCTGCAGCCCCTGGCCACCCTGTACCTGCTGGGCATGCTGGTGGCCTCCGTGCTGG
CCGTGGGCGACAACCTGTGGGTGACCGTGTACTACGGCGTGCCCGTGTGGAAGGAGGCCAAGACCACCCT
GTTCTGCGCCTCCGACGCCAAGGCCTACGAGCGCGAGGTGCACAACGTGTGGGCCACCCACGCCTGCGTG
CCCACCGACCCCAACCCCAGGAGATCGCCCTGGAGAACGTGACCGAGAACTTCAACATGTGGAAGAACA
ACATGGTGGACCAGATGCACGAGGACATCATCTCCCTGTGGGACCAGTCCCTGAAGCCCTGCGTGAAGCT
GACCCCCCTGTGCGTGACCCTGAACTGCACCAACGTGACCAAGAACGACACCAACGCCAACAACACCGCC
GAGGGCAAGGAGGAGCGCAAGAACTGCTCCTTCAACGCCACCACCGAGCTGCGCGACAAGAACCGCAAGG
TGTACGCCCTGTTCTACAAGCTGGACATCGTGCCCCTGAACCCCTCCAACAACTCCAACTCCTCCGGCCA
GTACCGCCTGATCACCTGCAACACCTCCGTGATCACCCAGGCCTGCCCCAAGATCATCTTCGACCCCATC
CCCATCCACTACTGCGCCCCCGCCGGCTACGCCATCCTGAAGTGCAACAACAAGACCTTCAACGGCACCG
GCCCCTGCAACAACGTGTCCACCGTGCAGTGCACCCACGGCATCAAGCCCGTGGTGTCCACCCAGCTGCT
GCTGAACGGCTCCCTGGCCGAGGAGGAGATCATCATCCGCTCCGAGAACCTGACCGACAACGTGAAGACC
ATCATCGTGCACCTGAACGAGTCCGTGATGATCAACTGCACCCGCCCCGGCAACAACACCCGCAAGTCCA
TCCGCATCGGCCCCGGCCAGACCTTCTACGCCCCCGGCGACATCATCGGCGACATCCGCCAGGCCCACTG
CAACATCTCCATCAACCAGTGGAACAACACCCTGCAGAAGATCGCCAAGAAGCTGCAGACCCGCTTCAAC
CGCCCCATCAAGTTCGAGCCCCACTCCGGCGGCGACCTGGAGATCACCACCCACTCCTTCAACTGCCGCG
GCGAGTTCTTCTACTGCAACACCTCCCAGCTGTTCAACGGCACCTACAACGGCACCTGGAACGGCCCCTG
GAACAACAACGAGTCCGACACCATCATCCTGCCCTGCCGCATCAAGCAGATCATCAACATGTGGCAGGAG
GTGGGCCGCGCCATGTACGCCCCCCCCATCGCCGGCAACATCACCTGCAAGTCCAACATCACCGGCCTGC
TGCTGACCCGCGACGGCGGCAAGAACGAGACCAACAACGGCACCGAaATCTTCCGCCCCGGCGGCGGCGA
CATGCGCGACAACTGGCGCTCCGAGCTGTACAAGTACAAGGTGGTGCAGATCGAGCCCCTGGGCGTGGCC
CCCACCAAGGCCAAGCGCCGCGTGGTGCAGGGCGGCGGCGGCTCCGGCGGCGGCGGCTCCGCCGTGGGCA
CCCTGGGCGCCATGTTCCTGGGCTTCCTGGGCGCCGCCGGCTCCACCATGGGCGCCGCCTCCGTGACCCT
GACCGTGCAGGCCCGCCAGCTGCTGTCCGGCATCGTGCAGCAGCAGAACAACCTGCTGAAGGCCCCCGAG
GCCCAGCAGCACCTGCTGCAGCTGACCGTGTGGGGCATCAAGCAGCTGCAGGCCCGCGTGCTGGCCATCG
AGCGCTACCTGAAGGACCAGCAGCTGCTGGGCCTGTGGGGCTGCTCCGGCAAGCTGATCTGCACCACCGC
CGTGCCCTGGAACGCCTCCTGGTCCAACAAGTCCCTGAACATGATCTGGGACAACATGACCTGGATGGAG
TGGGAGCGCGAGGTGTCCAACTACACCGACATCATCTACTCCCTGATCGAGGAGTCCCAGAACCAGCAGG
AGATGAACGAGAAGGAGCTGCTGGAGCTGGACGGCGGCGGCGGCTCCCACCACCACCACCACCACCACCA
C
```

FIG. 70A

EF117266-NFL2
```
ATGCCCATGGGCTCCCTGCAGCCCCTGGCCACCCTGTACCTGCTGGGCATGCTGGTGGCCTCCGTGCTGG
CCGTGGAGAACCTGTGGGTGACCGTGTACTACGGCGTGCCCGTGTGGAAGGAGGCCCGCACCACCCTGTT
CTGCGCCTCCGACGCCAAGGCCTACGAGACCGAGGTGCACAACGTGTGGGCCACCCACGCCTGCGTGCCC
ACCGACCCCAACCCCCAGGAGATGGTGCTGGGCAACGTGACCGAGAACTTCAACATGTGGAAGAACGACA
TGGTGGACCAGATGCACGAGGACGTGATCTCCCTGTGGGCCCAGTCCCTGAAGCCCTGCGTGAAGCTGAC
CCCCCTGTGCGTGACCCTGGAGTGCACCCAGGTGAACGCCACCCAGGGCAACACCACCCAGGTGAACGTG
ACCCAGGTGAACGGCGACGAGATGAAGAACTGCTCCTTCAACACCACCACCGAGATCCGCGACAAGAAGC
AGAAGGCCTACGCCCTGTTCTACCGCCTGGACCTGGTGCCCCTGGAGCGCGAGAACCGCGGCGACTCCAA
CTCCGCCTCCAAGTACATCCTGATCAACTGCAACACCTCCGCCATCACCCAGGCCTGCCCCAAGGTGAAC
TTCGACCCCATCCCCATCCACTACTGCACCCCCGCCGGCTACGCCATCCTGAAGTGCAACAACAAGACCT
TCAACGGCACCGGCTCCTGCAACAACGTGTCCACCGTGCAGTGCACCCACGGCATCAAGCCCGTGGTGTC
CACCCAGCTGCTGCTGAACGGCTCCCTGGCCGAGGAGGAGATCATCATCCGCTCCGAGAACCTGACCGAC
AACGTGAAGACCATCATCGTGCACCTGGACCAGTCCGTGGAGATCGTGTGCACCCGCCCCAACAACAACA
CCCGCAAGTCCATCCGCATCGGCCCCGGCCAGACCTTCTACGCCACCGGCGACATCATCGGCAACATCCG
CGAGGCCCACTGCAACATCTCCGAGAAGAAGTGGCACGAGATGCTGCGCCGCGTGTCCGAGAAGCTGGCC
GAGCACTTCCCCAACAAGACCATCAAGTTCACCTCCTCCTCCGGCGGCGACCTGGAGATCACCACCCACT
CCTTCAACTGCCGCGGCGAGTTCTTCTACTGCAACACCTCCGGCCTGTTCAACTCCACCTACATGCCCAA
CGGCACCTACATGCCCAACGGCACCAACAACTCCAACTCCACCATCATCCTGCCCTGCCGCATCAAGCAG
ATCATCAACATGTGGCAGGAGGTGGGCCGCGCCATGTACGCCCCCCCCATCGCCGGCAACATCACCTGCA
ACTCCAACATCACCGGCCTGCTGCTGGTGCGCGACGGCGGCAAGAACAACAACACCGAaATCTTCCGCCC
CGGCGGCGGCGACATGCGCGACAACTGGCGCTCCGAGCTGTACAAGTACAAGGTGGTGGAGATCAAGCCC
CTGGGCGTGGCCCCCACCCGCGCCAAGCGCCGCGTGGTGGAGGGCGGCGGCGGCTCCGGCGGCGGCGGCT
CCGCCGTGGGCCTGGGCGCCGTGTTCCTGGGCTTCCTGGGCGCCGCCGGCTCCACCATGGGCGCCGCCTC
CATCACCCTGACCGTGCAGGCCCGCCAGCTGCTGTCCGGCATCGTGCAGCAGCAGTCCAACCTGCTGCAG
GCCCCCGAGGCCCAGCAGCACCTGCTGCAGCTGACCGTGTGGGGCATCAAGCAGCTGCAGACCCGCGTGC
TGGCCATCGAGCGCTACCTGAAGGACCAGCAGCTGCTGGGCATCTGGGGCTGCTCCGGCAAGCTGATCTG
CACCACCGCCGTGCCCTGGAACTCCTCCTGGTCCAACAAGTCCCTGACCGACATCTGGGACAACATGACC
TGGATGCAGTGGGACCGCGAGGTGTCCAACTACACCGGCATCATCTACCGCCTGCTGGAGGACTCCCAGA
ACCAGCAGGAGCGCAACGAGCAGGACCTGCTGGCCCTGGACGGCGGCGGCGGCTCCCACCACCACCACCA
CCACCACCAC
```

FIG. 70B

AY423971-NFL2
ATGCCCATGGGCTCCCTGCAGCCCCTGGCCACCCTGTACCTGCTGGGCATGCTGGTGGCCTCCGTGCTGG
CCTCCCTGTGGGTGACCGTGTACTACGGCGTGCCCGTGTGGAAGGAGGCCAAGACCACCCTGTTCTGCGC
CTCCGACGCCAAGGCCTACGAGCGCGAGGTGCACAACGTGTGGGCCACCCACGCCTGCGTGCCCACCGAC
CCCAACCCCCAGGAGATGGTGCTGGAGAACGTGACCGAGAACTTCAACATGTGGAAGAACGACATGGTGG
ACCAGATGCACGAGGACATCATCTCCCTGTGGGACGAGTCCCTGAAGCCCTGCGTGAAGCTGACCCCCCT
GTGCGTGACCCTGAACTGCACCTTCATCACCAACACCACCGAGATCAAGAACTGCACCTTCAACATGACC
ACCGAGCTGCGCGACATCAAGCAGCAGGGCCGCGCCCTGTTCGACACCCTGGACATCGTGCCCCTGAAGC
CCCCCAACAACTCCTCCAACTACTCCGAGTACCGCCTGATCTCCTGCAACACCTCCACCATCACCCAGGC
CTGCCCCAAGGTGTCCTTCGACCCCATCCCCATCCACTACTGCGCCCCCGCCGGCTACGCCATCCTGAAG
TGCAACAACAAGACCTTCAACGGCCTGGGCCCCTGCAACAACGTGTCCACCGTGCAGTGCACCCACGGCA
TCAAGCCCGTGGTGTCCACCCAGCTGCTGCTGAACGGCTCCCTGGCCGAGGAGGAGATCATCATCCGCTC
CGAGAACCTGACCAACAACGTGAAGACCATCATCGTGCACCTGAACGAGCCCGTGTACATCGTGTGCACC
CGCCCCAACAACAACACCCGCAAGTCCATGCGCATCGGCCCCGGCCAGACCTTCTACGCCACCGGCGACA
TCATCGGCGACATCCGCCAGGCCCACTGCAACATCTCCATCGAGAAGTGGAACACCACCCTGGAGAAGGT
GAAGGAGCGCCTGAAGAAGCACTTCCCCAACAAGATCATCAAGTTCGAGCCCTCCTCCGGCGGCGACCTG
GAGATCACCACCCACTCCTTCAACTGCCGCGGCGAGTTCTTCTACTGCAACACCGCCAACCTGTTCAACG
AGACCTTCATGAACCAGACCGACGCCAACCAGACCAACGCCACCATCACCCTGCAGTGCCGCATCAAGCA
GATCATCAACATGTGGCAGGGCGTGGGCCGCGCCATGTACGCCCCCCCCATCCCCGGCCGCATCACCTGC
AACTCCTCCATCACCGGCCTGATCCTGACCCGCGACGGCGGCGAGAACACCACCGACAACGGCACCGAaA
TCTTCCGCCCCGGCGGCGGCGACATGCGCGACAACTGGCGCTCCGAGCTGTACAAGTACAAGGTGGTGGA
GATCAAGCCCCTGGGCATCGCCCCCACCGAGGCCAAGCGCCGCGTGGTGGAGGGCGGCGGCGGCTCCGGC
GGCGGCGGCTCCGCCGTGGGCATCGGCGCCGTGTTCCTGGGCTTCCTGGGCGCCGCCGGCTCCACCATGG
GCGCCGCCTCCATCACCCTGACCGTGCAGGCCCGCCAGCTGCTGTCCGGCATCGTGCAGCAGCAGTCCAA
CCTGCTGCGCGCCCCCGAGGCCCAGCAGCACATGCTGCAGCTGACCGTGTGGGGCATCAAGCAGCTGCAG
GCCCGCGTGCTGGCCATCGAGCGCTACCTGAAGGACCAGCAGCTGCTGGGCATCTGGGGCTGCTCCGGCA
AGCTGATCTGCACCACCAACGTGCCCTGGAACTCCTCCTGGTCCAACAAGTCCCTGGGCGACATCTGGGA
CAACATGACCTGGATGGAGTGGGACCGCGAaATCTCCAACTACACCAACATCATCTTCGGCCTGCTGGAG
GACTCCCAGAACCAGCAGGAGCGCAACGAGAAGGACCTGCTGGCCCTGGACGGCGGCGGCGGCTCCCACC
ACCACCACCACCACCACCAC

FIG. 70C

KC863309-NFL2
```
ATGCCCATGGGCTCCCTGCAGCCCCTGGCCACCCTGTACCTGCTGGGCATGCTGGTGGCCTCCGTGCTGG
CCGCCAACAACCTGTGGGTGACCGTGTACTACGGCGTGCCCGTGTGGCGCGACGCCGAGACCACCCTGTT
CTGCGCCTCCGACGCCAAGGCCTACGACACCGAGGTGCACAACGTGTGGGCCACCCACGCCTGCGTGCCC
ACCGACCCCGACCCCAGGAGATCGACCTGAAGAACGTGACCGAGGAGTTCAACATGTGGAAGAACAACA
TGGTGGAGCAGATGCACACCGACATCATCTCCCTGTGGGACCAGTCCCTGAAGCCCTGCGTGAAGCTGAC
CCACCTGTGCGTGACCCTGAACTGCTCCACCGCCAACGTGAACGTGACCGACTACAACATCACCACCGGC
GACAAGGAGGAGATCAAGAACTGCTCCTTCAACATGACCACCGAGCTGTCCGACAAGAAGCAGAAGGTGC
ACTCCCTGTTCTACCGCCTGGACGTGGTGCCCATCGAGCAGGACAACTCCAAGAACAACTCCAACTCCGG
CGACAACTCCTCCTACTCCTCCTACTCCAACTACCGCCTGATCAACTGCAACACCTCCGCCATCACCCAG
GCCTGCCCCAAGGTGACCTTCGACCCCATCCCCATCCACTACTGCGCCCCCGCCGGCTTCGCCATCCTGA
AGTGCAAGGACGACGGCTTCAACGGCACCGGCCCCTGCAAGAACGTGTCCTCCGTGCAGTGCACCCACGG
CATCAAGCCCGTGGTGTCCACCCAGCTGCTGCTGAACGGCTCCCTGGCCAAGGAGGGCATCCGCATCCGC
TCCGAGAACATCACCGACAACACCAAGACCATCATCGTGCAGCTGGACAAGCCCGTGCGCATCAACTGCA
CCCGCCCCAACAACAACACCCGCAAGTCCATGCGCATCGGCCCCGGCCAGACCTTCTTCGCCACCGGCGA
CATCATCGGCGACATCCGCAAGGCCCACTGCAACATCTCCATCTCCGAGTGGAACGAGACCCTGTACCGC
GTGGCCAAGCAGCTGGGCGGCATGATCGGCAACAAGACCGTGAAGTTCGACAACTCCTCCGGCGGCGACC
TGGAGATCACCACCCACTCCTTCAACTGCGGCGGCGAGTTCTTCTACTGCAACACCACCGACCTGTTCAA
GGGCACCTGGACCCCCAACACCTCCATCTGGAACGCCAACTGGAACGACTCCATCAAGTCCAACGACACC
TCCAACGCCAACATCACCATCCTGTGCAAGATCAAGCAGATCGTGCGCATGTGGCAGCGCGTGGAGCAGG
CCATGTACGCCCCCCCCATCCAGGGCGTGATCTCCTGCTCCTCCAACATCACCGGCCTGCTGCTGACCTC
CGACGGCGGCCGCAACACCTCCAACAACAACACCGAGACCTTCCGCCCCGGCGGCGGCGACATGCGCGAC
AACTGGCGCTCCGAGCTGTACAAGTACAAGGTGGTGAAGATCGAGCCCTGGGCGTGGCCCCACCCCCG
CCAAGCGCCGCGTGGTGGAGGGCGGCGGCGGCTCCGGCGGCGGCGGCTCCGCCGTGGGCCTGGGCGCCGT
GTTCATCGGCTTCCTGGGCGCCGCCGGCTCCACCATGGGCGCCGCCTCCGTGACCCTGACCGTGCAGGCC
CGCCAGCTGCTGACCGGCATCGTGCGCCAGCAGTCCAACCTGCTGAAGGCCCCCGAGGCCCAGCAGCACC
TGCTGCGCCTGACCGTGTGGGGCATCAAGCAGCTGCAGGCCCGCGTGCTGGCCGTGGAGCGCTACCTGAA
GGACCAGCAGCTGCTGGGCATCTGGGGCTGCTCCGGCAAGCTGATCTGCACCACCAACGTGCCCTGGAAC
TCCTCCTGGTCCAACAAGAACCAGTCCGAaATCTGGGACAACATGACCTGGCTGCAGTGGGACAAGGAGA
TCCACAACTACACCCAGATCATCTACGACCTGCTGGAGGAGTCCCAGAACCAGCAGGAGAAGAACGAGCA
GGAGCTGCTGGCCCTGGACGGCGGCGGCGGCTCCCACCACCACCACCACCACCAC
```

FIG. 70D

Single mutations involving only HR1 residues

| | 2G12 | VRCO6 | PGT145 | PGT151 | F105 | 19b |
|---|---|---|---|---|---|---|
| 16055_I548P | ++ | - | +/- | - | + | ++ |
| 16055_V549P | ++ | - | +/- | - | + | ++ |
| 16055_Q551P | ++ | +/- | +/- | - | +++ | +++ |
| 16055_L555P | ++ | + | + | - | +++ | +++ |
| 16055_L556P | ++ | +/- | +/- | - | +++ | +++ |
| 16055_A558P | ++ | +/- | +/- | - | +++ | +++ |
| 16055_I559P | ?? | +/- | +/- | - | ++ | n.d. |
| 16055_Q562P | ++ | + | + | +/- | +++ | +++ |
| 16055_Q563P | ++ | + | ++ | +/- | ++ | ++ |
| 16055_L565P | ++ | + | ++ | +/- | ++ | ++ |
| 16055_L566P | ++ | + | ++ | +/- | ++ | ++ |
| 16055_L568P | | | | | | |
| 16055_T569P | | | | | | |
| 16055_V570P | | | | | | |
| 16055_W571P | | | | | | |
| 16055_G572P | | | | | | |
| 16055_I573P | | | | | | |
| 16055_K574P | | | | | | |
| 16055_L576P | | | | | | |
| 16055_Q577P | | | | | | |
| 16055_R579P | | | | | | |
| 16055_V580P | | | | | | |
| 16055_V583P | | | | | | |
| 16055_E584P | | | | | | |
| 16055_Y586P | | | | | | |
| 16055_L587P | | | | | | |
| 16055_S649P | ++ | +/- | +/- | - | +++ | +++ |

FIG. 71A

Double mutations involving both, the HR1 and HR2 residues

| | 2G12 | VRC06 | PGT145 | PGT151 | F105 | 19b |
|---|---|---|---|---|---|---|
| 16055_L556P_S649D | ++ | - | +/- | - | ++ | ++ |
| 16055_A558P_S649D | ++ | + | +/- | - | +++ | +++ |
| 16055_I559P_S649D | ++ | + | + | +/- | ++ | ++ |
| 16055_L555P_S649E | ++ | + | + | - | ++ | ++ |
| 16055_L556P_S649E | ++ | - | +/- | - | +/- | +++ |
| 16055_A558P_S649E | ++ | ++ | + | +/- | +++ | +++ |
| 16055_I559P_S649E | +++ | +++ | ++ | +/- | +++ | +++ |

Clade C 16055 gp140-NFL2 Env

MPMGSLQPLATLYLLGMLVASVLAGNLWVTVYYGVPVWKEAKTTLFCASDAKAYEKEVHN
VWATHACVPTDPNPQEMVLENVTENFNMWKNDMVEQMHEDVISLWDQSLKPCVKLTPLCV
TLECRQVNTTNATSSVNVTNGEEIKNCSFNATTEIRDKKQKVYALFYRLDIVPLEEERKG
NSSKYRLINCNTSAITQACPKVTFDPIPIHYCAPAGYAILKCNNKTFNGTGPCNNVSTVQ
CTHGIKPVVSTQLLLNGSLAEGEIIIRSENLTNNVKTIIVHLNESVEIVCTRPNNNTRKS
IRIGPGQTFYATGDIIGNIRQAYCNIKKDDWIRTLQRVGKKLAEHFPRRIINFTSPAGGD
LEITTHSFNCRGEFFYCNTSSLFNSTYNPNDTNSNSSSSNSSLDITIPCRIKQIINMWQE
VGRAMYAPPIEGNITCKSNITGLLLVRDGGVESNETEIFRPGGGDMRNNWRSELYKYKVV
EIKPLGIAPTAAKRRVVEGGGGSGGGGSAVGLGAVIFGFLGAAGSTMGAASITLTVQARQ
LLSG███████████████████████████████████KDQQLLGIWGCSGKLI
CTTAVPWNSSWSNKSHDEIWGNMTWMQWDREISNYTNTIYRLL███████QQEQNEKDLLAL
DGGGGS████████-

The region of HR1 being studied in the proline screen to stabilize the trimer is highlighted in green and underlined.

The residues of HR2 involved in this study are highlighted in red and underlined.

FIG. 74

\>16055_SOSIP
MPMGSLQPLATLYLLGMLVASVLANGNLWVTVYYGVPVWKEAKTTLFCASDAKAYEKEVHNVWATHACVPTDPNPQEMVL
ENVTENFNMWKNDMVEQMHEDVISLWDQSLKPCVKLTPLCVTLECRQVNTTNATSSVNVTNGEEIKNCSFNATTEIRDKK
QKVYALFYRLDIVPLEEERKGNSSKYRLINCNTSAITQACPKVTFDPIPIHYCAPAGYAILKCNNKTFNGTGPCNNVSTV
QCTHGIKPVVSTQLLLNGSLAEGEIIIRSENLTNNVKTIIVHLNESVEIVCTRPNNNTRKSIRIGPGQTFYATGDIIGNI
RQAYCNIKKDDWIRTLQRVGKKLAEHFPRRIINFTSPAGGDLEITTHSFNCRGEFFYCNTSSLFNSTYNPNDTNSNSSSS
NSSLDITIPCRIKQIINMWQEVGRAMYAPPIEGNITCKSNITGLLLVRDGGVESNETEIFRPGGGDMRNNWRSELYKYKV
VEIKPLGIAPTACKRRVRRRKKRAVGLGAVIFGFLGAAGSTMGAASITLTVQARQLLSGIVQQQSNLLKAPEAQQHLLQL
TVWGIKQLQTRVLAIERYLKDQQLLGIWGCSGKLICCTAVPWNSSWSNKSHDEIWGNMTWMQWDREISNYTNTIYRLLED
SQNQQEQNEKDLLALGGGGHHHHHH*

\>CAP244_SOSIP
MPMGSLQPLATLYLLGMLVASVLAGQNLWVTVYYGVPVWKEAKTTLFCASNAKAYEKEVHNVWATHACVPTDPNPQEMVL
GNVTENFNMWKNDMVDQMHEDIISLWDESLKPCVKLTPLCVTLICTNVNHSSTNVSHSSTNVSQSSNSSQDNTTIDESMR
EEIKNCSYNSTTELWDKKQKEYALFYKLDIVPINGNASEYRLINCNTSTIKQACPKVTFEPIPIHYCAPAGYAILKCNNQ
TFNGTGPCTNVSTVQCTHGIKPVVSTQLLLNGSLAEKEIIISSENLTNNAKIIIVHLKDPVRIVCTRPNNNTRKSIRIGP
GQTFYATGDIIGDIRQAYCNISKGAWNKTLQQVGKKLQEHFPGKTIKFNSSSGGDLEITTHSFNCRGEFFYCNTSKLFNN
TYYNGTGNANSTHENITLPCRIKQIIRMWQKVGQAMYAPPIAGNITCTSNITGLLLVRDGGEANGTNNIETFRPGGGDMR
DNWRSELYKYKVVEIQPLGIAPTKCKRRVRRRKKRAVGIGAMFLGFLGAAGSTMGAASMALTVQSRQLLSGIVQQQSNLL
RAPEAQQHMLQLTVWGIKQLRARVVALERYLQDQQLLGIWGCSGKLICCTNVPWNSSWSNRSADIWDNLTWMQWEKEINN
YTDTIYQLLEESQIQQEKNEQDLLALGGGGHHHHHH*

\>CAP244_NFL2P
MPMGSLQPLATLYLLGMLVASVLAGQNLWVTVYYGVPVWKEAKTTLFCASNAKAYEKEVHNVWATHACVPTDPNPQEMVL
GNVTENFNMWKNDMVDQMHEDIISLWDESLKPCVKLTPLCVTLICTNVNHSSTNVSHSSTNVSQSSNSSQDNTTIDESMR
EEIKNCSYNSTTELWDKKQKEYALFYKLDIVPINGNASEYRLINCNTSTIKQACPKVTFEPIPIHYCAPAGYAILKCNNQ
TFNGTGPCTNVSTVQCTHGIKPVVSTQLLLNGSLAEKEIIISSENLTNNAKIIIVHLKDPVRIVCTRPNNNTRKSIRIGP
GQTFYATGDIIGDIRQAYCNISKGAWNKTLQQVGKKLQEHFPGKTIKFNSSSGGDLEITTHSFNCRGEFFYCNTSKLFNN
TYYNGTGNANSTHENITLPCRIKQIIRMWQKVGQAMYAPPIAGNITCTSNITGLLLVRDGGEANGTNNIETFRPGGGDMR
DNWRSELYKYKVVEIQPLGIAPTKAKRRVVEGGGGSGGGGSAVGIGAMFLGFLGAAGSTMGAASMALTVQSRQLLSGIVQ
QQSNLLRAPEAQQHMLQLTVWGIKQLRARVVALERYLQDQQLLGIWGCSGKLICTTNVPWNSSWSNRSADIWDNLTWMQW
EKEINNYTDTIYQLLEESQIQQEKNEQDLLALNGGGGSHHHHHH*

\>CAP244_NFL2P_BG7
MPMGSLQPLATLYLLGMLVASVLAGQNLWVTVYYGVPVWKDAETTLFCASNAKAYEKEKHNVWATHACVPTDPNPQEMVL
GNVTENFNMWKNDMVDQMHTDIISLWDESLKPCVKLTPLCVTLICTNVNHSSTNVSHSSTNVSQSSNSSQDNTTIDESMR
EEIKNCSYNSTTELWDKKQKEYALFYKLDIVPINGNASEYRLINCNTSTIKQACPKVTFEPIPIHYCAPAGYAILKCNNQ
TFNGTGPCTNVSTVQCTHGIKPVVSTQLLLNGSLAEKEIIISSENLTNNAKIIIVHLKDPVRIVCTRPNNNTRKSIRIGP
GQTFYATGDIIGDIRQAYCNISKGAWNKTLQQVGKKLQEHFPGKTIKFNSSSGGDLEITTHSFNCRGEFFYCNTSKLFNN
TYYNGTGNANSTHENITLPCRIKQIIRMWQRVGQAMYAPPIAGNITCTSNITGLLLVRDGGEANGTNNIETFRPGGGDMR
DNWRSELYKYKVVEIQPLGIAPTKAKRRVVEGGGGSGGGGSAVGIGAMFLGFLGAAGSTMGAASMALTVQSRQLLSGIVQ
QQSNLLRAPEAQQHMLQLTVWGIKQLRARVVALERYLQDQQLLGIWGCSGKLICTTNVPWNSSWSNRSADIWDNLTWMQW
EKEINNYTDTIYQLLEESQIQQEKNEQDLLALNGGGGSHHHHHH*

FIG. 75

SEQUENCE LISTING

```
<160> NUMBER OF SEQ ID NOS: 35

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 1

Arg Arg Arg Lys Lys Arg
1               5

<210> SEQ ID NO 2
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Gly Gly Gly Ser
1               5

<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Arg Glu Lys Arg
1

<210> SEQ ID NO 4
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 4

His His His His His His
1               5

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 8xHis tag"

<400> SEQUENCE: 5

His His His His His His His His
1               5

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Gly Gly Ser Gly Gly Gly Gly Ser
```

-continued

```
1               5                   10
```

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

```
Gly Gly Gly Gly Ser Gly Gly Gly Ser Gly Gly Gly Gly Ser
1               5                   10                  15
```

<210> SEQ ID NO 8
<211> LENGTH: 659
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
                20                  25                  30

Tyr Tyr Gly Val Pro Val Trp Lys Glu Ala Thr Thr Thr Leu Phe Cys
            35                  40                  45

Ala Ser Asp Ala Lys Ala Tyr Asp Thr Glu Val His Asn Val Trp Ala
        50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Ile Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270
```

-continued

```
Ala Lys Thr Ile Ile Val Gln Leu Lys Glu Ser Val Glu Ile Asn Cys
        275                 280                 285

Thr Arg Pro Asn Asn Thr Arg Lys Ser Ile His Ile Gly Pro Gly
290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
450                 455                 460

Trp Arg Ser Glu Leu Tyr Lys Tyr Lys Val Val Lys Ile Glu Pro Leu
465                 470                 475                 480

Gly Val Ala Pro Thr Lys Cys Lys Arg Arg Val Arg Arg Lys Lys
                485                 490                 495

Arg Ala Val Gly Ile Gly Ala Val Phe Leu Gly Phe Leu Gly Ala Ala
            500                 505                 510

Gly Ser Thr Met Gly Ala Ala Ser Met Thr Leu Thr Val Gln Ala Arg
        515                 520                 525

Leu Leu Leu Ser Gly Ile Val Gln Gln Gln Asn Asn Leu Leu Arg Ala
530                 535                 540

Pro Glu Ala Gln Gln Arg Met Leu Gln Leu Thr Val Trp Gly Ile Lys
545                 550                 555                 560

Gln Leu Gln Ala Arg Val Leu Ala Val Glu Arg Tyr Leu Gly Asp Gln
                565                 570                 575

Gln Leu Leu Gly Ile Trp Gly Cys Ser Gly Lys Leu Ile Cys Cys Thr
            580                 585                 590

Ala Val Pro Trp Asn Ala Ser Trp Ser Asn Lys Ser Leu Asp Arg Ile
        595                 600                 605

Trp Asn Asn Met Thr Trp Met Glu Trp Glu Arg Glu Ile Asp Asn Tyr
610                 615                 620

Thr Ser Glu Ile Tyr Thr Leu Ile Glu Glu Ser Gln Asn Gln Gln Glu
625                 630                 635                 640

Lys Asn Glu Gln Glu Leu Leu Glu Leu Gly Gly Gly His His His
                645                 650                 655

His His His
```

<210> SEQ ID NO 9
<211> LENGTH: 602
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

Met Pro Met Gly Ser Leu Gln Pro Leu Ala Thr Leu Tyr Leu Leu Gly
1               5                   10                  15

Met Leu Val Ala Ser Val Leu Ala Glu Ala Thr Thr Thr Leu Phe Cys
            20                  25                  30

Ala Ser Asp Ala Lys Ala Tyr Asp Thr Glu Val His Asn Val Trp Ala
        35                  40                  45

Thr His Ala Cys Val Pro Thr Asp Pro Asn Pro Gln Glu Val Val Leu
    50                  55                  60

Glu Asn Val Thr Glu His Phe Asn Met Trp Lys Asn Asn Met Val Glu
65                  70                  75                  80

Gln Met Gln Glu Asp Ile Ile Ser Leu Trp Asp Gln Ser Leu Lys Pro
                85                  90                  95

Cys Val Lys Leu Thr Pro Leu Cys Val Thr Leu Asn Cys Lys Asp Val
            100                 105                 110

Asn Ala Thr Asn Thr Thr Asn Asp Ser Glu Gly Thr Met Glu Arg Gly
        115                 120                 125

Glu Ile Lys Asn Cys Ser Phe Asn Ile Thr Thr Ser Ile Arg Asp Lys
130                 135                 140

Val Gln Lys Glu Tyr Ala Leu Phe Tyr Lys Leu Asp Val Val Pro Ile
145                 150                 155                 160

Asp Asn Asn Asn Thr Ser Tyr Arg Leu Ile Ser Cys Asp Thr Ser Val
                165                 170                 175

Ile Thr Gln Ala Cys Pro Lys Ile Ser Phe Glu Pro Ile Pro Ile His
            180                 185                 190

Tyr Cys Ala Pro Ala Gly Phe Ala Ile Leu Lys Cys Asn Asp Lys Thr
        195                 200                 205

Phe Asn Gly Lys Gly Pro Cys Lys Asn Val Ser Thr Val Gln Cys Thr
    210                 215                 220

His Gly Ile Arg Pro Val Val Ser Thr Gln Leu Leu Leu Asn Gly Ser
225                 230                 235                 240

Leu Ala Glu Glu Glu Val Val Ile Arg Ser Asp Asn Phe Thr Asn Asn
                245                 250                 255

Ala Lys Thr Ile Ile Val Gln Leu Lys Glu Ser Val Glu Ile Asn Cys
            260                 265                 270

Thr Arg Pro Asn Asn Asn Thr Arg Lys Ser Ile His Ile Gly Pro Gly
        275                 280                 285

Arg Ala Phe Tyr Thr Thr Gly Glu Ile Ile Gly Asp Ile Arg Gln Ala
    290                 295                 300

His Cys Asn Ile Ser Arg Ala Lys Trp Asn Asp Thr Leu Lys Gln Ile
305                 310                 315                 320

Val Ile Lys Leu Arg Glu Gln Phe Glu Asn Lys Thr Ile Val Phe Asn
                325                 330                 335

His Ser Ser Gly Gly Asp Pro Glu Ile Val Met His Ser Phe Asn Cys
            340                 345                 350

Gly Gly Glu Phe Phe Tyr Cys Asn Ser Thr Gln Leu Phe Asn Ser Thr
        355                 360                 365

Trp Asn Asn Asn Thr Glu Gly Ser Asn Asn Thr Glu Gly Asn Thr Ile
    370                 375                 380

-continued

Thr Leu Pro Cys Arg Ile Lys Gln Ile Ile Asn Met Trp Gln Glu Val
385                 390                 395                 400

Gly Lys Ala Met Tyr Ala Pro Pro Ile Arg Gly Gln Ile Arg Cys Ser
            405                 410                 415

Ser Asn Ile Thr Gly Leu Leu Leu Thr Arg Asp Gly Gly Ile Asn Glu
        420                 425                 430

Asn Gly Thr Glu Ile Phe Arg Pro Gly Gly Gly Asp Met Arg Asp Asn
    435                 440                 445

Trp Arg Ser Glu Leu Tyr Lys Tyr Lys Val Val Lys Ile Glu Pro Leu
450                 455                 460

Gly Val Ala Pro Val Thr Ile Met Phe Ile Val Asn Thr Asn Val Pro
465                 470                 475                 480

Arg Ala Ser Val Pro Asp Gly Phe Leu Ser Glu Leu Thr Gln Gln Leu
                485                 490                 495

Ala Gln Ala Thr Gly Lys Pro Pro Gln Tyr Ile Ala Val His Val Val
            500                 505                 510

Pro Asp Gln Leu Met Ala Phe Gly Gly Ser Ser Glu Pro Cys Ala Leu
        515                 520                 525

Cys Ser Leu His Ser Ile Gly Lys Ile Gly Gly Ala Gln Asn Arg Ser
530                 535                 540

Tyr Ser Lys Leu Leu Cys Gly Leu Leu Ala Glu Arg Leu Arg Ile Ser
545                 550                 555                 560

Pro Asp Arg Val Tyr Ile Asn Tyr Tyr Asp Met Asn Ala Ala Ser Val
                565                 570                 575

Gly Trp Asn Gly Gly Ala Lys Phe Val Ala Ala Trp Thr Leu Lys Ala
            580                 585                 590

Ala Ala Gly Gly His His His His His His
            595                 600

<210> SEQ ID NO 10
<211> LENGTH: 701
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Thr Glu Val His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

```
Asn Ala Thr Asn Thr Thr Asn Asp Ser Glu Gly Thr Met Glu Arg Gly
    130                 135                 140
Glu Ile Lys Asn Cys Ser Phe Asn Ile Thr Thr Ser Ile Arg Asp Lys
145                 150                 155                 160
Val Gln Lys Glu Tyr Ala Leu Phe Tyr Lys Leu Asp Val Val Pro Ile
                165                 170                 175
Asp Asn Asn Asn Thr Ser Tyr Arg Leu Ile Ser Cys Asp Thr Ser Val
                180                 185                 190
Ile Thr Gln Ala Cys Pro Lys Ile Ser Phe Glu Pro Ile Pro Ile His
            195                 200                 205
Tyr Cys Ala Pro Ala Gly Phe Ala Ile Leu Lys Cys Asn Asp Lys Thr
    210                 215                 220
Phe Asn Gly Lys Gly Pro Cys Lys Asn Val Ser Thr Val Gln Cys Thr
225                 230                 235                 240
His Gly Ile Arg Pro Val Val Ser Thr Gln Leu Leu Leu Asn Gly Ser
                245                 250                 255
Leu Ala Glu Glu Glu Val Val Ile Arg Ser Asp Asn Phe Thr Asn Asn
                260                 265                 270
Ala Lys Thr Ile Ile Val Gln Leu Lys Glu Ser Val Glu Ile Asn Cys
            275                 280                 285
Thr Arg Pro Asn Asn Asn Thr Arg Lys Ser Ile His Ile Gly Pro Gly
    290                 295                 300
Arg Ala Phe Tyr Thr Thr Gly Glu Ile Ile Gly Asp Ile Arg Gln Ala
305                 310                 315                 320
His Cys Asn Ile Ser Arg Ala Lys Trp Asn Asp Thr Leu Lys Gln Ile
                325                 330                 335
Val Ile Lys Leu Arg Glu Gln Phe Glu Asn Lys Thr Ile Val Phe Asn
            340                 345                 350
His Ser Ser Gly Gly Asp Pro Glu Ile Val Met His Ser Phe Asn Cys
    355                 360                 365
Gly Gly Glu Phe Phe Tyr Cys Asn Ser Thr Gln Leu Phe Asn Ser Thr
                370                 375                 380
Trp Asn Asn Asn Thr Glu Gly Ser Asn Asn Thr Glu Gly Asn Thr Ile
385                 390                 395                 400
Thr Leu Pro Cys Arg Ile Lys Gln Ile Ile Asn Met Trp Gln Glu Val
                405                 410                 415
Gly Lys Ala Met Tyr Ala Pro Pro Ile Arg Gly Gln Ile Arg Cys Ser
            420                 425                 430
Ser Asn Ile Thr Gly Leu Leu Leu Thr Arg Asp Gly Gly Ile Asn Glu
    435                 440                 445
Asn Gly Thr Glu Ile Phe Arg Pro Gly Gly Gly Asp Met Arg Asp Asn
450                 455                 460
Trp Arg Ser Glu Leu Tyr Lys Tyr Lys Val Val Lys Ile Glu Pro Leu
465                 470                 475                 480
Gly Val Ala Pro Thr Lys Ala Lys Arg Arg Val Val Gln Ser Glu Lys
                485                 490                 495
Ser Ala Val Gly Ile Gly Ala Val Phe Leu Gly Phe Leu Gly Ala Ala
            500                 505                 510
Gly Ser Thr Met Gly Ala Ala Ser Met Thr Leu Thr Val Gln Ala Arg
    515                 520                 525
Leu Leu Leu Ser Gly Ile Val Gln Gln Asn Asn Leu Leu Arg Ala
    530                 535                 540
Ile Glu Ala Gln Gln Arg Met Leu Gln Leu Thr Val Trp Gly Ile Lys
```

```
545                 550                 555                 560
Gln Leu Gln Ala Arg Val Leu Ala Val Glu Arg Tyr Leu Gly Asp Gln
                565                 570                 575

Gln Leu Leu Gly Ile Trp Gly Cys Ser Gly Lys Leu Ile Cys Thr Thr
                580                 585                 590

Ala Val Pro Trp Asn Ala Ser Trp Ser Asn Lys Ser Leu Asp Arg Ile
                595                 600                 605

Trp Asn Asn Met Thr Trp Met Glu Trp Glu Arg Glu Ile Asp Asn Tyr
        610                 615                 620

Thr Ser Glu Ile Tyr Thr Leu Ile Glu Glu Ser Gln Asn Gln Gln Glu
625                 630                 635                 640

Lys Asn Glu Gln Glu Leu Leu Glu Leu Asp Lys Trp Ala Ser Leu Trp
                645                 650                 655

Asn Trp Phe Asp Ile Thr Lys Trp Leu Trp Tyr Ile Lys Ile Phe Ile
                660                 665                 670

Met Ile Val Ala Lys Lys Ile Lys Lys Arg Leu Lys Lys Thr Lys Lys
                675                 680                 685

Ser Ile Lys Asn Arg Gly Gly His His His His His His
            690                 695                 700

<210> SEQ ID NO 11
<211> LENGTH: 701
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
                20                  25                  30

Tyr Tyr Gly Val Pro Val Trp Lys Glu Ala Thr Thr Thr Leu Phe Cys
            35                  40                  45

Ala Ser Asp Ala Lys Ala Tyr Asp Thr Glu Val His Asn Val Trp Ala
        50                  55                  60

Thr His Ala Cys Val Pro Thr Asp Pro Asn Pro Gln Glu Val Val Leu
65              70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
130                 135                 140

Glu Ile Lys Asn Cys Ser Phe Asn Ile Thr Thr Ser Ile Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205
```

```
Tyr Cys Ala Pro Ala Gly Phe Ala Ile Leu Lys Cys Asn Asp Lys Thr
    210                 215                 220
Phe Asn Gly Lys Gly Pro Cys Lys Asn Val Ser Thr Val Gln Cys Thr
225                 230                 235                 240
His Gly Ile Arg Pro Val Val Ser Thr Gln Leu Leu Leu Asn Gly Ser
            245                 250                 255
Leu Ala Glu Glu Glu Val Val Ile Arg Ser Asp Asn Phe Thr Asn Asn
                260                 265                 270
Ala Lys Thr Ile Ile Val Gln Leu Lys Glu Ser Val Glu Ile Asn Cys
        275                 280                 285
Thr Arg Pro Asn Asn Thr Arg Lys Ser Ile His Ile Gly Pro Gly
    290                 295                 300
Arg Ala Phe Tyr Thr Thr Gly Glu Ile Ile Gly Asp Ile Arg Gln Ala
305                 310                 315                 320
His Cys Asn Ile Ser Arg Ala Lys Trp Asn Asp Thr Leu Lys Gln Ile
            325                 330                 335
Val Ile Lys Leu Arg Glu Gln Phe Glu Asn Lys Thr Ile Val Phe Asn
                340                 345                 350
His Ser Ser Gly Gly Asp Pro Glu Ile Val Met His Ser Phe Asn Cys
        355                 360                 365
Gly Gly Glu Phe Phe Tyr Cys Asn Ser Thr Gln Leu Phe Asn Ser Thr
    370                 375                 380
Trp Asn Asn Asn Thr Glu Gly Ser Asn Asn Thr Glu Gly Asn Thr Ile
385                 390                 395                 400
Thr Leu Pro Cys Arg Ile Lys Gln Ile Ile Asn Met Trp Gln Glu Val
            405                 410                 415
Gly Lys Ala Met Tyr Ala Pro Pro Ile Arg Gly Gln Ile Arg Cys Ser
                420                 425                 430
Ser Asn Ile Thr Gly Leu Leu Leu Thr Arg Asp Gly Gly Ile Asn Glu
        435                 440                 445
Asn Gly Thr Glu Ile Phe Arg Pro Gly Gly Gly Asp Met Arg Asp Asn
    450                 455                 460
Trp Arg Ser Glu Leu Tyr Lys Tyr Lys Val Val Lys Ile Glu Pro Leu
465                 470                 475                 480
Gly Val Ala Pro Thr Lys Ala Lys Arg Arg Val Val Gln Ser Glu Lys
            485                 490                 495
Ser Ala Val Gly Ile Gly Ala Val Phe Leu Gly Phe Leu Gly Ala Ala
                500                 505                 510
Gly Ser Thr Met Gly Ala Ala Ser Met Thr Leu Thr Val Gln Ala Arg
        515                 520                 525
Leu Leu Leu Ser Gly Ile Val Gln Gln Gln Asn Asn Leu Leu Arg Ala
    530                 535                 540
Ile Glu Ala Gln Gln Arg Met Leu Gln Leu Thr Val Trp Gly Ile Lys
545                 550                 555                 560
Gln Leu Gln Ala Arg Val Leu Ala Val Glu Arg Tyr Leu Gly Asp Gln
            565                 570                 575
Gln Leu Leu Gly Ile Trp Gly Cys Ser Gly Lys Leu Ile Cys Thr Thr
                580                 585                 590
Ala Val Pro Trp Asn Ala Ser Trp Ser Asn Lys Ser Leu Asp Arg Ile
        595                 600                 605
Trp Asn Asn Met Thr Trp Met Glu Trp Glu Arg Glu Ile Asp Asn Tyr
    610                 615                 620
```

-continued

Thr Ser Glu Ile Tyr Thr Leu Ile Glu Glu Ser Gln Asn Gln Gln Glu
625                 630                 635                 640

Lys Asn Glu Gln Glu Leu Leu Glu Leu Asp Lys Trp Ala Ser Leu Trp
            645                 650                 655

Asn Trp Phe Asp Ile Thr Lys Trp Leu Trp Tyr Ile Lys Ile Lys Ile
            660                 665                 670

Lys Ile Val Ala Lys Lys Ile Lys Lys Arg Leu Lys Lys Thr Lys Lys
        675                 680                 685

Ser Ile Lys Asn Arg Gly Gly His His His His His
        690                 695                 700

<210> SEQ ID NO 12
<211> LENGTH: 683
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Thr Glu Val His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Ile Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys 275 280 285
Thr Arg Pro Asn Asn Thr Arg Lys Ser Ile His Ile Gly Pro Gly
290                 295                 300
Arg Ala Phe Tyr Thr Thr Gly Glu Ile Ile Gly Asp Ile Arg Gln Ala
305                 310                 315                 320
His Cys Asn Ile Ser Arg Ala Lys Trp Asn Asp Thr Leu Lys Gln Ile
                325                 330                 335
Val Ile Lys Leu Arg Glu Gln Phe Glu Asn Lys Thr Ile Val Phe Asn
            340                 345                 350
His Ser Ser Gly Gly Asp Pro Glu Ile Val Met His Ser Phe Asn Cys
            355                 360                 365
Gly Gly Glu Phe Phe Tyr Cys Asn Ser Thr Gln Leu Phe Asn Ser Thr
        370                 375                 380
Trp Asn Asn Asn Thr Glu Gly Ser Asn Asn Thr Glu Gly Asn Thr Ile
385                 390                 395                 400
Thr Leu Pro Cys Arg Ile Lys Gln Ile Ile Asn Met Trp Gln Glu Val
                405                 410                 415
Gly Lys Ala Met Tyr Ala Pro Pro Ile Arg Gly Gln Ile Arg Cys Ser
            420                 425                 430
Ser Asn Ile Thr Gly Leu Leu Leu Thr Arg Asp Gly Gly Ile Asn Glu
        435                 440                 445
Asn Gly Thr Glu Ile Phe Arg Pro Gly Gly Gly Asp Met Arg Asp Asn
450                 455                 460
Trp Arg Ser Glu Leu Tyr Lys Tyr Lys Val Val Lys Ile Glu Pro Leu
465                 470                 475                 480
Gly Val Ala Pro Thr Lys Ala Lys Arg Arg Val Val Gln Ser Glu Lys
                485                 490                 495
Ser Ala Val Gly Ile Gly Ala Val Phe Leu Gly Phe Leu Gly Ala Ala
            500                 505                 510
Gly Ser Thr Met Gly Ala Ala Ser Met Thr Leu Thr Val Gln Ala Arg
        515                 520                 525
Leu Leu Leu Ser Gly Ile Val Gln Gln Gln Asn Asn Leu Leu Arg Ala
    530                 535                 540
Ile Glu Ala Gln Gln Arg Met Leu Gln Leu Thr Val Trp Gly Ile Lys
545                 550                 555                 560
Gln Leu Gln Ala Arg Val Leu Ala Val Glu Arg Tyr Leu Gly Asp Gln
                565                 570                 575
Gln Leu Leu Gly Ile Trp Gly Cys Ser Gly Lys Leu Ile Cys Thr Thr
            580                 585                 590
Ala Val Pro Trp Asn Ala Ser Trp Ser Asn Lys Ser Leu Asp Arg Ile
        595                 600                 605
Trp Asn Asn Met Thr Trp Met Glu Trp Glu Arg Glu Ile Asp Asn Tyr
    610                 615                 620
Thr Ser Glu Ile Tyr Thr Leu Ile Glu Glu Ser Gln Asn Gln Gln Glu
625                 630                 635                 640
Lys Asn Glu Gln Glu Leu Leu Glu Leu Asp Lys Trp Ala Ser Leu Trp
                645                 650                 655
Asn Trp Phe Asp Ile Thr Lys Trp Leu Trp Tyr Ile Lys Ile Lys Ile
            660                 665                 670
Lys Ile Val Gly Gly His His His His His His
        675                 680

<210> SEQ ID NO 13

```
<211> LENGTH: 683
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
                20                  25                  30

Tyr Tyr Gly Val Pro Val Trp Lys Glu Ala Thr Thr Thr Leu Phe Cys
            35                  40                  45

Ala Ser Asp Ala Lys Ala Tyr Asp Thr Glu Val His Asn Val Trp Ala
        50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Ile Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365
```

```
Gly Gly Glu Phe Phe Tyr Cys Asn Ser Thr Gln Leu Phe Asn Ser Thr
        370                 375                 380

Trp Asn Asn Thr Glu Gly Ser Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430

Ser Asn Ile Thr Gly Leu Leu Leu Thr Arg Asp Gly Ile Asn Glu
        435                 440                 445

Asn Gly Thr Glu Ile Phe Arg Pro Gly Gly Gly Asp Met Arg Asp Asn
450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Arg Arg Val Val Gln Ser Glu Lys
                485                 490                 495

Ser Ala Val Gly Ile Gly Ala Val Phe Leu Gly Phe Leu Gly Ala Ala
            500                 505                 510

Gly Ser Thr Met Gly Ala Ala Ser Met Thr Leu Thr Val Gln Ala Arg
        515                 520                 525

Leu Leu Leu Ser Gly Ile Val Gln Gln Gln Asn Asn Leu Leu Arg Ala
530                 535                 540

Ile Glu Ala Gln Gln Arg Met Leu Gln Leu Thr Val Trp Gly Ile Lys
545                 550                 555                 560

Gln Leu Gln Ala Arg Val Leu Ala Val Glu Arg Tyr Leu Gly Asp Gln
                565                 570                 575

Gln Leu Leu Gly Ile Trp Gly Cys Ser Gly Lys Leu Ile Cys Thr Thr
            580                 585                 590

Ala Val Pro Trp Asn Ala Ser Trp Ser Asn Lys Ser Leu Asp Arg Ile
        595                 600                 605

Trp Asn Asn Met Thr Trp Met Glu Trp Glu Arg Glu Ile Asp Asn Tyr
610                 615                 620

Thr Ser Glu Ile Tyr Thr Leu Ile Glu Glu Ser Gln Asn Gln Gln Glu
625                 630                 635                 640

Lys Asn Glu Gln Glu Leu Leu Glu Leu Asp Lys Asn Ala Ser Leu Trp
                645                 650                 655

Asn Trp Phe Asn Ile Thr Lys Trp Leu Trp Tyr Ile Lys Ile Asn Ile
            660                 665                 670

Thr Ile Val Gly Gly His His His His His
        675                 680

<210> SEQ ID NO 14
<211> LENGTH: 664
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Glu Ala Thr Thr Thr Leu Phe Cys
```

-continued

```
                35                  40                  45
Ala Ser Asp Ala Lys Ala Tyr Asp Thr Glu Val His Asn Val Trp Ala
             50                  55                  60
Thr His Ala Cys Val Pro Thr Asp Pro Asn Pro Gln Glu Val Val Leu
 65                  70                  75                  80
Glu Asn Val Thr Glu His Phe Asn Met Trp Lys Asn Asn Met Val Glu
                 85                  90                  95
Gln Met Gln Glu Asp Ile Ile Ser Leu Trp Asp Gln Ser Leu Lys Pro
            100                 105                 110
Cys Val Lys Leu Thr Pro Leu Cys Val Thr Leu Asn Cys Lys Asp Val
            115                 120                 125
Asn Ala Thr Asn Thr Thr Asn Asp Ser Glu Gly Thr Met Glu Arg Gly
130                 135                 140
Glu Ile Lys Asn Cys Ser Phe Asn Ile Thr Thr Ser Ile Arg Asp Lys
145                 150                 155                 160
Val Gln Lys Glu Tyr Ala Leu Phe Tyr Lys Leu Asp Val Val Pro Ile
                165                 170                 175
Asp Asn Asn Asn Thr Ser Tyr Arg Leu Ile Ser Cys Asp Thr Ser Val
                180                 185                 190
Ile Thr Gln Ala Cys Pro Lys Ile Ser Phe Glu Pro Ile Pro Ile His
            195                 200                 205
Tyr Cys Ala Pro Ala Gly Phe Ala Ile Leu Lys Cys Asn Asp Lys Thr
210                 215                 220
Phe Asn Gly Lys Gly Pro Cys Lys Asn Val Ser Thr Val Gln Cys Thr
225                 230                 235                 240
His Gly Ile Arg Pro Val Val Ser Thr Gln Leu Leu Leu Asn Gly Ser
                245                 250                 255
Leu Ala Glu Glu Glu Val Val Ile Arg Ser Asp Asn Phe Thr Asn Asn
            260                 265                 270
Ala Lys Thr Ile Ile Val Gln Leu Lys Glu Ser Val Glu Ile Asn Cys
            275                 280                 285
Thr Arg Pro Asn Asn Asn Thr Arg Lys Ser Ile His Ile Gly Pro Gly
290                 295                 300
Arg Ala Phe Tyr Thr Thr Gly Glu Ile Ile Gly Asp Ile Arg Gln Ala
305                 310                 315                 320
His Cys Asn Ile Ser Arg Ala Lys Trp Asn Asp Thr Leu Lys Gln Ile
                325                 330                 335
Val Ile Lys Leu Arg Glu Gln Phe Glu Asn Lys Thr Ile Val Phe Asn
            340                 345                 350
His Ser Ser Gly Gly Asp Pro Glu Ile Val Met His Ser Phe Asn Cys
            355                 360                 365
Gly Gly Glu Phe Phe Tyr Cys Asn Ser Thr Gln Leu Phe Asn Ser Thr
            370                 375                 380
Trp Asn Asn Asn Thr Glu Gly Ser Asn Asn Thr Glu Gly Asn Thr Ile
385                 390                 395                 400
Thr Leu Pro Cys Arg Ile Lys Gln Ile Ile Asn Met Trp Gln Glu Val
                405                 410                 415
Gly Lys Ala Met Tyr Ala Pro Pro Ile Arg Gly Gln Ile Arg Cys Ser
            420                 425                 430
Ser Asn Ile Thr Gly Leu Leu Leu Thr Arg Asp Gly Gly Ile Asn Glu
            435                 440                 445
Asn Gly Thr Glu Ile Phe Arg Pro Gly Gly Gly Asp Met Arg Asp Asn
450                 455                 460
```

Trp Arg Ser Glu Leu Tyr Lys Tyr Lys Val Val Lys Ile Glu Pro Leu
465                 470                 475                 480

Gly Val Ala Pro Thr Lys Ala Lys Arg Arg Val Val Gln Gly Gly Gly
            485                 490                 495

Gly Ser Ala Val Gly Ile Gly Ala Val Phe Leu Gly Phe Leu Gly Ala
            500                 505                 510

Ala Gly Ser Thr Met Gly Ala Ala Ser Met Thr Leu Thr Val Gln Ala
            515                 520                 525

Arg Leu Leu Leu Ser Gly Ile Val Gln Gln Gln Asn Asn Leu Leu Arg
            530                 535                 540

Ala Pro Glu Ala Gln Gln Arg Met Leu Gln Leu Thr Val Trp Gly Ile
545                 550                 555                 560

Lys Gln Leu Gln Ala Arg Val Leu Ala Val Glu Arg Tyr Leu Gly Asp
                565                 570                 575

Gln Gln Leu Leu Gly Ile Trp Gly Cys Ser Gly Lys Leu Ile Cys Thr
            580                 585                 590

Thr Ala Val Pro Trp Asn Ala Ser Trp Ser Asn Lys Ser Leu Asp Arg
            595                 600                 605

Ile Trp Asn Asn Met Thr Trp Met Glu Trp Arg Glu Ile Asp Asn
610                 615                 620

Tyr Thr Ser Glu Ile Tyr Thr Leu Ile Glu Glu Ser Gln Asn Gln Gln
625                 630                 635                 640

Glu Lys Asn Glu Gln Glu Leu Leu Glu Leu Asp Gly Gly Gly Ser
                645                 650                 655

His His His His His His His His
            660

<210> SEQ ID NO 15
<211> LENGTH: 669
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Thr Glu Val His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

```
Glu Ile Lys Asn Cys Ser Phe Asn Ile Thr Thr Ser Ile Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Arg Arg Val Val Gln Gly Gly Gly
                485                 490                 495

Gly Ser Gly Gly Gly Ser Ala Val Gly Ile Gly Ala Val Phe Leu
            500                 505                 510

Gly Phe Leu Gly Ala Ala Gly Ser Thr Met Gly Ala Ala Ser Met Thr
    515                 520                 525

Leu Thr Val Gln Ala Arg Leu Leu Ser Gly Ile Val Gln Gln Gln
        530                 535                 540

Asn Asn Leu Leu Arg Ala Pro Glu Ala Gln Gln Arg Met Leu Gln Leu
545                 550                 555                 560

Thr Val Trp Gly Ile Lys Gln Leu Gln Ala Arg Val Leu Ala Val Glu
```

```
                          565                 570                 575

Arg Tyr Leu Gly Asp Gln Gln Leu Leu Gly Ile Trp Gly Cys Ser Gly
                580                 585                 590

Lys Leu Ile Cys Thr Thr Ala Val Pro Trp Asn Ala Ser Trp Ser Asn
                595                 600                 605

Lys Ser Leu Asp Arg Ile Trp Asn Asn Met Thr Trp Met Glu Trp Glu
                610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Glu Leu Asp
                645                 650                 655

Gly Gly Gly Gly Ser His His His His His His
                660                 665

<210> SEQ ID NO 16
<211> LENGTH: 674
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
                20                  25                  30

Tyr Tyr Gly Val Pro Val Trp Lys Glu Ala Thr Thr Thr Leu Phe Cys
                35                  40                  45

Ala Ser Asp Ala Lys Ala Tyr Asp Thr Glu Val His Asn Val Trp Ala
            50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
                100                 105                 110

Cys Val Lys Leu Thr Pro Leu Cys Val Thr Leu Asn Cys Lys Asp Val
                115                 120                 125

Asn Ala Thr Asn Thr Thr Asn Asp Ser Glu Gly Thr Met Glu Arg Gly
            130                 135                 140

Glu Ile Lys Asn Cys Ser Phe Asn Ile Thr Thr Ser Ile Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
                180                 185                 190

Ile Thr Gln Ala Cys Pro Lys Ile Ser Phe Glu Pro Ile Pro Ile His
                195                 200                 205

Tyr Cys Ala Pro Ala Gly Phe Ala Ile Leu Lys Cys Asn Asp Lys Thr
            210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255
```

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Arg Arg Val Val Gln Gly Gly Gly
                485                 490                 495

Gly Ser Gly Gly Gly Gly Ser Gly Gly Gly Gly Ser Ala Val Gly Ile
            500                 505                 510

Gly Ala Val Phe Leu Gly Phe Leu Gly Ala Ala Gly Ser Thr Met Gly
        515                 520                 525

Ala Ala Ser Met Thr Leu Thr Val Gln Ala Arg Leu Leu Leu Ser Gly
    530                 535                 540

Ile Val Gln Gln Gln Asn Asn Leu Leu Arg Ala Pro Glu Ala Gln Gln
545                 550                 555                 560

Arg Met Leu Gln Leu Thr Val Trp Gly Ile Lys Gln Leu Gln Ala Arg
                565                 570                 575

Val Leu Ala Val Glu Arg Tyr Leu Gly Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ala Ser Trp Ser Asn Lys Ser Leu Asp Arg Ile Trp Asn Asn Met Thr
    610                 615                 620

Trp Met Glu Trp Glu Arg Glu Ile Asp Asn Tyr Thr Ser Glu Ile Tyr
625                 630                 635                 640

Thr Leu Ile Glu Glu Ser Gln Asn Gln Gln Glu Lys Asn Glu Gln Glu
                645                 650                 655

Leu Leu Glu Leu Asp Gly Gly Gly Gly Ser His His His His His His
            660                 665                 670

His His

<210> SEQ ID NO 17
<211> LENGTH: 674
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Met Pro Met Gly Ser Leu Gln Pro Leu Ala Thr Leu Tyr Leu Gly
1               5                   10                  15

Met Leu Val Ala Ser Val Leu Ala Gly Asn Leu Trp Val Thr Val Tyr
            20                  25                  30

Tyr Gly Val Pro Val Trp Lys Glu Ala Lys Thr Thr Leu Phe Cys Ala
            35                  40                  45

Ser Asp Ala Lys Ala Tyr Glu Lys Glu Val His Asn Val Trp Ala Thr
        50                  55                  60

His Ala Cys Val Pro Thr Asp Pro Asn Pro Gln Glu Met Val Leu Glu
65                  70                  75                  80

Asn Val Thr Glu Asn Phe Asn Met Trp Lys Asn Asp Met Val Glu Gln
                85                  90                  95

Met His Glu Asp Val Ile Ser Leu Trp Asp Gln Ser Leu Lys Pro Cys
            100                 105                 110

Val Lys Leu Thr Pro Leu Cys Val Thr Leu Glu Cys Arg Gln Val Asn
            115                 120                 125

Thr Thr Asn Ala Thr Ser Ser Val Asn Val Thr Asn Gly Glu Glu Ile
        130                 135                 140

Lys Asn Cys Ser Phe Asn Ala Thr Thr Glu Ile Arg Asp Lys Lys Gln
145                 150                 155                 160

Lys Val Tyr Ala Leu Phe Tyr Arg Leu Asp Ile Val Pro Leu Glu Glu
                165                 170                 175

Glu Arg Lys Gly Asn Ser Ser Lys Tyr Arg Leu Ile Asn Cys Asn Thr
            180                 185                 190

Ser Ala Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
            210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Gly Glu Ile Ile Ile Arg Ser Glu Asn Leu Thr
            260                 265                 270

Asn Asn Val Lys Thr Ile Ile Val His Leu Asn Glu Ser Val Glu Ile
        275                 280                 285

Val Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asn Ile Arg
305                 310                 315                 320

Gln Ala Tyr Cys Asn Ile Lys Lys Asp Asp Trp Ile Arg Thr Leu Gln
                325                 330                 335

Arg Val Gly Lys Lys Leu Ala Glu His Phe Pro Arg Arg Ile Ile Asn
            340                 345                 350
```

Phe Thr Ser Pro Ala Gly Gly Asp Leu Glu Ile Thr Thr His Ser Phe
          355                 360                 365

Asn Cys Arg Gly Glu Phe Phe Tyr Cys Asn Thr Ser Ser Leu Phe Asn
370                 375                 380

Ser Thr Tyr Asn Pro Asn Asp Thr Asn Ser Asn Ser Ser Ser Ser Asn
385                 390                 395                 400

Ser Ser Leu Asp Ile Thr Ile Pro Cys Arg Ile Lys Gln Ile Ile Asn
                405                 410                 415

Met Trp Gln Glu Val Gly Arg Ala Met Tyr Ala Pro Pro Ile Glu Gly
            420                 425                 430

Asn Ile Thr Cys Lys Ser Asn Ile Thr Gly Leu Leu Leu Val Arg Asp
            435                 440                 445

Gly Gly Val Glu Ser Asn Glu Thr Glu Ile Phe Arg Pro Gly Gly Gly
        450                 455                 460

Asp Met Arg Asn Asn Trp Arg Ser Glu Leu Tyr Lys Tyr Lys Val Val
465                 470                 475                 480

Glu Ile Lys Pro Leu Gly Ile Ala Pro Thr Ala Ala Lys Arg Arg Val
                485                 490                 495

Val Glu Gly Gly Gly Ser Gly Gly Gly Ser Ala Val Gly Leu
            500                 505                 510

Gly Ala Val Ile Phe Gly Phe Leu Gly Ala Ala Gly Ser Thr Met Gly
        515                 520                 525

Ala Ala Ser Ile Thr Leu Thr Val Gln Ala Arg Gln Leu Leu Ser Gly
        530                 535                 540

Ile Val Gln Gln Gln Ser Asn Leu Leu Lys Ala Pro Glu Ala Gln Gln
545                 550                 555                 560

His Leu Leu Gln Leu Thr Val Trp Gly Ile Lys Gln Leu Gln Thr Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ser Ser Trp Ser Asn Lys Ser His Asp Glu Ile Trp Gly Asn Met Thr
        610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Gln Asn Glu Lys Asp
                645                 650                 655

Leu Leu Ala Leu Asp Gly Gly Gly Ser His His His His His His
            660                 665                 670

His His

<210> SEQ ID NO 18
<211> LENGTH: 675
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val

```
            20                  25                  30
Tyr Tyr Gly Val Pro Val Trp Lys Asp Ala Glu Thr Thr Leu Phe Cys
            35                  40                  45

Ala Ser Asp Ala Lys Ala Tyr Glu Thr Glu Lys His Asn Val Trp Ala
50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
            115                 120                 125

Thr Asn Asn Ile Thr Asp Asp Met Arg Gly Glu Leu Lys Asn Cys Ser
            130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
            195                 200                 205

Ile His Tyr Cys Ala Pro Ala Gly Phe Ala Ile Leu Lys Cys Lys Asp
            210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
            275                 280                 285

Asn Cys Thr Arg Pro Asn Asn Asn Thr Arg Lys Ser Ile Arg Ile Gly
            290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
            355                 360                 365

Phe Asn Cys Gly Gly Glu Phe Phe Tyr Cys Asn Thr Ser Gly Leu Phe
            370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
            435                 440                 445
```

```
Asp Gly Gly Ser Thr Asn Ser Thr Glu Thr Phe Arg Pro Gly Gly
        450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Gly Gly Gly Ser Gly Gly Gly Ser Ala Val Gly
                500                 505                 510

Ile Gly Ala Val Phe Leu Gly Phe Leu Gly Ala Ala Gly Ser Thr Met
        515                 520                 525

Gly Ala Ala Ser Met Thr Leu Thr Val Gln Ala Arg Asn Leu Leu Ser
530                 535                 540

Gly Ile Val Gln Gln Gln Ser Asn Leu Leu Arg Ala Pro Glu Ala Gln
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
                580                 585                 590

Ile Trp Gly Cys Ser Gly Lys Leu Ile Cys Thr Thr Asn Val Pro Trp
        595                 600                 605

Asn Ser Ser Trp Ser Asn Arg Asn Leu Ser Glu Ile Trp Asp Asn Met
610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp Gly Gly Gly Ser His His His His
                660                 665                 670

His His His
        675

<210> SEQ ID NO 19
<211> LENGTH: 2031
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
atgcctatgg gatcactgca gcctctggca actctgtatc tgctggggat gctggtcgca      60
agcgtcctgg ccgccgaaaa tctgtgggtg accgtctact atggcgtgcc tgtctggaag     120
gacgccgaaa ccacactgtt ctgcgccagc gatgctaagg catacgaaac agagaaacac     180
aatgtgtggg caactcatgc ctgtgtccca accgacccaa acccccagga aatccacctg     240
gagaatgtga ctgaggagtt caacatgtgg aagaacaata tggtgagcca gatgcatacc     300
gacatcattt ccctgtggga tcagtctctg aagccttgcg tgaaactgac tccactgtgc     360
gtcaccctgc agtgtaccaa cgtgacaaac aatatcaccg acgatatgag gggagaactg     420
aagaattgtt cattcaacat gactaccgag ctgcgagaca gaaacagaa agtgtacagc     480 ctgttttatc ggctggatgt ggtccagatc aatgaaaacc agggcaatcg cagtaacaat     540
tcaaacaagg agtaccgact gatcaattgc aacactagcg ctattaccca ggcatgtcca     600
aaagtgtcct tcgagcctat cccaattcat tattgcgccc ccgctggctt cgccatcctg     660
```

```
aagtgtaaag ataagaagtt caacgggaca ggaccctgcc cttcagtgag cacagtccag    720
tgtactcacg ggattaagcc agtggtcagt actcagctgc tgctgaatgg atcactggcc    780
gaggaagaag tgatgatccg gtctgagaac atcacaaaca acgctaagaa catcctggtg    840
cagttcaaca ctcccgtcca gattaattgc acaagaccta acaataacac tcgaaaatcc    900
atccggattg ccctggcca ggcttttat gcaaccgggg acatcattgg cgacatccgc    960
caggcacact gcaatgtgtc taaggctacc tggaacgaga cactgggaaa ggtggtcaaa   1020
cagctgcgga acatttcgg caataacacc atcattagat ttgccaatag ctccggcggg   1080
gacctggaag tgacaactca ctccttcaac tgcggaggcg agttctttta ctgtaacaca   1140
agtggcctgt ttaattcaac atggatcagc aacacttccg tgcagggctc caattctact   1200
gggtctaacg atagtatcac cctgccctgc aggattaagc agatcattaa tatgtggcag   1260
cgcattggac aggccatgta tgctcccct atccagggcg tgattagatg tgtcagtaat   1320
atcaccgggc tgattctgac aagggacggg ggatcaacca acagcaccac agagaccttc   1380
cggcccggcg gaggagacat gagagataac tggaggagcg aactgtacaa gtataaagtg   1440
gtcaagatcg agccactggg agtggcacca acccgcgcta acgaagagt ggtcggagga   1500 ggaggaggga gcggaggagg aggcagcgct gtgggaattg gcgcagtctt cctggggttt   1560
ctgggagccg ctggctcaac aatgggcgca gccagcatga cactgactgt ccaggcccgc   1620
aatctgctgt ccgggatcgt gcagcagcag tctaacctgc tgcgagcacc tgaagcccag   1680
cagcacctgc tgaagctgac cgtgtggggg atcaaacagc tgcaggcacg ggtgctggcc   1740
gtcgagagat acctgcgcga tcagcagctg ctggggatct ggggatgcag cggcaagctg   1800
atttgtacta ccaatgtgcc ttggaactct agttggtcta atagaaacct gagtgaaatc   1860
tgggacaata tgacctggct gcagtgggat aaggagattt ctaactacac acagatcatc   1920
tacggcctgc tggaagagag tcagaatcag caggagaaga acgagcagga cctgctggcc   1980
ctggatggcg gaggaggctc ccaccatcat caccaccatc accattgctg a             2031
```

<210> SEQ ID NO 20
<211> LENGTH: 2040
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

```
atgcctatgg gatcactgca gcctctggca actctgtatc tgctggggat gctggtcgca     60
agcgtcctgg ccgccgaaaa tctgtgggtg accgtctact atggcgtgcc tgtctggaag    120
gacgccgaaa ccacactgtt ctgcgccagc gatgctaagg catacgaaac agagaaacac    180
aatgtgtggg caactcatgc ctgtgtccca accgacccaa accccagga atccacctg      240 gagaatgtga ctgaggagtt caacatgtgg aagaacaata tggtggagca gatgcatacc    300
gacatcattt ccctgtggga tcagtctctg aagccttgcg tgaaactgac tccactgtgc    360
gtcaccctgc agtgtaccaa cgtgacaaac aatatcaccg acgatatgag gggagaactg    420
aagaattgtt cattcaacat gactaccgag ctgcgagaca gaaacagaa agtgtacagc    480 ctgttttatc ggctggatgt ggtccagatc aatgaaaacc agggcaatcg cagtaacaat    540
tcaaacaagg agtaccgact gatcaattgc aacactagcg ctattaccca ggcatgtcca    600
```

```
aaagtgtcct tcgagcctat cccaattcat tattgcgccc ccgctggctt cgccatcctg    660
aagtgtaaag ataagaagtt caacgggaca ggaccctgcc cttcagtgag cacagtccag    720
tgtactcacg ggattaagcc agtggtcagt actcagctgc tgctgaatgg atcactggcc    780
gaggaagaag tgatgatccg gtctgagaac atcacaaaca acgctaagaa catcctggtg    840
cagttcaaca ctcccgtcca gattaattgc acaagaccta acaataacac tcgaaaatcc    900
atccggattg ccctggcca ggcttttat gcaaccgggg acatcattgg cgacatccgc       960
caggcacact gcaatgtgtc taaggctacc tggaacgaga cactgggaaa ggtggtcaaa   1020
cagctgcgga acatttcgg caataacacc atcattagat ttgccaatag ctccggcggg    1080
gacctggaag tgacaactca ctccttcaac tgcggaggcg agttctttta ctgtaacaca   1140
agtggcctgt ttaattcaac atggatcagc aacacttccg tgcagggctc caattctact   1200
gggtctaacg atagtatcac cctgccctgc aggattaagc agatcattaa tatgtggcag   1260
cgcattggac aggccatgta tgctccccct atccagggcg tgattagatg tgtcagtaat   1320
atcaccgggc tgattctgac aagggacggg ggatcaacca acagcaccac agagaccttc   1380
cggcccggcg gaggagacat gagagataac tggaggagcg aactgtacaa gtataaagtg   1440
gtcaagatcg agccactggg agtggcacca acccgcgcta acgaagagt ggtcggagga    1500 ggaggaggga gcggaggagg aggcagcgct gtgggaattg gcgcagtctt cctggggttt   1560
ctgggagccg ctggctcaac aatgggcgca gccagcatga cactgactgt ccaggcccgc   1620
aatctgctgt ccgggatcgt gcagcagcag tctaacctgc tgcgagcacc tgaagcccag   1680
cagcacctgc tgaagctgac cgtgtggggg atcaaacagc tgcaggcacg ggtgctggcc   1740
gtcgagagat acctgcgcga tcagcagctg ctggggatct ggggatgcag cggcaagctg   1800
atttgtacta ccaatgtgcc ttggaactct agttggtcta atagaaacct gagtgaaatc   1860
tgggacaata tgacctggct gcagtgggat aaggagattt ctaactacac acagatcatc   1920 tacgcctgc tggaagagag tcagaatcag caggagaaga acgagcagga cctgctggcc    1980
ctggatggcg gaggaggctc ccaccatcat caccaccatc accatggatc cggctgctga   2040
```

<210> SEQ ID NO 21
<211> LENGTH: 2031
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

```
atgcccatgg ctccctgca gcccctggcc accctgtacc tgctgggcat gctggtggcc      60
tccgtgctgg ccgtgggcga caacctgtgg gtgaccgtgt actacggcgt gcccgtgtgg   120
aaggaggcca agaccaccct gttctgcgcc tccgacgcca aggcctacga gcgcgaggtg   180
cacaacgtgt gggccaccca cgcctgcgtg cccaccgacc caacccccca ggagatcgcc   240
ctggagaacg tgaccgagaa cttcaacatg tggaagaaca catggtgga ccagatgcac   300 gaggacatca tctcccctgtg ggaccagtcc ctgaagccct gcgtgaagct gacccccctg   360
tgcgtgaccc tgaactgcac caacgtgacc aagaacgaca ccaacgccaa caacaccgcc   420
gagggcaagg aggagcgcaa gaactgctcc ttcaacgcca ccaccgagct gcgcgacaag   480
aaccgcaagg tgtacgccct gttctacaag ctggacatcg tgcccctgaa ccctccaac    540 aactccaact cctccggcca gtaccgcctg atcacctgca cacctccgt gatcacccag    600
```

```
gcctgcccca agatcatctt cgaccccatc cccatccact actgcgcccc cgccggctac      660
gccatcctga agtgcaacaa caagaccttc aacggcaccg ccccctgcaa caacgtgtcc      720
accgtgcagt gcacccacgg catcaagccc gtggtgtcca cccagctgct gctgaacggc      780
tccctggccg aggaggagat catcatccgc tccgagaacc tgaccgacaa cgtgaagacc      840
atcatcgtgc acctgaacga gtccgtgatg atcaactgca cccgccccgg caacaacacc      900
cgcaagtcca tccgcatcgg ccccggccag accttctacg cccccggcga catcatcggc      960
gacatccgcc aggcccactg caacatctcc atcaaccagt ggaacaacac cctgcagaag     1020
atcgccaaga gctgcagac ccgcttcaac cgccccatca gttcgagcc ccactccggc      1080 ggcgacctgg agatcaccac ccactccttc aactgccgcg gcgagttctt ctactgcaac     1140
acctcccagc tgttcaacgg cacctacaac ggcacctgga acggccctg aacaacaac      1200 gagtccgaca ccatcatcct gccctgccgc atcaagcaga tcatcaacat gtggcaggag     1260
gtgggccgcg ccatgtacgc cccccccatc gccggcaaca tcacctgcaa gtccaacatc     1320
accggcctgc tgctgacccg cgacggcggc aagaacgaga ccaacaacgg caccgaaatc     1380
ttccgccccg gcggcggcga catgcgcgac aactggcgct ccgagctgta caagtacaag     1440
gtggtgcaga tcgagcccct gggcgtggcc cccaccaagg ccaagcgccg cgtggtgcag     1500
ggcggcggcg gctccggcgg cggcggctcc gccgtgggca ccctgggcgc catgttcctg     1560
ggcttcctgg gcgccgccgg ctccaccatg ggcgccgcct ccgtgaccct gaccgtgcag     1620
gcccgccagc tgctgtccgg catcgtgcag cagcagaaca acctgctgaa ggccccggag     1680
gcccagcagc acctgctgca gctgaccgtg tggggcatca agcagctgca ggcccgcgtg     1740
ctggccatcg agcgctacct gaaggaccag cagctgctgg gcctgtgggg ctgctccggc     1800
aagctgatct gcaccaccgc cgtgccctgg aacgcctcct ggtccaacaa gtccctgaac     1860
atgatctggg acaacatgac ctggatggag tgggagcgcg aggtgtccaa ctacaccgac     1920
atcatctact ccctgatcga ggagtcccag aaccagcagg agatgaacga gaaggagctg     1980
ctggagctgg acggcggcgg cggctcccac caccaccacc accaccaca c               2031
```

<210> SEQ ID NO 22
<211> LENGTH: 2040
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
atgcccatgg gctccctgca gcccctggcc accctgtacc tgctgggcat gctggtggcc       60
tccgtgctgg ccgtggagaa cctgtgggtg accgtgtact acggcgtgcc cgtgtggaag      120
gaggcccgca ccaccctgtt ctgcgcctcc gacgccaagg cctacgagac cgaggtgcac      180
aacgtgtggg ccacccacgc ctgcgtgccc accgacccca ccccagga gatggtgctg       240 ggcaacgtga ccgagaactt caacatgtgg aagaacgaca tggtggacca gatgcacgag      300
gacgtgatct ccctgtgggc ccagtccctg aagccctgcg tgaagctgac ccccctgtgc      360 gtgacccctgg agtgcaccca ggtgaacgcc acccagggca caccaccca ggtgaacgtg     420 acccaggtga acggcgacga gatgaagaac tgctccttca acaccaccac cgagatccgc      480
gacaagaagc agaaggccta cgccctgttc taccgcctgg acctggtgcc cctggagcgc      540
```

```
gagaaccgcg gcgactccaa ctccgcctcc aagtacatcc tgatcaactg caacacctcc      600
gccatcaccc aggcctgccc caaggtgaac ttcgacccca tccccatcca ctactgcacc      660
cccgccggct acgccatcct gaagtgcaac aacaagacct tcaacggcac cggctcctgc      720
aacaacgtgt ccaccgtgca gtgcacccac ggcatcaagc ccgtggtgtc cacccagctg      780
ctgctgaacg gctccctggc cgaggaggag atcatcatcc gctccgagaa cctgaccgac      840
aacgtgaaga ccatcatcgt gcacctggac cagtccgtgg agatcgtgtg cacccgcccc      900
aacaacaaca cccgcaagtc catccgcatc ggccccggcc agaccttcta cgccaccggc      960
gacatcatcg gcaacatccg cgaggcccac tgcaacatct ccgagaagaa gtggcacgag     1020
atgctgcgcc gcgtgtccga aagctggcc gagcacttcc ccaacaagac catcaagttc     1080
acctcctcct ccggcggcga cctggagatc accacccact ccttcaactg ccgcggcgag     1140
ttcttctact gcaacacctc cggcctgttc aactccacct acatgcccaa cggcacctac     1200
atgcccaacg gcaccaacaa ctccaactcc accatcatcc tgccctgccg catcaagcag     1260
atcatcaaca tgtggcagga ggtgggccgc gccatgtacg ccccccccat cgccggcaac     1320
atcacctgca actccaacat caccggcctg ctgctggtgc gcgacggcgg caagaacaac     1380
aacaccgaaa tcttccgccc cggcggcggc gacatgcgcg acaactggcg ctccgagctg     1440
tacaagtaca aggtggtgga gatcaagccc ctgggcgtgg cccccacccg cccaagcgc     1500 cgcgtggtgg agggcggcgg cggctccggc ggcggcggct ccgccgtggg cctgggcgcc     1560
gtgttcctgg gcttcctggg cgccgccggc tccaccatgg gcgccgcctc catcaccctg     1620
accgtgcagg cccgccagct gctgtccggc atcgtgcagc agcagtccaa cctgctgcag     1680
gcccccgagg cccagcagca cctgctgcag ctgaccgtgt ggggcatcaa gcagctgcag     1740
acccgcgtgc tggccatcga gcgctacctg aaggaccagc agctgctggg catctggggc     1800
tgctccggca gctgatctg caccaccgcc gtgccctgga actcctcctg gtccaacaag     1860
tccctgaccg acatctggga caacatgacc tggatgcagt gggaccgcga ggtgtccaac     1920
tacaccggca tcatctaccg cctgctggag gactcccaga accagcagga gcgcaacgag     1980
caggacctgc tggcccctgga cggcggcggc ggctcccacc accaccacca ccaccaccac     2040
```

<210> SEQ ID NO 23
<211> LENGTH: 1980
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

```
atgcccatgg gctccctgca gccctggcc accctgtacc tgctgggcat gctggtggcc       60
tccgtgctgg cctccctgtg ggtgaccgtg tactacggcg tgcccgtgtg gaaggaggcc      120
aagaccaccc tgttctgcgc ctccgacgcc aaggcctacg agcgcgaggt gcacaacgtg      180
tgggccaccc acgcctgcgt gcccaccgac cccaaccccc aggagatggt gctggagaac      240
gtgaccgaga acttcaacat gtggaagaac gacatggtgg accagatgca cgaggacatc      300
atctccctgt gggacgagtc cctgaagccc tgcgtgaagc tgaccccct gtgcgtgacc      360 ctgaactgca ccttcatcac caacaccacc gagatcaaga actgcacctt caacatgacc      420
accgagctgc gcgacatcaa gcagcagggc cgcgccctgt cgacaccct ggacatcgtg      480 cccctgaagc ccccaacaa ctcctccaac tactccgagt accgcctgat ctcctgcaac      540
```

```
acctccacca tcacccaggc ctgcccaag gtgtccttcg accccatccc catccactac    600 tgcgccccg ccggctacgc catcctgaag tgcaacaaca agaccttcaa cggcctgggc    660
ccctgcaaca acgtgtccac cgtgcagtgc acccacggca tcaagcccgt ggtgtccacc    720
cagctgctgc tgaacggctc cctggccgag gaggagatca tcatccgctc cgagaacctg    780
accaacaacg tgaagaccat catcgtgcac ctgaacgagc ccgtgtacat cgtgtgcacc    840
cgccccaaca caacacccg caagtccatg cgcatcggcc ccggccagac cttctacgcc    900
accggcgaca tcatcggcga catccgccag gcccactgca acatctccat cgagaagtgg    960
aacaccaccc tggagaaggt gaaggagcgc ctgaagaagc acttccccaa caagatcatc   1020
aagttcgagc cctcctccgg cggcgacctg gagatcacca cccactcctt caactgccgc   1080
ggcgagttct tctactgcaa caccgccaac ctgttcaacg agaccttcat gaaccagacc   1140
gacgccaacc agaccaacgc caccatcacc ctgcagtgcc gcatcaagca gatcatcaac   1200
atgtggcagg gcgtgggccg cgccatgtac gccccccca tccccggccg catcacctgc   1260
aactcctcca tcaccggcct gatcctgacc cgcgacggcg gcgagaacac caccgacaac   1320
ggcaccgaaa tcttccgccc cggcggcggc gacatgcgcg acaactggcg ctccgagctg   1380
tacaagtaca aggtggtgga gatcaagccc ctgggcatcg cccccaccga ggccaagcgc   1440
cgcgtggtgg agggcggcgg cggctccggc ggcggcggct ccgccgtggg catcggcgcc   1500
gtgttcctgg gcttcctggg cgccgccggc tccaccatgg gcgccgcctc catcacctg   1560 accgtgcagg cccgccagct gctgtccggc atcgtgcagc agcagtccaa cctgctgcgc   1620
gcccccgagg cccagcagca catgctgcag ctgaccgtgt ggggcatcaa gcagctgcag   1680
gcccgcgtgc tggccatcga gcgctacctg aaggaccagc agctgctggg catctggggc   1740
tgctccggca agctgatctg caccaccaac gtgccctgga actcctcctg gtccaacaag   1800
tccctgggcg acatctggga caacatgacc tggatggagt gggaccgcga aatctccaac   1860
tacaccaaca tcatcttcgg cctgctggag gactcccaga accagcagga gcgcaacgag   1920
aaggacctgc tggccctgga cggcggcggc ggctcccacc accaccacca ccaccaccac   1980
```

<210> SEQ ID NO 24
<211> LENGTH: 2088
<212> TYPE: DNA
<213> ORGANISM: Artificial Sequence
<220> FEATURE:
<221> NAME/KEY: source
<223> OTHER INFORMATION: /note="Description of Artificial Sequence:
   Synthetic polynucleotide"

<400> SEQUENCE: 24

```
atgcccatgg ctccctgca gccctggcc accctgtacc tgctgggcat gctggtggcc     60
tccgtgctgg ccgccaacaa cctgtgggtg accgtgtact acggcgtgcc cgtgtggcgc    120
gacgccgaga ccaccctgtt ctgcgcctcc gacgccaagg cctacgacac cgaggtgcac    180
aacgtgtggg ccacccacgc ctgcgtgccc accgacccg accccagga gatcgacctg    240 aagaacgtga ccgaggagtt caacatgtgg aagaacaaca tggtggagca gatgcacacc    300
gacatcatct ccctgtggga ccagtccctg aagccctgcg tgaagctgac ccacctgtgc    360
gtgaccctga actgctccac cgccaacgtg aacgtgaccg actacaacat caccaccggc    420
gacaaggagg agatcaagaa ctgctccttc aacatgacca ccgagctgtc cgacaaggag    480
cagaaggtgc actccctgtt ctaccgcctg gacgtggtgc ccatcgagca ggacaactcc    540
```

-continued

| | |
|---|---|
| aagaacaact ccaactccgg cgacaactcc tcctactcct cctactccaa ctaccgcctg | 600 |
| atcaactgca acacctccgc catcacccag gcctgcccca aggtgacctt cgaccccatc | 660 |
| cccatccact actgcgcccc cgccggcttc gccatcctga agtgcaagga cgacggcttc | 720 |
| aacggcaccg cccctgcaa gaacgtgtcc tccgtgcagt gcaccacgg catcaagccc | 780 |
| gtggtgtcca cccagctgct gctgaacggc tccctggcca aggagggcat ccgcatccgc | 840 |
| tccgagaaca tcaccgacaa caccaagacc atcatcgtgc agctggacaa gcccgtgcgc | 900 |
| atcaactgca cccgccccaa caacaacacc cgcaagtcca tgcgcatcgg ccccggccag | 960 |
| accttcttcg ccaccggcga catcatcggc gacatccgca aggcccactg caacatctcc | 1020 |
| atctccgagt ggaacgagac cctgtaccgc gtggccaagc agctgggcgg catgatcggc | 1080 |
| aacaagaccg tgaagttcga caactcctcc ggcggcgacc tggagatcac cacccactcc | 1140 |
| ttcaactgcg gcggcgagtt cttctactgc aacaccaccg acctgttcaa gggcacctgg | 1200 |
| accccaaca cctccatctg gaacgccaac tggaacgact ccatcaagtc caacgacacc | 1260 |
| tccaacgcca acatcaccat cctgtgcaag atcaagcaga tcgtgcgcat gtggcagcgc | 1320 |
| gtggagcagg ccatgtacgc cccccccatc cagggcgtga tctcctgctc ctccaacatc | 1380 |
| accggcctgc tgctgacctc cgacggcggc cgcaacacct ccaacaacaa caccgagacc | 1440 |
| ttccgccccg cggcggcga catgcgcgac aactggcgct ccgagctgta caagtacaag | 1500 |
| gtggtgaaga tcgagcccct gggcgtggcc ccacccccg ccaagcgccg cgtggtggag | 1560 |
| ggcggcggcg gctccggcgg cggcggctcc gccgtgggcc tgggcgccgt gttcatcggc | 1620 |
| ttcctgggcg ccgccggctc caccatgggc gccgcctccg tgaccctgac cgtgcaggcc | 1680 |
| cgccagctgc tgaccggcat cgtgcgccag cagtccaacc tgctgaaggc ccccgaggcc | 1740 |
| cagcagcacc tgctgcgcct gaccgtgtgg ggcatcaagc agctgcaggc ccgcgtgctg | 1800 |
| gccgtggagc gctacctgaa ggaccagcag ctgctgggca tctggggctg ctccggcaag | 1860 |
| ctgatctgca ccaccaacgt gccctggaac tcctcctggt ccaacaagaa ccagtccgaa | 1920 |
| atctgggaca acatgacctg gctgcagtgg gacaaggaga tccacaacta cacccagatc | 1980 |
| atctacgacc tgctggagga gtcccagaac cagcaggaga gaacgagca ggagctgctg | 2040 |
| gccctggacg gcggcggcgg ctcccaccac caccaccacc accaccac | 2088 |

<210> SEQ ID NO 25
<211> LENGTH: 674
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

Met Pro Met Gly Ser Leu Gln Pro Leu Ala Thr Leu Tyr Leu Leu Gly
1               5                   10                  15

Met Leu Val Ala Ser Val Leu Ala Gly Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Glu Lys Glu Val His Asn Val Trp Ala Thr
    50                  55                  60

His Ala Cys Val Pro Thr Asp Pro Asn Pro Gln Glu Met Val Leu Glu
65                  70                  75                  80

-continued

```
Asn Val Thr Glu Asn Phe Asn Met Trp Lys Asn Asp Met Val Glu Gln
                 85                  90                  95
Met His Glu Asp Val Ile Ser Leu Trp Asp Gln Ser Leu Lys Pro Cys
            100                 105                 110
Val Lys Leu Thr Pro Leu Cys Val Thr Leu Glu Cys Arg Gln Val Asn
        115                 120                 125
Thr Thr Asn Ala Thr Ser Ser Val Asn Val Thr Asn Gly Glu Glu Ile
130                 135                 140
Lys Asn Cys Ser Phe Asn Ala Thr Thr Glu Ile Arg Asp Lys Lys Gln
145                 150                 155                 160
Lys Val Tyr Ala Leu Phe Tyr Arg Leu Asp Ile Val Pro Leu Glu Glu
                165                 170                 175
Glu Arg Lys Gly Asn Ser Ser Lys Tyr Arg Leu Ile Asn Cys Asn Thr
            180                 185                 190
Ser Ala Ile Thr Gln Ala Cys Pro Lys Val Thr Phe Asp Pro Ile Pro
        195                 200                 205
Ile His Tyr Cys Ala Pro Ala Gly Tyr Ala Ile Leu Lys Cys Asn Asn
    210                 215                 220
Lys Thr Phe Asn Gly Thr Gly Pro Cys Asn Asn Val Ser Thr Val Gln
225                 230                 235                 240
Cys Thr His Gly Ile Lys Pro Val Val Ser Thr Gln Leu Leu Leu Asn
                245                 250                 255
Gly Ser Leu Ala Glu Gly Glu Ile Ile Ile Arg Ser Glu Asn Leu Thr
            260                 265                 270
Asn Asn Val Lys Thr Ile Ile Val His Leu Asn Glu Ser Val Glu Ile
        275                 280                 285
Val Cys Thr Arg Pro Asn Asn Asn Thr Arg Lys Ser Ile Arg Ile Gly
    290                 295                 300
Pro Gly Gln Thr Phe Tyr Ala Thr Gly Asp Ile Ile Gly Asn Ile Arg
305                 310                 315                 320
Gln Ala Tyr Cys Asn Ile Lys Lys Asp Asp Trp Ile Arg Thr Leu Gln
                325                 330                 335
Arg Val Gly Lys Lys Leu Ala Glu His Phe Pro Arg Arg Ile Ile Asn
            340                 345                 350
Phe Thr Ser Pro Ala Gly Gly Asp Leu Glu Ile Thr Thr His Ser Phe
        355                 360                 365
Asn Cys Arg Gly Glu Phe Phe Tyr Cys Asn Thr Ser Ser Leu Phe Asn
    370                 375                 380
Ser Thr Tyr Asn Pro Asn Asp Thr Asn Ser Asn Ser Ser Ser Ser Asn
385                 390                 395                 400
Ser Ser Leu Asp Ile Thr Ile Pro Cys Arg Ile Lys Gln Ile Ile Asn
                405                 410                 415
Met Trp Gln Glu Val Gly Arg Ala Met Tyr Ala Pro Pro Ile Glu Gly
            420                 425                 430
Asn Ile Thr Cys Lys Ser Asn Ile Thr Gly Leu Leu Leu Val Arg Asp
        435                 440                 445
Gly Gly Val Glu Ser Asn Glu Thr Glu Ile Phe Arg Pro Gly Gly Gly
    450                 455                 460
Asp Met Arg Asn Asn Trp Arg Ser Glu Leu Tyr Lys Tyr Lys Val Val
465                 470                 475                 480
Glu Ile Lys Pro Leu Gly Ile Ala Pro Thr Ala Ala Lys Arg Arg Val
                485                 490                 495
Val Glu Gly Gly Gly Gly Ser Gly Gly Gly Gly Ser Ala Val Gly Leu
```

```
                500                 505                 510
Gly Ala Val Ile Phe Gly Phe Leu Gly Ala Ala Gly Ser Thr Met Gly
            515                 520                 525

Ala Ala Ser Ile Thr Leu Thr Val Gln Ala Arg Gln Leu Leu Ser Gly
        530                 535                 540

Ile Val Gln Gln Gln Ser Asn Leu Leu Lys Ala Ile Glu Ala Gln Gln
545                 550                 555                 560

His Leu Leu Gln Leu Thr Val Trp Gly Ile Lys Gln Leu Gln Thr Arg
            565                 570                 575

Val Leu Ala Ile Glu Arg Tyr Leu Lys Asp Gln Gln Leu Leu Gly Ile
        580                 585                 590

Trp Gly Cys Ser Gly Lys Leu Ile Cys Thr Thr Ala Val Pro Trp Asn
        595                 600                 605

Ser Ser Trp Ser Asn Lys Ser His Asp Glu Ile Trp Gly Asn Met Thr
    610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Gln Asn Glu Lys Asp
            645                 650                 655

Leu Leu Ala Leu Asp Gly Gly Gly Ser His His His His His His
        660                 665                 670

His His
```

<210> SEQ ID NO 26
<211> LENGTH: 665
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Met Pro Met Gly Ser Leu Gln Pro Leu Ala Thr Leu Tyr Leu Leu Gly
1               5                   10                  15

Met Leu Val Ala Ser Val Leu Ala Asn Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
            85                  90                  95

Gln Met His Glu Asp Val Ile Ser Leu Trp Asp Gln Ser Leu Lys Pro
        100                 105                 110

Cys Val Lys Leu Thr Pro Leu Cys Val Thr Leu Glu Cys Arg Gln Val
    115                 120                 125

Asn Thr Thr Asn Ala Thr Ser Ser Val Asn Val Thr Asn Gly Glu Glu
130                 135                 140

Ile Lys Asn Cys Ser Phe Asn Ala Thr Thr Glu Ile Arg Asp Lys Lys
            145                 150                 155                 160

Gln Lys Val Tyr Ala Leu Phe Tyr Arg Leu Asp Ile Val Pro Leu Glu
        165                 170                 175
```

-continued

```
Glu Glu Arg Lys Gly Asn Ser Ser Lys Tyr Arg Leu Ile Asn Cys Asn
                180                 185                 190
Thr Ser Ala Ile Thr Gln Ala Cys Pro Lys Val Thr Phe Asp Pro Ile
            195                 200                 205
Pro Ile His Tyr Cys Ala Pro Ala Gly Tyr Ala Ile Leu Lys Cys Asn
        210                 215                 220
Asn Lys Thr Phe Asn Gly Thr Gly Pro Cys Asn Asn Val Ser Thr Val
225                 230                 235                 240
Gln Cys Thr His Gly Ile Lys Pro Val Val Ser Thr Gln Leu Leu Leu
                245                 250                 255
Asn Gly Ser Leu Ala Glu Gly Glu Ile Ile Arg Ser Glu Asn Leu
            260                 265                 270
Thr Asn Asn Val Lys Thr Ile Ile Val His Leu Asn Glu Ser Val Glu
            275                 280                 285
Ile Val Cys Thr Arg Pro Asn Asn Asn Thr Arg Lys Ser Ile Arg Ile
        290                 295                 300
Gly Pro Gly Gln Thr Phe Tyr Ala Thr Gly Asp Ile Ile Gly Asn Ile
305                 310                 315                 320
Arg Gln Ala Tyr Cys Asn Ile Lys Lys Asp Asp Trp Ile Arg Thr Leu
                325                 330                 335
Gln Arg Val Gly Lys Lys Leu Ala Glu His Phe Pro Arg Arg Ile Ile
            340                 345                 350
Asn Phe Thr Ser Pro Ala Gly Gly Asp Leu Glu Ile Thr Thr His Ser
        355                 360                 365
Phe Asn Cys Arg Gly Glu Phe Phe Tyr Cys Asn Thr Ser Ser Leu Phe
370                 375                 380
Asn Ser Thr Tyr Asn Pro Asn Asp Thr Asn Ser Asn Ser Ser Ser
385                 390                 395                 400
Asn Ser Ser Leu Asp Ile Thr Ile Pro Cys Arg Ile Lys Gln Ile Ile
                405                 410                 415
Asn Met Trp Gln Glu Val Gly Arg Ala Met Tyr Ala Pro Pro Ile Glu
            420                 425                 430
Gly Asn Ile Thr Cys Lys Ser Asn Ile Thr Gly Leu Leu Leu Val Arg
        435                 440                 445
Asp Gly Gly Val Glu Ser Asn Glu Thr Glu Ile Phe Arg Pro Gly Gly
450                 455                 460
Gly Asp Met Arg Asn Asn Trp Arg Ser Glu Leu Tyr Lys Tyr Lys Val
465                 470                 475                 480
Val Glu Ile Lys Pro Leu Gly Ile Ala Pro Thr Ala Cys Lys Arg Arg
                485                 490                 495
Val Arg Arg Arg Lys Arg Ala Val Gly Leu Gly Ala Val Ile Phe
            500                 505                 510
Gly Phe Leu Gly Ala Ala Gly Ser Thr Met Gly Ala Ala Ser Ile Thr
        515                 520                 525
Leu Thr Val Gln Ala Arg Gln Leu Leu Ser Gly Ile Val Gln Gln Gln
        530                 535                 540
Ser Asn Leu Leu Lys Ala Pro Glu Ala Gln Gln His Leu Leu Gln Leu
545                 550                 555                 560
Thr Val Trp Gly Ile Lys Gln Leu Gln Thr Arg Val Leu Ala Ile Glu
                565                 570                 575
Arg Tyr Leu Lys Asp Gln Gln Leu Leu Gly Ile Trp Gly Cys Ser Gly
            580                 585                 590
Lys Leu Ile Cys Cys Thr Ala Val Pro Trp Asn Ser Ser Trp Ser Asn
```

```
                    595                 600                 605
Lys Ser His Asp Glu Ile Trp Gly Asn Met Thr Trp Met Gln Trp Asp
        610                 615                 620

Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Gly
                645                 650                 655

Gly Gly Gly His His His His His
        660                 665

<210> SEQ ID NO 27
<211> LENGTH: 676
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Met Pro Met Gly Ser Leu Gln Pro Leu Ala Thr Leu Tyr Leu Leu Gly
1               5                   10                  15

Met Leu Val Ala Ser Val Leu Ala Gly Gln Asn Leu Trp Val Thr Val
                20                  25                  30

Tyr Tyr Gly Val Pro Val Trp Lys Glu Ala Lys Thr Thr Leu Phe Cys
            35                  40                  45

Ala Ser Asn Ala Lys Ala Tyr Glu Lys Glu Val His Asn Val Trp Ala
        50                  55                  60

Thr His Ala Cys Val Pro Thr Asp Pro Asn Pro Gln Glu Met Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Glu Ser Leu Lys Pro
            100                 105                 110

Cys Val Lys Leu Thr Pro Leu Cys Val Thr Leu Ile Cys Thr Asn Val
        115                 120                 125

Asn His Ser Ser Thr Asn Val Ser His Ser Ser Thr Asn Val Ser Gln
    130                 135                 140

Ser Ser Asn Ser Ser Gln Asp Asn Thr Thr Ile Asp Glu Ser Met Arg
145                 150                 155                 160

Glu Glu Ile Lys Asn Cys Ser Tyr Asn Ser Thr Thr Glu Leu Trp Asp
                165                 170                 175

Lys Lys Gln Lys Glu Tyr Ala Leu Phe Tyr Lys Leu Asp Ile Val Pro
            180                 185                 190

Ile Asn Gly Asn Ala Ser Glu Tyr Arg Leu Ile Asn Cys Asn Thr Ser
        195                 200                 205

Thr Ile Lys Gln Ala Cys Pro Lys Val Thr Phe Glu Pro Ile Pro Ile
    210                 215                 220

His Tyr Cys Ala Pro Ala Gly Tyr Ala Ile Leu Lys Cys Asn Asn Gln
225                 230                 235                 240

Thr Phe Asn Gly Thr Gly Pro Cys Thr Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Lys Glu Ile Ile Ile Ser Ser Glu Asn Leu Thr Asn
        275                 280                 285
```

Asn Ala Lys Ile Ile Ile Val His Leu Lys Asp Pro Val Arg Ile Val
            290                 295                 300

Cys Thr Arg Pro Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala Tyr Cys Asn Ile Ser Lys Gly Ala Trp Asn Lys Thr Leu Gln Gln
                340                 345                 350

Val Gly Lys Lys Leu Gln Glu His Phe Pro Gly Lys Thr Ile Lys Phe
            355                 360                 365

Asn Ser Ser Gly Gly Asp Leu Glu Ile Thr Thr His Ser Phe Asn
370                 375                 380

Cys Arg Gly Glu Phe Phe Tyr Cys Asn Thr Ser Lys Leu Phe Asn Asn
385                 390                 395                 400

Thr Tyr Tyr Asn Gly Thr Gly Asn Ala Asn Ser Thr His Glu Asn Ile
                405                 410                 415

Thr Leu Pro Cys Arg Ile Lys Gln Ile Ile Arg Met Trp Gln Lys Val
                420                 425                 430

Gly Gln Ala Met Tyr Ala Pro Pro Ile Ala Gly Asn Ile Thr Cys Thr
            435                 440                 445

Ser Asn Ile Thr Gly Leu Leu Leu Val Arg Asp Gly Gly Glu Ala Asn
450                 455                 460

Gly Thr Asn Asn Ile Glu Thr Phe Arg Pro Gly Gly Gly Asp Met Arg
465                 470                 475                 480

Asp Asn Trp Arg Ser Glu Leu Tyr Lys Tyr Lys Val Val Glu Ile Gln
                485                 490                 495

Pro Leu Gly Ile Ala Pro Thr Lys Cys Lys Arg Arg Val Arg Arg Arg
            500                 505                 510

Lys Lys Arg Ala Val Gly Ile Gly Ala Met Phe Leu Gly Phe Leu Gly
            515                 520                 525

Ala Ala Gly Ser Thr Met Gly Ala Ala Ser Met Ala Leu Thr Val Gln
            530                 535                 540

Ser Arg Gln Leu Leu Ser Gly Ile Val Gln Gln Ser Asn Leu Leu
545                 550                 555                 560

Arg Ala Pro Glu Ala Gln Gln His Met Leu Gln Leu Thr Val Trp Gly
                565                 570                 575

Ile Lys Gln Leu Arg Ala Arg Val Val Ala Leu Glu Arg Tyr Leu Gln
                580                 585                 590

Asp Gln Gln Leu Leu Gly Ile Trp Gly Cys Ser Gly Lys Leu Ile Cys
            595                 600                 605

Cys Thr Asn Val Pro Trp Asn Ser Ser Trp Ser Asn Arg Ser Ala Asp
610                 615                 620

Ile Trp Asp Asn Leu Thr Trp Met Gln Trp Glu Lys Glu Ile Asn Asn
625                 630                 635                 640

Tyr Thr Asp Thr Ile Tyr Gln Leu Leu Glu Glu Ser Gln Ile Gln Gln
                645                 650                 655

Glu Lys Asn Glu Gln Asp Leu Leu Ala Leu Gly Gly Gly Gly His His
            660                 665                 670

His His His His
            675

<210> SEQ ID NO 28
<211> LENGTH: 684

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28
```

Met Pro Met Gly Ser Leu Gln Pro Leu Ala Thr Leu Tyr Leu Leu Gly
1               5                   10                  15

Met Leu Val Ala Ser Val Leu Ala Gly Gln Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asn Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Gly Asn Val Thr Glu Asn Phe Asn Met Trp Lys Asn Asp Met Val Asp
                85                  90                  95

Gln Met His Glu Asp Ile Ile Ser Leu Trp Asp Glu Ser Leu Lys Pro
            100                 105                 110

Cys Val Lys Leu Thr Pro Leu Cys Val Thr Leu Ile Cys Thr Asn Val
        115                 120                 125

Asn His Ser Ser Thr Asn Val Ser His Ser Ser Thr Asn Val Ser Gln
    130                 135                 140

Ser Ser Asn Ser Ser Gln Asp Asn Thr Thr Ile Asp Glu Ser Met Arg
145                 150                 155                 160

Glu Glu Ile Lys Asn Cys Ser Tyr Asn Ser Thr Thr Glu Leu Trp Asp
                165                 170                 175

Lys Lys Gln Lys Glu Tyr Ala Leu Phe Tyr Lys Leu Asp Ile Val Pro
            180                 185                 190

Ile Asn Gly Asn Ala Ser Glu Tyr Arg Leu Ile Asn Cys Asn Thr Ser
        195                 200                 205

Thr Ile Lys Gln Ala Cys Pro Lys Val Thr Phe Glu Pro Ile Pro Ile
210                 215                 220

His Tyr Cys Ala Pro Ala Gly Tyr Ala Ile Leu Lys Cys Asn Asn Gln
225                 230                 235                 240

Thr Phe Asn Gly Thr Gly Pro Cys Thr Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Lys Glu Ile Ile Ile Ser Ser Glu Asn Leu Thr Asn
        275                 280                 285

Asn Ala Lys Ile Ile Ile Val His Leu Lys Asp Pro Val Arg Ile Val
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala Tyr Cys Asn Ile Ser Lys Gly Ala Trp Asn Lys Thr Leu Gln Gln
            340                 345                 350

Val Gly Lys Lys Leu Gln Glu His Phe Pro Gly Lys Thr Ile Lys Phe
        355                 360                 365

Asn Ser Ser Ser Gly Gly Asp Leu Glu Ile Thr Thr His Ser Phe Asn

```
                    370                 375                 380
Cys Arg Gly Glu Phe Phe Tyr Cys Asn Thr Ser Lys Leu Phe Asn Asn
385                 390                 395                 400

Thr Tyr Tyr Asn Gly Thr Gly Asn Ala Asn Ser Thr His Glu Asn Ile
                405                 410                 415

Thr Leu Pro Cys Arg Ile Lys Gln Ile Arg Met Trp Gln Lys Val
            420                 425                 430

Gly Gln Ala Met Tyr Ala Pro Pro Ile Ala Gly Asn Ile Thr Cys Thr
                435                 440                 445

Ser Asn Ile Thr Gly Leu Leu Leu Val Arg Asp Gly Gly Glu Ala Asn
            450                 455                 460

Gly Thr Asn Asn Ile Glu Thr Phe Arg Pro Gly Gly Asp Met Arg
465                 470                 475                 480

Asp Asn Trp Arg Ser Glu Leu Tyr Lys Tyr Lys Val Val Glu Ile Gln
                485                 490                 495

Pro Leu Gly Ile Ala Pro Thr Lys Ala Lys Arg Arg Val Val Glu Gly
                500                 505                 510

Gly Gly Gly Ser Gly Gly Gly Ser Ala Val Gly Ile Gly Ala Met
            515                 520                 525

Phe Leu Gly Phe Leu Gly Ala Ala Gly Ser Thr Met Gly Ala Ala Ser
            530                 535                 540

Met Ala Leu Thr Val Gln Ser Arg Gln Leu Leu Ser Gly Ile Val Gln
545                 550                 555                 560

Gln Gln Ser Asn Leu Leu Arg Ala Pro Glu Ala Gln Gln His Met Leu
                565                 570                 575

Gln Leu Thr Val Trp Gly Ile Lys Gln Leu Arg Ala Arg Val Val Ala
            580                 585                 590

Leu Glu Arg Tyr Leu Gln Asp Gln Gln Leu Leu Gly Ile Trp Gly Cys
            595                 600                 605

Ser Gly Lys Leu Ile Cys Thr Thr Asn Val Pro Trp Asn Ser Ser Trp
            610                 615                 620

Ser Asn Arg Ser Ala Asp Ile Trp Asp Asn Leu Thr Trp Met Gln Trp
625                 630                 635                 640

Glu Lys Glu Ile Asn Asn Tyr Thr Asp Thr Ile Tyr Gln Leu Leu Glu
                645                 650                 655

Glu Ser Gln Ile Gln Gln Glu Lys Asn Glu Gln Asp Leu Leu Ala Leu
                660                 665                 670

Asn Gly Gly Gly Gly Ser His His His His His
            675                 680

<210> SEQ ID NO 29
<211> LENGTH: 684
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Pro Met Gly Ser Leu Gln Pro Leu Ala Thr Leu Tyr Leu Leu Gly
1               5                   10                  15

Met Leu Val Ala Ser Val Leu Ala Gly Gln Asn Leu Trp Val Thr Val
                20                  25                  30

Tyr Tyr Gly Val Pro Val Trp Lys Asp Ala Glu Thr Thr Leu Phe Cys
            35                  40                  45
```

-continued

```
Ala Ser Asn Ala Lys Ala Tyr Glu Lys Glu Lys His Asn Val Trp Ala
         50                  55                  60
Thr His Ala Cys Val Pro Thr Asp Pro Asn Pro Gln Glu Met Val Leu
 65                  70                  75                  80
Gly Asn Val Thr Glu Asn Phe Asn Met Trp Lys Asn Asp Met Val Asp
                 85                  90                  95
Gln Met His Thr Asp Ile Ile Ser Leu Trp Asp Glu Ser Leu Lys Pro
                100                 105                 110
Cys Val Lys Leu Thr Pro Leu Cys Val Thr Leu Ile Cys Thr Asn Val
            115                 120                 125
Asn His Ser Ser Thr Asn Val Ser His Ser Ser Thr Asn Val Ser Gln
    130                 135                 140
Ser Ser Asn Ser Ser Gln Asp Asn Thr Thr Ile Asp Glu Ser Met Arg
145                 150                 155                 160
Glu Glu Ile Lys Asn Cys Ser Tyr Asn Ser Thr Thr Glu Leu Trp Asp
                165                 170                 175
Lys Lys Gln Lys Glu Tyr Ala Leu Phe Tyr Lys Leu Asp Ile Val Pro
                180                 185                 190
Ile Asn Gly Asn Ala Ser Glu Tyr Arg Leu Ile Asn Cys Asn Thr Ser
            195                 200                 205
Thr Ile Lys Gln Ala Cys Pro Lys Val Thr Phe Glu Pro Ile Pro Ile
    210                 215                 220
His Tyr Cys Ala Pro Ala Gly Tyr Ala Ile Leu Lys Cys Asn Asn Gln
225                 230                 235                 240
Thr Phe Asn Gly Thr Gly Pro Cys Thr Asn Val Ser Thr Val Gln Cys
                245                 250                 255
Thr His Gly Ile Lys Pro Val Val Ser Thr Gln Leu Leu Leu Asn Gly
            260                 265                 270
Ser Leu Ala Glu Lys Glu Ile Ile Ile Ser Ser Glu Asn Leu Thr Asn
    275                 280                 285
Asn Ala Lys Ile Ile Ile Val His Leu Lys Asp Pro Val Arg Ile Val
290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala Tyr Cys Asn Ile Ser Lys Gly Ala Trp Asn Lys Thr Leu Gln Gln
                340                 345                 350
Val Gly Lys Lys Leu Gln Glu His Phe Pro Gly Lys Thr Ile Lys Phe
            355                 360                 365
Asn Ser Ser Ser Gly Gly Asp Leu Glu Ile Thr Thr His Ser Phe Asn
    370                 375                 380
Cys Arg Gly Glu Phe Phe Tyr Cys Asn Thr Ser Lys Leu Phe Asn Asn
385                 390                 395                 400
Thr Tyr Tyr Asn Gly Thr Gly Asn Ala Asn Ser Thr His Glu Asn Ile
                405                 410                 415
Thr Leu Pro Cys Arg Ile Lys Gln Ile Ile Arg Met Trp Gln Arg Val
            420                 425                 430
Gly Gln Ala Met Tyr Ala Pro Pro Ile Ala Gly Asn Ile Thr Cys Thr
    435                 440                 445
Ser Asn Ile Thr Gly Leu Leu Leu Val Arg Asp Gly Gly Glu Ala Asn
450                 455                 460
```

-continued

```
Gly Thr Asn Asn Ile Glu Thr Phe Arg Pro Gly Gly Asp Met Arg
465                 470                 475                 480

Asp Asn Trp Arg Ser Glu Leu Tyr Lys Tyr Lys Val Val Glu Ile Gln
            485                 490                 495

Pro Leu Gly Ile Ala Pro Thr Lys Ala Lys Arg Arg Val Val Glu Gly
                500                 505                 510

Gly Gly Gly Ser Gly Gly Gly Ser Ala Val Gly Ile Gly Ala Met
        515                 520                 525

Phe Leu Gly Phe Leu Gly Ala Ala Gly Ser Thr Met Gly Ala Ala Ser
        530                 535                 540

Met Ala Leu Thr Val Gln Ser Arg Gln Leu Leu Ser Gly Ile Val Gln
545                 550                 555                 560

Gln Gln Ser Asn Leu Leu Arg Ala Pro Glu Ala Gln Gln His Met Leu
                565                 570                 575

Gln Leu Thr Val Trp Gly Ile Lys Gln Leu Arg Ala Arg Val Val Ala
            580                 585                 590

Leu Glu Arg Tyr Leu Gln Asp Gln Gln Leu Leu Gly Ile Trp Gly Cys
        595                 600                 605

Ser Gly Lys Leu Ile Cys Thr Thr Asn Val Pro Trp Asn Ser Ser Trp
610                 615                 620

Ser Asn Arg Ser Ala Asp Ile Trp Asp Asn Leu Thr Trp Met Gln Trp
625                 630                 635                 640

Glu Lys Glu Ile Asn Asn Tyr Thr Asp Thr Ile Tyr Gln Leu Leu Glu
                645                 650                 655

Glu Ser Gln Ile Gln Gln Glu Lys Asn Glu Gln Asp Leu Leu Ala Leu
            660                 665                 670

Asn Gly Gly Gly Gly Ser His His His His His His
        675                 680

<210> SEQ ID NO 30
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Val Asn Ala Thr
1

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Phe Asn Ile Thr Thr Ser Ile
1               5

<210> SEQ ID NO 32
<211> LENGTH: 6
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 32

Arg Ala Phe Tyr Thr Thr
1               5

<210> SEQ ID NO 33
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Val Thr Asn Asn
1

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Phe Asn Met Thr Thr Glu Leu
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gln Ala Phe Tyr Ala Thr
1               5
```

SOLUBLE HIV-1 ENVELOPE GLYCOPROTEIN TRIMERS

RELATED APPLICATIONS AND/OR INCORPORATION BY REFERENCE

This application claims priority to and benefit of U.S. provisional patent application Ser. No. 62/054,727 filed Sep. 24, 2014, 62/032,507 filed Aug. 1, 2014, 61/941,101 filed Feb. 18, 2014 and 61/887,618 filed Oct. 7, 2013.

Reference is also made to international patent application Serial No. PCT/US11/26862 filed Mar. 2, 2011 which published as international patent publication WO 2011/109511 on Sep. 9, 2011 and claims priority to U.S. provisional patent application Ser. No. 61/309,685 filed Mar. 2, 2010. Reference is also made to U.S. provisional patent application Ser. No. 61/664,990 and 61/722,739 filed Jun. 27, 2012 and Nov. 5, 2012, respectively.

FEDERAL FUNDING LEGEND

This invention was made with government support under Grant Numbers Al100663 and Al104722 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 6, 2015, is named 43094.80.2028_SL.txt and is 114,793 bytes in size.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This application relates to a novel HIV-1 envelope glycoprotein which may be utilized as an HIV-1 vaccine immunogen, as a native Env trimer mimic, for identification of small molecules for use as immunogen that bind specific HIV-1 broad neutralizing antibodies, for identification of small molecules for use as anti-viral compound that bind specific HIV-1 envelope glycoprotein monomer and/or trimer, as antigens for crystallization and electron microscopy (EM) structural analysis and for the identification of broad neutralizing antibodies from HIV-1 infected individuals or vaccinated subjects or antibody or ligand libraries.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The poi gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4$^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells.

In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been daunting task (Phogat S, Wyatt R. Curr Pharm Des. 2007; 13:213-27, Phogat S, et al. J Intern Med. 2007 262:26-43, Karlsson Hedestam G B, et al Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNAbs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens. Presumably, due to the ability of these bNabs to recognize conserved recessed targets on HIV Env which are either inaccessible by elicited antibodies or difficult to precisely redesign and present to the immune system.

Recently using a sensitive high-throughput micro-neutralization screening of supernatants from approximately 30,000 IgG+memory B cells from a HIV-1 clade A-infected African donor, Applicants identified two new bNabs PG9 and PG16 that are broad and exceptionally potent neutralizing antibodies (Walker L, Phogat S, et al. Science. 2009; 326:285-9. Epub 2009 Sep. 3). These antibodies recognize a new conserved, yet accessible, vaccine target (consisting of conserved elements on the variable loops 2 and 3) on the Env and show preferential binding to HIV Env trimer (Model of PG9 and 16 epitopes on HIV-1 trimer.). When tested for binding, these antibodies did not show binding to many empirically designed soluble (Env gp140) HIV Env trimer thought to be mimics of the native HIV-1 Env spike, suggesting that either these Env designs are either incorrect or they are fixed in a form not recognized by PG9 and PG16.

Citation or identification of any document in this application is not an admission that such document is available as prior art to the present invention.

SUMMARY OF THE INVENTION

A first embodiment of the present invention relates to an engineered or non-naturally occurring SOSIP trimer. The SOSIP trimer may be a JRFL SOSIP trimer. The JRFL SOSIPtrimer may be truncated, for example at residue 663 (JRFL SOSIP.663 trimer). The JRFL SOSIP may be stabilized by disulfide linkages, for example, at residues 201-433 (1st disulfide) and/or at 163-309 (2nd disulfide). The SOSIP trimer may also be a 16055 SOSIP trimer. The 16055 SOSIP trimer may be truncated, for example at residue 663 (16055 SOSIP.663 trimer).

A second embodiment of the present invention relates to an engineered or non-naturally occurring native flexible linker (NFL) gp140 trimer. In one embodiment, the trimer may be mutated. The mutation may be, for example, a proline substitution. The mutation may be selected from the group consisting of S649D, S649E, L555P, L556P, A558P and I559P. The mutation may be a double mutant containing combinations of 649D or E with the other HR1 P mutations. The mutation may be selected from the group consisting of E47D, K49E, V65K, E106T, I165L, E429R, R432Q. The mutation may also be selected from the group consisting of L555P, Q652P, Q653P, L565P and L566P or any combination thereof. The mutation may also be a double mutant selected from the group consisting of 558P-S649D, A558P-S649E and I559P-S649E. In another embodiment, the trimer may be a BG505 trimer or a trimer homologous to BG505. In another embodiment, the trimer may comprise a free cysteine.

A third embodiment of the present invention encompasses methods of eliciting an immune response which may comprise administering to a mammal the any of the trimers disclosed herein. The method may further comprise adding an adjuvant. The adjuvant may be a lecithin and may optionally be combined with an acrylic polymer, a lecithin coated oil droplet in an oil-in-water emulsion or a lecithin and an acrylic polymer in an oil-in-water emulsion. The adjuvant may be ISCOMATRIX or Adjuplex. In another embodiment, the adjuvant may comprise alum.

In another embodiment, the trimer may be administered in a liposome or a nanoparticle. In another embodiment, the trimer may be fixed, for example, in glutaraldehyde.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which:

FIGS. 4A-B depict gp120 trimers matrices with JRFL and BG505. FIG. 4A discloses the consecutive V1 positions as SEQ ID NOS 30-31 and the consecutive V3 positions as SEQ ID NO: 32 and FIG. 4B discloses the consecutive V1 positions as SEQ ID NOS 33-34 and the consecutive V3 positions as SEQ ID NO: 35.

FIG. 5 depicts a JRFL SOSIP E168K dMPER sequence (SEQ ID NO: 8).

FIG. 6 depicts a JRFL MIF gp120 V1-V3 Cys-Cys linkage sequence (SEQ ID NO: 9) and a matrix depicting possible mutations. Residues in bold magenta are V1 residues for mutation to Cys and residues in bold italic green are V3 residues for mutation to Cys.

FIG. 7 depicts a JRFL HPTM gp145 sequence (SEQ ID NO: 10). A modified transmembrane domain is in bold italic magenta and a cleavage site is in bold cyan.

FIG. 8 depicts sequences of Variants HPTM2 (SEQ ID NO: 11), HPTM2s (SEQ ID NO: 12) and HPTM2s N666 N674 N685 (SEQ ID NO: 13). A modified transmembrane domain is in bold italic magenta, cleavage site is in bold cyan is modified to RRRKKR (SEQ ID NO: 1) and introduced glycosylation sites are in underlined green.

FIG. 9 depicts a schematic of NFL trimer design. The G$_4$S (SEQ ID NO: 2) linkers are ~6, 18 and 33 Angstroms linker wherein the 1 (SEQ ID NO: 2), 2 (SEQ ID NO: 6) and 3 (SEQ ID NO: 7) repeats are minus the REKR (SEQ ID NO: 3) 4 residues C-terminus gp120 and ~12 Angstroms (4 amino acids) deleted from linkers of 15, 30 and 45 Angstroms. ("HHHHHHHH" is disclosed as SEQ ID NO: 5).

FIG. 10 depicts an amino acid sequence of a JR-FL gp140-NFL1P construct (SEQ ID NO: 14). Linkers are in bold, underlined green, I559P change and a His-tag is in bold yellow.

FIG. 11 depicts an amino acid sequence of a JR-FL gp140-NFL2P construct (SEQ ID NO: 15). Linkers are in bold, underlined green, I559P change and a His-tag is in bold yellow.

FIG. 12 depicts an amino acid sequence of a JR-FL gp140-NFL3P construct (SEQ ID NO: 16). Linkers are in bold, underlined green, I559P change and a His-tag is in bold yellow.

FIG. 13 depicts an amino acid sequence of a Clade C 16055 gp140-NFL2P construct (SEQ ID NO: 17). 16055 gp140-NFL2P has a I559P mutation (highlighted in green and underlined).

FIG. 14 depicts an amino acid sequence of a Clade A BG505 gp140-NFL2P construct (SEQ ID NO: 18). Linkers are in green. BG505 gp140-NFL2P has a I559P mutation and T332N change (highlighted in green and underlined).

FIG. 15 depicts immunoprecipitation of JRFL gp140-NFL1P with selected mAbs from the crude culture supernatant. The gp140 NFL1P trimer band intensities are low with trimer specific bNAbs VRCO6, PGT145, PGT151 and PG16 compared to that of b12, 2G12 and VRCO1.

FIG. 19A depicts JRFL gp140-NFL2P well recognized by the trimer/cleavage-specific bNAbs. FIG. 19B depicts VRCO1, b12 and 2G12 mAbs recognize the JR-FL gp140-NFL2P trimers similar to JRFL SOSIP. FIG. 19C depicts JRFL gp140-NFL2P trimers not recognized by F105, some F240 recognition. F240 cluster 1 binding to these trimers unclear; the epitope is disrupted in SOSIP.

FIG. 25A depicts binding of selected Trimer specific broadly neutralizing Abs with BG505 gp140-NFL2P analyzed by Octet. FIG. 25B depicts binding of selected broadly neutralizing Abs with BG505 gp140-NFL2P analyzed by Octet. FIG. 25C depicts binding of selected non-neutralizing Abs (F105 and b6) with BG505gp140-NFL2P analyzed by Octet.

FIGS. 28A-C depict a SOSIP purification strategy. (A) 293F cells were co-transfected with plasmid DNA encoding both SOSIPs and furin sequences and cultured for 5-6 days before collection of supernatants. Filtered supernatants were run over a lectin affinity chromatography column and the eluate containing the overexpressed soluble SOSIP.663 molecules were resolved by SEC to isolate the trimer containing fractions. Lastly, these fractions were passed over a protein A column immobilized with F105 for JRFL or GE136 for 16055 to negatively select the disordered oligomers that are retained on the column from the well-ordered trimer fractions that flow through the column. (B) Blue-native gel analysis of JRFL and 16055 gp120 monomers and SOSIP oligomers. Molecular weight markers (MW) are in the first lane, the lectin-purified SOSIP oligomers are in the second lane, revealing three prominent bands corresponding to trimeric, dimeric and monomeric SOSIP forms. The third lane labeled "SEC" contains one predominant band corresponding to trimeric SOSIP forms, including well-ordered and disordered trimers. Faint bands corresponding to dimer and monomer contaminants were detected. The fourth lane containing negative-selected samples ("Neg. Sel.") displayed mostly one prominent band corresponding to the expected size of the SOSIP.663 trimer. The last lane contains the monomeric gp120 control and faint band corresponding to gp120 dimers. (C) SEC profiles of the lectin-purified JRFL and 16055 SOSIP.663 samples (top panels). JRFL displayed a dominant peak corresponding to the trimeric form and a smaller shoulder to the right of the peak corresponding to dimeric and monomeric forms of SOSIP. The 16055 SOSIP trimer, dimer and monomer peak are overlapping and of similar size. The bottom panels displayed negatively selected SOSIP trimer samples as a homogeneous highly symmetric peak.

FIGS. 29A-B depict SOSIP EM micrographs and 2D class averages. (A) In the SEC isolated trimer fraction, disordered oligomers along with well-ordered trimeric proteins (circled) are detected (left). The negatively selected samples display a majority of well-ordered trimeric proteins (right). (B) EM 2D class averages of SOSIP.663 trimers after negative selection.

FIGS. 33A-B depict EM 3D reconstructions of VRC01- and VRC03-liganded SOSIP.663 trimers. (A) Top and side views of the 3D reconstruction EM densities of the VRC01-liganded (top) and VRC03-liganded (bottom) JRFL and 16055 SOSIP.663 trimers in grey with the high resolution cryo-EM structure of the PGV04-liganded BG505 SOSIP.663 (PDB 3J5M, gp120 in blue with V1V2 in magenta, V2 in green, gp41 in brown and the PGV04 Fab in red) fitted within. To the right, top and side views of the liganded 16055 SOSIP.663 EM density (bronze) superimposed onto the liganded JRFL SOSIP.663 (grey). Arrows indicate differences between the EM densities of the two VRC01-liganded trimers. (B) Comparison of thermodynamic parameters, represented here as bar graphs, resulting from ITC measurements obtained when SOSIP.663 trimers interact with sCD4 and VRC01.

FIGS. 34A-B depict EM 2D class averages and 3D reconstructions of the trimer-preferred cleavage-specific PGT151-bound SOSIP.663 trimers. (A) EM 2D class averages of PGT151-bound JRFL and 16055 SOSIP.663 trimers (left and right, respectively). Red arrows indicate the density corresponding to a PGT151 Fab and the blue arrows indicate the density corresponding to the trimeric proteins. (B) Top and side views of 3D reconstruction EM densities of PGT151-bound JRFL-SOSIP.663 and JRFL-ENV (grey) with the BG505 SOSIP.663 cryo-EM structure (PDB ID 3J5M, gp120 in blue, V1V2 in magenta, V3 in green and gp41 in brown) fitted within. To the right, top and side views of the liganded JRFL SOSIP.663 EM density (grey) superimposed onto the liganded JRFL-ENV EM density (bronze).

FIGS. 35A-B depict an analysis of SOSIP.663 trimers thermal stability by DSC and DSF. (A) DSC analysis of the negatively selected JRFL and 16055 SOSIP.663 trimers and its gp120 monomer controls. (B) DSF analysis of JRFL and 16055 SOSIP.663 trimers alone and pre-incubated with a 2 M excess of selected Fabs.

FIGS. 36A-C depict a SOSIP design template and SDS-PAGE analysis of JRFL- and 16055-derived proteins. (A) Cartoon representation of the JRFL and 16055 SOSIP.663 linear organization and design modifications ("506RRRKKR511" is disclosed as SEQ ID NO: 1). (B) SDS-PAGE gel shows bands corresponding to g120 protein captured by non-bNAbs and bands for the heavy and light chain of the mAb following immuno-precipitation from 1 mL of cell culture supernatant from cells expressing JRFL or 16055 SOSIP.663 glycoproteins (left). Binding kinetic parameters of non-bNAbs F105, GE136 and GE148 to monomeric JRFL and 16055 gp120 (right). (C) SDS-PAGE gel analyzing both negatively selected JRFL and 16055 SOSIP.663 trimers with and without DTT. A strong band corresponding to gp120 and a faint band corresponding to the gp41 ectodomain migrated at the expected molecular weight (MW) in the presence of the reducing reagent (DTT). A higher MW band consistent with a disulfide linked gp120-gp41 is observed in the absence of DTT. Uncleaved JRFL gp140-Foldon trimers and corresponding JRFL and 16055 gp120 monomers are shown as controls.

FIG. 47 depicts a summary of the HR1 proline screen in BG505NFL2 backbone. L555P, L556P and L566P almost behave like I559P in terms of antigenic profile and trimer formation.

FIG. 50 depicts an estimation of protein molecules per liposome.

FIG. 55 depicts that well-ordered NFL trimers densely arrayed on liposomes by EM.

A schematic of nanotechnology-based drug delivery platforms and nanocarrier-based drugs on the market are presented in Nanomedicine, 2012, 7 (8), 1253-1271.

Figure 56A:
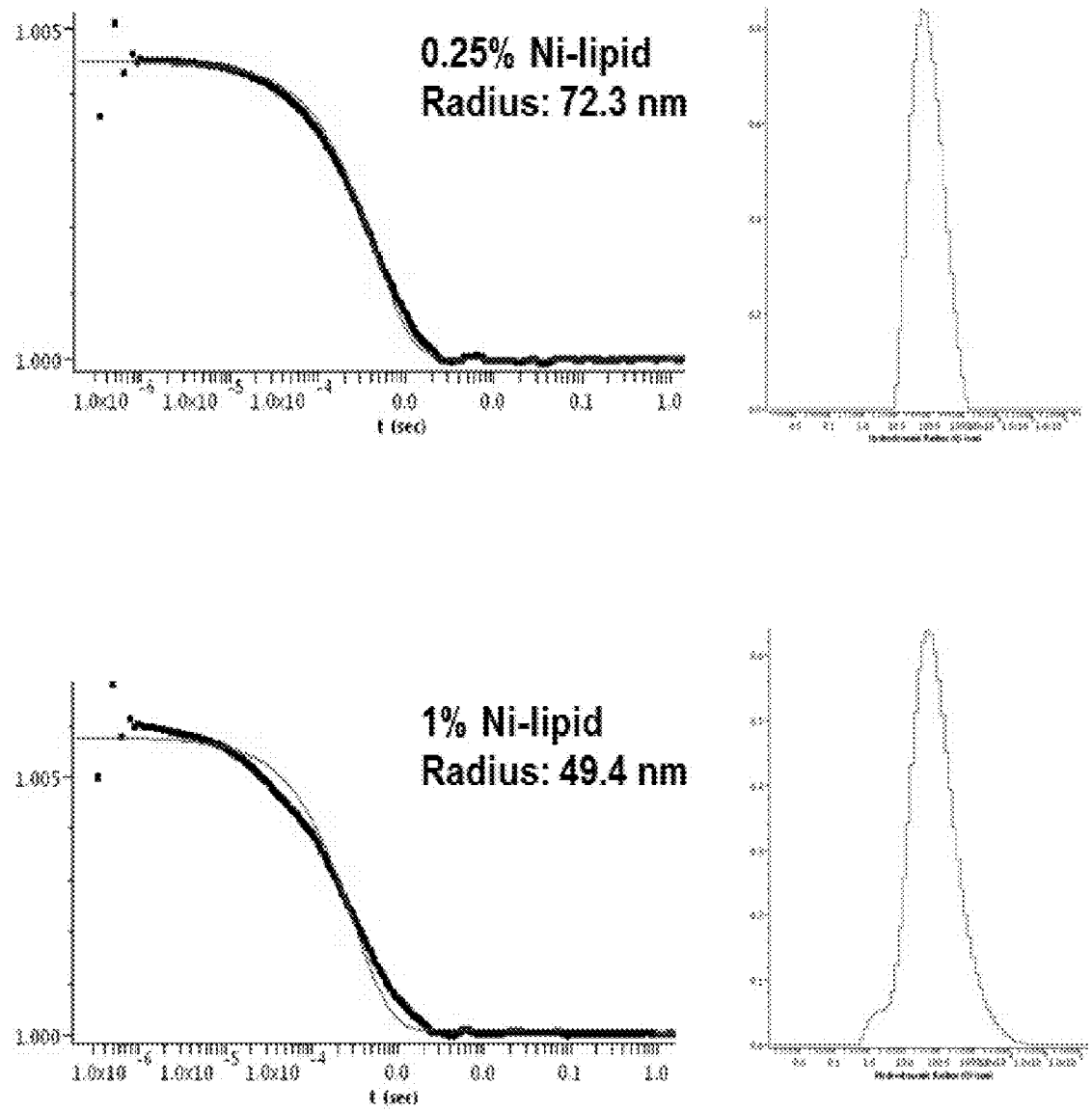
Figure 56B:
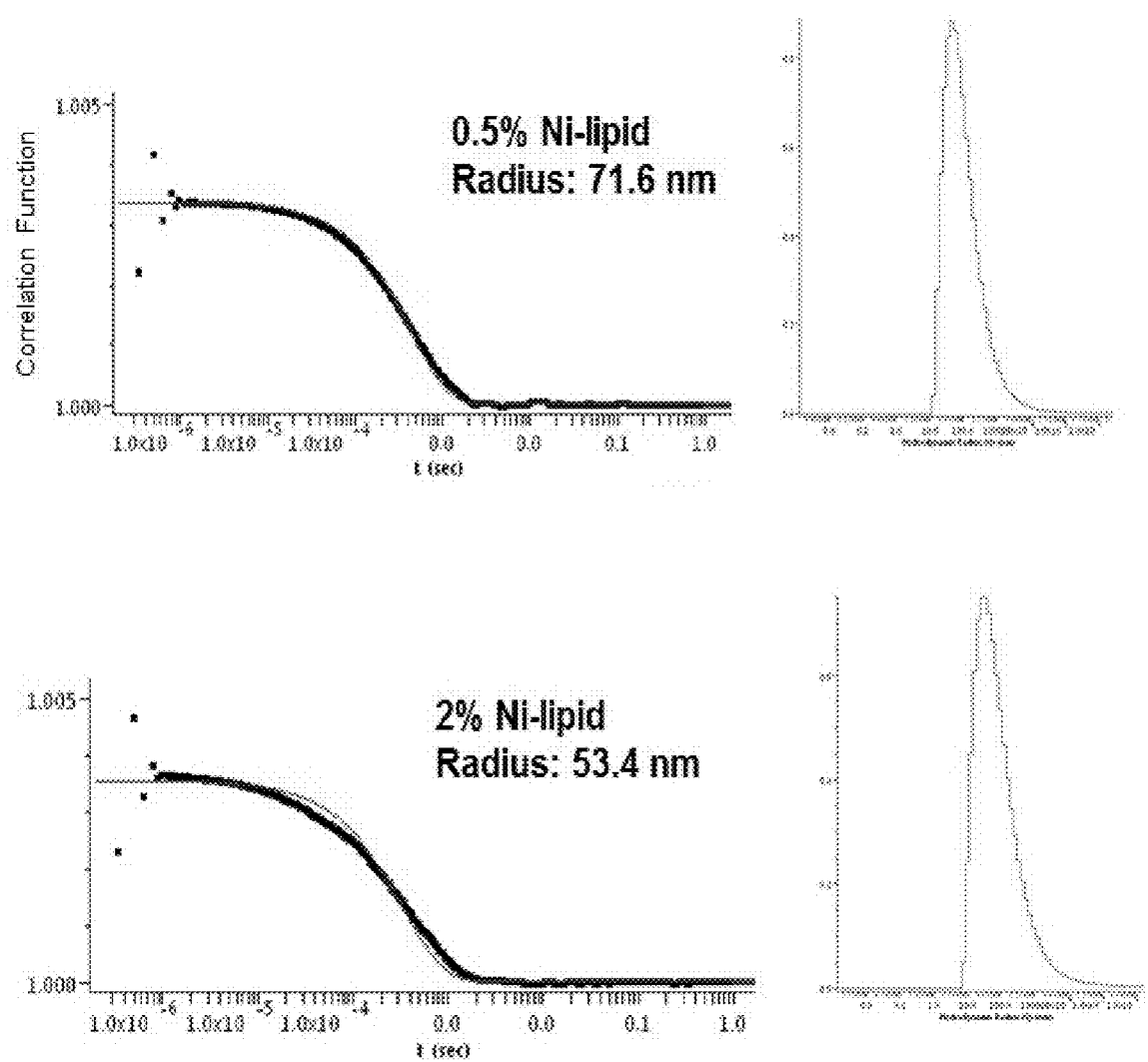
Figure 56C:
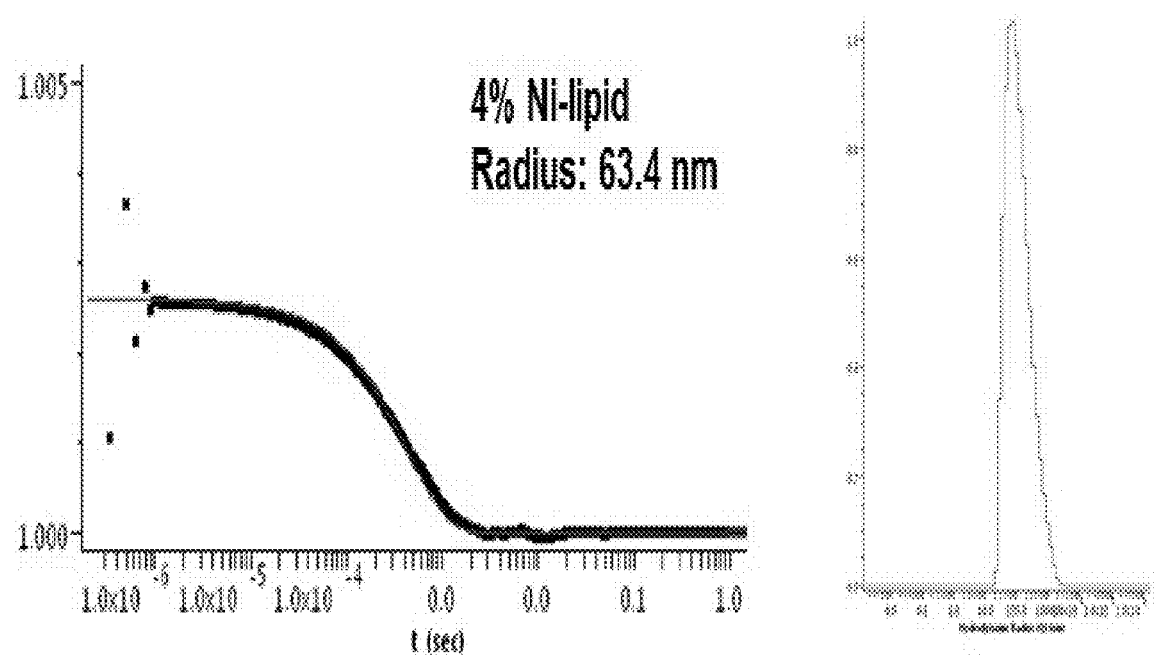

FIGS. 56A-C depicts DLS profiles estimate size and reveals no free protein.

Figure 57:
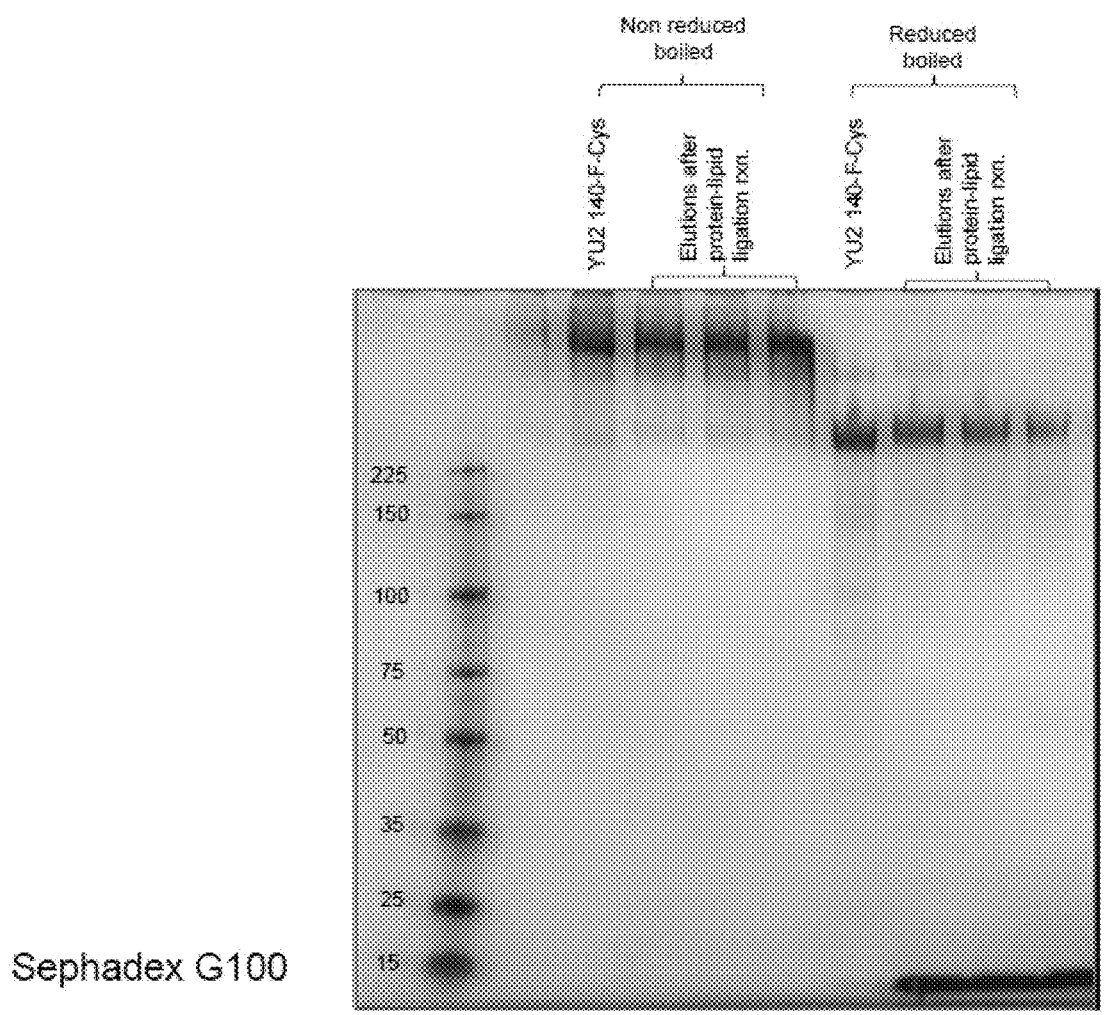

FIG. 57 depicts conjugation of Cys-protein to maleimide-PEG-lipid.

Figure 58:
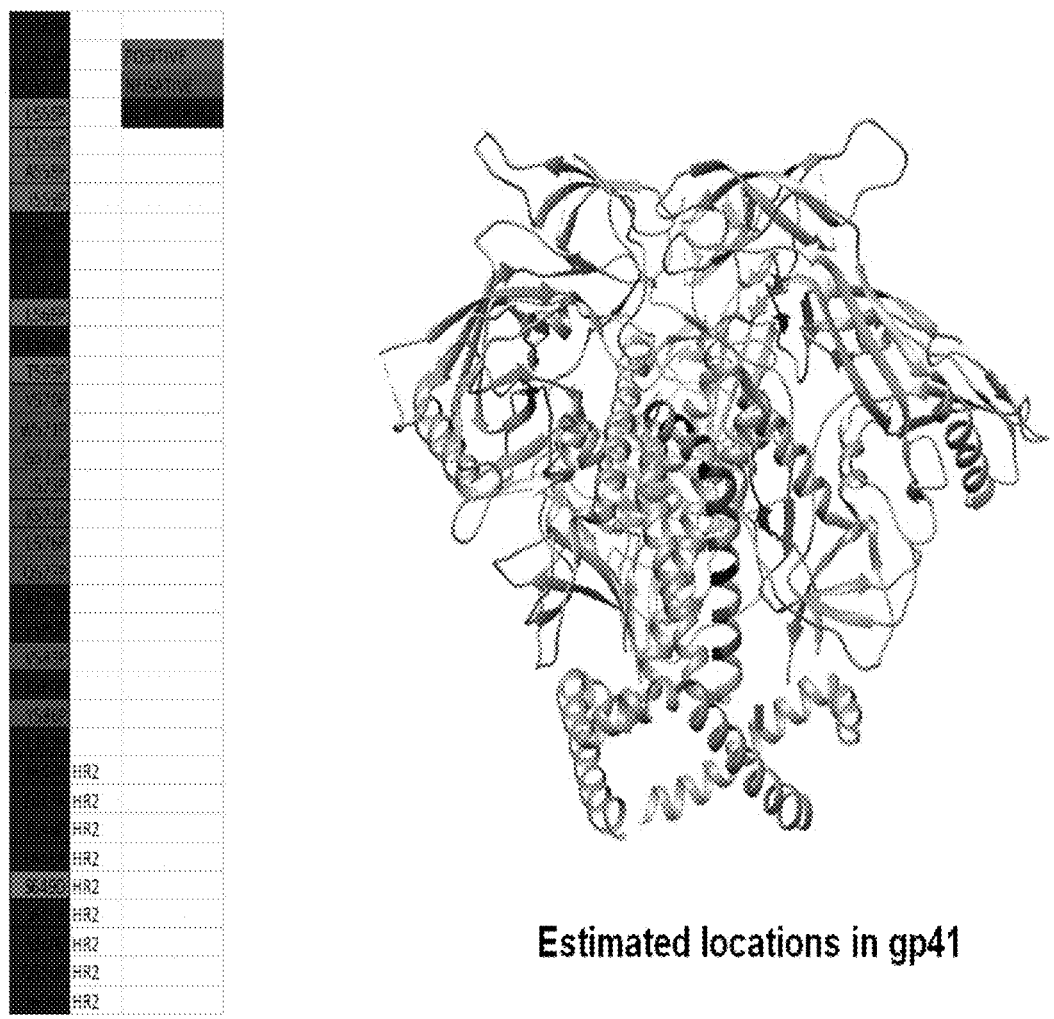

FIG. 58 depicts a gp41 screen in NFL for Substitutions for transfer to other Envs. These are the proline substitutions screened in the BG505 NFL context.

Figure 59:
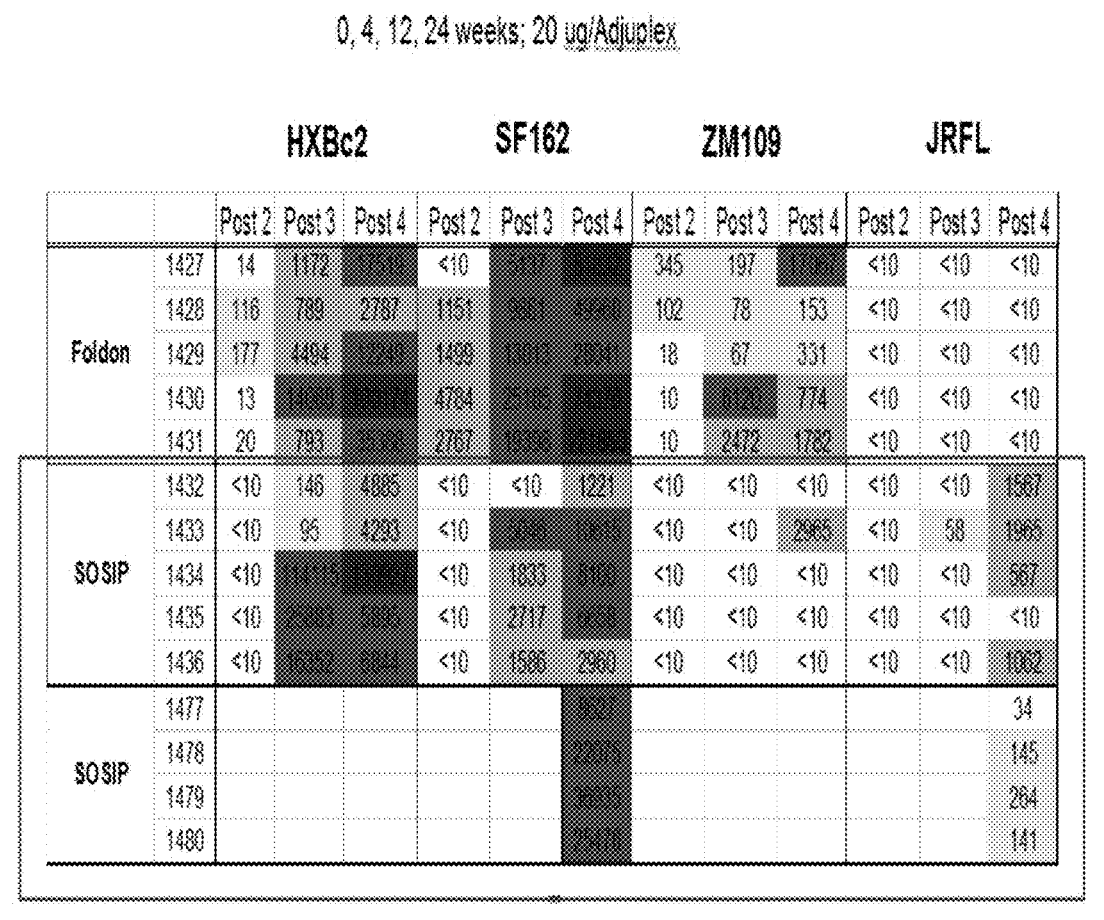

FIG. 59 depicts negatively selected JRFL SOSIP trimers elicit homologous JRFL neutralization.

Figure 60:
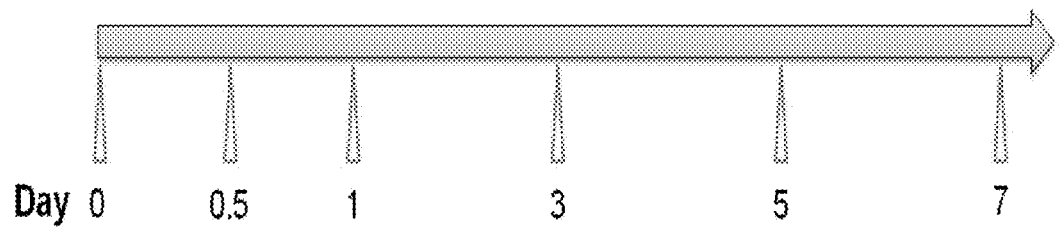

FIG. 60 depicts a stability assay.

Figure 61:
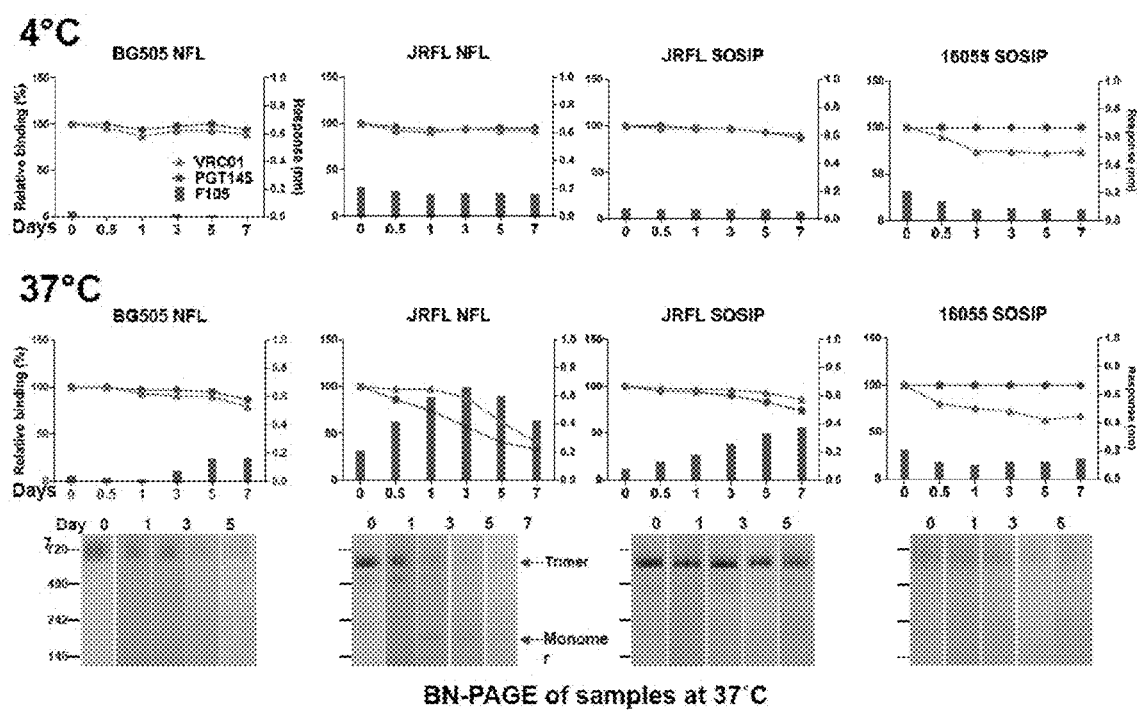

FIG. 61 depicts that trimers are stable at 4° C. and 37° C.'

FIG. 62 depicts that trimers are relative stable in ISCO-MATRIX at 37° C.

FIG. 63 depicts Fixation of well-ordered trimers. The fixation protocol involves: 1. 5 mM of GLA (Glutaraldehyde, homobifunctional crosslinker) at RT for 5 min; 2. 50 mM of Glycine to quench the reaction and 3. Negative selection and Gel filtration.

Figure 64:
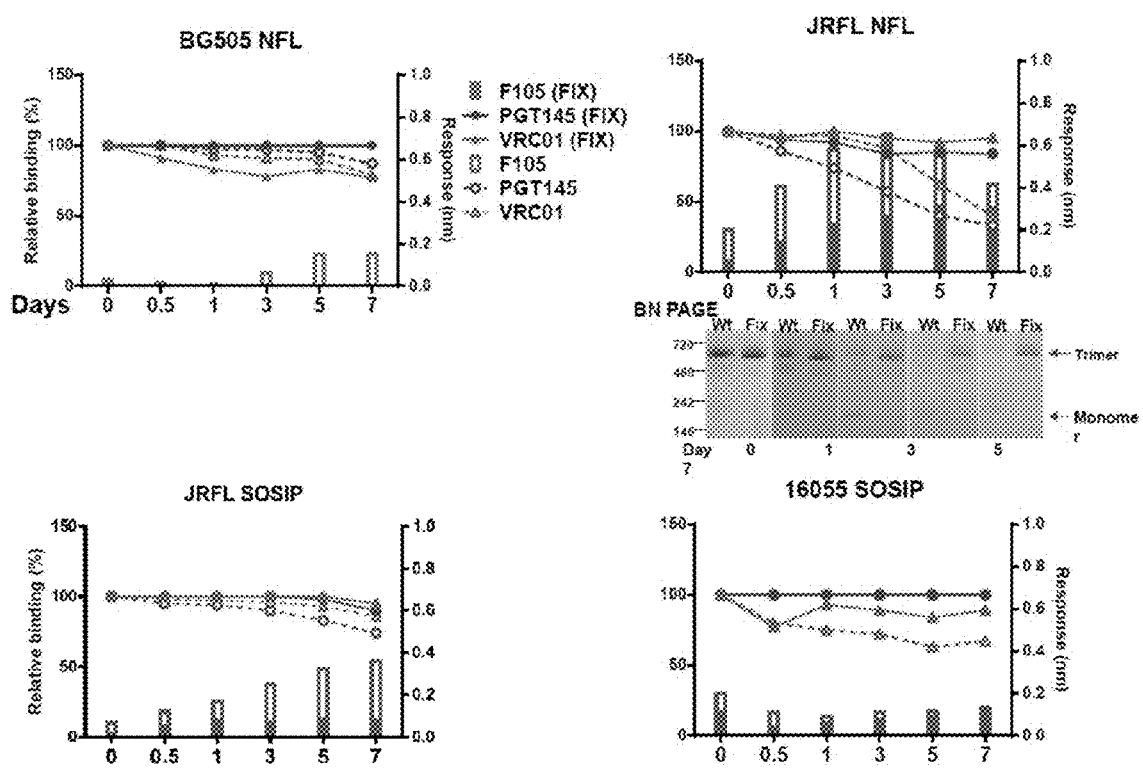

FIG. 64 depicts that fixation improves trimer stability at 37° C.

Figure 65:
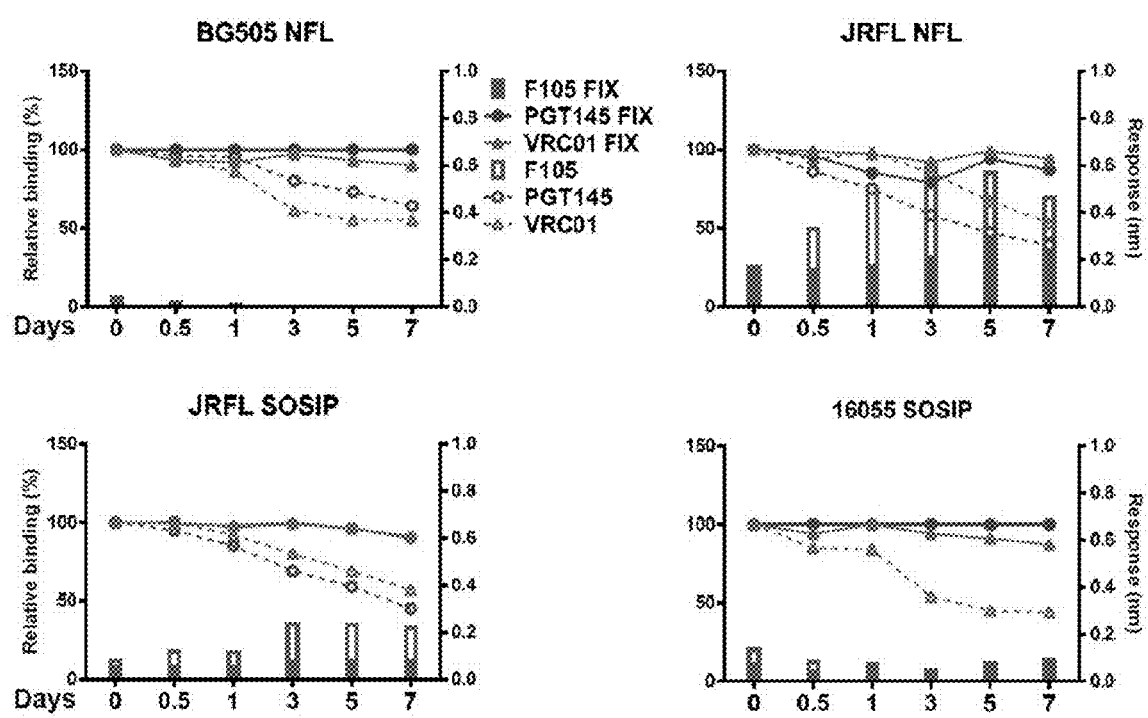

FIG. 65 depicts that fixation improves trimer stability in ISCOMATRIX at 37° C.

Figure 66:
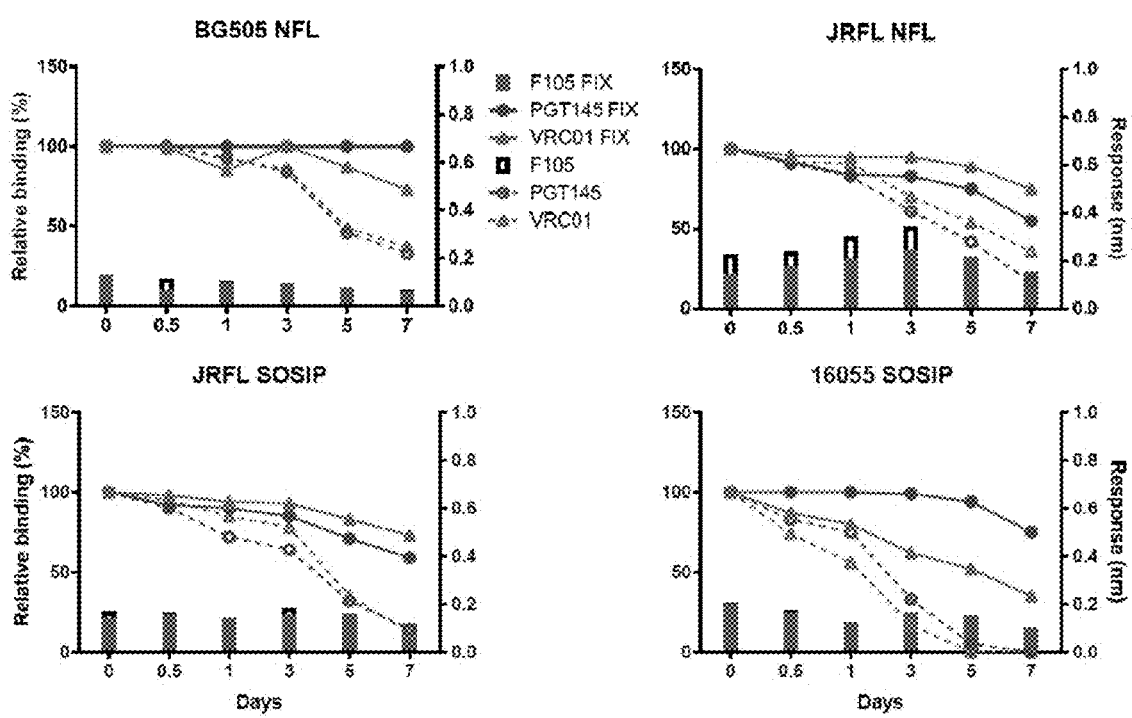

FIG. 66 depicts that fixation improves trimer stability in Adjuplex at 37° C.

Figure 67A:
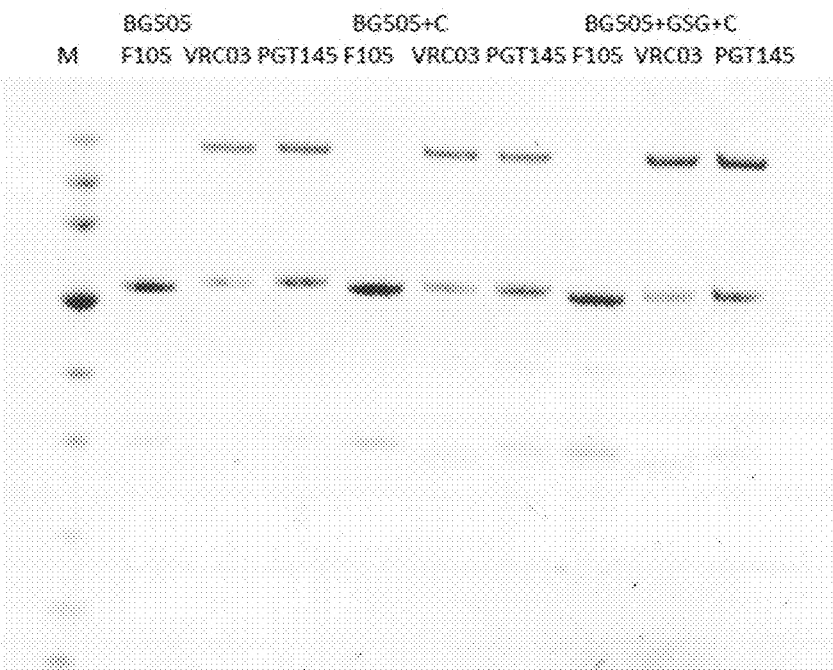

FIG. 67A depicts immunoprecipitation with BG505+cysteine trimers.

Figure 67B:
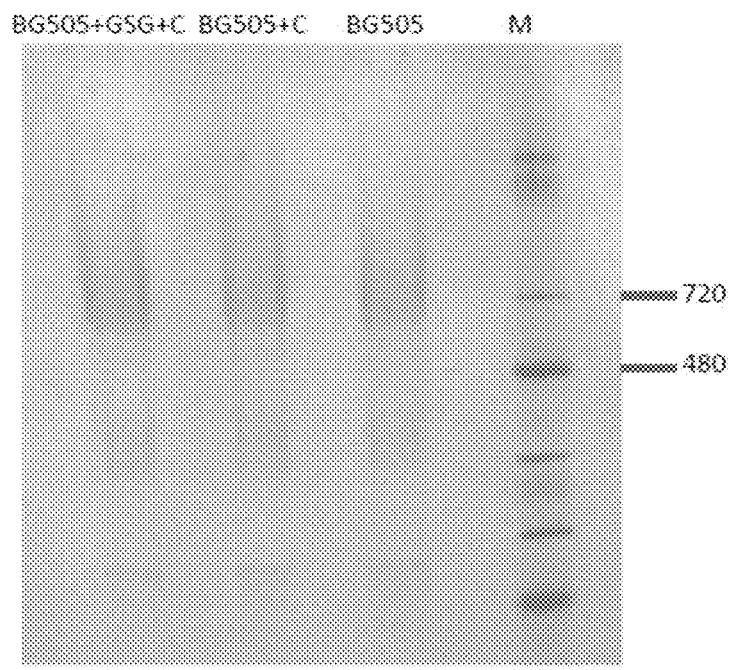

FIG. 67B depicts a blue native gel with BG505+cysteine trimers.

Figure 68:
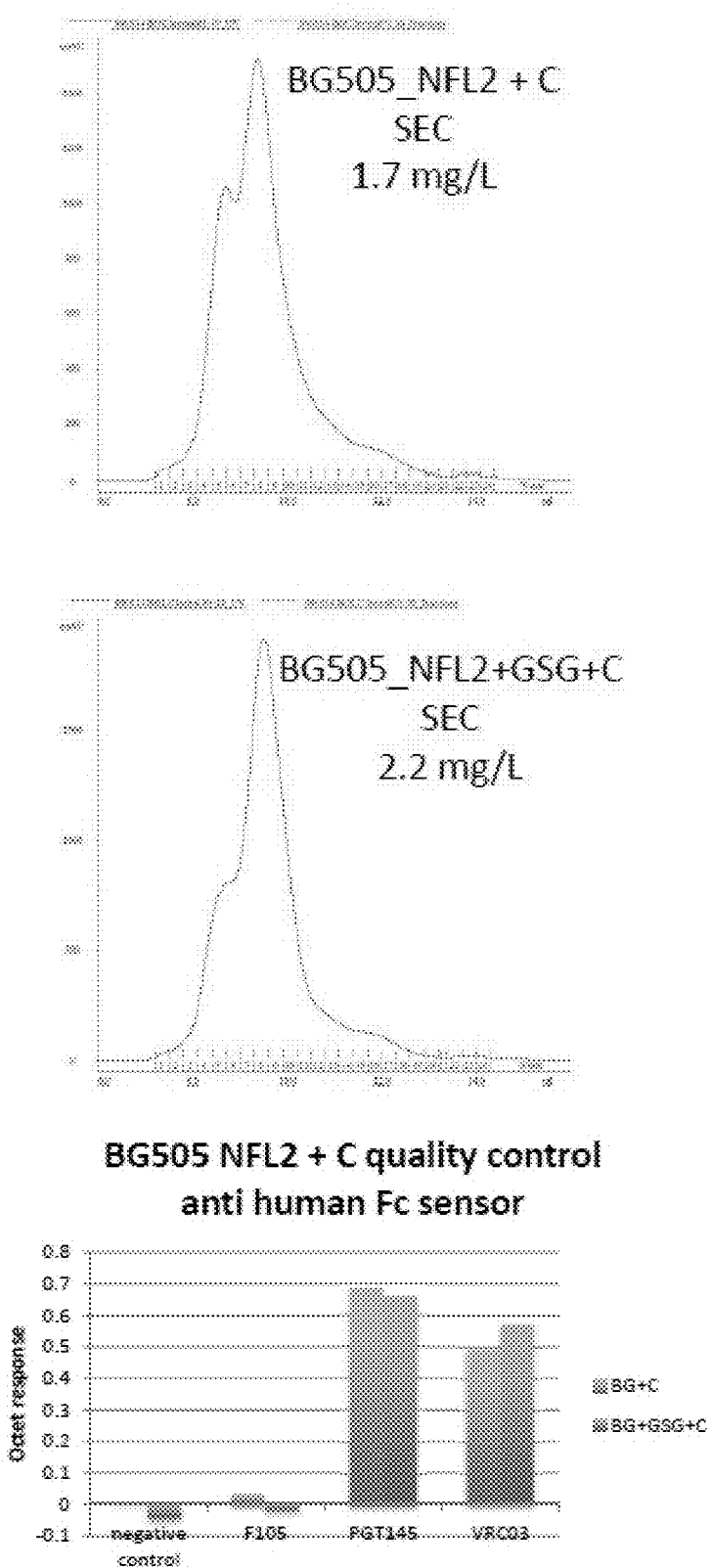

FIG. 68 depicts BG505 NFL2+C quality control anti human Fc sensor.

FIG. 69 depicts a sequence of BL505NFL2P with a free cysteine (SEQ ID NOS 19-20).

FIGS. 70A-D depicts a sequence (SEQ ID NOS 21-24) of Clade C NFLs for CMVR derived from clade C Envs with high homology to BG505 to make NFL trimers.

FIGS. 71A-B depicts a summary of the ongoing HR1 proline screen in the 16055 gp140-NFL2 construct: based on the initial immunoprecipitation and initial octet binding data. FIG. 71A depicts single mutations involving only HR1 residues and FIG. 71B depicts double mutations involving both, the HR1 and HR2 residues. Green indicates a positive result, red indicates a negative result and blue indicates an experiment in progress. Five single proline mutants (L555P, Q652P, Q653P, L565P and L566P) stabilize the clade C 16055-NFL2 Env trimers in the native-like conformations. Five double mutants stabilize and induce native-like trimer formation in 16055-NFL2 Env.

Figure 72:
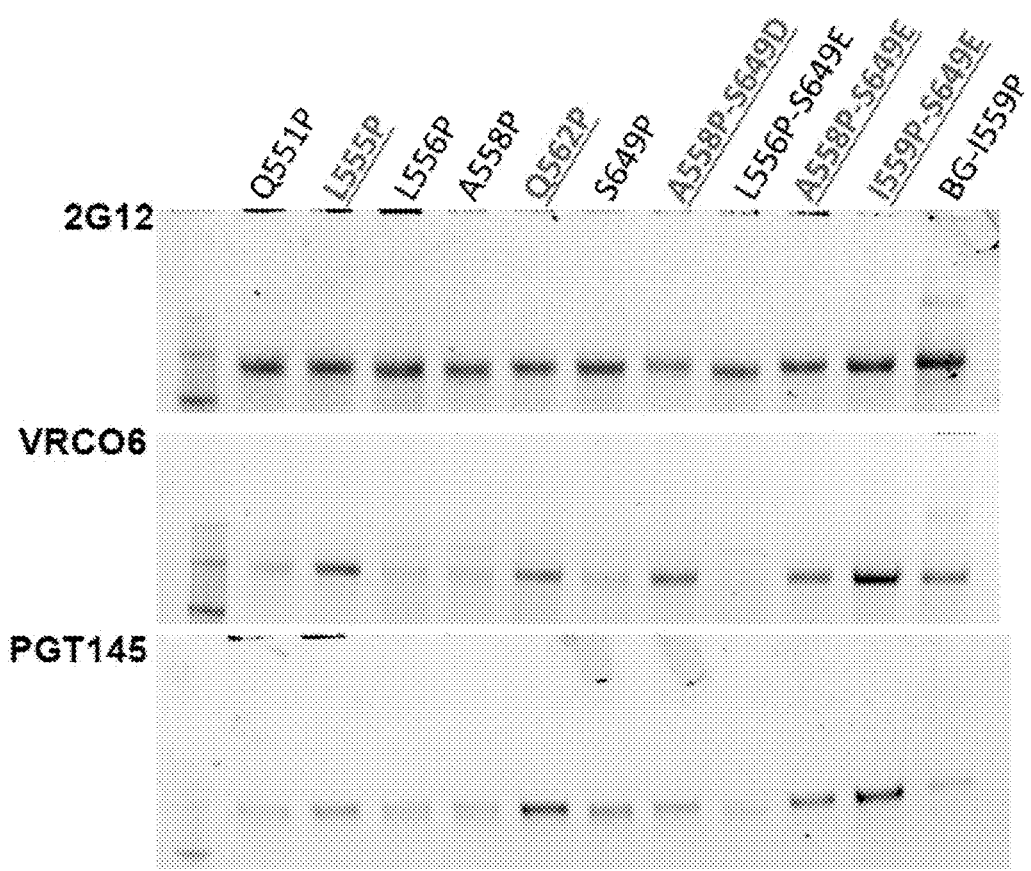

FIG. 72 depicts immunoprecipitation with selected trimer sensitive bNAbs (VRCO6 and PGT145) which suggest that L555P, Q652P, A558P-S649D, A558P-S649E and I559P-S649E are making well ordered trimers in solution.

Figure 73:
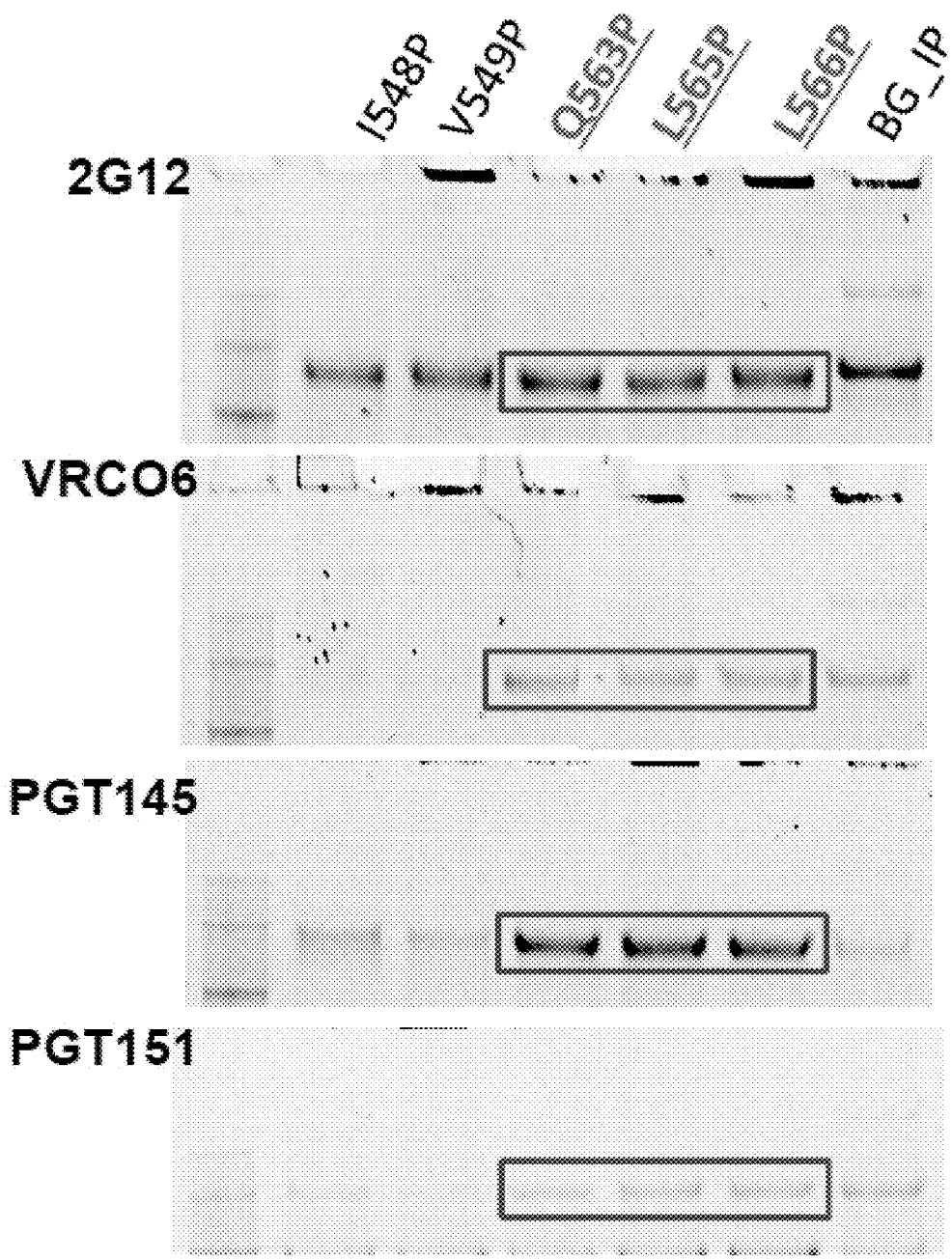

FIG. 73 depicts immunoprecipitation with selected trimer sensitive bNAbs clearly indicate that Q653P, L565P and L566P are destabilizing the formation of 6 HB bundle resulting in the formation of well-ordered native-like 16055 gp140-NFL2 Env trimers.

FIG. 74 depicts a sequence of Clade C 16055 gp140-NFL2 Env (SEQ ID NO: 25). The region of HR1 studied in the proline screen to stabilize the trimer is highlighted in green and underlined. The residues of HR2 involved in this study are highlighted in red and underlined.

FIG. 75 depicts clade C sequences (SEQ ID NOS 26-29) homologous to BG505.

Figure 76A:
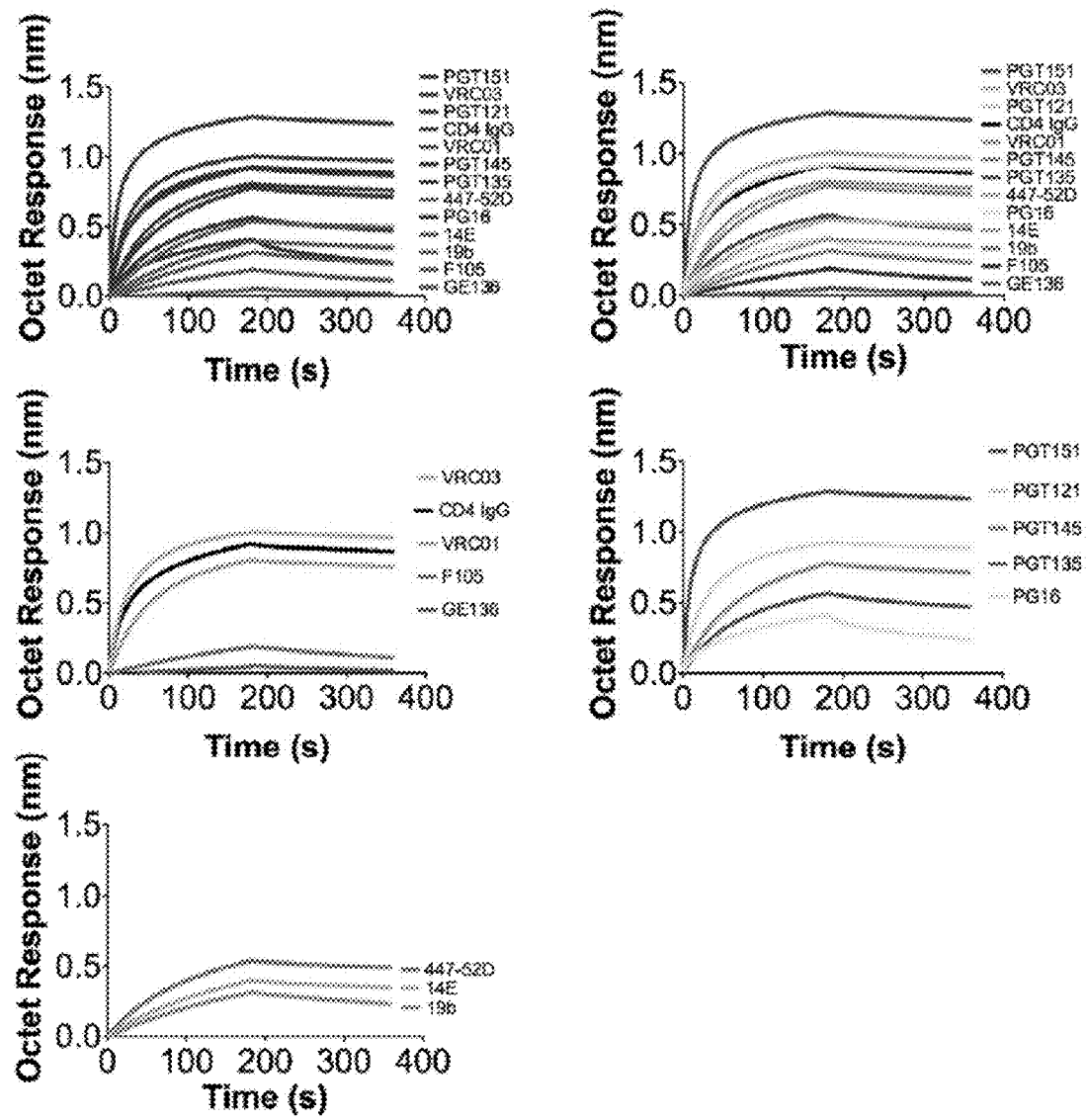
Figure 76B:
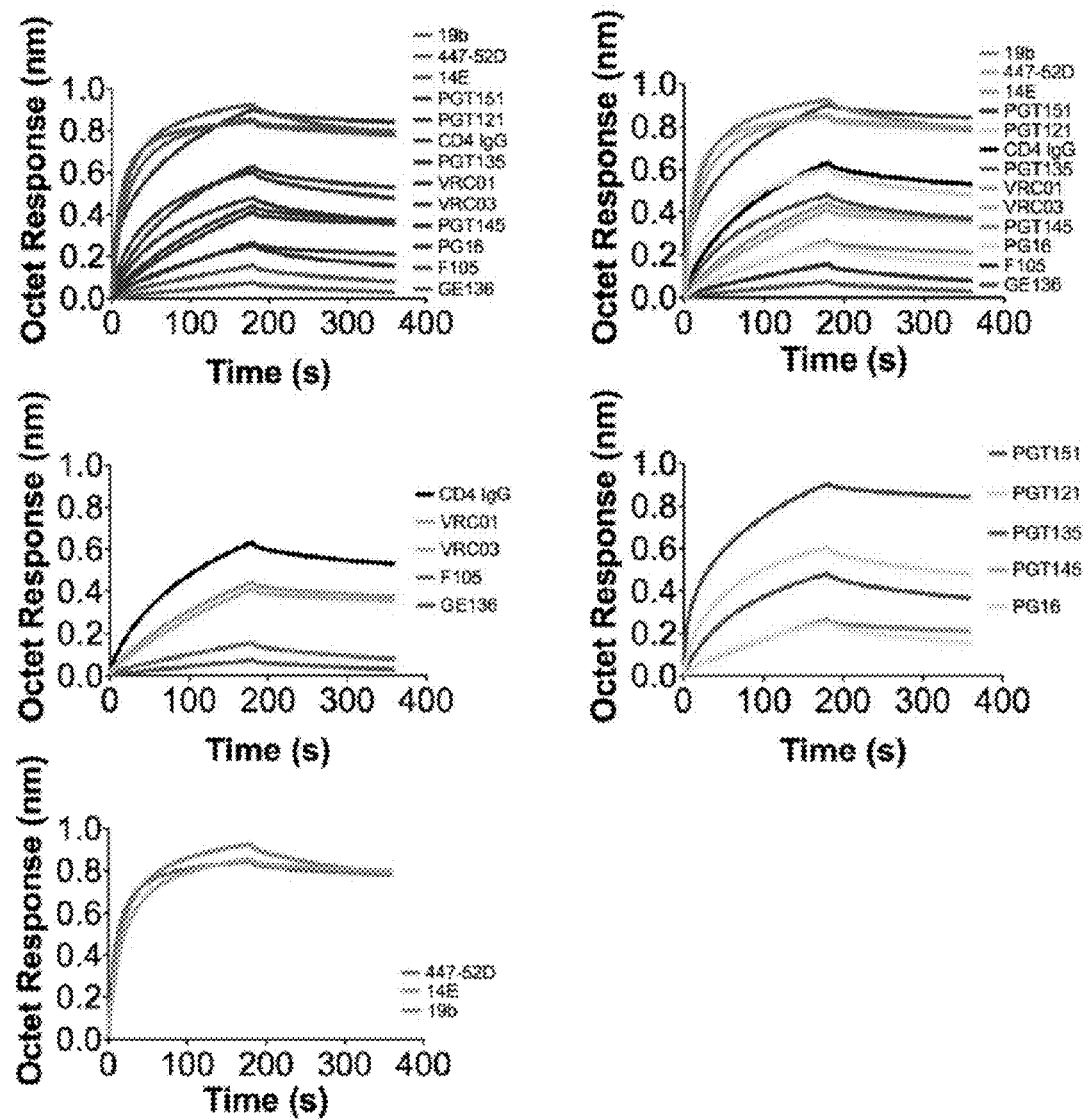
Figure 76C:
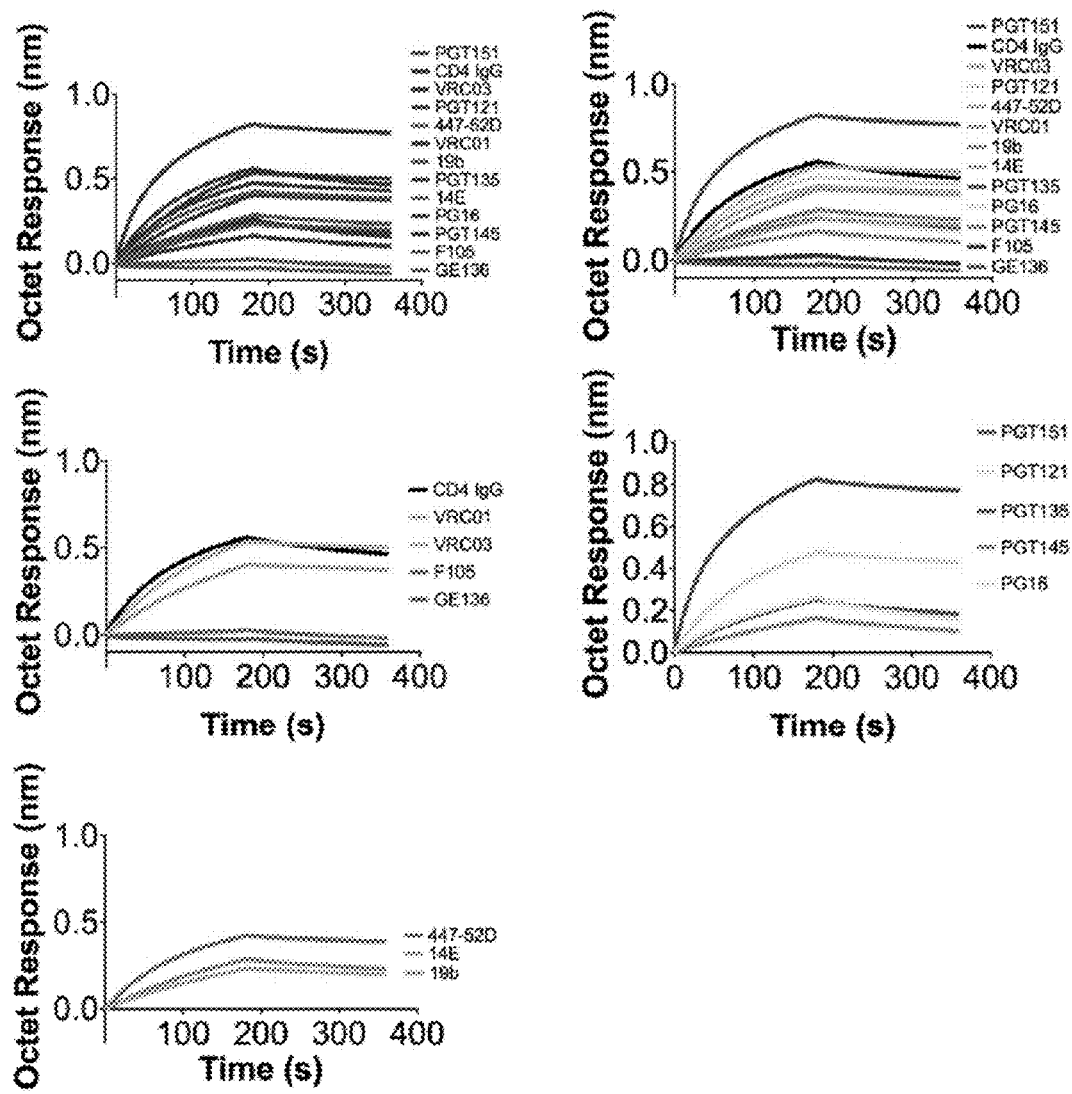
Figure 76D:
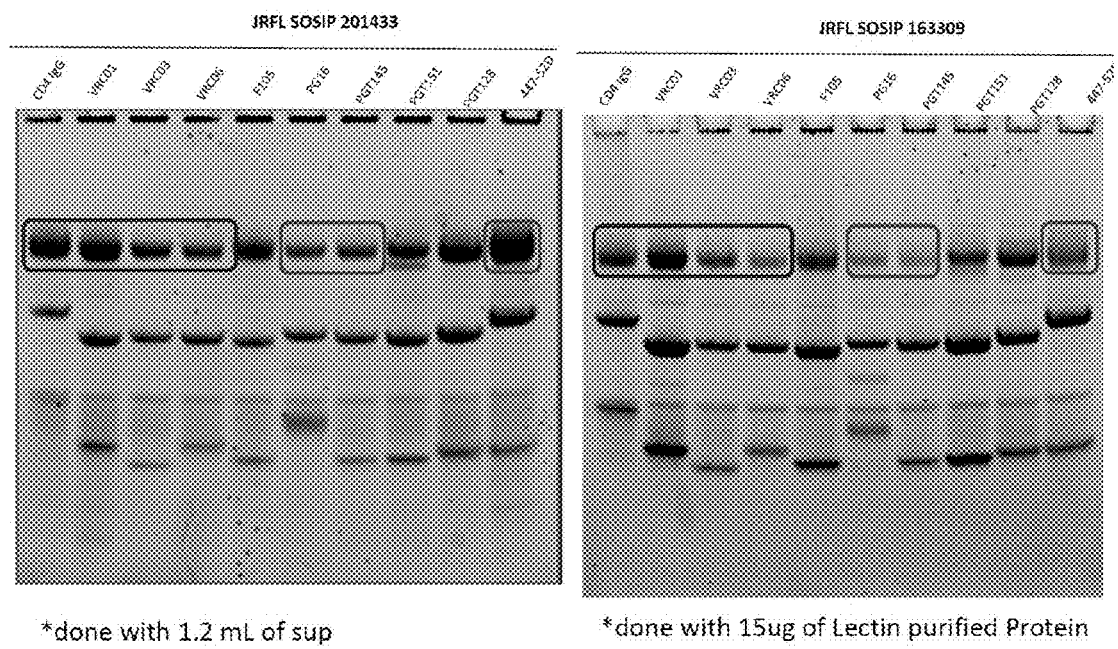

FIGS. 76A-D depicts binding data on two versions of the JRFL SOSIP stabilized by disulfide linkages at residues 201-433 (1st disulfide) and at 163-309 (2nd disulfide). FIG. 76A depicts JRFL SOSIP WT octet data with an anti-human Fc sensor, IgG immobilized 5 ug/mL and trimer in solution at 400 nM. FIG. 76B depicts JRFL SOSIP I201C A433C octet data with an anti-human Fc sensor, IgG immobilized 5 ug/mL and trimer in solution at 400 nM. FIG. 76C depicts JRFL SOSIP T163C I309C octet data with an anti-human Fc sensor, IgG immobilized 5 ug/mL and trimer in solution at 200 nM. FIG. 76D depicts a 4-12% SDS PAGE of JRFL SOSIP disulfide stabilizations.

DETAILED DESCRIPTION

Soluble, stabilized, proteolytically cleaved, trimeric gp41 proteins can be generated by engineering an intermolecular disulphide bond between gp120 and gp41 (SOS), combined with a single residue change, I559P, within gp41 (SOSIP). Applicants have developed a purification method of homogenous trimers from a mixture of trimers derived from the JRFL clade B virus strain Env. These trimers, known as JRFL SOSIPs may comprise a cysteine pair covalently linking gp120 to gp41, a poly R cleavage site, MPER deletion, a 168 E/K change or a combination thereof. The purification method is scalable, avoids the published 2G12 monoclonal antibody column purification and employs antibody-mediated negative selection to rescue JRFL SOSIP trimers from a heterogenous mixture of trimers in different and 'random' conformation to a high degree of conformational and structural homogeneity, which is expandable to other strains and clades of HIV.

The present invention also encompasses SOSIP trimer molecules derived from the B subtype strain, JRFL, and the subtype C strain, 16055. Applicants selected these two Envs for the initial results reported in this study as follows. The JRFL SOSIP trimer, truncated at residue 663 (JRFL SOSIP.663) derives from the JRFL HIV-1 strain isolated from the frontal lobe (FL) of an HIV-1-infected individual. This Env is often used because it displays the unusual property that its gp160 Env precursor is efficiently cleaved into the gp120 and gp41 subunits when expressed on the cell surface of 293F HEK cells (Pancera M & Wyatt R (2005) Virology 332(1):145-156). The 16055 SOSIP.663 trimer, also truncated at residue 663, derives from a HIV-1 Indian strain and displays the unusual property that its monomeric gp120 is recognized by the quaternary epitope-preferring bNAbs, PG9 and PG16, which is relatively infrequent amongst most HIV-1 Env sequences (McLellan J S, et al. (2011) Nature 480(7377):336-343), and is also observed for BG505 gp120 (Julien J P, et al. (2013) Proc Natl Acad Sci USA 110(11):4351-4356; Hoffenberg S, et al. (2013) J Virol 87(10):5372-5383).

Applicants have designed and purified HIV gp145 trimers possessing a hydrophilic transmembrane region re-engineered from the previously hydrophobic TM. This allows secretion of either uncleaved or cleaved gp145 trimers, not previously possible. This should be expandable to other strains and clades of HIV.

Applicants have designed and developed HIV gp120 trimers stabilized by engineered variable region cysteine pairs and by appending a heterologous trimerization motif selected from the pdb.

Applicants have also designed and developed a new method to produce soluble, fully uncleaved, homogeneous, highly stable gp140s trimers as a native spike mimetics. In this method the native-like gp120 subunit is covalently linked to gp41 via peptide based flexible linkers and the method is easily expandable to other strains and clades of HIV.

The SOSIP envelope glycoproteins identified as a part of this invention show significantly better binding to new identified broad neutralizing antibodies PG9 and/or PG16 and are well recognized by all known broadly neutralizing antibodies (bNAbs). The JRFL HPTMs and gp120 MIFs may be recognized by trimer-specific bNabs and likely recognized by bNAbs of other specificities. The envelope glycoproteins Envs have value (a) as reagents for screening of broad neutralizing antibodies (bNAbs), such as but not limited to, PG9 and PG16, the PGT145 family, the PGT128 family and for the SOSIPs the VRC01-like mabs including VRC06, (b) as reagents for screening of small molecules that compete binding of broad neutralizing antibodies, such as but not limited to, PG9 and PG16, (c) as monomer and native envelope trimer mimic for crystallization studies and (d) as immunogens in different forms to use as HIV-1 vaccine components, for example, to elicit broadly neutralizing antibodies.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus, the BG505 virus or the Zm109F virus.

In a particularly advantageous embodiment, the trimer protein, is prepared, purified and formulated for immunization in a human.

In another particularly advantageous embodiment, the trimer protein, is formulated for immunization in a human to contain an adjuvant. A number of adjuvants are well known to those investigating vaccines but could include but are not limited to those containing alum.

In another particularly advantageous embodiment, the trimer protein is further attached to a particle such that multiple copies of the trimer are attached and this material is prepared and formulated for immunization in a human.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or the specification.

Another advantageous embodiment encompasses a stable soluble HIV-1 envelope glycoprotein trimer mimic.

Applicants have designed completely new gp120 and gp145 trimers based upon the cryo-EM densities of the HIV-1 functional spike, as well as based upon Applicants' means of producing and purifying JRFL SOSIP trimers (residue 168 E to K modified for PG9/16 recognition) to a high degree of homogeneity. For gp120 trimer de novo design, using SOSIP EM structures, and Applicants' densities, Applicants have appended new trimer motifs completing replacing gp41 (and the need for cleavage) in combination with structure-guided cysteine pairs to lock down the metastable variable (V) loops on gp120.

Using this design strategy, Applicants have generated gp120 trimers that express well, appear trimeric by EM, and are efficiently recognized preferentially by the broadly neutralizing mAbs as opposed to non-neutralizing mAbs.

Applicants have very recently successfully produced gp145 trimers that contain the entire ectodomains of gp120 and gp41 by modifying the usually hydrophobic transmembrane (TM) region to be hydrophilic and allowing secretion rather than membrane attachment. Applicants have made several by systematic TM deletions and site directed, sequence specific N-glycan additions.

To a varying degree, and especially for the JRFL SOSIPs, all three of these trimers display the epitopes of virtually all the broadly neutralizing HIV-1 mAbs, including the extremely potent, glycan-dependent PGT mAbs. An objective of the present invention is to render all three trimers with these recognition properties.

Second generation soluble trimers display desired structural features and antigenic profile. They are used as immunogens in animal models to elicit improved neutralizing antibodies. The soluble trimers are assessed in combination with the ability of genetic Env trimer expression to prime (or boost) neutralizing antibody responses to HIV-1 Env. The influence of trimer modifications using previous analyses of trimer-elicited responses in NHPs directed toward the CD4bs are pursued in parallel to improve the elicitation of neutralizing antibodies. Recent analysis of trimer-elicited CD4bs-directed mAbs indicates that they approach the HIV spike "from the top" rather than accessing the CD4bs "from the side" as do the broadly neutralizing mAbs such as VRC01 and PGV04, dictating immunogen re-design (manuscript in Appendix). In addition, the commonly elicited NHP CD4bs mAbs possess hydrophobic HCDR3s which often interact with the Phe 43 cavity, indicating that filling of this cavity with less hydrophobic residues should be revisited for immunogen modification in either the 1st generation or the future generations of trimer design and development.

Due to the structural limitations of the first generation gp140 foldon trimers and their inability so far to elicit broadly neutralizing antibodies, Applicants designed native-like gp140 trimers in which gp120 is covalently attached to gp41 via a peptide flexible linker (native flexible linker trimers termed gp140-NFL). Applicants developed this new trimer design pathway to make soluble mimetics of the native HIV-1 envelope glycoprotein spike for structural, biophysical and antigenic analysis. A subset of these new trimers that are well-ordered and present trimer-specific neutralizing determinants as HIV vaccine candidates to elicit neutralizing antibodies. Applicants expanded these initial designs to clade C and A virus-derived envelope glycoproteins, and to assess these trimers as soluble immunogens. Applicants also assess immunogenicity of these trimers by particulate, high-density array on liposomes or other particles already under development. In one non-limiting example, nickel chromatography may be accomplished with nickel containing lipids in the formulation at 1-2% and then capturing a His6-tagged ("His6" disclosed as SEQ ID NO: 4) trimer by nickel chelation.

Applicants designed the native, flexible linked (NFL) trimers by appending a flexible linker between gp120 and gp4 and are optimizing their design (FIG. 9). The rationale was to provide flexibility at the cleavage site to allow native rearrangement of gp120 and gp41 trimeric subunits: as it happens after cleavage by furin. The linker used was $G_4S$ (SEQ ID NO: 2) with 1 (SEQ ID NO: 2), 2 (SEQ ID NO: 6) and 3× (SEQ ID NO: 7) repeats. The MPER is deleted at position 664 as per SOSIP (for better expression) The trimers have an E168K mutation to potentially restore PG9/16 recognition and I559P mutation to increase the trimer stability. There is no exogenous trimerization domain or foldon or other stabilizing mutations. The vector is a CMV-driven expression vector.

Initially Applicants inserted G45 (SEQ ID NO: 2) (glycin/serine) linkers of three different lengths between gp120 and gp41, deleting 4 residues (REKR) (SEQ ID NO: 3) at the gp120 C-terminus that comprise the normal furin cleavage site. The strategy is by covalent linker attachment, this will allow the gp120 and gp41 subunits to assume their natural trimeric association that approximates the HIV functional spike. Leveraging off the screening and purification procedures developed with the JRFL SOSIPs, Applicants expressed the gp140-NFL trimers following transient transfection of 293 HEK cells, secretion into serum-free media, and then purified the NFL trimers by lectin chromatography, size exclusion chromatography and F105-based affinity column negative selection.

The design and amino acid sequence of flexible length (NFL) gp140 trimers are exemplified in FIGS. 10-14 which include JR-FL gp140-NFLP (with 1×, 2× and 3× linkers), Clade C 16055 gp140-NFL2P and Clade A BG505 gp140-NFL2P.

Immunogens in different forms to use as HIV-1 vaccine components to elicit bNabs. The different forms of the HIV-1 envelope are used in a prime, as DNA/vector expressing the protein/protein and as a boost as protein. The envelopes could also be used as particulate immunogen by cross linking to virus particles like Qbeta, cow pea mosaic virus, CRM, HPV, HBsAg etc.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus.

HIV type 1 (HIV-1) envelope is a noncovalent trimer of gp120-gp41 heterodimers, and its lability has hindered structural studies. SOSIP gp140 is a soluble, proteolytically mature form of the HIV-1 envelope wherein gp120-gp41 interactions are stabilized via a disulfide bond and gp41 contains an additional trimer-stabilizing point mutation. The isolation of a substantially pure preparation of SOSIP gp140 trimers derived from KNH1144, a subtype A isolate was described in Iyer S P et al., AIDS Res Hum Retroviruses. 2007 June; 23(6):817-28. Following initial purification, the only significant contaminant was higher-order gp140 aggregates; however, 0.05% Tween 20 quantitatively converted these aggregates into trimers. The surfactant effect was rapid, dose dependent, and similarly effective for a subtype B SOSIP gp140. Surfactant-treated SOSIP gp140 retained favorable antigenicity and formed compact trimers 12-13 nm in size as determined by electron microscopy. Iyer S P et al., AIDS Res Hum Retroviruses. 2007 June; 23(6):817-28 provides a description of homogeneous, cleaved HIV-1 envelope trimers. These proteins may be useful as vaccine immunogens and for studying structure-function relationships within the HIV-1 envelope glycoproteins.

Soluble, stabilized, proteolytically cleaved, trimeric proteins may be generated by engineering an intermolecular disulphide bond between gp120 and gp41 (SOS), combined with a single residue change, I559P, within gp41 (SOSIP). SOSIP gp140 proteins based on the subtype A HIV-1 strain KNH1144 form particularly homogenous trimers compared to a prototypic strain (JR-FL, subtype B). Described in U.S. Pat. No. 7,939,083 are the determinants of this enhanced stability which are located in the N-terminal region of KNH11144 gp41 and that, when substituted into heterologous Env sequences (e.g., JR-FL and Ba-L) they have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

The trimers of the present invention also include flexible length (NFL) gp140 trimers exemplified in FIGS. 10-14 which include JR-FL gp140-NFLP (with 1×, 2× and 3× linkers), Clade C 16055 gp140-NFL2P and Clade A BG505 gp140-NFL2P.

The structure of BG505 gp140 SOSIP, a soluble mimic of the native HIV-1 envelope glycoprotein (Env), marks the beginning of new era in Env structure-based immunogen design. Displaying a well-ordered quaternary structure, these subtype A-derived trimers display an excellent antigenic profile, discriminating recognition by broadly neutralizing antibodies (bNAbs) from non-broadly neutralizing antibodies (non-bNAbs), and provide a solid Env-based immunogenic platform starting point. Even with this important advance, obtaining homogeneous well-ordered soluble SOSIP trimers derived from other subtypes remains challenging. Here, Applicants report the "rescue" of homogeneous well-ordered subtype B and C SOSIP trimers from a heterogeneous Env mixture using CD4 binding site-directed (CD4bs) non-bNAbs in a negative-selection purification process. These non-bNAbs recognize the primary receptor CD4bs only on disordered trimers but not on the native Env spike or well-ordered soluble trimers due to steric hindrance. Following negative selection to remove disordered oligomers, Applicants demonstrated recovery of well-ordered, homogeneous trimers by electron microscopy (EM). Applicants obtained 3D EM reconstructions of unliganded trimers, as well as in complex with sCD4, a panel of CD4bs-directed bNAbs, and the cleavage-dependent, trimer-specific bNAb, PGT151. Using bio-layer light interferometry Applicants obtained a full antigenic profile, demonstrating that the well-ordered trimers were avidly recognized by bNAbs and poorly recognized by non-bNAbs. Biophysical characterization was consistent with thermostability of a homogeneous species that could be further stabilized by specific bNAbs. Applicants establish a new means to obtain soluble Env mimetics derived from both subtypes B and C for expanded use as candidate vaccine immunogens.

This study presents an artful means using HIV non-broadly neutralizing antibodies to isolate new well-ordered trimers engineered to mimic the virus surface protein. These soluble spike mimetics, called SOSIPs, derive from different genetic HIV subtypes B and C, and complement the recently described subtype A-derived BG505 SOSIP. The comprehensive biochemical analysis presented demonstrates that these new homogeneous soluble trimers are faithful mimics of the HIV spike and more importantly provides a novel means to purify a wider array of soluble Env trimers for future structural and immunogenicity studies. Possessing soluble and stable mimics of the HIV spike derived from diverse strains will improve both Applicants' knowledge of HIV spike architecture and extend the geographical/genetic coverage of future vaccine candidates.

The HIV-1 envelope glycoprotein (Env) is a trimer of heterodimers composed of two non-covalently associated subunits; the receptor-binding gp120, and the fusion machinery-containing gp41. Each subunit is derived from a gp160 precursor glycoprotein following cleavage by cellular furins (Wyatt R & Sodroski J (1998) Science 280(5371): 1884-1888). HIV-1 gp120 binds the CD4 molecule on the surface of human target T cells to initiate the viral entry process, and following co-receptor engagement, fusion is mediated by gp41 (Dalgleish A G, et al. (1984) Nature 312(5996):763-767; McDougal J S, et al. (1986) J Immunol 137(9):2937-2944; mKarlsson Hedestam G B, et al. (2008) Nat Rev Microbiol 6(2):143-155). The surface-exposed HIV-1 Env trimer is the sole target for antibodies capable of neutralizing the virus (Burton D R, et al. (2004) Nat Immunol 5(3):233-236). Recently, a myriad of Env-directed broadly neutralizing antibodies (bNAbs) were isolated from numerous HIV-1-infected individuals, demonstrating that the human B cell response can effectively inhibit this variable pathogen (Wu X, et al. (2010) Science 329(5993):856-861; Walker L M, et al. (2009) Science 326(5950):285-289; Walker L M, et al. (2011) Nature 477(7365):466-470; Huang J, et al. (2012) Nature 491(7424):406-412; Scharf L, et al. (2014) Antibody 8ANC195 reveals a site of broad vulnerability on the HIV-1 envelope spike. Cell reports 7(3):785-795; Klein F, et al. (2012) J Exp Med 209(8):1469-1479). Infection of macaques by a chimeric model virus, SHIV, can be prevented by prior passive immunization of all bNAbs so far tested, confirming the capacity of neutralizing antibodies to prevent HIV infection (Mascola J R, et al. (1999) J Virol 73(5):4009-4018; Hessell A J, et al. (2009) PLoS Pathog 5(5):e1000433; Moldt B, et al. (2012) Proc Natl Acad Sci USA 109(46):18921-18925; Barouch D H, et al. (2013) Therapeutic efficacy of potent neutralizing HIV-1-specific monoclonal antibodies in SHIV-infected rhesus monkeys. Nature 503(7475):224-228).

Along with virus-specific T cells, an efficacious HIV-1 vaccine therefore would likely need to generate bNAbs targeting Env. Although the premise is simple, in actuality, it is a tremendous challenge without precedent in the history of vaccinology. The difficulty to vaccinate against HIV arises from the extensive variability of Env present on the large number of HIV-1 isolates simultaneously circulating in the human population as well as other mechanisms of immune evasion selected for by strong pressure from the human immune system.

Generally, vaccine-generated antibodies using either or both gp120 or gp41 sequences do not recognize native Env on the surface of cells or virus, do not neutralize primary isolates in vitro, and do not prevent infection in laboratory animals (Burton D R, et al. (2011) Proc Natl Acad Sci USA 108(27):11181-11186; Sundling C, et al. (2012) Science translational medicine 4(142):142ra196; Tran K, et al. (2014) Vaccine-elicited primate antibodies use a distinct approach to the HIV-1 primary receptor binding site informing vaccine redesign. Proc Natl Acad Sci USA 111(7):E738-747). Non-neutralizing antibodies directed to the major variable region two (V2) of gp120 are associated with modest efficacy in a single human clinical trial (Haynes B F, et al. (2012) N Engl J Med 366(14):1275-1286; Zolla-Pazner S, et al. (2014) Vaccine-induced IgG antibodies to V1V2 regions of multiple HIV-1 subtypes correlate with decreased risk of HIV-1 infection. PLoS One 9(2):e87572), while, in general, Env-elicited antibodies fail to demonstrate protection in previous human clinical trials (Jones N G, et al. (2009) Vaccine 27(7):1136-1140; Rerks-Ngarm S, et al. (2009) N Engl J Med 361(23):2209-2220; Yates N L, et al. (2014) Vaccine-induced Env V1-V2 IgG3 correlates with lower HIV-1 infection risk and declines soon after vaccination. Science translational medicine 6(228):228ra239).

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci USA 111(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-1 primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci USA 109(30):12111-12116; Nkolola J P, et al. (2014) Comparison of multiple adjuvants on the stability and immunogenicity of a clade C HIV-1 gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bNAbs, (GE148 and GE136) generated following immunization of uncleaved gp140 trimers (YU2 gp140-foldon) in non-human primates (NHP). Non-bNAbs, represented by GE136 and 148, can only neutralize the sensitive so-called "tier 1 viruses" that are not representative of the more neutralization resistant tier 2-like primary isolates circulating in the human population. Using crystallography, EM reconstructions, paratope scanning and molecular modeling Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci USA 111(7):E738-747).

The cumulative historical data have led to the hypothesis that a more faithful mimic of the HIV-1 spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNH1144 SOSIP is also available but does not provide atomic level details (Bartesaghi A, Merk A, Borgnia M J, Milne it, & Subramaniam S (2013) Nat Struct Mol Biol 20(12):1352-1357). The BG505 SOSIP and KNH1144 SOSIP trimers are derived from the Env sequences of the subtype A BG505 and KNH1144 strains. These soluble trimers possess an engineered disulfide linkage between the gp120 and gp41 (at residues 501C and 605C, respectively) and an additional mutation in the heptad repeat 1 (HR1) of gp41 (I559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-1 primary strains were attempted over the past decade, the BG505- and KNH1144-derived SOSIP trimers are the two limited examples of SOSIPs that yield homogeneous trimers suitable for high resolution biophysical and structural analysis. The structural explanation for the difficulty to readily transfer the SOSIP design to other HIV-1 strain-derived sequences is not yet fully understood and would be valuable information to broaden the trimer design horizon.

Here, Applicants describe two SOSIP trimer molecules derived from the B subtype strain, JRFL, and the subtype C strain, 16055. Applicants selected these two Envs for the initial results reported in this study as follows. The JRFL SOSIP trimer, truncated at residue 663 (JRFL SOSIP.663) derives from the JRFL HIV-1 strain isolated from the frontal lobe (FL) of an HIV-1-infected individual. This Env is often used because it displays the unusual property that its gp160 Env precursor is efficiently cleaved into the gp120 and gp41 subunits when expressed on the cell surface of 293F HEK cells (Pancera M & Wyatt R (2005) Virology 332(1):145-156). The 16055 SOSIP.663 trimer, also truncated at residue 663, derives from a HIV-1 Indian strain and displays the unusual property that its monomeric gp120 is recognized by the quaternary epitope-preferring bNAbs, PG9 and PG16, which is relatively infrequent amongst most HIV-1 Env sequences (McLellan J S, et al. (2011) Nature 480(7377): 336-343), and is also observed for BG505 gp120 (Julien J P, et al. (2013) Proc Natl Acad Sci USA 110(11):4351-4356; Hoffenberg S, et al. (2013) J Virol 87(10):5372-5383).

Applicants demonstrate that the JRFL and 16055 SOSIP.663 trimers were purified to homogeneity by a novel means of isolation that utilizes non-bNAbs targeting the CD4-binding site (CD4bs) in a negative-selection process that effectively separates well-ordered trimers from a mixture also containing disordered trimers and other oligomeric states of Env. By binding kinetic analysis, Applicants demonstrated that the purified JRFL and 16055 SOSIP.663 trimers were efficiently recognized by bNAbs but were poorly recognized by the non-bNAbs. By negative stain EM, Applicants confirmed that negative selection results in homogeneous, three-fold symmetric JRFL and 16055 SOSIP.663 trimers resembling the native HIV spike and the previously described subtype A SOSIPs. Applicants obtained 3D EM reconstructions of the unliganded and liganded JRFL and 16055 SOSIP.663 trimers and demonstrated that the negatively selected trimers adopt conformational changes upon sCD4 engagement that emulate those of the native HIV spike (Liu J, et al. (2008) Nature 455(7209): 109-113). Differential scanning calorimetry (DSC) and differential scanning fluorimetry (DSF) revealed that the negatively selected JRFL and 16055 SOSIP.663 trimers were stable at temperatures exceeding 55 and 63° C., respectively. Applicants conclude that the negative-selection process resulted in highly homogenous well-ordered JRFL and 16055.663 trimers, expanding the SOSIP family of Env mimetics to HIV-1 subtypes B and C. This advance provides opportunities for HIV Env structural comparisons at high resolution as well as a wider array of ordered trimers for sequential or simultaneous inoculation regimens to evaluate enhanced immunogenicity toward more broadly effective antibody responses.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or specification.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. J. Virol. 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

In another embodiment of the present invention, the soluble envelope glycoproteins of the present invention may be crystallized in the combination with PG9 or PG16 or with any other neutralizing antibodies, including those identified by the above methods, to determine the exact molecular surface where the soluble envelope glycoprotein binds with the neutralizing antibody to design HIV-1 immunogens.

Crystals of the invention may be obtained by conventional means as are well-known in the art of protein crystallography, including batch, liquid bridge, dialysis, vapor diffusion and hanging drop methods (see, e.g., Johnson et al., Biochemistry. 1982 Sep. 28; 21(20):4839-43; Brayer & McPherson, J Biol Chem. 1982 Apr. 10; 257(7):3359-61; McPherson & Weickmann, J Biomol Struct Dyn. 1990 April; 7(5):1053-60; and Koszelak et al., J Mol Biol. 1989 Sep. 20; 209(2):323-5; Weber et al., Acta Crystallogr B. 1991 Feb. 1; 47 (Pt 1):116-27 and Weber, Methods Enzymol. 1991; 202:727-41).

Generally, the crystals of the invention are grown by dissolving a substantially pure neutralizing antibody, such as PG9 or PG16, and soluble envelope glycoprotein in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to a neutralizing antibody, such as PG9 or PG16, and thus are useful to elicit anti-HIV antibodies. Such compounds may be useful in eliciting clade B and C anti-HIV antibodies, however variants may be useful in eliciting clade A, D or E anti-HIV antibodies.

The structure co-ordinates may be used as phasing models in determining the crystal structures of a synthetic or mutated neutralizing antibody, such as PG9 or PG16, domains, as well as the structures of co-crystals of such domains with ligands.

The provision of the crystal structure of a neutralizing antibody, such as PG9 or PG16, complexed with a soluble envelope glycoprotein provide the skilled artisan with a detailed insight into the mechanisms of action of a neutralizing antibody, such as PG9 or PG16. This insight provides a means to design compounds that bind to a neutralizing antibody, such as PG9 or PG16, and thus to certain anti-HIV antibodies, and therefore compounds that elicit anti-HIV antibodies, which are useful in diagnosis, treatment, or prevention of HIV in an individual in need thereof.

The provision of the crystal structure of a neutralizing antibody, such as PG9 or PG16, complexed with a soluble envelope glycoprotein allows a novel approach for drug or compound discovery, identification, and design for compounds that bind to a neutralizing antibody, such as PG9 or PG16, and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of a neutralizing antibody, such as PG9 or PG16, complex as defined by the co-ordinates or the identifying co-ordinates, providing a structure of a candidate compound; and fitting the structure of the candidate to the structure of a neutralizing antibody, such as PG9 or PG16.

In an alternative aspect, the method may use the co-ordinates of atoms of interest of a neutralizing antibody, such as PG9 or PG16, which are in the vicinity of the active site or binding region in order to model the pocket in which the substrate or ligand binds. These co-ordinates may be used to define a space which is then screened "in silico" against a candidate molecule. Thus, the invention provides a computer-based method of rational drug or compound design or identification which comprises: providing the co-ordinates of at least selected co-ordinates; providing the structure of a candidate compound; and fitting the structure of the candidate to the selected co-ordinates.

In practice, it may be desirable to model a sufficient number of atoms of a neutralizing antibody, such as PG9 or PG16, as defined by its co-ordinates which represent the active site or binding region. Thus, there can be provided the co-ordinates of at least 5, advantageously at least 10, more advantageously at least 50 and even more advantageously at least 100 atoms of the structure.

Accordingly, the methods of the invention can employ a sub-domain of interest of a neutralizing antibody, such as PG9 or PG16, which is in the vicinity of the active site or binding region, and the invention can provide a computer-based method for identifying or rationally designing a compound or drug which comprises: providing the coordinates of at least a sub-domain of; providing the structure of a candidate modulator or inhibitor of a neutralizing antibody, such as PG9 or PG16; and fitting the structure of the candidate to the co-ordinates of the sub-domain provided.

The invention further provides a method for determining the structure of a binder of a neutralizing antibody, such as PG9 or PG16, bound to a neutralizing antibody, such as PG9 or PG16, comprising: providing a crystal of a neutralizing antibody, such as PG9 or PG16, e.g., according to the invention, soaking the crystal with the binder, and determining the structure of the neutralizing antibody-binder complex. Alternatively or additionally the neutralizing antibody, such as PG9 or PG16, and the binder may be co-crystallized.

The invention also provides a method of analyzing a complex of a neutralizing antibody, such as PG9 or PG16, and a potential binder comprising: employing X-ray crystallographic diffraction data from the complex and a three-dimensional structure of a neutralizing antibody, such as PG9 or PG16, or at least a sub-domain thereof, to generate a different Fourier electron density map of the complex; advantageously, the three-dimensional structure being as defined by its atomic co-ordinate data.

Such complexes can be crystallized and analyzed using X-ray diffraction methods, e.g., according to the approaches described by Greer et al., 1994, and difference Fourier electron density maps can be calculated based on X-ray diffraction patterns of soaked or co-crystallized neutralizing antibody, such as PG9 or PG16, and the solved structure of an uncomplexed neutralizing antibody, such as PG9 or PG16. These maps can then be used to determine whether and where a particular potential binder binds to a neutralizing antibody, such as PG9 or PG 16, and/or changes the conformation of a neutralizing antibody, such as PG9 or PG16. Electron density maps can be calculated using programs such as those from the CCP4 computer package (Collaborative Computing Project, No. 4. The CCP4 Suite:

Programs for Protein Crystallography, Acta Crystallographica, D50, 1994, 760-763). For map visualization and model building programs such as "QUANTA" (1994, San Diego, Calif.: Molecular Simulations, Jones et al., 1991) can be used.

Determination of the 3D structure of a neutralizing antibody, such as PG9 or PG16, provides important information about the likely active/binding site(s) of a neutralizing antibody, such as PG9 or PG16. This information may be used for rational design of neutralizing antibody binders, e.g., by computational techniques that identify possible binding ligands for the active site(s), by enabling linked-fragment approaches to drug design, and by enabling the identification and location of bound ligands using analyses such as X-ray crystallographic analysis.

In yet another embodiment, the present invention also encompassed the use of the soluble envelope glycoproteins described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

F(ab')$_2$, the fragment of the antibody that can be obtained by treating whole antibody with the enzyme pepsin without subsequent reduction; F(ab')$_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus F with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions are generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

In an advantageous embodiment, the mutation is a proline substitution. Stabilization of the native Env trimer in the "NFL" platform involves and encompases a HR1 destabilization screen with proline substitutions.

Figure 44:
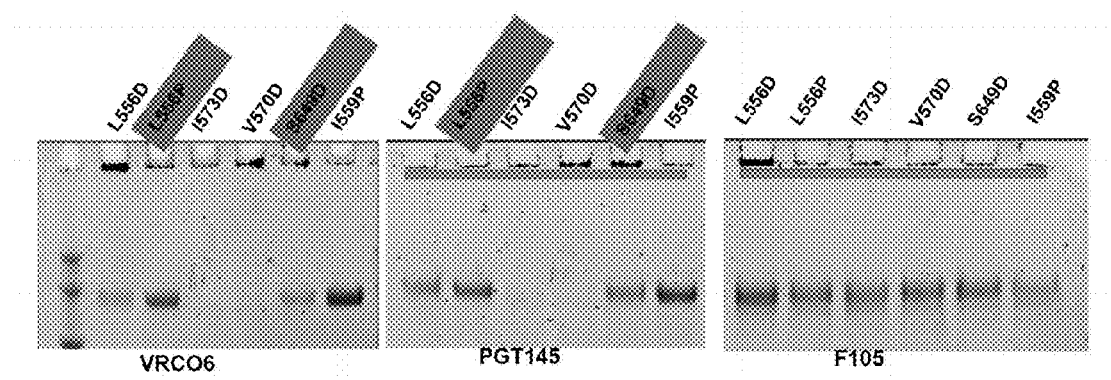
FIG. 44 depicts a HR1 destabilization screen suggesting that BG505 NFL2-L556P and S649D are involved in stabilzation of the trimers. In particular, L556P and S649D make well-ordered trimers.

FIG. 44 depicts a HR1 destabilization screen suggesting that BG505 NFL2-L556P and S649D are involved in stabilzation of the trimers. In particular, L556P and S649D make well-ordered trimers.

Figure 45:
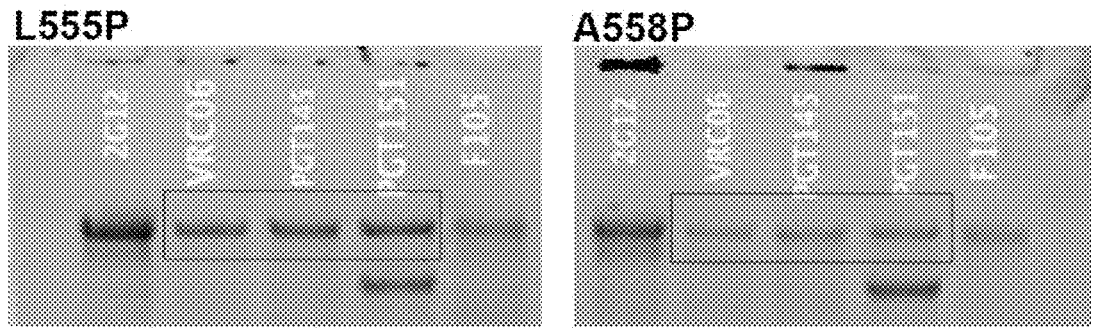
FIG. 45 depicts that immunoprecipitation (IP) results indicate that L555P and A558P are making well-ordered trimers. In particular, L555P and A558P looks similar to I559P.

FIG. 45 depicts that immunoprecipitation (IP) results indicate that L555P and A558P are making well-ordered trimers. In particular, L555P and A558P looks similar to I559P.

Figure 46:
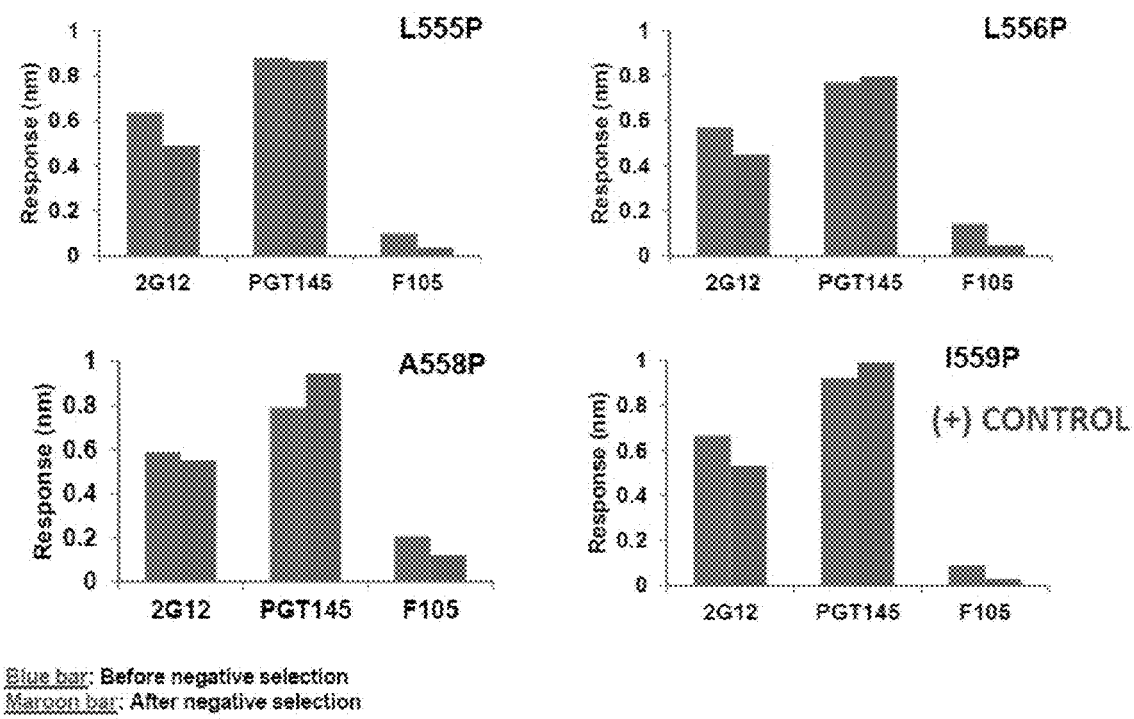
FIG. 46 depicts that octet binding data suggest that there is no appreciable difference in the antigenicity of L555P, L556P, and A558P after negative selection. L555P, L556P, A558P bind strongly with PGT145 and show almost no binding with F105 and the pattern is very similar to I559P suggesting that they are making well-ordered, native-like BG505-NFL2 trimers.

FIG. 46 depicts that octet binding data suggest that there is no appreciable difference in the antigenicity of L555P, L556P, and A558P after negative selection. L555P, L556P, A558P bind strongly with PGT145 and show almost no binding with F105 and the pattern is very similar to I559P suggesting that they are making well-ordered, native-like BG505-NFL2 trimers.

FIG. 47 depicts a summary of the HR1 proline screen in BG505NFL2 backbone. L555P, L556P and L566P almost behave like I559P in terms of antigenic profile and trimer formation.

In the initial 15 residues of the HR1 proline screen, Applicants have six positive hits, which are behaving similar to BG505 gp140-NFL2P.

FIG. 58 depicts a gp41 screen in NFL for substitutions for transfer to other Envs. These are the proline substitutions screened in the BG505 NFL context.

The present invention also encompasses the I559P change in the BG505 NFL trimers.

The present invention also involves stabilizing the clade C 16055 Env trimers in their native-like conformation in the NFL platform and to find out a common proline mutation that can be easily translated to stabilize majority of the ENV trimers spanning different clades.

In the native spike, the gp41 subunit exists in a metastable conformation and it favorably forms a stable post-fusion six-helix bundle (6HB), which is composed of trimers of HR1 (N-heptad repeat) and HR2 C-heptad repeat) heterodimers facilitating the fusion of HIV with the host CD4 T cells. The formation the 6HB is a irreversible process destabilizing the native trimer resulting in exposure of immunodominant and non-neutralizing epitopes to the immune system. Ideally, any mutation in the HR1 or HR2 that can destabilize the 6HB formation will stabilize the ENV trimers in native-like conformation.

In the initial screen 30 residues from HR1 and 3 residues from HR2 were selected. The HR1 residues were mutated individually to proline. The HR2 residues were mutated to proline and other charged residues (Aspartic acid, Glutamic acid and Arginines).

A summary of the ongoing HR1 proline screen in the 16055 gp140-NFL2 construct: based on the initial immunoprecipitation and initial octet binding data is presented in FIG. 71. FIG. 71A depicts single mutations involving only HR1 residues and FIG. 71B depicts double mutations involving both, the HR1 and HR2 residues. Green indicates a positive result, red indicates a negative result and blue indicates an experiment in progress.

So far, five single proline mutants (L555P, Q652P, Q653P, L565P and L566P) stabilize the clade C 16055-NFL2 Env trimers in the native-like conformations. So far, five double mutants stabilize and induce native-like trimer formation in 16055-NFL2 Env.

FIG. 72 depicts immunoprecipitation with selected trimer sensitive bNAbs (VRCO6 and PGT145) which suggest that L555P, Q652P, A558P-S649D, A558P-S649E and I559P-S649E are making well ordered trimers in solution.

FIG. 73 depicts immunoprecipitation with selected trimer sensitive bNAbs clearly indicate that Q653P, L565P and L566P are destabilizing the formation of 6 HB bundle resulting in the formation of well-ordered native-like 16055 gp140-NFL2 Env trimers.

FIG. 74 depicts a sequence of Clade C 16055 gp140-NFL2 Env. The region of HR1 studied in the proline screen to stabilize the trimer is highlighted in green and underlined. The residues of HR2 involved in this study are highlighted in red and underlined.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284;

6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof; buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum*, *Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524, 584; 6,645,495), monophosphoryl lipid A, in particular, 3-de-O-acylated monophosphoryl lipid A (3D-MPL), imiquimod (also known in the art as IQM and commercially available as Aldarag; U.S. Pat. Nos. 4,689,338; 5,238,944; Zuber, A. K. et al (2004) 22(13-14): 1791-8), and the CCR5 inhibitor CNIPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

The invention will now be further described by way of the following non-limiting examples.

Example 1: JRFL SOSIP Trimers

Applicants are characterizating the second generation stable and soluble Env spikes that are faithful mimetics of the native spike than are the first generation foldon trimers. Applicants apply several means of analysis of second generation soluble Env trimers including antigenic profiling, biophysical assessments, EM and crystallography. Applicants are producing modified JRFL SOSIP trimers that are purified by negative selection to generate highly homogenous trimers by EM (FIG. 1) and binding kinetics. The present invention also encompasses negative selection with F015, and non-neutralizing CD4 binding site mabs.

Currently, Applicants have produced the JRFL SOSIP trimers by transient transfection that contain the previously described gp120-to-gp41 cysteine pair linkage and the gp41 I/P change, which enhances trimer formation. The JRFL SOSIPs also contain a 168 E/K mutation to restore PG9/16 binding and are deleted of the MPER to enhance expression, have a poly R cleavage site between gp120 and gp41 and are co-transfected with furin to achieve cleavage.

Applicants developed a means of isolating the fraction of well-ordered JRFL trimers by negative selection (see FIG. 1, upper left panels) and Applicants define their complete antigenic profile by Octet with a panel of neutralizing and non-neutralizing mAbs. Applicants define thermal stability by differential scanning calorimetry, the impact of ligand binding by isothermal titration calorimetry, pursue high resolution EM and crystallography of these trimers for those that Applicants can obtain sufficient quantities of protein. Expansion of this protocol to other clade C versions of such trimers are actively pursued in parallel by the same means of design and purification procedures in parallel with sufficient resources.

Figure 2:
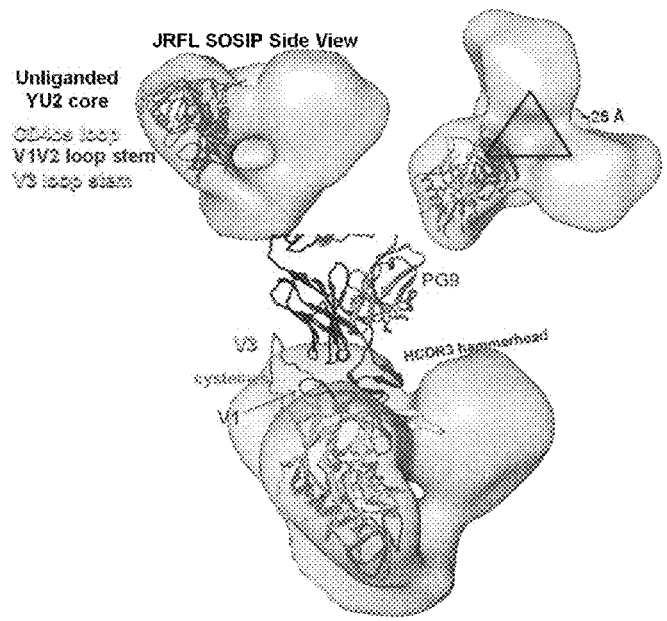
FIG. 2 depicts 3D reconstructions of modified JRFL SOSIP trimer to guide gp120 trimer design.
Figure 3A:
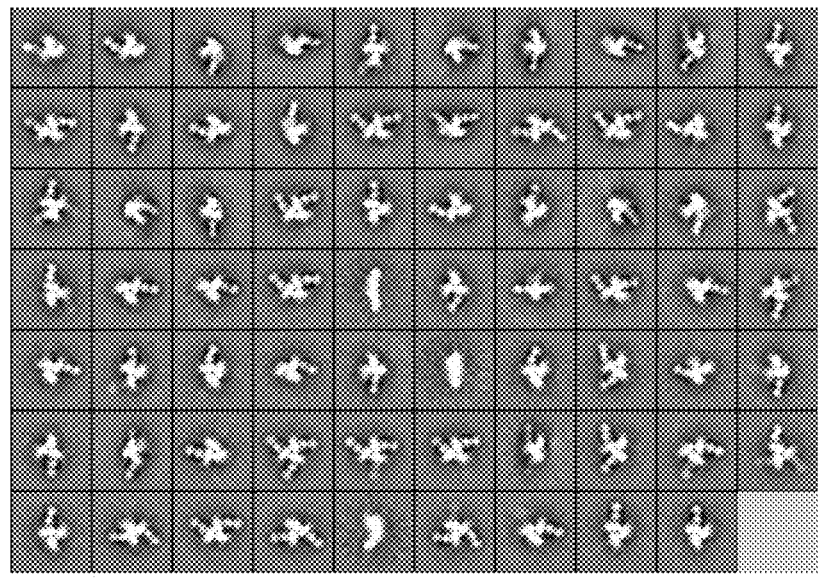
FIGS. 3A-E depict 2D template stacks of the homogenous JRFL trimers in complex with selected Fabs.
Figure 3B:
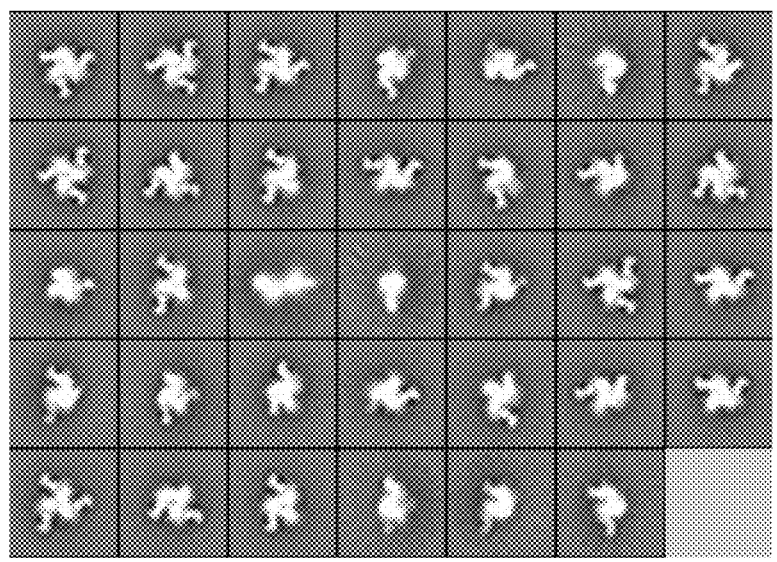
Figure 3C:
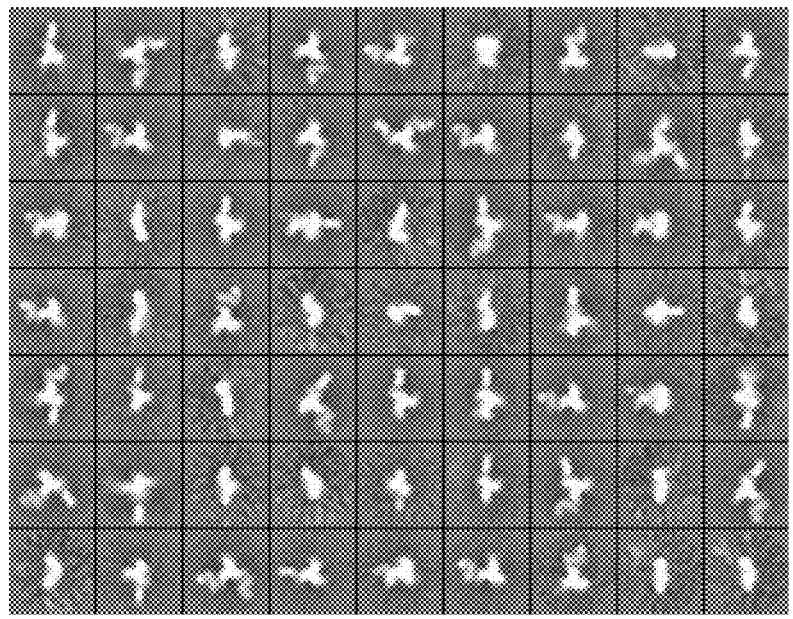
Figure 3D:
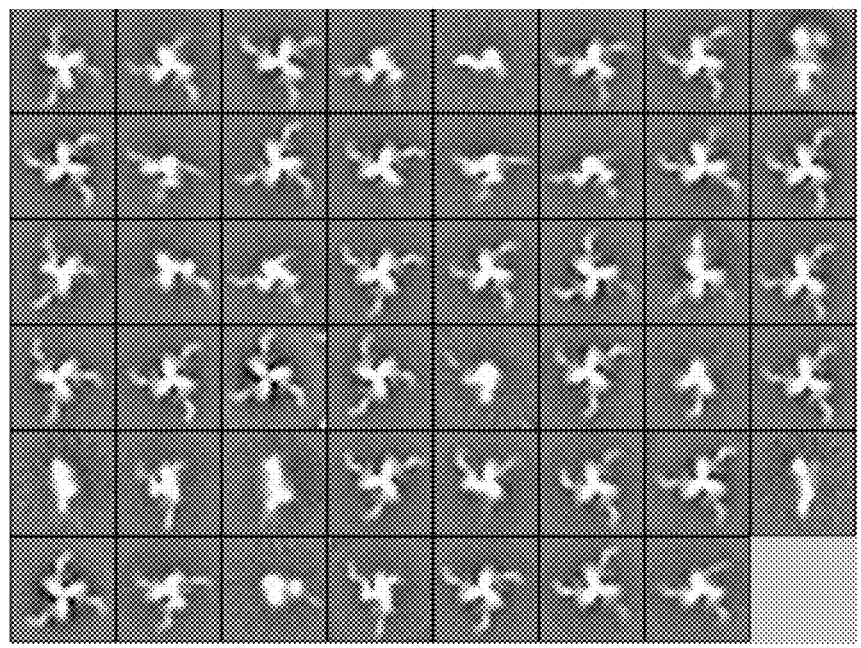
Figure 3E:
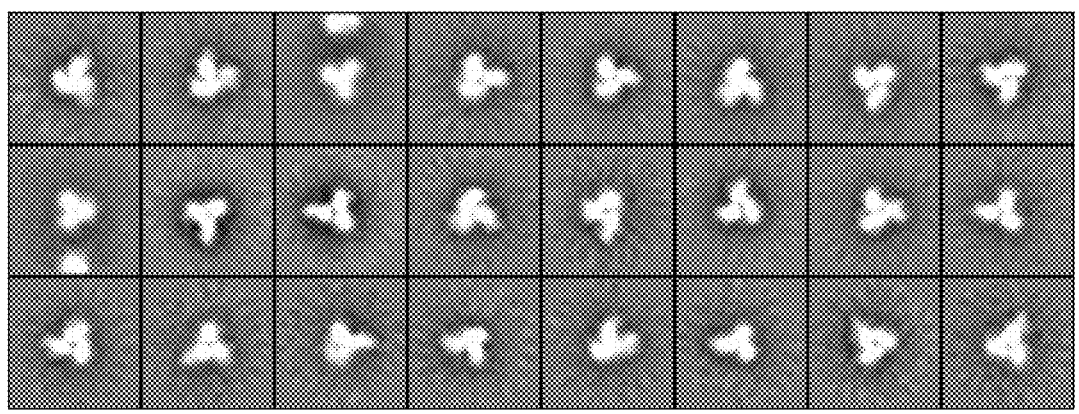

JRFL SOSIP trimers containing the modifications described above were expressed by transient transfection, purified by 2G12 affinity chromatography (or lectin and His-bind affinity chromatography) followed by size-exclusion chromatography as previously described followed by negative-selection over an F105 column. Using negative staining EM, Applicants generated 3D trimer reconstructions (FIG. 2). Using this reconstruction data, Applicants fit in the several HIV cores (core +V3), and using the published PG9-V1V2 scaffold structure, coupled with PG9-BG505 SOSIP, Applicants oriented the variable (V) 3 and V1 loops in close proximity (see FIG. 2, right). Applicants then scanned these loops for C—C linkages with the goal of locking down the "spring-loaded" V3 by cross-linking to V1. Applicants narrowed the search assuming that the conserved V3 tip would be buried in primary isolates, as would that of V1, and concentrated on the flanks of both of these V regions.

In FIG. 2, one can see that V3 protrudes from the density, but Applicants hypothesize that in native spike, V3 "tucks under" V1, which was the rationale for the C—C linkages (marked in magenta). Applicants also used this density to assign an approximate 3-fold axis of symmetry of the gp120 trimer (FIG. 2, upper right) and appended several trimerization domains present in the structural pdb on to the C-terminus of gp120, replacing completely all of the gp41 ectodomain. These MIF gp120 trimers formed well-ordered trimers in roughly 10% of the molecules by EM (FIG. 1, middle left), allowing 3D reconstruction (FIG. 1, middle right) and Applicants are assessing how to isolate such trimers from the mixture, likely by some means of negative selection. The advantage of these trimers is that they express well, do not require cleavage or the co-expression of exogenous furin and should be transplantable to other Envs from clade C and A. Applicants continue to use this information and emerging structural information to also stabilize the trimer via interprotomer stabilizing cross linkages. These design approaches are important advances toward the goal of soluble stable trimers that better mimic the functional spike.

Applicants have generated gp145 soluble trimers by hydrophilic modification of the putative helical transmembrane region of gp41 that, following lectin purification and negative F105 selection, appear well-ordered by EM analysis. These trimers are pursued as a third pathway of trimer design/production (see FIG. 1, lower right). The exciting aspect of this approach is that Applicants are utilizing the natural trimerization elements in the TM to generate soluble and stable trimers by an innovative but rational means of design. EM 3D reconstructions of these full-length, soluble trimers are attempted and should be informative on several levels. For example, these trimers contain the entire gp41 ectodomain, and these fully natural trimers validate the engineered but unnatural mutations that are introduced in the SOSIP design pathway. In the best case scenario, the soluble gp145 trimer pathway should be transferable to many Envs, including clade C or A candidates, and may as well benefit from the inclusion of the SOS mutations for stability following full precursor cleavage. Currently, their level of expression is somewhat limiting but should be sufficient for EM analysis and for immunogenicity following DNA priming with cell-surface Env or other trimers that are better expressed.

Figure 1:
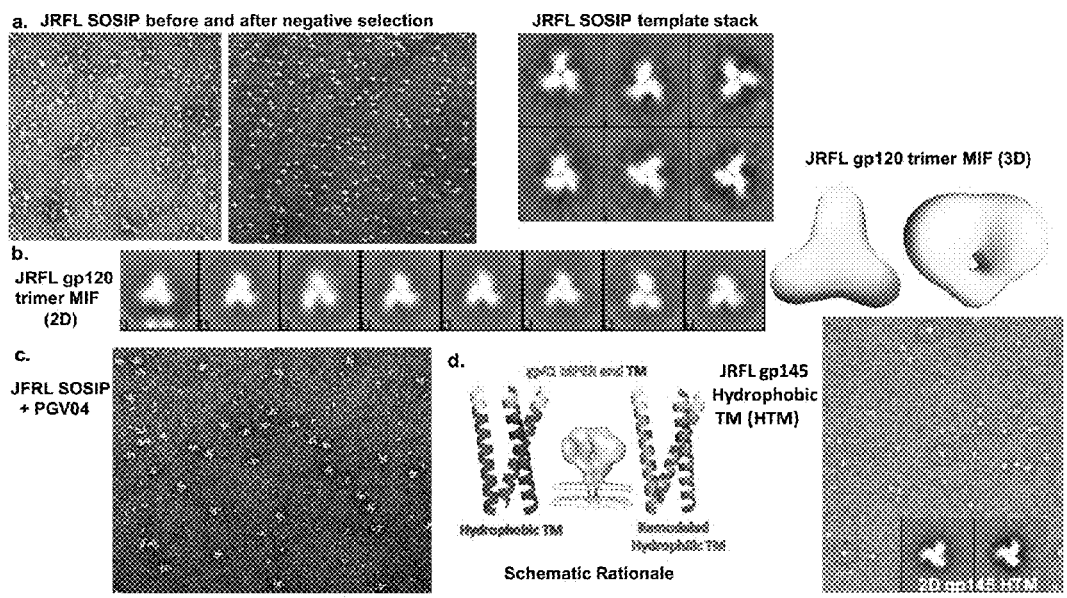
FIG. 1 depicts EM negative staining as labeled and schematic of the redesigned gp41 transmembrane (TM) region (lower right).

The EM images of each of these trimers are shown in FIG. 1 and are described in brief therein. Applicants aim to produce these trimers at higher quantities by a transient transfection system (pTT vector and cells) that replicates that DNA so that daughter cells retain the episomal plasmid to boost protein production, licensed from National Research Council Canada. This system can also be utilized to generate stable cell lines if so desired.

Applicants assess immunogenicity of selected trimers in relevant animal models, such as NHPs or hu-Ig mice, to assess the elicitation of neutralizing antibodies as a primary means of readout. To guide future trimer immunogens and immunogenicity Applicants characterize at a high level of resolution the B cell responses and antibodies elicited by trimers in NHPs or he huIg mice. Applicants perform deep sequencing analysis and Env-specific B cell sorting to define the "elicit-ome" generated by HIV Env trimers in NHPs and to assess their V-D-J usage, level of SHM, length of the HCDR3 loops and other relevant parameters such as epitope specificity and angle of approach to the HIV-1 Env spike as Applicants have recently done for NHP mAbs specific for the CD4 binding site. Once Applicants have selected, well-ordered trimers, the immunogenicity analysis requires as many if not more resources to inform iterative immunogen design in to develop broadly effective vaccine candidates. In addition, using novel probes, some of which are derived directly from the well-ordered trimers, Applicants isolate broadly neutralizing antibodies from Env-immunized NHPs or Ig-humanized mice whether they are detectable at the serum level, or not.

FIGS. 3A-E provide initial 2D template stacks of the homogenous JRFL trimers in complex with selected Fabs.

Example 2: gp140 Native, Flexible Linker (NFL) Trimers

Due to the structural limitations of the first generation gp140 foldon trimers and their inability so far to elicit broadly neutralizing antibodies, Applicants designed native-like gp140 trimers in which gp120 is covalently attached to gp41 via a flexible linker (native flexible linker trimers termed gp140-NFL). Applicants developed this new trimer design pathway to make soluble mimetics of the native HIV-1 envelope glycoprotein spike for structural, biophysical and antigenic analysis. A subset of these new trimers that are well-ordered and present trimer-specific neutralizing determinants as HIV vaccine candidates to elicit neutralizing antibodies. Applicants expanded these initial designs to clade C and A virus-derived envelope glycoproteins, and to assess these trimers as soluble immunogens. Applicants also assess immunogenicity of these trimers by particulate, high-density array on liposomes or other particles already under development.

Applicants designed the native, flexible linked (NFL) trimers by appending a flexible linker between gp120 and gp4 and are optimizing their design (FIG. 9). The rationale was to provide flexibility at the cleavage site to allow native rearrangement of gp120 and gp41 trimeric subunits: as it happens after cleavage by furin. The linker used was $G_4S$ (SEQ ID NO: 2) with 1 (SEQ ID NO: 2), 2 (SEQ ID NO: 6) and 3× (SEQ ID NO: 7) repeats. The MPER is deleted at 664 as per SOSIP (for better expression) The trimers have an E168K mutation to potentially restore PG9/16 recognition and I559P mutation for trimer stability. There is no exogenous trimerization domain or foldon or other stabilizing mutations. The vector is a CMV-driven expression vector.

Initially Applicants inserted G45 (SEQ ID NO: 2) (glycin/serine) linkers of three different lengths between gp120 and gp41, deleting 4 residues (REKR) (SEQ ID NO: 3) at the gp120 C-terminus that comprise the normal furin cleavage site. The strategy is by covalent linker attachment, this will allow the gp120 and gp41 subunits to assume their natural trimeric association that approximates the HIV functional spike. Leveraging off the screening and purification procedures developed with the JRFL SOSIPs, Applicants expressed the gp140-NFL trimers following transient transfection of 293 HEK cells, secretion into serum-free media, and then purified the NFL trimers by lectin chromatography, size exclusion chromatography and F105-based affinity column negative selection.

The design and amino acid sequence of native flexible length (NFL) gp140 trimers are presented below:

Design/sequence of the JR-FL gp140-NFL1P construct (FIG. 10)

1. Introduction of E168K in gp120 V2 region to restore PG9/PG16 binding
2. Removal of "REKR" (SEQ ID NO: 3) cleavage site, the last 4 residues of full length gp120
3. Introduction of I559P mutation for trimer stability
4. Insertion of 1×$G_4S$ [GGGGS] (SEQ ID NO: 2) linker "in the place of REKR" in gp120
   a. Results in 2 additional residues end of gp120 or approximately 6 angstroms extra length beyond the natural gp120 C-terminus
5. Removal of gp41 MPER region so that the HIV trimer amino acid sequence ends at residue Asp-664
6. A GGGGS (SEQ ID NO: 2) linker followed by His tag (8× H residues) (SEQ ID NO: 5) at the C-terminus of gp41

Design/sequence of JR-FL gp140-NFL2P construct (FIG. 11)

1. Introduction of E168K in gp120 V2 region to restore PG9/PG16 binding
2. Removal of "REKR" (SEQ ID NO: 3) cleavage site, the last 4 residues of full length gp120
3. Introduction of I559P mutation for trimer stability
4. Insertion of 2×$G_4S$ $[GGGGS]_2$ (SEQ ID NO: 6) linker "in the place of REKR" (SEQ ID NO: 3) in gp120
   a. Results in 6 additional residues end of gp120 or approximately 18 angstroms extra length beyond natural gp120 C-terminus
5. Removal of gp41 MPER region so that the HIV trimer amino acid sequence ends at residue Asp-664
6. A GGGGS (SEQ ID NO: 2) linker followed by His tag (8× H residues) (SEQ ID NO: 5) at the C-terminus of gp41

Design of JR-FL gp140-NFL3P construct (FIG. 12)

1. Introduction of E168K in gp120 V2 region to restore PG9/PG16 binding
2. Removal of "REKR" (SEQ ID NO: 3) cleavage site, the last 4 residues of full length gp120
3. Introduction of I559P mutation for trimer stability
4. Insertion of 3×$G_4S$ $[GGGGS]_2$ (SEQ ID NO: 7) linker "in the place of REKR" (SEQ ID NO: 3) in gp120
   a. Results in 11 additional residues end of gp120 or approximately 33 angstroms extra length beyond natural gp120 C-terminus
5. Removal of gp41 MPER region so that the HIV trimer amino acid sequence ends at residue Asp-664
6. A GGGGS (SEQ ID NO: 2) linker followed by His tag (8× H residues) (SEQ ID NO: 5) at the C-terminus of gp41

Design of Clade C 16055 gp140-NFL2P construct (FIG. 13)

1. PG9/PG16 recognition is inherent in 16055, no restoration required
2. Removal of "REKR" (SEQ ID NO: 3) cleavage site, the last 4 residues of full length gp120
3. Introduction of I559P mutation for trimer stability
4. Insertion of 2×$G_4S$ $[GGGGS]_2$ (SEQ ID NO: 6) linker "in the place of REKR" (SEQ ID NO: 3) in gp120
   a. Results in 6 additional residues end of gp120 or approximately 18 angstroms extra length beyond natural gp120 C-terminus
5. Removal of gp41 MPER region so that the HIV trimer amino acid sequence ends at residue Asp-664

6. A GGGGS (SEQ ID NO: 2) linker followed by His tag (8× H residues) (SEQ ID NO: 5) at the C-terminus of gp41

Design of Clade A BG505 gp140-NFL2P construct (FIG. 14)
1. PG9/PG16 recognition is inherent in BG505, no restoration required
2. Removal of "REKR" cleavage site, the last 4 residues of full length gp120
3. Introduction of I559P mutation for trimer stability
4. T332N mutation for restoration of glycan supersite
5. Insertion of 2×G$_4$S [GGGGS]$_2$ (SEQ ID NO: 6) linker "in the place of REKR" (SEQ ID NO: 3) in gp120
    a. Results in 6 additional residues end of gp120 or approximately 18 angstroms extra length beyond natural gp120 C-terminus
6. Removal of gp41 MPER region so that the HIV trimer amino acid sequence ends at residue Asp-664
7. A GGGGS (SEQ ID NO: 2) linker followed by His tag (8× H residues) (SEQ ID NO: 5) at the C-terminus of gp41

Flexible linkage of JRFL gp140 trimers as native spike mimetics is discussed below:

Applicants analyzed these trimers further by binding analysis (Octet) and EM negative staining to obtain preliminary 3D reconstructions. The candidate trimers were expressed in HEK-293F cells and purified by lectin affinity and size exclusion chromatography. Trimer peaks were pooled and further purified by negative selection to get well-folded, well-ordered JR-FL NFL2P trimers, which were analyzed by (a) immunoprecipitation from the crude supernatants (initial screen), (b) EM screening (negative staining), (c) octet binding with various broadly neutralizing mAbs and (d) EM 2D and 3D classifications.

FIG. 15 depicts immunoprecipitation of JRFL gp140-NFL1P with selected mAbs from the crude culture supernatant. The gp140 NFL1 trimer band intensities are low with VRCO6, PGT145, PGT151 and PG16 compared to that of b12, 2G12 and VRCO1.

Figure 16:
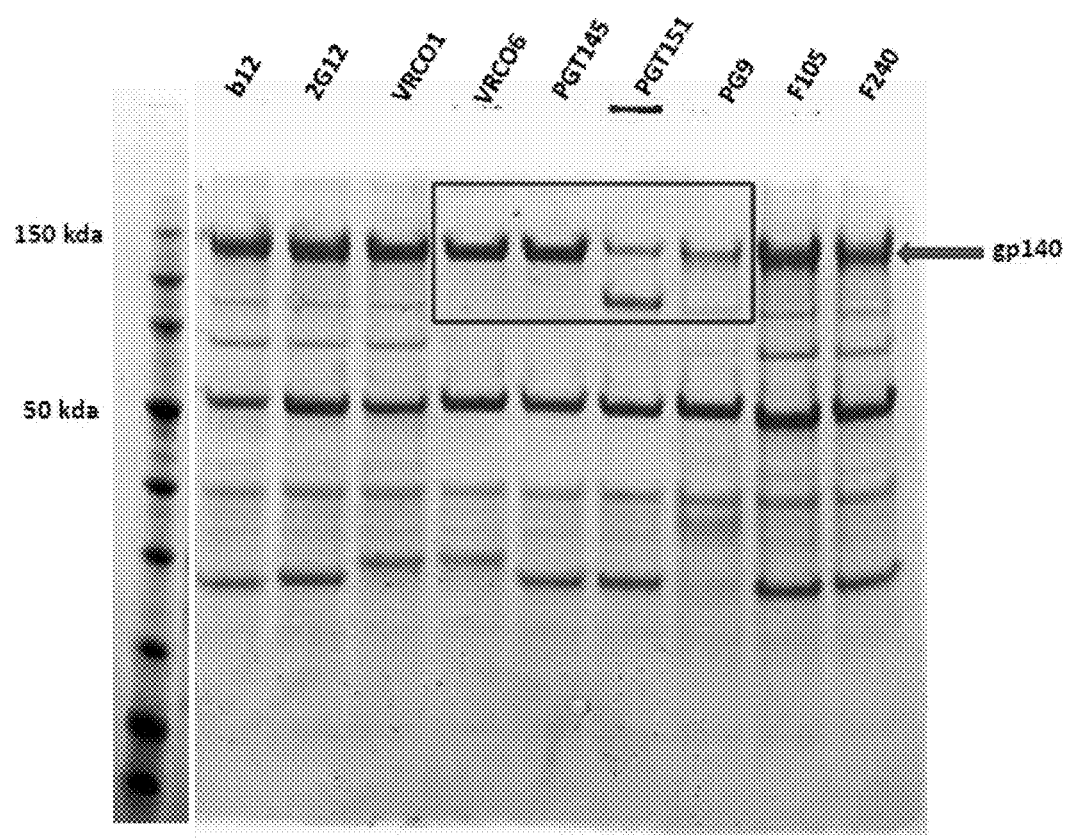
FIG. 16 depicts VRCO6, PGT145 immunoprecipitated gp140-NFL2P band intensities close to that of b12, 2G12 and VRCO1. IP band intensities for PGT151 and PG9 are also good, suggesting that the NFL2P preparation may have a reasonably high percentage of well-ordered trimers.

FIG. 16 depicts VRC06, PGT145 immunoprecipitated gp140-NFL2P band intensities close to that of b12, 2G12 and VRCO1. IP band intensities for PGT151 and PG9 are also good, suggesting that the NFL2 preparation may have a reasonable percentage of well-ordered trimers.

Figure 17:
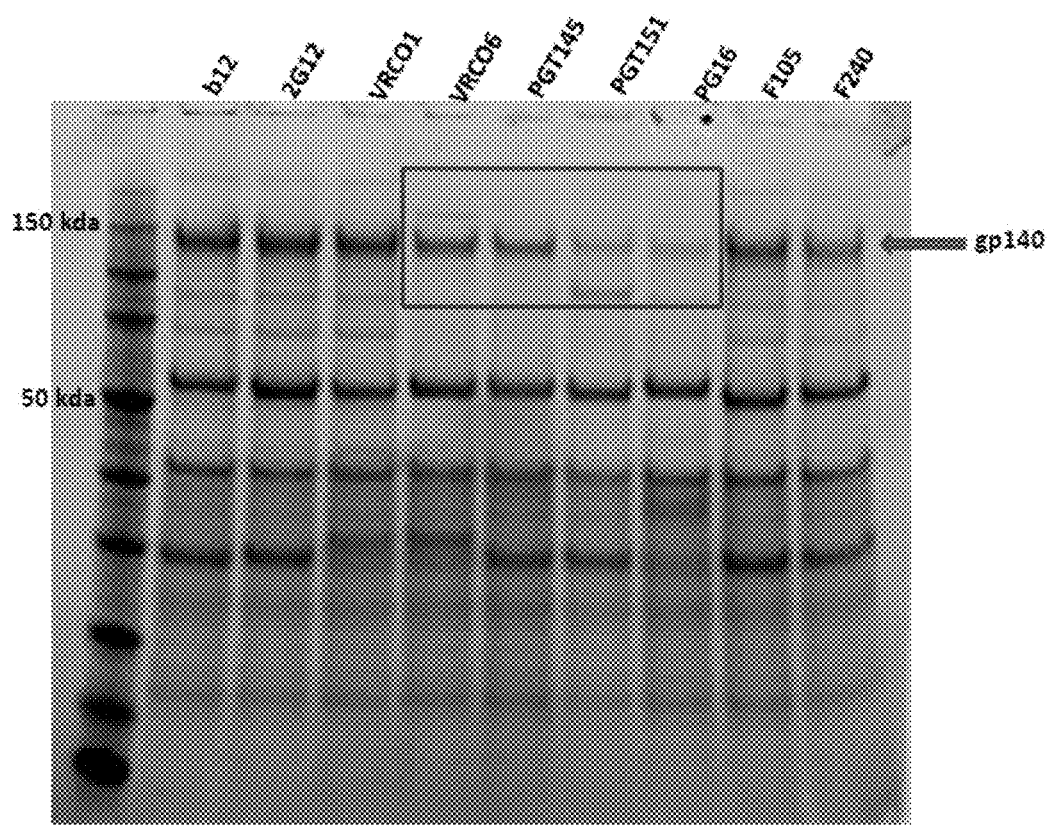
FIG. 17 depicts increasing the linker length to 3× appears to decrease the well-ordered trimers in the NFL3P preparation. IP band intensities for VRCO6 and PGT 145 for the JRFL gp140-NFL3P are less relative to b12, 2G12 and VRCO1 but there may be reasonable percentage of well-ordered trimers.

FIG. 17 depicts increasing the linker length to 3× appears to decrease the well-ordered trimers in the NFL3 preparation. IP band intensities for VRCO6 and PGT 145 for the JRFL gp140-NFL3 are less relative to b12, 2G12 and VRCO1 but there may be some well-ordered trimers.

Figure 18:
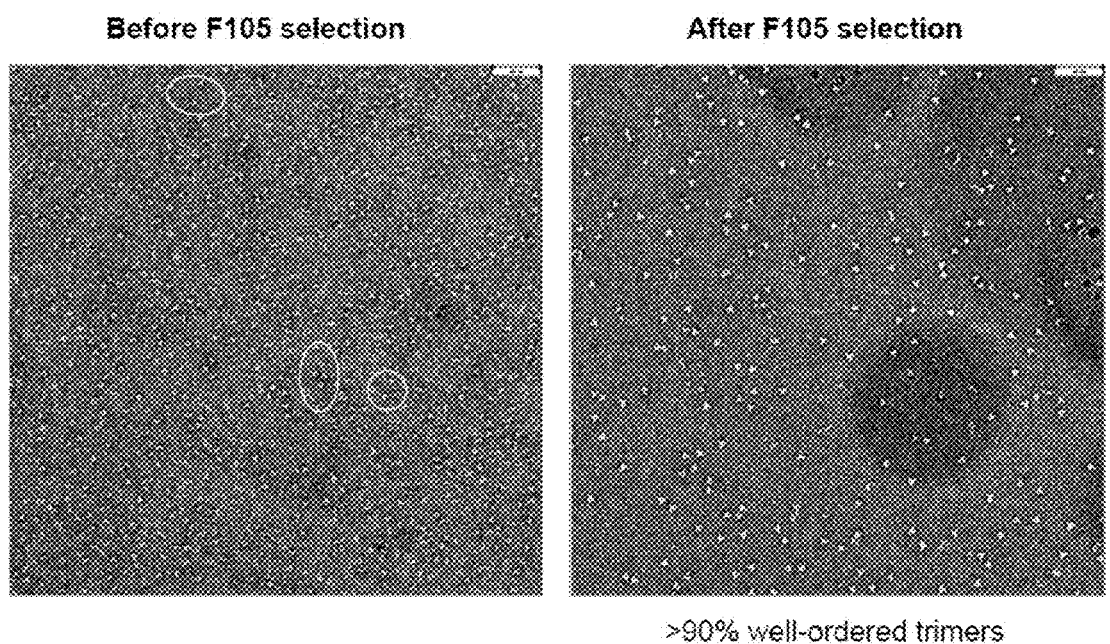
FIG. 18 depicts JRFL gp140-NFL2P form well-ordered trimers by negative staining EM following F105 negative selection. After F105 selection depicts greater than 90% well-ordered trimers.

FIG. 18 depicts JRFL gp140-NFL2P form well-ordered trimers by negative staining EM following F105 negative selection. After F105 selection depicts greater than 90% well-ordered trimers.

Figure 19A:
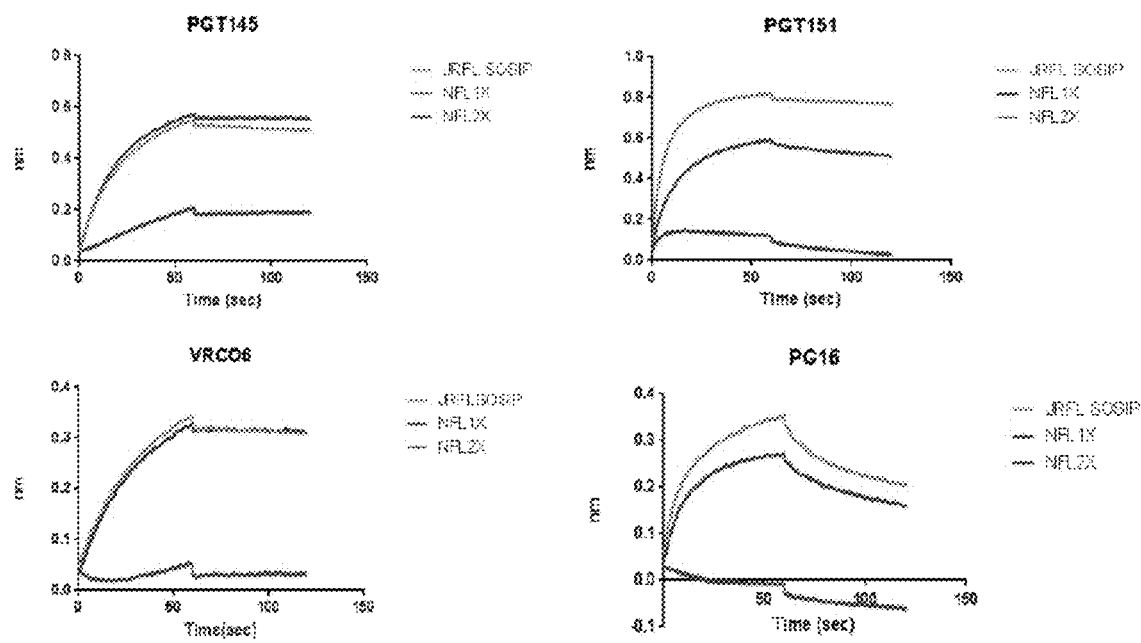
FIGS. 19A-C depicts antigenic analysis of JRFL gp140 SOSIP, NFL1P and NFL2P trimers (after negative selection) with selected mAbs by Octet.
Figure 19B:
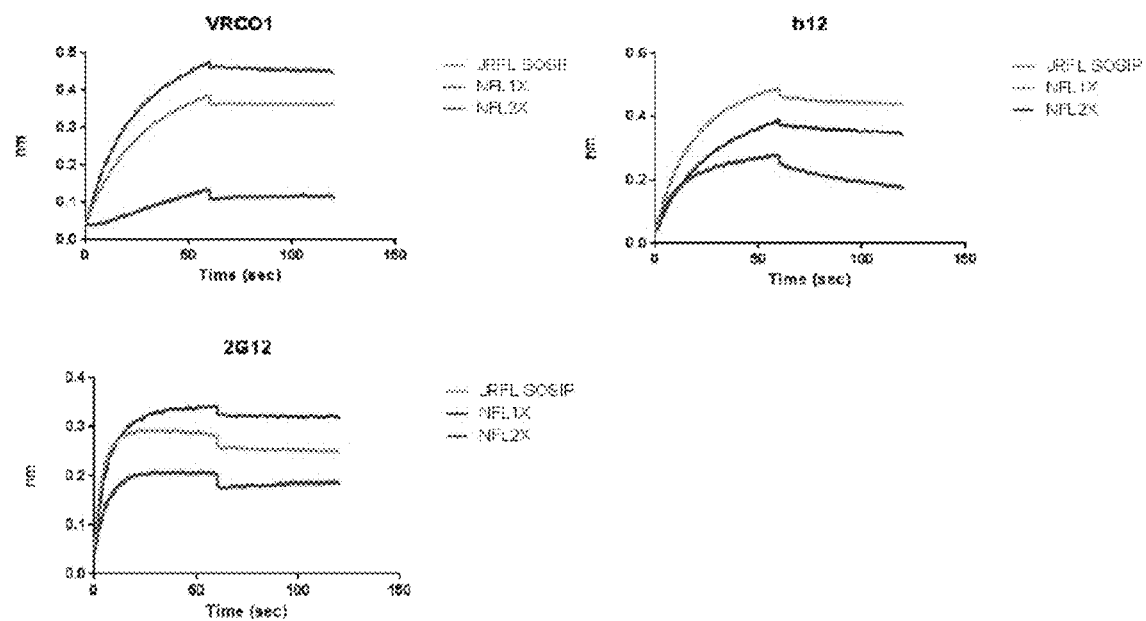
Figure 19C:
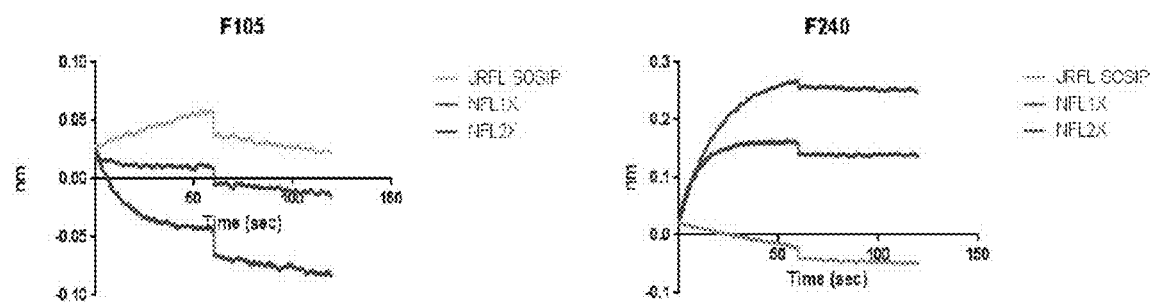

FIGS. 19A-B depicts antigenic analysis of JRFL gp140 SOSIP, NFL1P and NFL2P trimers (after negative selection) with selected mAbs by Octet. FIG. 19A depicts JRFL gp140-NFL2P well recognized by the trimer/cleavage-specific bNAbs. FIG. 19B depicts VRCO1, b12 and 2G12 mAbs recognize the JRFL NFL2P trimers similar to JRFL SOSIP. FIG. 19C depicts JRFL gp140-NFLP trimers not recognized by F105, some F240 recognition. F240 cluster 1 binding to these trimers unclear; the epitope is disrupted in SOSIP.

Figure 20:
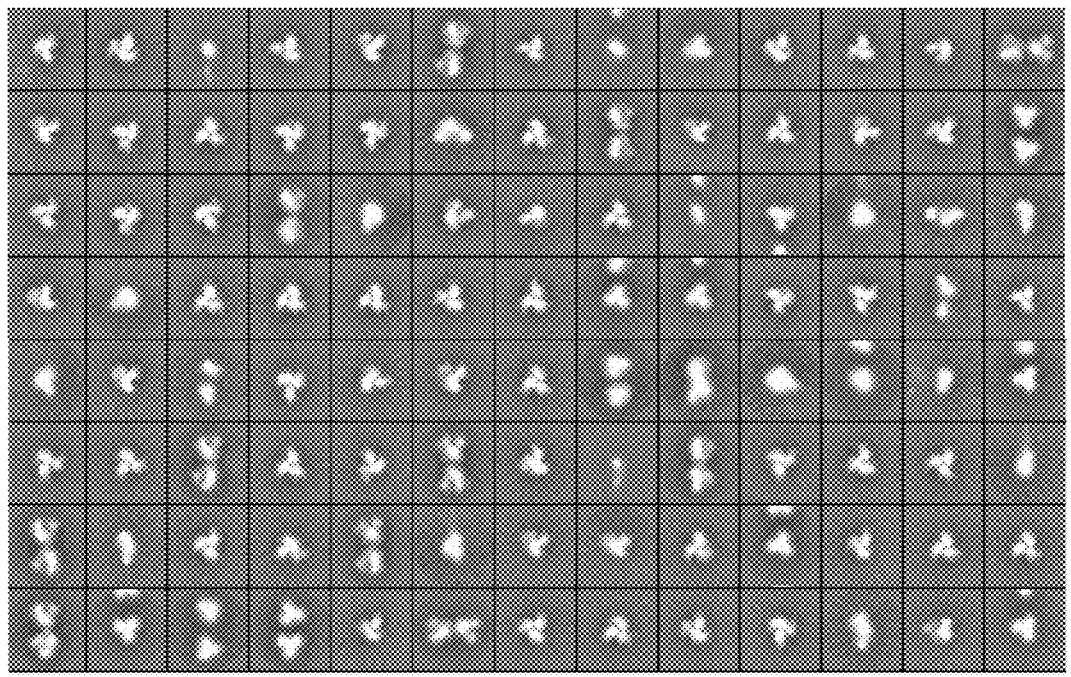
FIG. 20 depicts 2D class averages for JRFL gp140-NFL2P trimers.

FIG. 20 depicts 2D class averages for JRFL gp140-NFL2P trimers.

To summarize, the 2× linker length is so far the best of the first generation NFL trimer design, "uncleaved" JRFL gp140 trimers immunogen approximate the JRFL SOSIP trimers, JRFL gp140-NFL2P shows a (preliminary) binding pattern similar to the cleaved trimers, furin is not needed and initial yields are reasonable, negative selection greatly improves the percentage of well-ordered/folded trimers and initial EM micrographs are encouraging and in agreement with the biochemical and initial binding data.

Figure 21:
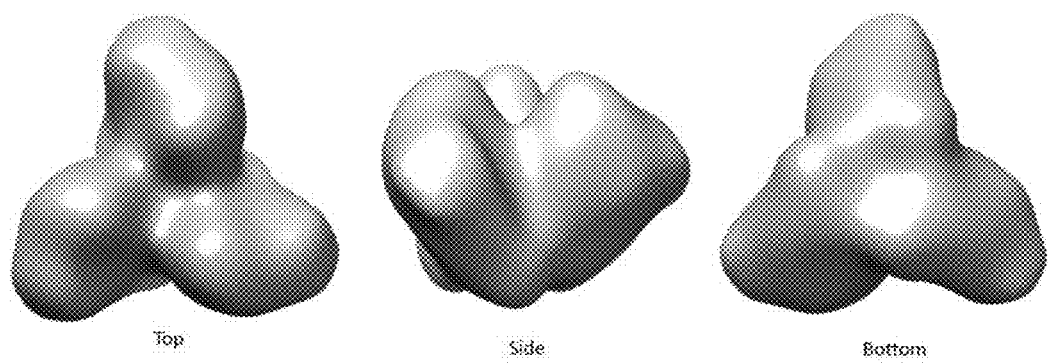
FIG. 21 depicts EM analysis of JRFL gp140-NFL trimers, specifically a 3D reconstruction of an EMAN2 common lines model using 29376 particles of JRFL gp140-NFL2P trimers.
Figure 22A:
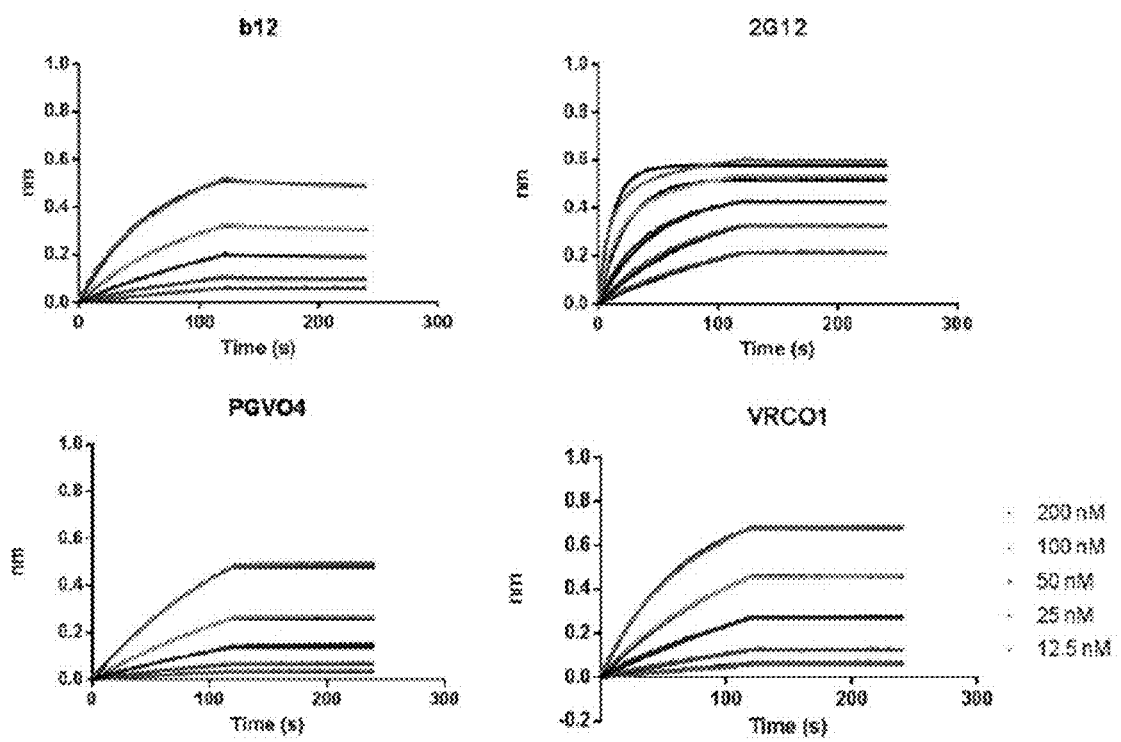
FIGS. 22A-C depict an antigenicity study of JRFL gp140-NFL2P trimers by Bio-Layer Interferometry (BLI or Octet). The binding kinetics of selected panel of broadly neutralizing antibodies (bNAbs; b12, 2G12, VRCO1 and PGVO4), trimer-specific or cleavage-specific bNAbs (PGT145 and PG16; VRCO6 and PGT151) and non-broadly neutralizing CD4 binding site mAbs (F105 and b6) and non-neutralizing gp41 mAbs (F240 and 22B) were studied by BLI. The antibodies were captured on the anti-human IgG Fc sensor and the binding of JR-FL gp140-NFL2 was studied at 5 different protein concentrations as an analyte (200 nM, 100 nM, 50 nM, 25 nM and 12.5 nM). As is evident from the binding curves, JRFL gp140-NFL2 is well recognized by all four of the bNAbs tested as well as with the four trimer-specific bNAbs. Low level recognition was detected with the non-broadly neutralizing or non-neutralizing Abs. The strongest binding was observed with trimer-specific bNAb PGT145. The binding study confirms that the soluble JR-FL gp140-NFL2 trimers present a relevant conformation that is consistent with that of the functional viral spike.
Figure 22B:
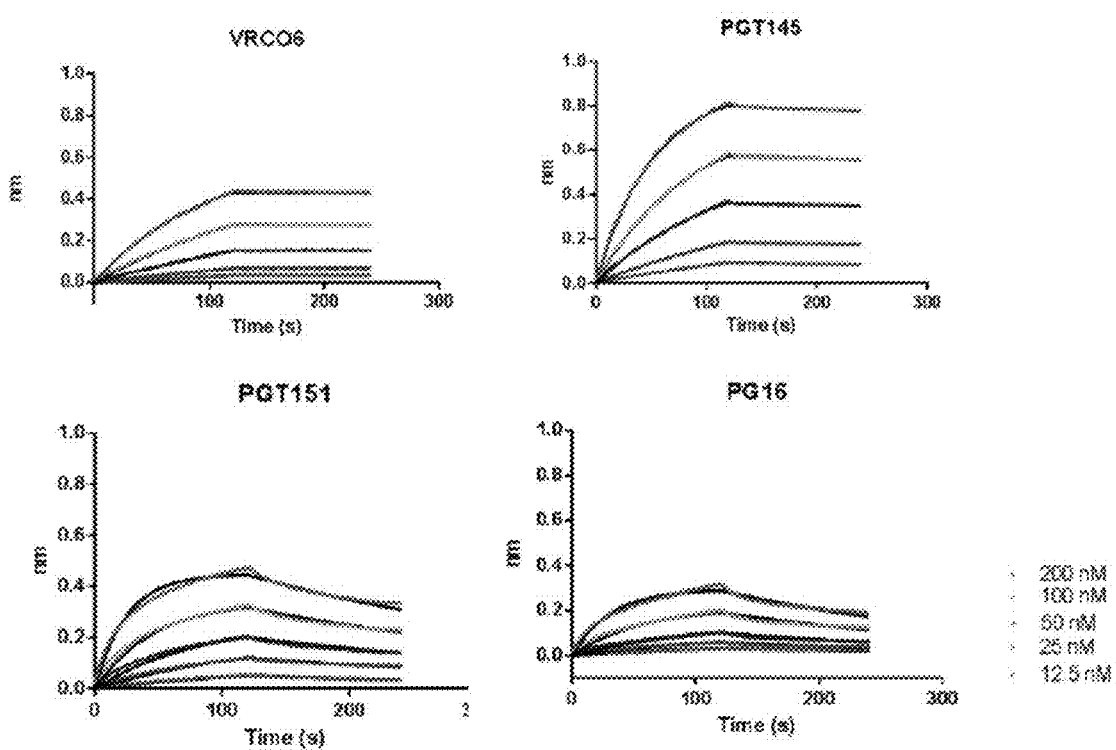
Figure 22C:
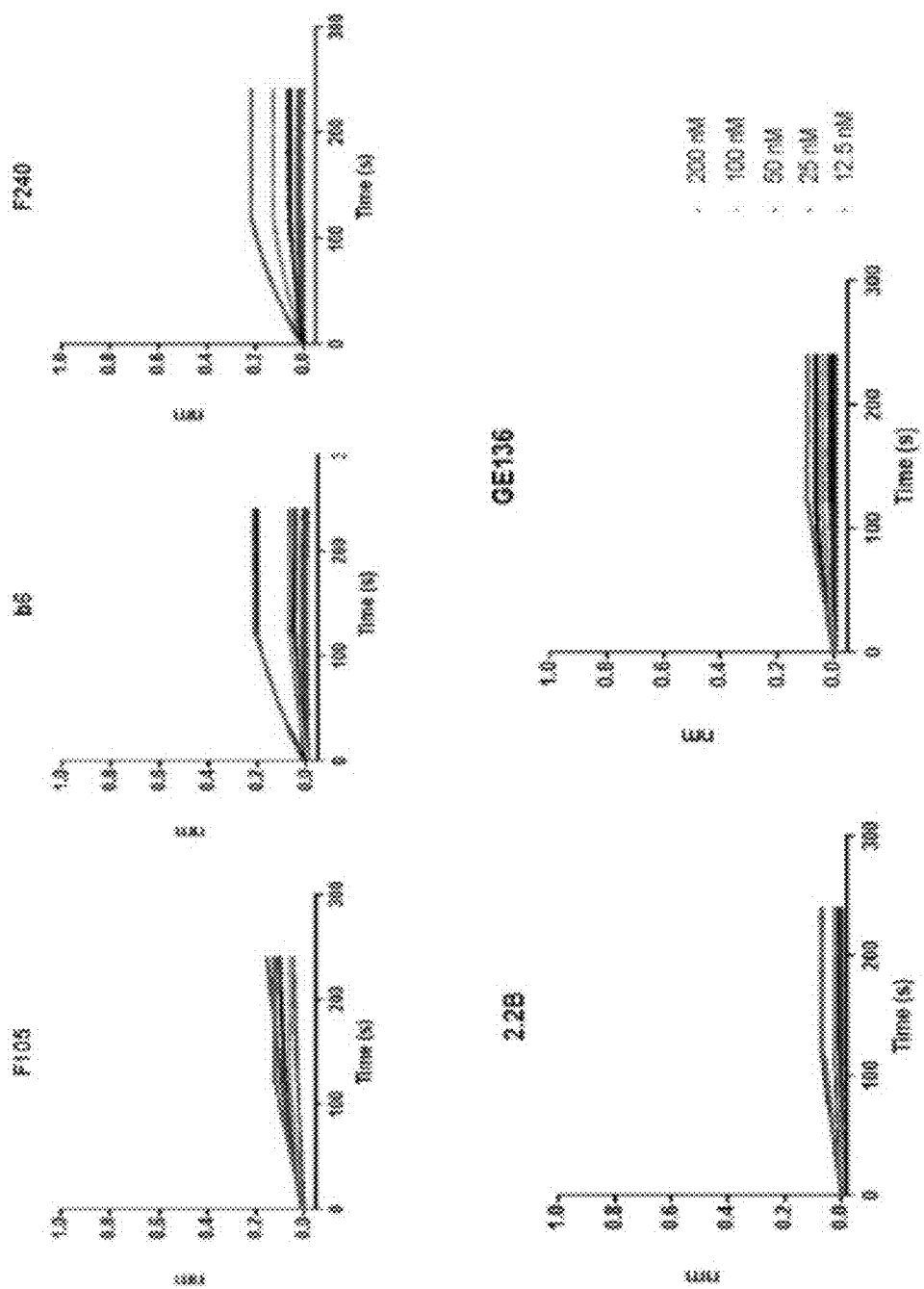
Figure 23:
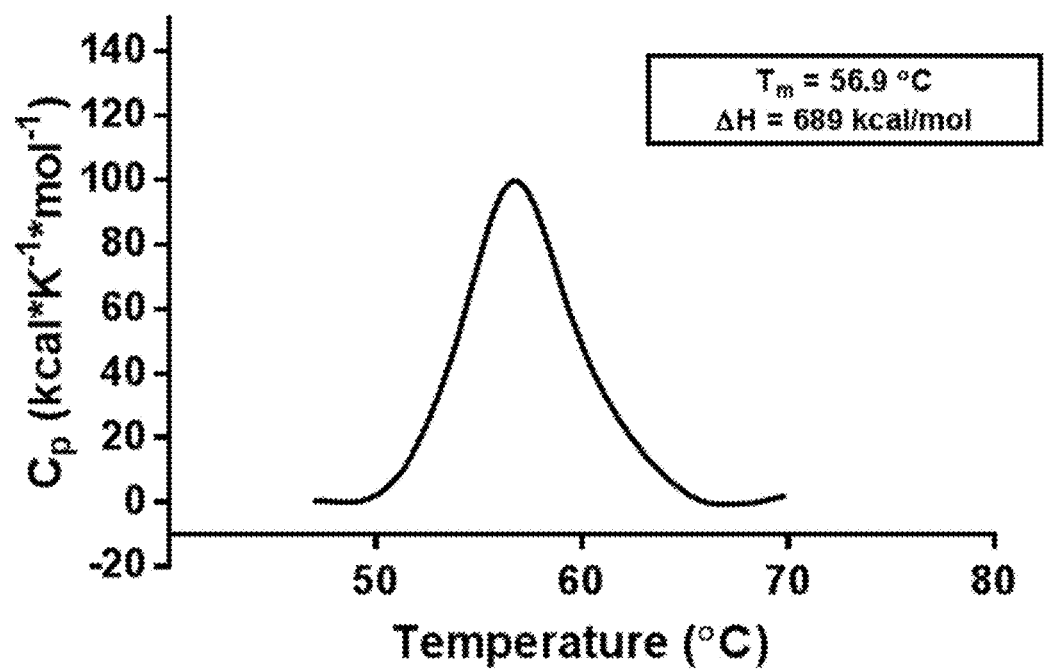
FIG. 23 depicts a thermal stability of the JRFL gp140-NFL2 trimers. The thermal stability of the JRFL gp140-NFL2 trimers was analyzed by Differential Scanning calorimetry (DSC), the thermogram presented here a uniform single melting peak with the thermal denaturation midpoint or melting temperature (Tm) of 56.9° C. suggesting that the protein is homogeneous and is stable at a relatively high temperature.

FIG. 21 depicts a 3D reconstruction of an EMAN2 common lines model using 29376 particles of JRFL gp140-NFL2P trimers.

Example 3: BG505 gp140-NFL2P Trimers

The data in FIGS. 27-30 suggests that BG505 gp140-NFL2P trimers are well behaved native like and homogeneous trimers and they do not need F105 negative selection.

Figure 24:
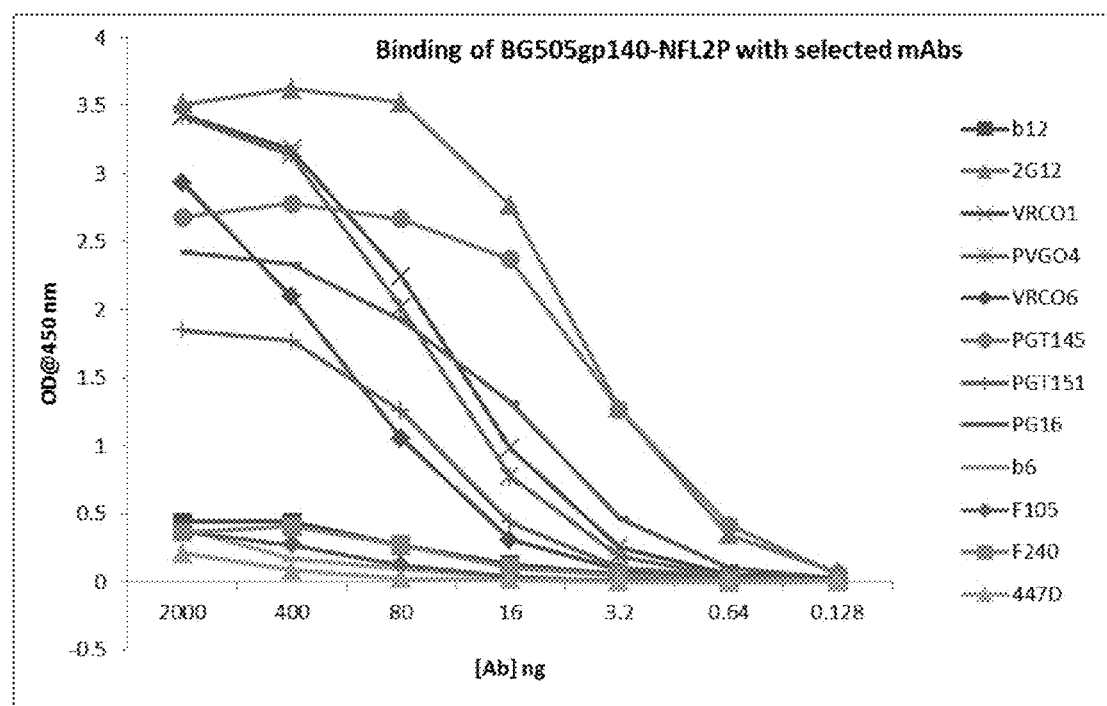
FIG. 24 depicts ELISA binding studies of BG505 gp140-NFL2P with selected mAbs. BG505 gp140-NFL2P was captured on anti-His Abs coated plate and was directly used from the trimer fraction of the SEC column. The ELISA plate was pre-coated with anti-His mAbs. The BG505 gp140-NFL2P trimers (taken directly from the SEC trimer fraction and before F105 negative selection) were captured on the plate by the anti-His Abs. The binding of selected panel of broadly neutralizing (bNAbs; b12, 2G12, VRCO1 and PGVO4), quaternary structure dependent or trimer specific bNAbs (VRCO6, PGT145, PGT151 and PG16) and non-neutralizing monoclonal antibodies (F105, b6 and F240) and V3 mAb, 447-D were studied by ELISA. As is evident from the binding curves, BG505-gp140 NFL2P shows very strong binding with all the bNAbs (except for b12 probably because b12 doesn't neutralize BG505) and also with the trimer specific bNAbs but almost no binding with the non-neutralizing Abs and the V3 Ab. The ELISA binding study confirms that BG505 gp140-NFL2P trimers is mimicking the native-like trimer conformation and represent the epitopes for the bNAbs, non-neutralizing epitopes are occluded and another advantage of this immunogen is that V3 loop seems to be buried, and thus BG505 gp140-NFL2P represent itself as a most suitable immunogen for further animal studies.

FIG. 24 depicts an antigenicity study of BG505 gp140-NFL2P trimers by ELISA: The ELISA plate was pre-coated with anti-His mAbs. The BG505 gp140-NFL2P trimers (taken directly from the SEC trimer fraction and before F105 negative selection) were captured on the plate by the anti-His Abs. The binding of selected panel of broadly neutralizing (bNAbs; b12, 2G12, VRCO1 and PGVO4), quaternary structure dependent or trimer specific bNAbs (VRCO6, PGT145, PGT151 and PG16) and non-neutralizing monoclonal antibodies (F105, b6 and F240) and V3 mAb, 447-D were studied by ELISA. As is evident from the binding curves, BG505-gp140 NFL2P shows very strong binding with all the bNAbs (except for b12 probably because b12 doesn't neutralize BG505) and also with the trimer specific bNAbs but almost no binding with the non-neutralizing Abs and the V3 Ab. The ELISA binding study confirms that BG505 gp140-NFL2P trimers is mimicking the native-like trimer conformation and represent the epitopes for the bNAbs, non-neutralizing epitopes are occluded and another advantage of this immunogen is that V3 loop seems to be buried, and thus BG505 gp140-NFL2P represent itself as a most suitable immunogen for further animal studies.

Figure 25A:
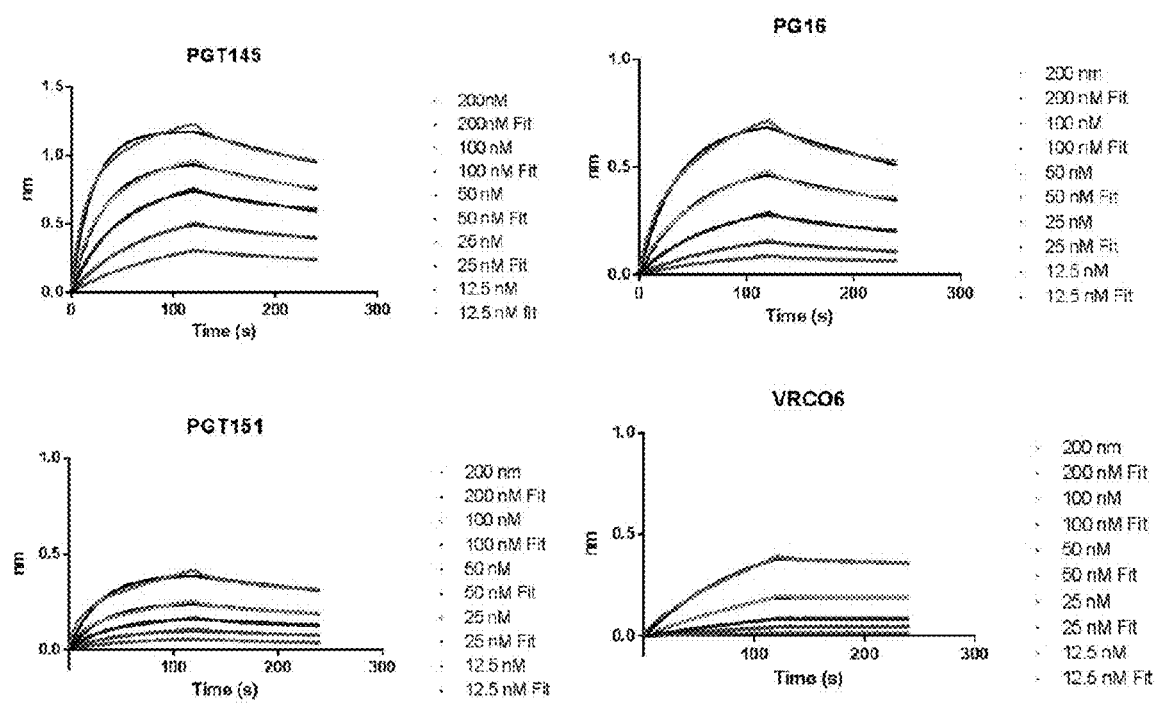
FIGS. 25A-C depict an antigenicity study of BG505 gp140-NFL2P trimers by Bio-Layer Interferometry technology (Octet): The binding of selected panel of broadly neutralizing (bNAbs; 2G12, VRCO1, PGVO4 and PGT121), quaternary structure dependent or trimer specific bNAbs (VRCO6, PGT145, PGT151 and PG16) and non-neutralizing monoclonal antibodies (F105 and b6) were studied by octet. The antibodies were captured on the anti-human IgG Fc sensor and the binding of BG505 gp140-NFL2P was studied at 5 different concentrations (200 nM, 100 nM, 50 nM, 25 nM and 12.5 nM). As is evident from the binding curves, BG505 gp140-NFL2P shows very strong binding with all the four bNAbs and also with the trimer specific bNAbs but very poor binding with the non-neutralizing Abs. The strongest binding was observed with trimer specific bNAb PGT145. The binding study confirms that BG505 gp140-NFL2P is present in a physiologically relevant trimeric conformation and represent the epitopes for the bNAbs and as desired for a bonafide immunogen it shows minimal binding with non-neutralizing Abs.
Figure 25B:
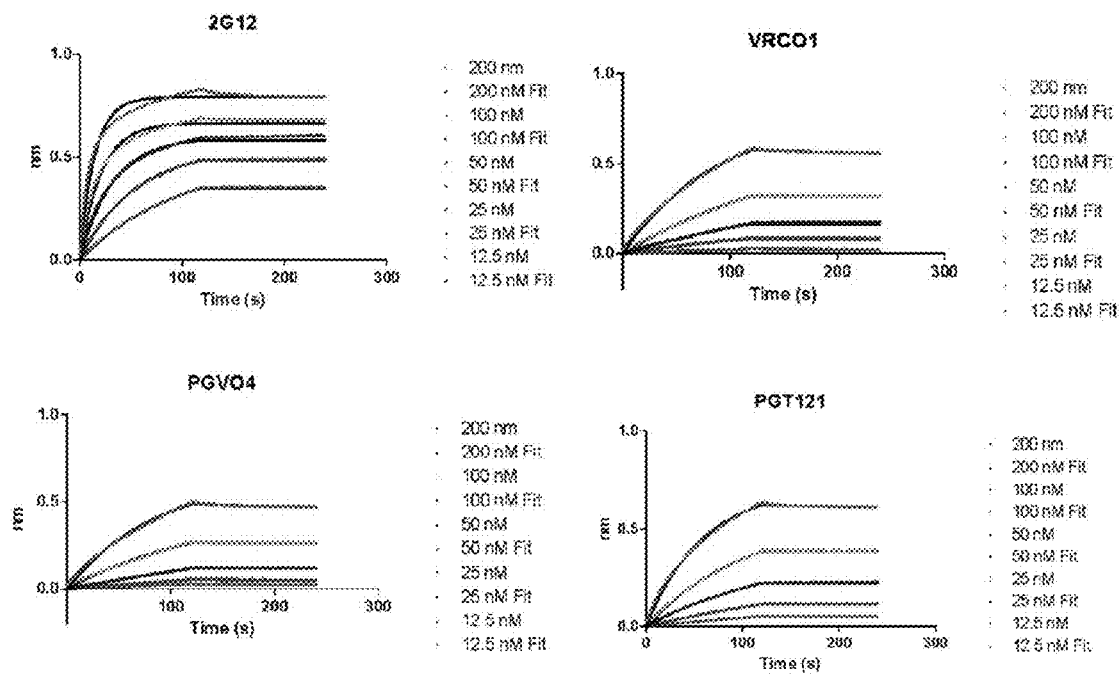
Figure 25C:
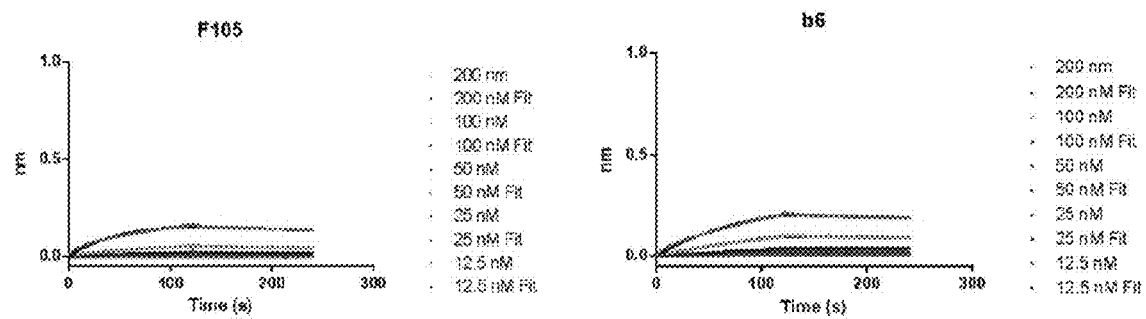

FIGS. 25A-C depict an antigenicity study of BG505 gp140-NFL2P trimers by Bio-Layer Interferometry technology (Octet): The binding of selected panel of broadly neutralizing (bNAbs; 2G12, VRCO1, PGVO4 and PGT121), quaternary structure dependent or trimer specific bNAbs (VRCO6, PGT145, PGT151 and PG16) and non-neutralizing monoclonal antibodies (F105 and b6) were studied by octet. The antibodies were captured on the anti-human IgG Fc sensor and the binding of BG505 gp140-NFL2P was studied at 5 different concentrations (200 nM, 100 nM, 50 nM, 25 nM and 12.5 nM). As is evident from the binding curves, BG505 gp140-NFL2P shows very strong binding with all the four bNAbs and also with the trimer specific bNAbs but very poor binding with the non-neutralizing Abs. The strongest binding was observed with trimer specific bNAb PGT145. The binding study confirms that BG505 gp140-NFL2P is present in a physiologically relevant trimeric conformation and represent the epitopes for the bNAbs and as desired for a bonafide immunogen it shows minimal binding with non-neutralizing Abs.

Figure 26:
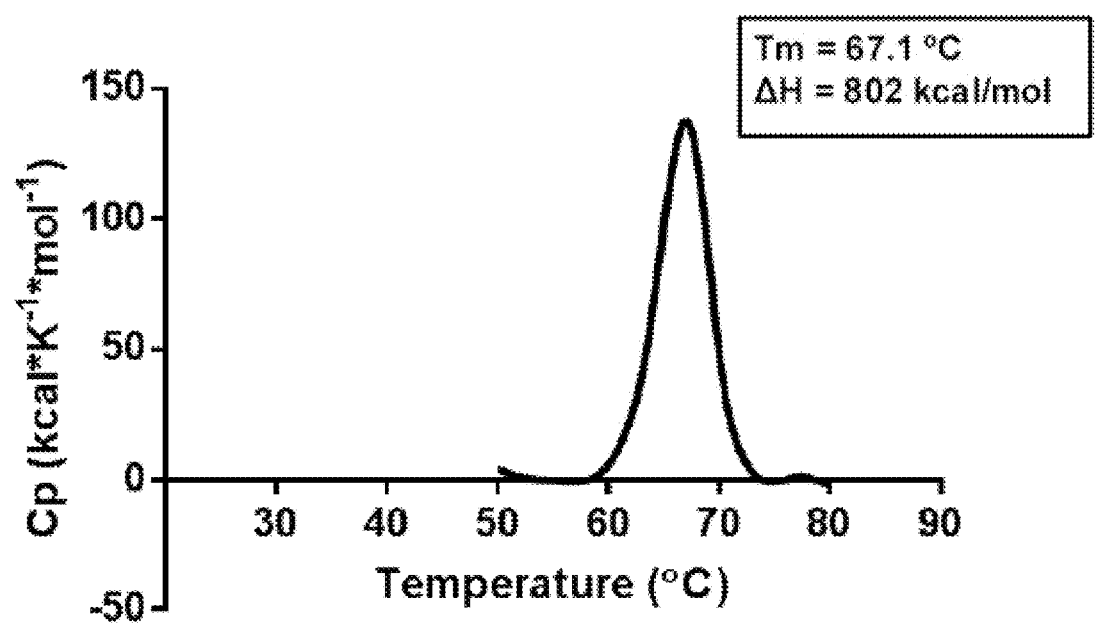
FIG. 26 depicts a DSC thermogram of BG505 gp140-NFL2P. The thermal stability of the BG505 gp140-NFL2P protein was analyzed by Differential Scanning calorimetry (DSC), the thermogram presented here a uniform single melting peak with the thermal denaturation midpoint or melting temperature (Tm) of 67.1° C. suggesting that the protein is homogeneous and considerably stable at high temperature.

FIG. 26 depicts thermal stability of BG505 gp140-NFL2P. The thermal stability of the BG505 gp140-NFL2P protein was analyzed by Differential Scanning calorimetry (DSC), the thermogram presented here a uniform single melting peak with the thermal denaturation midpoint or melting temperature (Tm) of 67.1° C. suggesting that the protein is homogeneous and considerably stable at high temperature.

Figure 27:
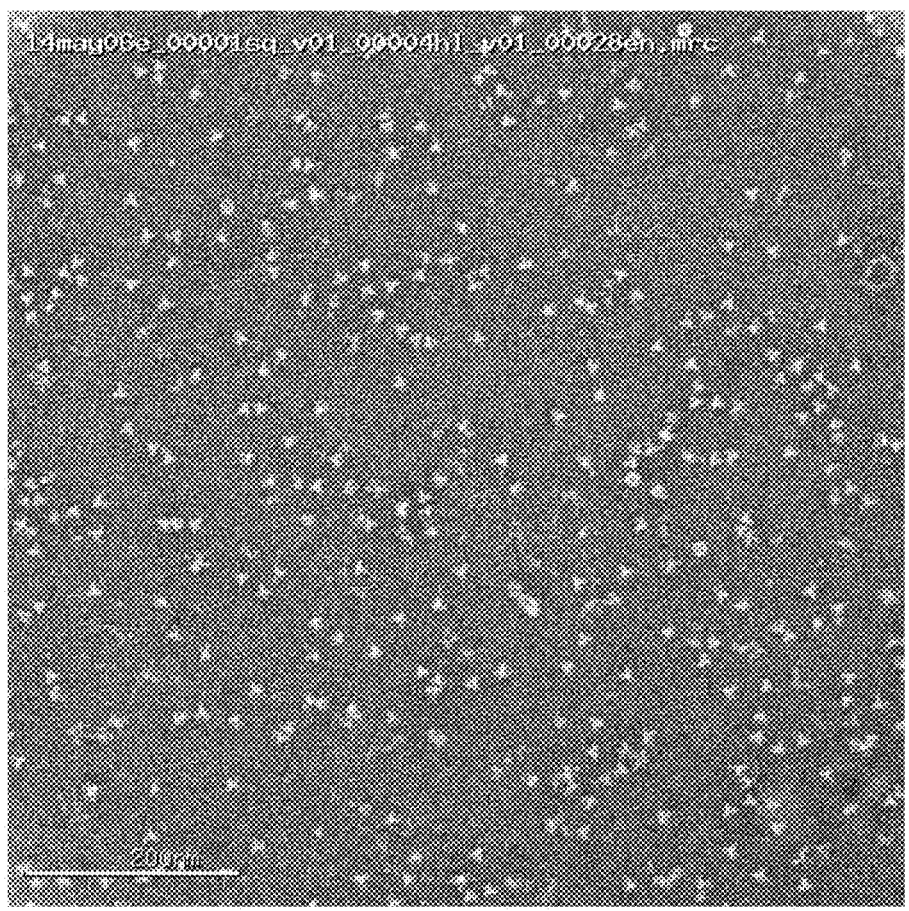
FIG. 27 depicts a negative stained EM micrograph of BG505 gp140-NFL2P env which confirms that almost all of the trimers are in native like well folded conformation. The sample used here was taken directly from the trimer peak of the SEC column and was not cleaned up by F105 negative selection. This suggests that for BG505 gp140-NFL2P there is no need to do negative selection.

FIG. 27 depicts a negative stained EM micrograph of BG505 gp140-NFL2P env confirms that almost all of the trimers are in native like well folded conformation. The sample used here was taken directly from the trimer peak of the SEC column and was not cleaned up by F105 negative selection. This suggests that for BG505 gp140-NFL2P there is no need to do negative selection.

Example 4: Isolation of Subtype B and C HIV-1 Spike Soluble Mimetics Using Negative Selection by Non-Neutralizing Antibodies The structure of BG505 gp140 SOSIP, a soluble mimic of the native HIV-1 envelope glycoprotein (Env), marks the beginning of new era in Env structure-based immunogen design. Displaying a well-ordered quaternary structure, these subtype A-derived trimers display an excellent antigenic profile, discriminating recognition by broadly neutralizing antibodies (bNAbs) from non-broadly neutralizing antibodies (non-bNAbs), and provide a solid Env-based immunogenic platform starting point. Even with this important advance, obtaining homogeneous well-ordered soluble SOSIP trimers derived from other subtypes remains challenging. Here, Applicants report the "rescue" of homogeneous well-ordered subtype B and C SOSIP trimers from a heterogeneous Env mixture using CD4 binding site-directed (CD4bs) non-bNAbs in a negative-selection purification process. These non-bNAbs recognize the primary receptor CD4bs only on disordered trimers but not on the native Env spike or well-ordered soluble trimers due to steric hindrance. Following negative selection to remove disordered oligomers, Applicants demonstrated recovery of well-ordered, homogeneous trimers by electron microscopy (EM). Applicants obtained 3D EM reconstructions of unliganded trimers, as well as in complex with sCD4, a panel of CD4bs-directed bNAbs, and the cleavage-dependent, trimer-specific bNAb, PGT151. Using bio-layer light interferometry Applicants obtained a full antigenic profile, demonstrating that the well-ordered trimers were avidly recognized by bNAbs and poorly recognized by non-bNAbs. Biophysical characterization was consistent with thermostability of a homogeneous species that could be further stabilized by specific bNAbs. Applicants establish a new means to obtain soluble Env mimetics derived from both subtypes B and C for expanded use as candidate vaccine immunogens.

This study presents an artful means using HIV non-broadly neutralizing antibodies to isolate new well-ordered trimers engineered to mimic the virus surface protein. These soluble spike mimetics, called SOSIPs, derive from different genetic HIV subtypes B and C, and complement the recently described subtype A-derived BG505 SOSIP. The comprehensive biochemical analysis presented demonstrates that these new homogeneous soluble trimers are faithful mimics of the HIV spike and more importantly provides a novel means to purify a wider array of soluble Env trimers for future structural and immunogenicity studies. Possessing soluble and stable mimics of the HIV spike derived from diverse strains will improve both Applicants' knowledge of HIV spike architecture and extend the geographical/genetic coverage of future vaccine candidates.

The HIV-1 envelope glycoprotein (Env) is a trimer of heterodimers composed of two non-covalently associated subunits; the receptor-binding gp120, and the fusion machinery-containing gp41. Each subunit is derived from a gp160 precursor glycoprotein following cleavage by cellular furins (Wyatt R & Sodroski J (1998) Science 280(5371): 1884-1888). HIV-1 gp120 binds the CD4 molecule on the surface of human target T cells to initiate the viral entry process, and following co-receptor engagement, fusion is mediated by gp41 (Dalgleish A G, et al. (1984) Nature 312(5996):763-767; McDougal J S, et al. (1986) J Immunol 137(9):2937-2944; mKarlsson Hedestam G B, et al. (2008) Nat Rev Microbiol 6(2):143-155). The surface-exposed HIV-1 Env trimer is the sole target for antibodies capable of neutralizing the virus (Burton D R, et al. (2004) Nat Immunol 5(3):233-236). Recently, a myriad of Env-directed broadly neutralizing antibodies (bNAbs) were isolated from numerous HIV-1-infected individuals, demonstrating that the human B cell response can effectively inhibit this variable pathogen (Wu X, et al. (2010) Science 329(5993):856-861; Walker L M, et al. (2009) Science 326(5950):285-289; Walker L M, et al. (2011) Nature 477(7365):466-470; Huang J, et al. (2012) Nature 491(7424):406-412; Scharf L, et al. (2014) Antibody 8ANC195 reveals a site of broad vulnerability on the HIV-1 envelope spike. Cell reports 7(3):785-795; Klein F, et al. (2012) J Exp Med 209(8):1469-1479). Infection of macaques by a chimeric model virus, SHIV, can be prevented by prior passive immunization of all bNAbs so far tested, confirming the capacity of neutralizing antibodies to prevent HIV infection (Mascola J R, et al. (1999) J Virol 73(5):4009-4018; Hessell A J, et al. (2009) PLoS Pathog 5(5):e1000433; Moldt B, et al. (2012) Proc Natl Acad Sci USA 109(46):18921-18925; Barouch D H, et al. (2013) Therapeutic efficacy of potent neutralizing HIV-1-specific monoclonal antibodies in SHIV-infected rhesus monkeys. Nature 503(7475):224-228).

Along with virus-specific T cells, an efficacious HIV-1 vaccine therefore would likely need to generate bNAbs targeting Env. Although the premise is simple, in actuality, it is a tremendous challenge without precedent in the history of vaccinology. The difficulty to vaccinate against HIV arises from the extensive variability of Env present on the large number of HIV-1 isolates simultaneously circulating in the human population as well as other mechanisms of immune evasion selected for by strong pressure from the human immune system.

Generally, vaccine-generated antibodies using either or both gp120 or gp41 sequences do not recognize native Env on the surface of cells or virus, do not neutralize primary isolates in vitro, and do not prevent infection in laboratory animals (Burton D R, et al. (2011) Proc Natl Acad Sci USA 108(27):11181-11186; Sundling C, et al. (2012) Science translational medicine 4(142):142ra196; Tran K, et al. (2014) Vaccine-elicited primate antibodies use a distinct approach to the HIV-1 primary receptor binding site informing vaccine redesign. Proc Natl Acad Sci USA 111(7):E738-747). Non-neutralizing antibodies directed to the major variable region two (V2) of gp120 are associated with modest efficacy in a single human clinical trial (Haynes B F, et al. (2012) N Engl J Med 366(14):1275-1286; Zolla-Pazner S, et al. (2014) Vaccine-induced IgG antibodies to V1V2 regions of multiple HIV-1 subtypes correlate with decreased risk of HIV-1 infection. PLoS One 9(2):e87572), while, in general, Env-elicited antibodies fail to demonstrate protection in previous human clinical trials (Jones N G, et al. (2009) Vaccine 27(7):1136-1140; Rerks-Ngarm S, et al. (2009) N Engl J Med 361(23):2209-2220; Yates N L, et al. (2014) Vaccine-induced Env V1-V2 IgG3 correlates with lower HIV-1 infection risk and declines soon after vaccination. Science translational medicine 6(228):228ra239).

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci USA 111(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-1 primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci USA 109(30):12111-12116; Nkolola J P, et al. (2014) Comparison of multiple adjuvants on the stability and immunogenicity of a clade C HIV-1 gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bNAbs, (GE148 and GE136) generated following immunization of uncleaved gp140 trimers (YU2 gp140-foldon) in non-human primates (NHP). Non-bNAbs, represented by GE136 and 148, can only neutralize the sensitive so-called "tier 1 viruses" that are not representative of the more neutralization resistant tier 2-like primary isolates circulating in the human population. Using crystallography, EM reconstructions, paratope scanning and molecular modeling Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci USA 111(7):E738-747).

The cumulative historical data have led to the hypothesis that a more faithful mimic of the HIV-1 spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNH1144 SOSIP is also available but does not provide atomic level details (Bartesaghi A, Merk A, Borgnia M J, Milne it, & Subramaniam S (2013) Nat Struct Mol Biol 20(12):1352-1357). The BG505 SOSIP and KNH1144 SOSIP trimers are derived from the Env sequences of the subtype A BG505 and KNH1144 strains. These soluble trimers possess an engineered disulfide linkage between the gp120 and gp41 (at residues 501C and 605C, respectively) and an additional mutation in the heptad repeat 1 (HR1) of gp41 (I559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-1 primary strains were attempted over the past decade, the BG505- and KNH1144-derived SOSIP trimers are the two limited examples of SOSIPs that yield homogeneous trimers suitable for high resolution biophysical and structural analysis. The structural explanation for the difficulty to readily transfer the SOSIP design to other HIV-1 strain-derived sequences is not yet fully understood and would be valuable information to broaden the trimer design horizon.

Here, Applicants describe two SOSIP trimer molecules derived from the B subtype strain, JRFL, and the subtype C strain, 16055. Applicants selected these two Envs for the initial results reported in this study as follows. The JRFL SOSIP trimer, truncated at residue 663 (JRFL SOSIP.663) derives from the JRFL HIV-1 strain isolated from the frontal lobe (FL) of an HIV-1-infected individual. This Env is often used because it displays the unusual property that its gp160 Env precursor is efficiently cleaved into the gp120 and gp41 subunits when expressed on the cell surface of 293F HEK cells (Pancera M & Wyatt R (2005) Virology 332(1):145-156). The 16055 SOSIP.663 trimer, also truncated at residue 663, derives from a HIV-1 Indian strain and displays the unusual property that its monomeric gp120 is recognized by the quaternary epitope-preferring bNAbs, PG9 and PG16, which is relatively infrequent amongst most HIV-1 Env sequences (McLellan J S, et al. (2011) Nature 480(7377): 336-343), and is also observed for BG505 gp120 (Julien J P, et al. (2013) Proc Natl Acad Sci USA 110(11):4351-4356; Hoffenberg S, et al. (2013) J Virol 87(10):5372-5383).

In the current study, Applicants demonstrate that the JRFL and 16055 SOSIP.663 trimers were purified to homogeneity by a novel means of isolation that utilizes non-bNAbs targeting the CD4-binding site (CD4bs) in a negative-selection process that effectively separates well-ordered trimers from a mixture also containing disordered trimers and other oligomeric states of Env. By binding kinetic analysis, Applicants demonstrated that the purified JRFL and 16055 SOSIP.663 trimers were efficiently recognized by bNAbs but were poorly recognized by the non-bNAbs. By negative stain EM, Applicants confirmed that negative selection results in homogeneous, three-fold symmetric JRFL and 16055 SOSIP.663 trimers resembling the native HIV spike and the previously described subtype A SOSIPs. Applicants obtained 3D EM reconstructions of the unliganded and liganded JRFL and 16055 SOSIP.663 trimers and demonstrated that the negatively selected trimers adopt conformational changes upon sCD4 engagement that emulate those of the native HIV spike (Liu J, et al. (2008) Nature 455(7209): 109-113). Differential scanning calorimetry (DSC) and differential scanning fluorimetry (DSF) revealed that the negatively selected JRFL and 16055 SOSIP.663 trimers were stable at temperatures exceeding 55 and 63° C., respectively. Applicants conclude that the negative-selection process resulted in highly homogenous well-ordered JRFL and 16055.663 trimers, expanding the SOSIP family of Env mimetics to HIV-1 subtypes B and C. This advance provides opportunities for HIV Env structural comparisons at high resolution as well as a wider array of ordered trimers for sequential or simultaneous inoculation regimens to evaluate enhanced immunogenicity toward more broadly effective antibody responses.

Figure 36A:
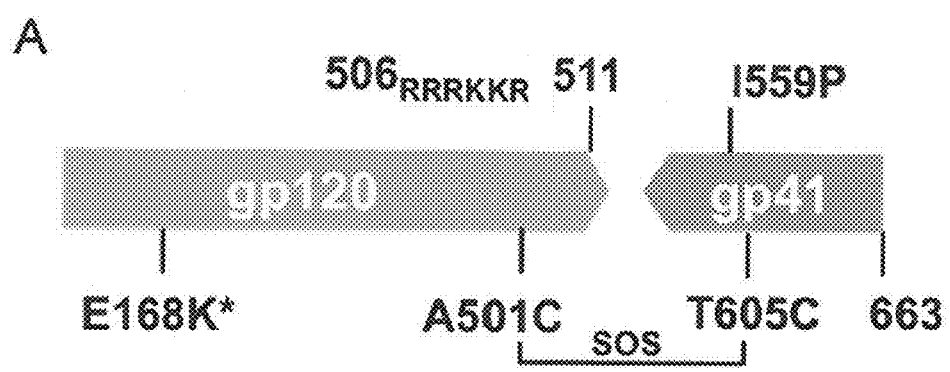

Purification of the SOSIP trimers by negative selection results in well-ordered trimers. As an overall approach, the JRFL SOSIP.663 and 16055 SOSIP.663 trimer glycoproteins, designed on the established SOSIP template as described in Methods and FIG. 36A, were purified in three steps consisting of lectin-affinity chromatography, followed by size exclusion chromatography (SEC), followed by a final negative-selection procedure (FIG. 28A schematic). Blue native polyacrylamide gel electrophoresis (BN-PAGE) analysis of the lectin-purified proteins revealed bands corresponding to the expected size of SOSIP.663 trimers, along with undesired monomers, dimers and higher-order oligomeric forms. The distribution of oligomers was slightly different for JRFL SOSIP.663 than for 16055 SOSIP.663. The JRFL SOSIP.663 glycoproteins presented as a predominant band corresponding to the trimeric species with lower intensity bands corresponding to dimeric and momeric forms. In contrast, 16055 SOSIP.663 displayed bands of similar magnitude for all oligomeric forms detected (FIG. 28B). The lectin-purified glycoproteins of both SOSIP types were subjected to SEC and the corresponding chromatograms corroborated the distribution of oligomeric forms observed by BN-PAGE. Specifically, the JRFL SOSIP protein peak corresponding to the trimeric form of SOSIP.663 eluted at approximately 11 ml, with a shoulder at 12 ml, corresponding to dimers, with a smaller peak at 13 ml corresponding to monomers (FIG. 28C). The 16055 SOSIP SEC profile showed three overlapping peaks of similar magnitude, suggesting a less efficient tendency of this Env to form SOSIP trimers compared to JRFL (FIG. 28C). Elution fractions containing the expected trimers (elution volume 10-12 ml) were collected and contained primarily trimers along with associated dimers and monomers that could not be resolved by SEC.

With the goal of resolving the mixture of SOSIP oligomeric states, Applicants reasoned that the CD4bs-directed non-bNAbs GE136 or GE148 might be able to absorb out disordered trimers and monomers. Applicants also included the similar, but infection-elicited CD4bs-directed non-bNAb, F105, in Applicants' analysis. Each of these non-bNAbs inefficiently target the CD4bs on the trimeric HIV spike with a vertical angle of approach that clashes with the variable region cap on well-ordered trimers (Tran K, et al. (2014) Proc Natl Acad Sci USA 111(7):E738-747) and therefore do not neutralize either JRFL or 16055 virus. Applicants sought to use these CD4bs-directed non-bNAbs to remove the disordered, and presumably more conformationally open, trimers, dimers and monomers from the oligomeric mixture in a negative-selection purification step. To begin, Applicants first assessed which non-bNAb most efficiently immune-precipitated the unresolved Env forms from the mixture, selecting F105 for JRFL and GE136 for 16055, which displayed favorable binding kinetic parameters for the respective gp120s (FIG. 36B). F105 did not efficiently immune-precipitated 16055 Env forms and also displayed a faster dissociation rate for 16055 gp120 (FIG. 36B). Subsequently, lectin- and SEC-purified SOSIP samples were flowed over protein A affinity columns with F105 or GE136 previously immobilized on this matrix. Analyzing the flow through from the affinity-column, Applicants observed that the SOSIP.663 trimers migrated as a highly homogenous single peak by SEC, suggesting that negative-selection approach removed aggregates, dimers, and monomers (FIG. 28C). Negative selection retained disordered trimers, dimers and monomers on the solid phase, presumably by allowing the non-bNAbs F105 or GE136 access to the CD4bs on these aberrant forms of Env. This retention is readily apparent for 16055, where the disappearance of the dimer and monomer bands on the BN-PAGE gel can be observed following negative selection compared to before (FIG. 28B). BN-PAGE analysis of the lectin- and SEC-purified, negatively selected JRFL and 16055 SOSIP.663 trimers revealed a single band corresponding to the expected size of a trimeric SOSIP.663 protein (FIG. 28B). To confirm the effectiveness of the separation process, Applicants examined the SOSIP.663 samples before and after the negative-selection affinity chromatography process by negative stain EM. Visual inspection of the EM micrographs showed a pronounced reduction of aberrant or disordered SOSIP oligomers following negative selection (FIG. 29A). Negative selection yielded nearly 100% highly homogeneous well-ordered native-like trimers in the respective eluates based on EM 2D classification (FIG. 29B). As expected, reducing SDS-PAGE revealed that both negatively selected JRFL and 16055 SOSIP.663 trimers appeared as two bands on the gel, corresponding to Env glycoprotein subunits gp120 and gp41, indicating effective Furin cleavage of the SOSIPs (FIG. 36C).

Figure 30:
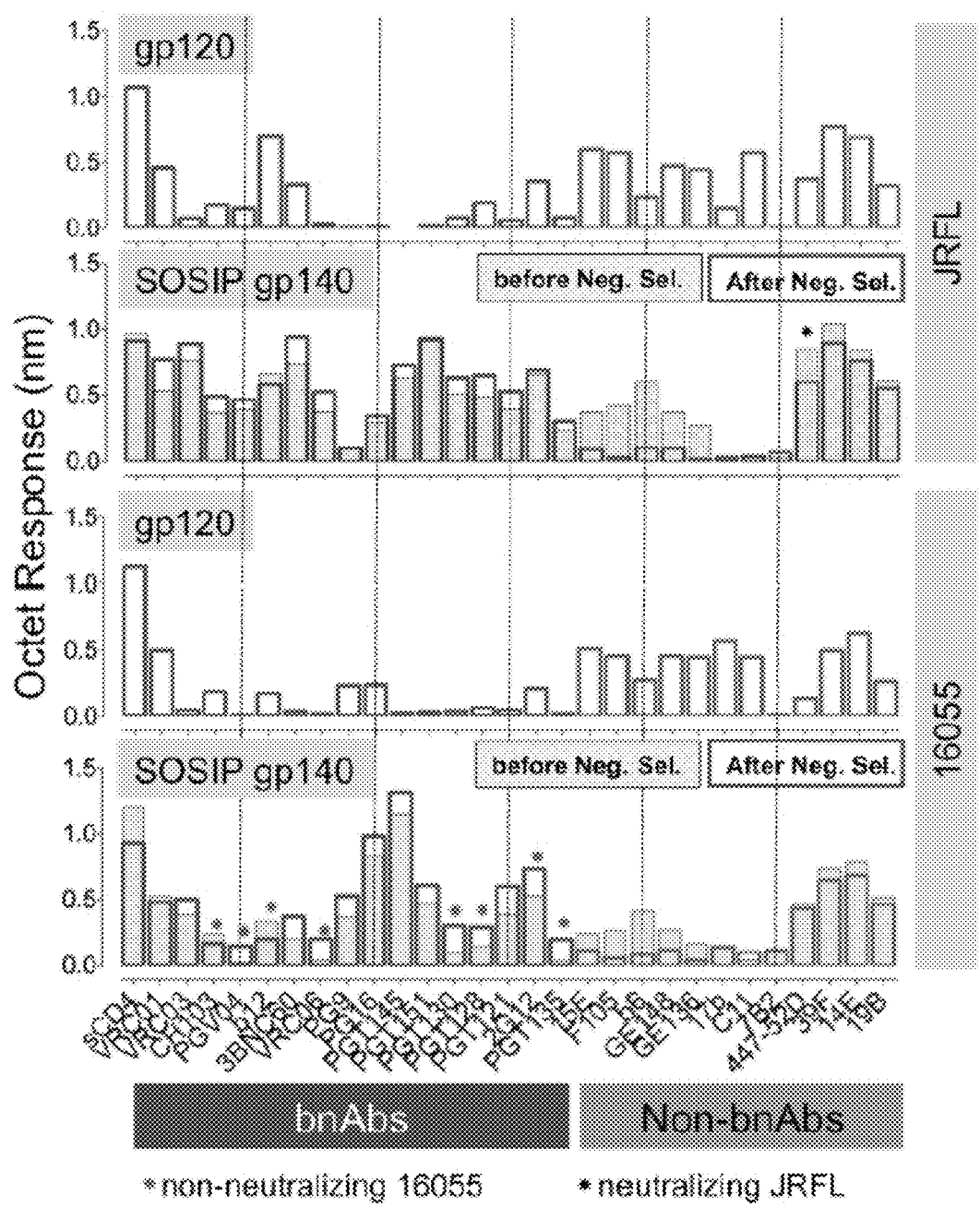
FIG. 30 depicts overall antigenic profiles of SOSIP trimers and gp120 control monomers. Bars represent Octet response values obtained when either SOSIP.663 trimers (200 nM) or gp120 monomers (600 nM) in solution were run over an anti-human IgG Fc sensor immobilized with a panel of well-characterized anti-HIV-1 Env monoclonal antibodies with diverse specificities and neutralization capacities. The blue bars represent BLI response values obtained against a panel of broadly neutralizing antibodies whereas the red bars denote BLI response values generated by non-bNAb or non-neutralizing monoclonal antibodies. The grey dotted bars on the SOSIP.663 gp140 samples represent values obtained before negative selection.

Antigenic analysis of JRFL and 16055 SOSIP.663 by bio-layer interferometry (BLI) confirms recognition by bNAbs. Applicants next investigated the effect of negative-selection on trimer antigenicity and binding kinetics using a set of bNAbs and non-bNAb monoclonal antibodies (mAbs) directed toward different Env epitopes. The CD4bs-directed mAbs such as VRC01, b12, F105, b6 and the quaternary epitope preferring PG9, PG16, PGT151, VRC06 and PGT145, were especially useful for this analysis. Their recognition of the SOSIP trimers, or lack thereof, provided a means to discern between an "open" or disordered conformation of the trimer compared to a well-ordered, native-like trimer conformation where binding of the non-bNAbs would be minimal and the bNAbs, including those trimer-preferring, would bind avidly. Applicants employed BLI (Octet) to assess mAb binding to JRFL and 16055 SOSIP.663 trimers in solution, before and after negative selection, and to their respective gp120 monomers as controls. Applicants plotted the BLI maximal response values as a bar graph, permitting a semi-quantitative relative assessment of overall affinity for each mAb's recognition of Env (FIG. 30). Using monomeric gp120 as the analyte eliminates potentially confounding avidity effects and clearly demarks mAbs with a preference for quaternary, trimer-dependent epitopes. The antigenic profile comparing binding to monomeric gp120 and SOSIP.663 trimers before and after negative selection is shown in FIG. 30. Negatively selected SOSIP.663 trimers displayed the most desirable antigenic profile, displaying strong recognition by most bNAbs while not being recognized by most non-bNAbs. JRFL SOSIP.663 had a more extensive coverage of bNAbs than 16055 SOSIP.663 since the latter was not recognized by some of the subtype B infection-derived bNAbs targeting the CD4bs.

Figure 31:
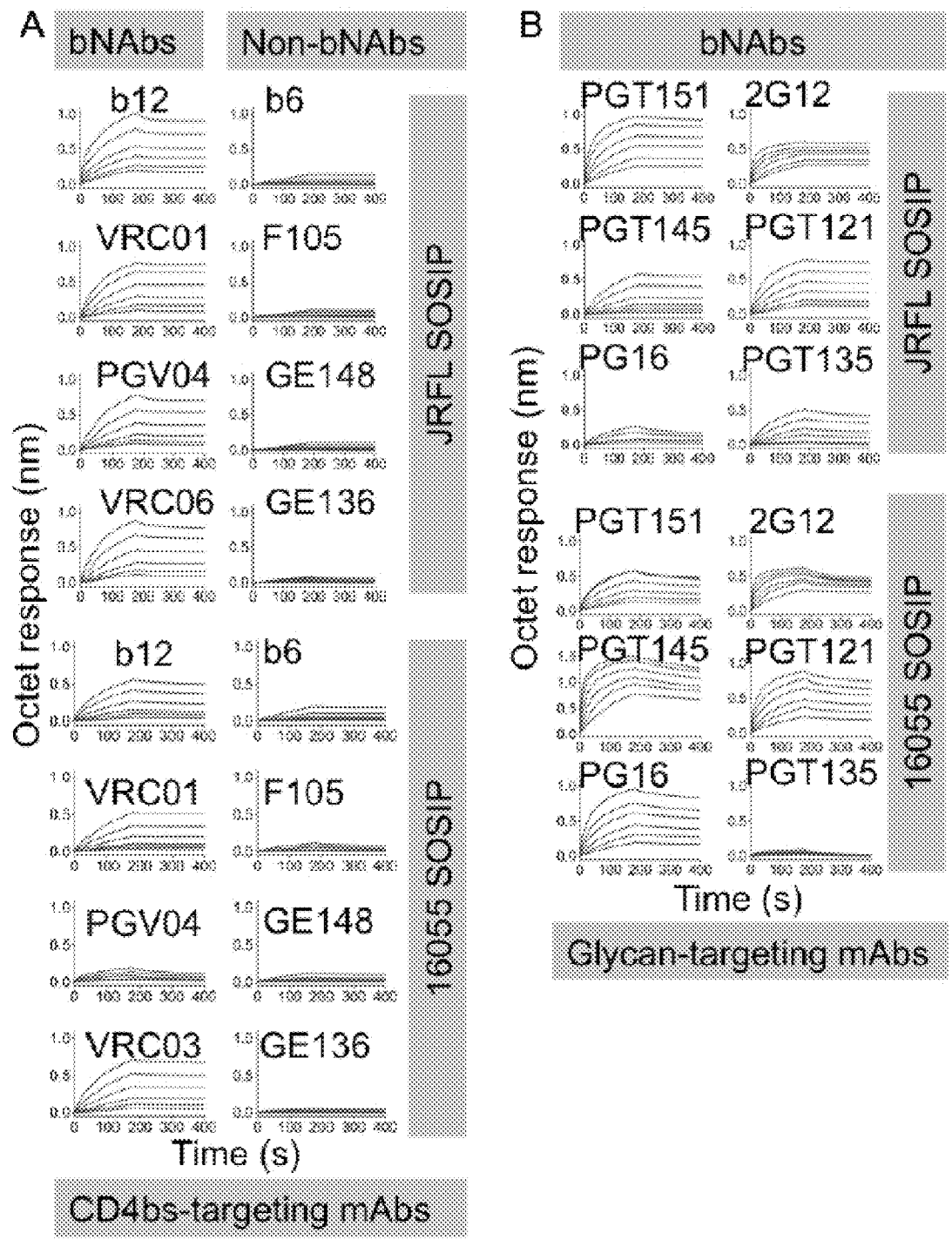
FIGS. 31A-B depict bio-layer interferometry (BLI) analysis of CD4bs- and glycan-targeting mAbs. (A) BLI curves generated with a panel of CD4bs-targeting antibodies immobilized on anti-human IgG Fc sensors and a serial dilution (200 nM-6.25 nM) of negatively selected SOSIP.663 trimers in solution as the analyte. (B) Similar BLI curves obtained with glycan-targeting bNAbs.
Figure 37:
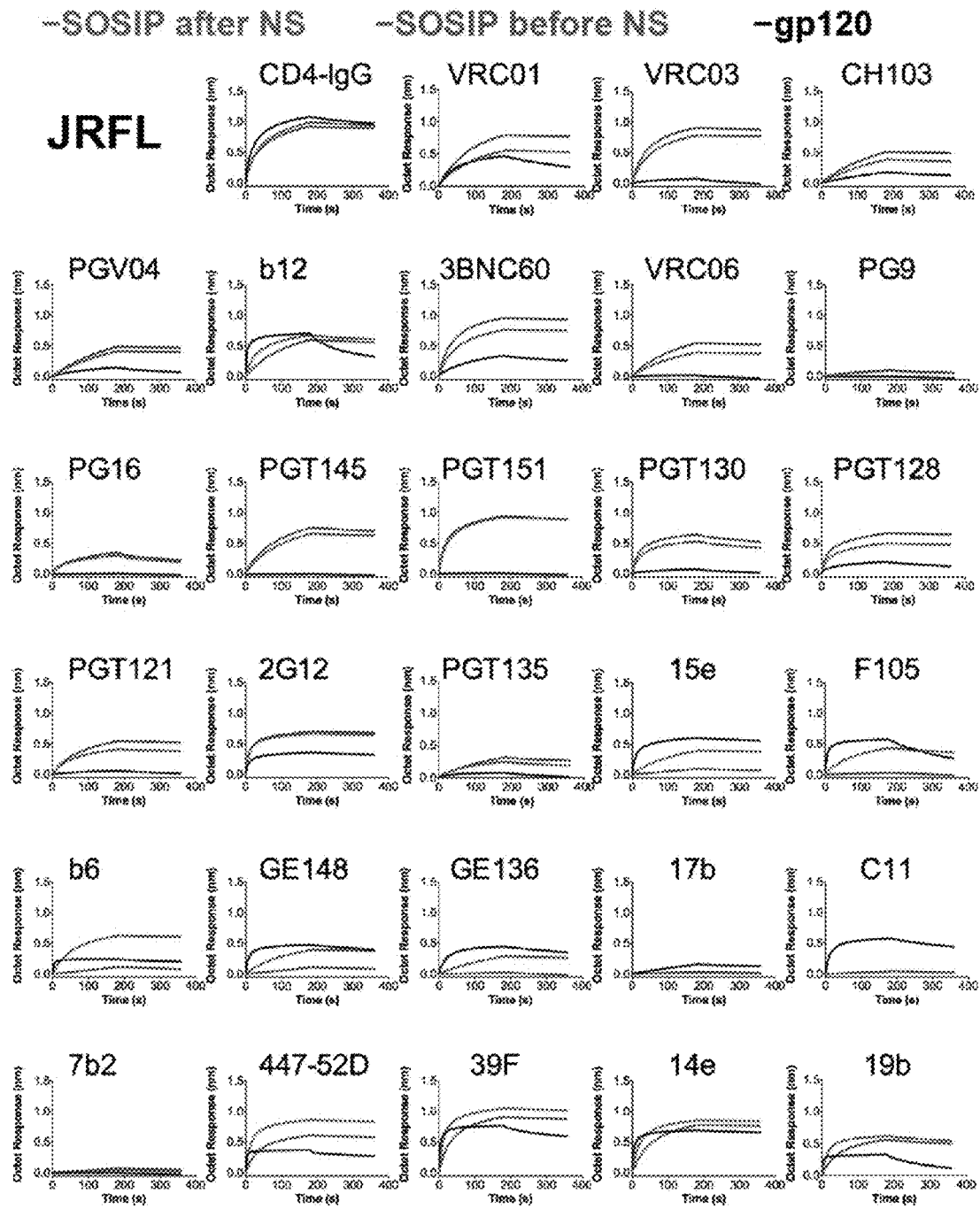
FIG. 37 depicts a bio-layer interferometry (BLI) analysis of JRFL SOSIP.663 trimers and gp120 monomers. A panel of HIV-1 mAb IgGs were immobilized on an anti-human IgG Fc sensor. JRFL SOSIP.663 mixtures before negative selection (200 nM) and after negative selection JRFL SOSIP.663 (200 nM), and monomeric JRFL gp120 (600 nM) were assessed as analytes in solution (PBS pH 7.4) to generate the BLI curves. CD4-IG was used to estimate the concentration of gp120 that would give a similar magnitude response relative to SOSIP.663 trimeric protein. Black curves represent avidity-free binding events between monomeric gp120 in solution and the corresponding immobilized ligand. The red and blue curves represent binding parameters of the SOSIP.663 trimeric proteins before and after negative selection. The association and dissociation phases were 180s each in duration.
Figure 38:
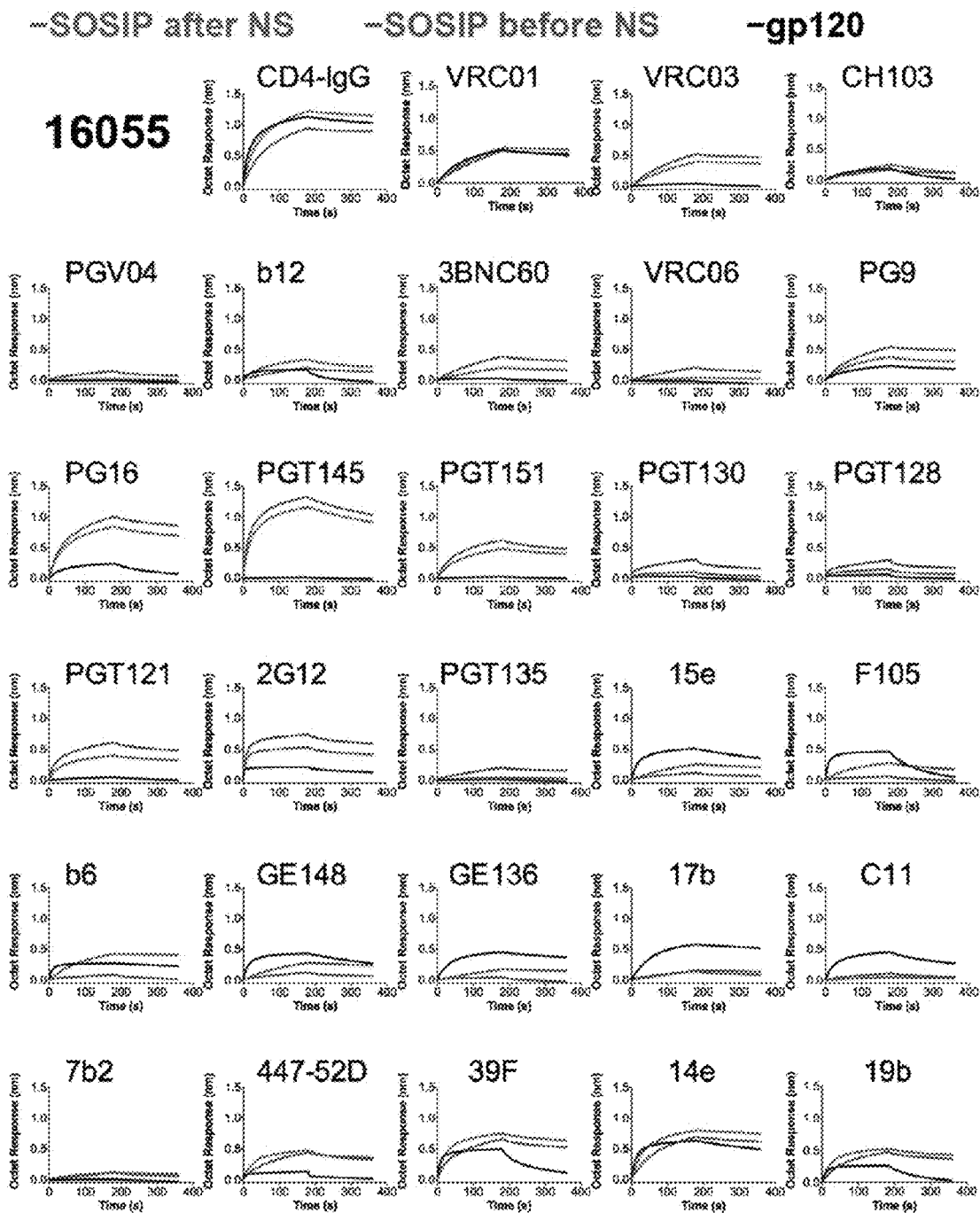
FIG. 38 depicts a BLI analysis of 16055 SOSIP.663 trimers and gp120 monomers.

Applicants observed that negative selection almost completely abrogated recognition of JRFL and 16055 SOSIP.663 trimers by the CD4bs-directed non-bNAbs ("F105-like"), compared to before negative selection. By inspection, the overall recognition of the SOSIPS by most bNAbs was relatively avid (FIG. 30 and FIG. 31A). The preferential recognition by bNAbs following negative selection suggested that this process efficiently eliminated disordered oligomers. In sum, mAbs 15e, F105, b6, GE136 and GE148 strongly bound gp120 and SOSIP samples before negative-selection, but only gp120 following SOSIP negative selection (FIG. 30 and FIG. 31A). Every CD4bs-directed bNAb tested efficiently recognized the negatively selected JRFL SOSIP trimers, however, 16055 SOSIP trimers were only recognized by VRC01, VRC03 and 3BNC60 while b12, PGV04, CH103 and VRC06 binding was minimal (FIG. 30, FIG. 37 and FIG. 38). This is likely because b12, PGV04, CH103 and VRC06 do not neutralize the subtype C HIV-1 strain, 16055, consistent with the lack of binding to the negatively selected and well-ordered 16055 SOSIP trimers (Table 51).

The bNAbs PG9, PG16, PGT145 and PGT151 are known for their quaternary epitope specificity and, as such, they do not efficiently recognize monomeric gp120 (Walker L M, et al. (2011) Nature 477(7365):466-470; Blattner C, et al. (2014) Immunity; Falkowska E, et al. (2014) Immunity; Walker L M, et al. (2009) Science 326(5950):285-289). Using monomeric gp120 as an analyte for binding analysis suggested that antibodies PGT121, PGT130 and PGT135 may also have preference for quaternary epitopes or a gp120 conformation as in the native spike since they each displayed almost no detectable on-rate for monomeric gp120 (FIG. 37 and FIG. 38) (Julien J P, et al. (2013) Crystal structure of a soluble cleaved HIV-1 envelope trimer. Science 342(6165):1477-1483; Hoffenberg S, et al. (2013) J Virol 87(10):5372-5383; Julien J P, et al. (2013) PLoS Pathog 9(5):e1003342; Kong L, et al. (2013) Nat Struct Mol Biol 20(7):796-803). These data were consistent with similar data for VRC06, which is trimer-preferring (Li Y, et al. (2012) J Virol 86(20):11231-11241). Not surprisingly, the VRC06-related mAb, VRC03, displayed similar binding properties (FIG. 37 and FIG. 38). In fact, all of these putative trimer-preferring antibodies showed increased recognition of SOSIP trimers, as compared with monomeric gp120 (FIG. 30, FIG. 31B, FIG. 37 and FIG. 38). Negative selection enhanced trimer-preferring mAb binding, consistent with efficient removal of the disordered oligomers (FIG. 30).

Applicants also assessed binding of bNAbs 2G12, PGT121, PGT128, PGT130 and PGT135 that target an array of glycans clustered around the N332 glycan. While the subtype B JRFL isolate is naturally glycosylated at the N332 site, the subtype C 16055 Env lacks this N-linked glycan. JRFL SOSIP.663 was robustly recognized by all glycan-dependent bNAbs tested, whereas 16055 SOSIP.663 trimers were poorly recognized by mAbs PGT128, PGT30 and PGT135. However, 2G12 and PGT121 binding remained relatively strong, despite faster off-rates compared to JRFL SOSIP.663, suggesting that the latter two antibodies may use other glycans that compensate for the missing 16055 332 N-linked glycan, as recently suggested for PGT121 (FIG. 30, FIG. 31B, FIG. 37 and FIG. 38) (Sok D, et al. (2014) Science translational medicine 6(236):236ra263). PGT121 is the only antibody that Applicants tested targeting this N332 glycan "site of vulnerability" that neutralizes the HIV-1 subtype C strain, 16055 (Table 51).

Figure 39:
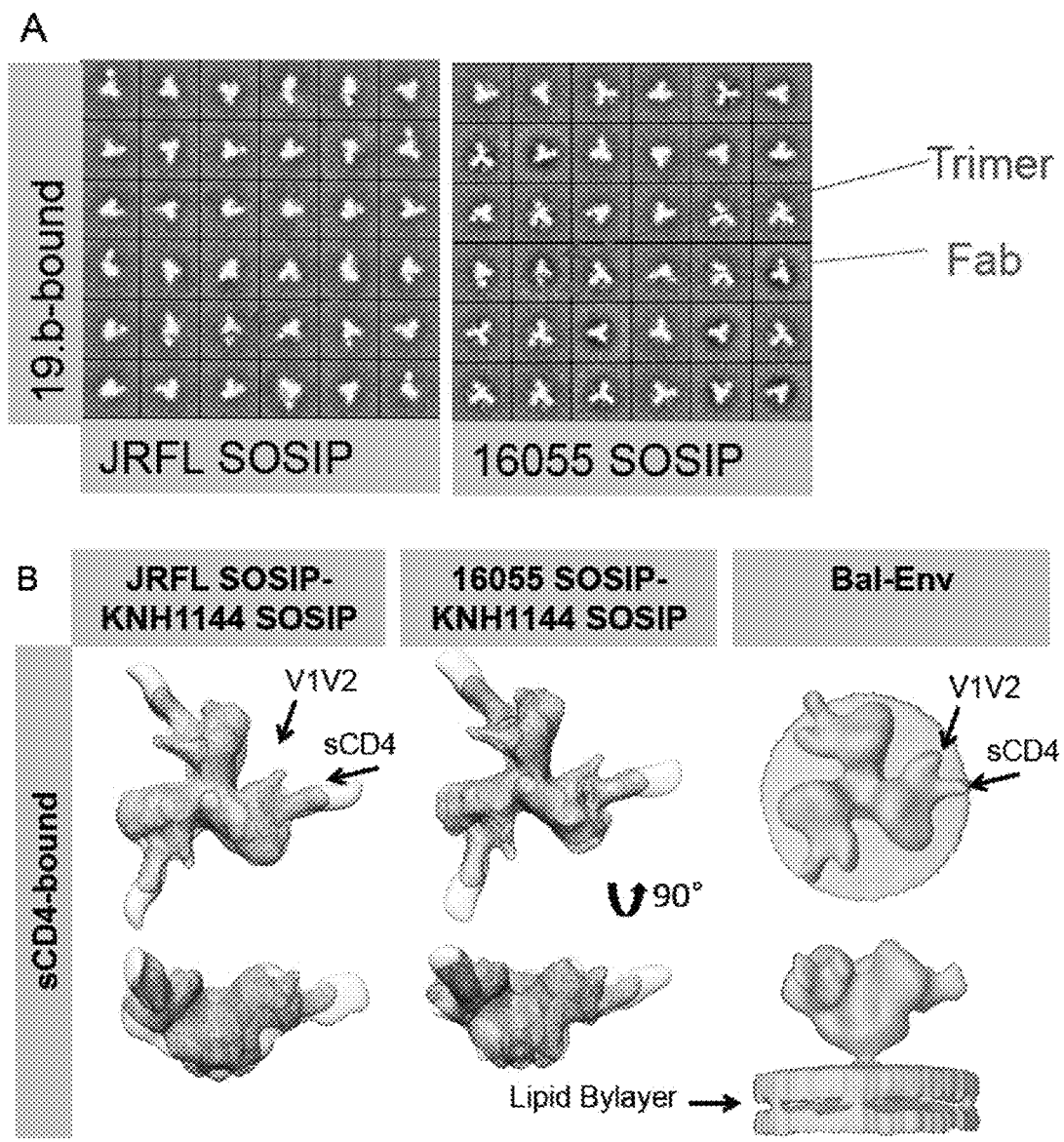
FIGS. 39A-B depict an EM 2D class averages of 19b-bound SOSIP.663 trimers and comparison of sCD4-bound trimer 3D EM models. (A) Negatively selected JRFL SOSIP.663 and 16055 SOSIP.663 trimers incubated with the V3-directed non-bNAb, 19b. The blue arrow indicates a trimer and the red arrow indicates a Fab. (B) Superimposition of four-domain sCD4-bound JRFL SOSIP.663 (left) and 16055 SOSIP.663 (middle) in grey over the two-domain sCD4-bound KNH1144 SOSIP.664 in orange (EMD 5708). For comparison, on the right is the two-domain sCD4-liganded native BaL Env (EMD 5455).

Non-neutralizing mAbs targeting other Env sites, such as 17b, C11, 7b2, did not recognize the negatively selected JRFL and 16055 SOSIP.663 trimers. The V3-directed non-bNAbs 447-52D, 39F, 14e and 19b did recognize the SOSIP.663 trimers even after F105 or GE136 negative selection (FIG. 30, FIG. 37 and S3). However, negative selection reduced recognition by these antibodies, as assessed by an overall decrease in the Octet response values (FIG. 30). By EM, the 19b Fab infrequently bound the negatively selected JRFL or 16055 SOSIP.663, demonstrating binding by only one Fab to 25 and 22% of trimers, respectively (FIG. 39A). This occupancy was comparable to that displayed by the BG505 SOSIP.664 where 30% of the trimers bound one V3-directed Fab (Sanders R W, et al. (2013) PLoS Pathog 9(9):e1003618). Recognition by the V3 antibodies as assessed by BLI with the multivalent SOSIP trimers as an analyte, may increase the sensitivity of detection due to avidity effects that are eliminated with the Fab in the EM context.

Figure 32:
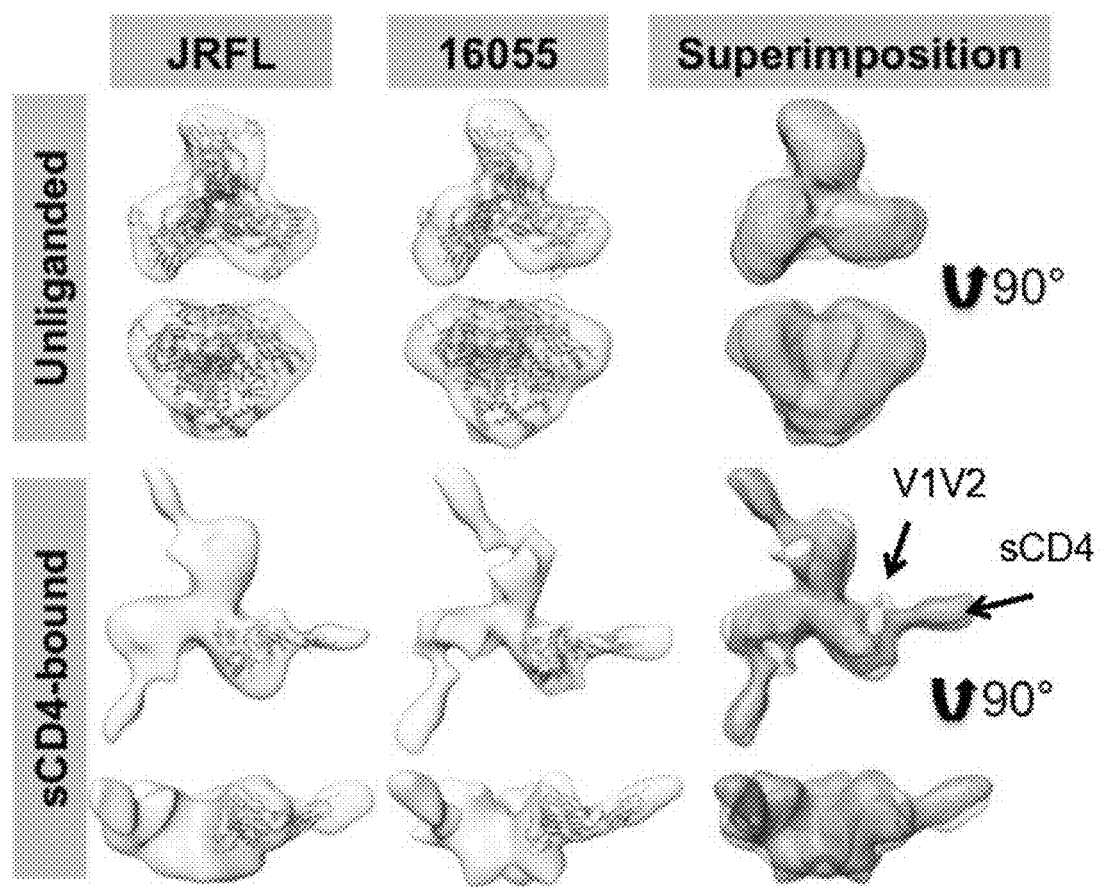
FIG. 32 depicts EM 3D reconstructions of unliganded and sCD4-liganded SOSIP.663 trimers. Top panels display top and side views of the unliganded JRFL and 16055 SOSIP.663 trimers 3D reconstruction EM densities in gray with the BG505 SOSIP.664 EM structure (PDB ID 3J5M, gp120 in blue, V1V2 in magenta, V3 in green and gp41 in brown) fitted within. Bottom panel displays top and side views of the four-domain soluble CD4-liganded SOSIP.663 trimers with the sCD4-bound gp120 core crystal structure (PDB ID 1GC1, gp120 in blue and sCD4 in red) fitted in the EM density. To the right, top and side views of the 16055 SOSIP.663 EM density (bronze) superimposed over the JRFL SOSIP.663 EM density (in grey). The 2D class averages and Fourier Shell Correlation (FSC) are included in the supporting information.

Analysis of JRFL AND 16055 SOSIP.663 trimers by EM reveals well-ordered trimers. Applicants obtained EM 3D reconstructions of the SOSIP trimers in the unliganded state by EM negative stain (FIG. 32). The overall morphology of the unliganded JRFL and 16055 SOSIP trimers at 21 Å and 18 Å resolution, respectively, is similar to that previously described for BG505 SOSIP.664. All trimers display three-fold symmetric lobes and overall density that is wider at the top and narrower at the bottom (FIG. 32) (Sanders R W, et al. (2013) PLoS Pathog 9(9):e1003618). Applicants fitted the EM high-resolution structure of BG505 SOSIP.664 (PDB 3J5M) within the JRFL AND 16055 SOSIP.663 EM reconstructions to demonstrate that no gross differences were observed. A superimposition of the unliganded JRFL and 16055 SOSIP.663 densities, however, revealed small differences when comparing their surface contours (FIG. 32, right panel). These differences may be in large part due to the low resolution of the reconstructions. Applicants do however note that there are differences in the glycosylation patterns of the two trimers, as the 16055 HIV-1 Env possesses 28 glycosylation sites while JRFL Env has 25 glycosylation sites, and that difference may account for some differences in surface contours.

Applicants compared the unliganded state to complexes with a soluble version of the HIV-1 primary receptor, soluble four-domain CD4 (sCD4) (FIG. 32). The 3D reconstructions of the JRFL and 16055 SOSIP.663 trimers liganded with sCD4 at 21 Å and 23 Å resolution, respectively, show conformational changes in agreement with cryo-EM images of the sCD4-liganded native Bal Env and the previously published KNH144 SOSIP:CD4 complexes (FIG. 39B) (Liu J et al. (2008) Nature 455(7209):109-113; Khayat R, et al. (2013) J Virol 87(17):9865-9872). During natural infection, such conformational changes presumably follow the engagement of the cellular receptor, CD4, to form or expose the co-receptor binding site. By EM analysis, CD4-induced conformational changes result in the lateral movement of the gp120 subunits and the appearance of a protrusion attributed to the displacement of the V1V2 loops (FIG. 32 and FIG. 39B) (Liu J et al. (2008) Nature 455(7209):109-113; Khayat R, et al. (2013) J Virol 87(17):9865-9872). Also, in the current analysis of the JRFL and 16055 soluble spike mimetics, the putative gp41 density, located at the bottom of the trimer, opened and flattened when in complex with sCD4 (FIG. 32). As expected from previous results, CD4 engagement did not abrogate trimerization of the SOSIP.663 trimers despite the large conformational changes observed and despite the truncation of the MPER in these constructs. sCD4 displayed the same angle of approach to the CD4bs in both CD4-liganded JRFL and 16055 SOSIP trimers, consistent with the previous KNH144 SOSIP-sCD4 and BaL-Env EM analysis (FIG. 39B) (Liu J et al. (2008) Nature 455 (7209):109-113; Khayat R, et al. (2013) J Virol 87(17):9865-9872).

Figure 40:
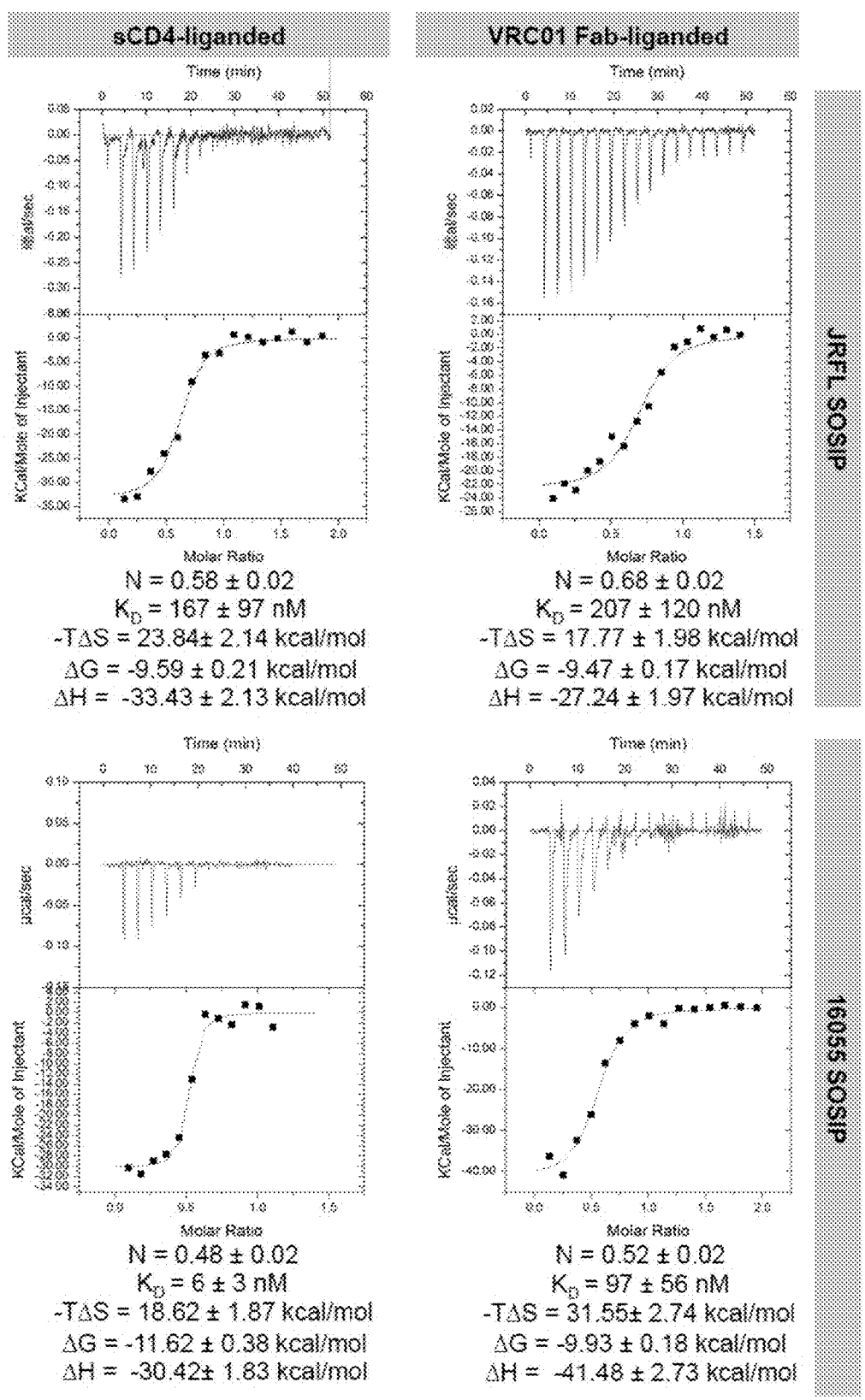
FIG. 40 depicts thermodynamic measurements for sCD4- and VRC01-liganded SOSIP.663 trimers. Panels depict raw data corresponding to the interaction of four-domain sCD4 (left) and VRC01 Fab (right) with JRFL SOSIP.663 (top) and 16055 SOSIP.663 (bottom). Below each panel are displayed the thermodynamic parameters for each measurement.

Applicants investigated if the bNAb VRC01, which also targets the CD4bs, resulted in similar quaternary conformational changes in the trimer architecture as those induced by sCD4. Accordingly, Applicants obtained 3D reconstructions of VRC01-liganded JRFL and 16055 SOSIP.663 at 20 Å and 22 Å resolution, respectively (FIG. 33A). VRC01 did not induce any apparent conformational changes in the overall architecture of the JRFL SOSIP.663 trimer at the resolution obtained in this study. However, Applicants did observe conformational changes induced by VRC01 interaction with the 16055 SOSIP.663 trimers. These conformational changes were not as pronounced as those induced following engagement with sCD4, however, substantial differences between JRFL and 16055 are observed in the superimposition of the two complexes (FIG. 33A). Specifically, VRC01 adopts a slightly more horizontal angle of approach when bound to 16055 SOSIP.663 as compared to its interaction with the JRFL SOSIP.663 trimers. VRC01 also produced conformational changes in the gp41 subunit of 16055 SOSIP.663 that resembled those induced by sCD4 (FIG. 33A). To investigate further differential conformational changes induced by VRC01 Fab on the JRFL versus 16055 SOSIP.663 trimers, Applicants performed isothermal titration calorimetry (ITC). Applicants detected much larger favorable enthalpy and unfavorable entropy changes induced by VRC01 Fab in complex with the 16055 SOSIP.663 trimers relative to the JRFL SOSIP.663 trimers, consistent with the EM analysis (FIG. 33B and FIG. 40). In contrast, ITC parameters assessed with sCD4 were similar for both trimers (FIG. 33B and FIG. 40).

Next, Applicants investigated if the conformational flexibility exhibited by the 16055 SOSIP.663 trimers was a result of specific interactions with VRC01 or an intrinsic property encoded by the 16055 primary sequence and subsequent quaternary assembly. Applicants used VRC03, a VRC01-related bNAb also targeting the CD4bs that, unlike VRC01, showed preferential binding to the trimer relative to the monomer by BLI (FIG. 30, FIG. 37 and FIG. 38). Applicants obtained 3D reconstructions of JRFL and 16055 SOSIP.663 trimers in complex with VRC03 at 20 Å and 19 Å resolution, respectively, revealing that VRC03 binding did not result in any apparent conformational changes in either of the SOSIP.663 trimers (FIG. 33A). Unlike the VRC01 densities, the superimposition of the two VRC03-bound trimer densities was highly concordant and the angle of approach of VRC03 was the same for both JRLF and 16055 SOSIP.663 trimers. Taken together, these data suggest that the conformational changes observed in 16055 SOSIP.663 upon VRC01 binding are specifically induced by the interaction of the mAb with these soluble trimers and not due to increased flexibility of the 16055 SOSIP.663 trimers themselves, consistent with the ITC data (FIG. 33B).

To solidify that these two SOSIP.663 trimers faithfully mimic the virion native spike conformation, Applicants made complexes with the recently described, trimer-preferring and cleavage-specific bNAb PGT151. This bNAb binds specific N-linked glycans at the interface of four Env subunits, two gp120 and two gp41 protomers (Blattner C, et al. (2014) Immunity; Falkowska E, et al. (2014) Immunity). The EM 2D class averages of PGT151 in complex with JRFL and 16055 SOSIP.663 trimers revealed mostly two or one Fabs per trimer (FIG. 34A). Computed stoichiometries based on EM micrographs revealed that 36% of the JRFL SOSIP.663 trimers possessed two Fabs, 28% with one bound Fab and 11% with 3 bound Fabs (Table S1). PGT151 displayed similar stoichiometry in its interaction with the native JRFL envelope extracted from the cell membrane, as recently described (Blattner C, et al. (2014) Immunity). The subtype C 16055 SOSIP.663 2D class averages displayed mostly one PGT151 Fab bound per trimer, although two Fabs were occasionally detected (FIG. 34A) and the computed stoichiometry was slightly different than for JRFL (~34% with one bound Fab, 20% with two Fabs and 0% with three Fabs) (Table S1). The lower stoichiometry for 16055 is consistent with the observation that in 60% of cases, only one PGT151 Fab bound the subtype C C22 Env following extraction from the cell membrane (Blattner C, et al. (2014) Immunity). Based on the more favorable stoichiometry with PGT151 and on the availability of the native JRFL Env-PGT151 complex EM density (Blattner C, et al. (2014) Immunity), Applicants obtained a 3D EM model of the JRLF SOSIP.663 bound to PGT151 at 24 Å resolution (FIG. 34B). This 3D model displays two Fabs bound per trimer and its superimposition with that of the JRFL cleaved full-length Env purified in complex with PGT151 showed a high degree of correspondence, with the expected exceptions of the MPER and TM gp41 regions lacking in the SOSIP.663 trimers (FIG. 34B). Applicants also superimposed the JRFL SOSIP-PGT151 3D reconstruction with that of the published BG505 SOSIP-PGT151 density and, as expected, they were highly concordant (FIG. 56A).

Different levels of stability are displayed by the JRFL and 16055 SOSIP.663 trimers as assessed by biophysical measurements. Applicants assessed the stability of the negatively selected SOSIP.663 trimers by two biophysical methods, differential scanning calorimetry (DSC) and differential scanning fluorimetry (DSF). By DSC, the JRFL SOSIP.663 trimer displayed a melting temperature (Tm) of 58.5° C., about 1° C. higher than the JRFL gp120 monomeric Tm of 57.1° C. In contrast, the 16055 SOSIP.663 trimer melted at 63.7° C., approximately 6 degrees higher than the 16055 gp120 monomer (57.6° C.) (FIG. 35A). Just as some mAbs can induce conformational changes on the trimer, Applicants reasoned that some might also stabilize the trimeric ground-state. Accordingly, Applicants used DSF to measure melting temperatures in the context of liganded-SOSIP.663 trimers, a comparable method to DSC that requires less protein and is more amenable to higher throughput analysis. DSF employs a real-time PCR instrument to detect fluorescence emission of a dye with specificity for hydrophobic residues. The exposure of hydrophobic residues as the protein unfolds with increasing temperature/energy results in a sigmoidal curve that allows the determination of the protein melting temperature. By DSF, the melting temperatures of the JRFL and 16055 SOSIP.663 trimers alone were 55.1° C. and 62.8° C., respectively, comparable to those determined by DSC (FIG. 35B). Applicants selected the CD4bs-directed bNAbs (VRC01, PGV04 and VRC06) and the trimer-preferring mAb (PGT151) to investigate their stabilizing or destabilizing effect on the SOSIP.663 trimers. While VRC01 and VRC06 had no significant effect in trimer stability, the antibodies PGT151 and PGV04 increased the Tm of the JRFL SOSIP-mAb complex by 2.1 and 3.6° C., respectively (FIG. 35B). These data may be of value for subsequent immunogenicity assessments using immune complexes to enhance SOSIP stability in vivo. In contrast, 16055 SOSIP.663 trimers in complex with either VRC01 or PGT151 mAbs did not increase the Tm beyond that of the trimer alone (FIG. 35B).

Figure 42:
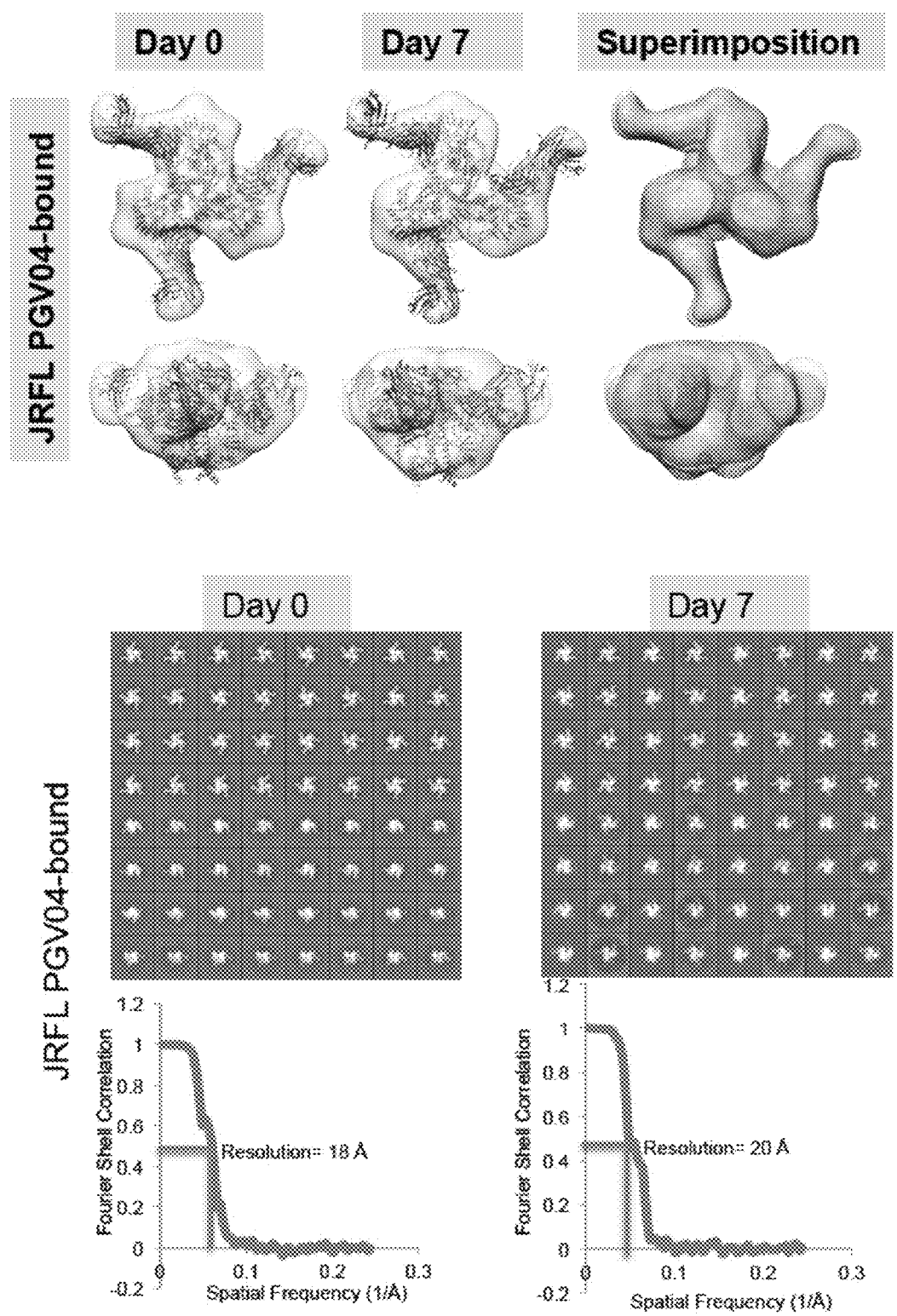
FIG. 42 depicts an EM 3D reconstructions of PGV04-liganded JRFL SOSIP.663 trimer before and after a 7 day incubation. To the left, top and side views of the EM 3D reconstruction densities of the PGV04-liganded JRFL SOSIP.663 trimer at day 0. In the middle, top and side views of the 3D reconstruction EM densities of the PGV04-liganded trimer at day 7. JRFL SOSIP.663 in grey with the high resolution cryo-EM structure of the PGV04-liganded BG505 SOSIP.664 (PDB 3J5M, gp120 in blue with V1V2 in magenta, V2 in green, gp41 in brown and the PGV04 Fab in red) fitted within. To the right, top and side views of the liganded JRFL SOSIP.663 at 7 days (bronze) superimposed onto the liganded JRFL SOSIP.663 at day 0 (grey).

In addition, to further assess trimer stability by EM, Applicants compared the 3D models of JRFL SOSIP.663 bound to the PGV04 Fabs at days 0 and 7 following "timer alone" incubation at 4° C. Applicants observed that the trimeric complexes appeared similar at both time points, indicating no deterioration in quaternary structure over this time interval (FIG. 42).

In this study, Applicants selected two HIV-1 Env sequences from subtypes B and C to produce soluble SOSIP trimers to complement the already available subtype A BG505 SOSIP trimer. Obtaining soluble mimetics of the native HIV-1 spike from subtypes representing the majority of global infections is of high interest for additional structural analysis as well as preclinical immunogenicity studies and candidate vaccine trials. The JRFL and 16055 SOSIPs did form homogeneous trimers, but not as readily as the subtype A SOSIP trimers derived from the BG505 Env sequences (Chakrabarti B K, et al. (2013) J Virol 87(24):

13239-13251; Sanders R W, et al. (2013) PLoS Pathog 9(9):e1003618). Since, following SEC, Applicants observed well-ordered trimers with three-fold symmetry in the EM negative stain micrographs within a mixture of dis-ordered oligomeric forms, Applicants used negative selection to purify the JRFL and 16055 SOSIPs to a high level of conformational homogeneity. Applicants then were able to obtain 3D reconstructions of these trimers in both the unliganded state and in complex with sCD4 and selected bNAbs. By EM, Applicants demonstrated that sCD4 induced conformational changes in these SOSIP.663 trimers that parallel those observed for the native BaL-Env spike. In addition, the cleavage- and trimer-specific bNAb PGT151 recognized the JRFL SOSIP.663 trimers in a manner similar to its recognition of the native JRFL Env spike. Applicants demonstrated that the antigenic profile of the negatively selected trimers was consistent with a well-ordered state, mimicking the viral spike and that the trimers exhibited degrees of thermostability consistent with a homogenous species by calorimetry and fluorimetry.

To obtain the well-ordered trimers, Applicants used CD4bs-directed non-bNAbs to selectively adsorb the disordered oligomers to the solid phase. F105 readily removed the disordered oligomers from the JRFL SOSIP.663 mixture but was insufficient for 16055, likely due to its faster off-rate for the 16055 monomer. GE136 was a better negative selecting agent for the 16055 mixture showing a considerably slower dissociation rate for monomeric 16055 gp120 (FIG. 36B and FIG. 38). A slower dissociation rate of a given mAb for the monomer or disordered oligomers is likely advantageous to efficiently capture the disordered oligomers on the protein A column and may be a key factor for successful negative selection using a given mAb.

Following negative selection, Applicants isolated highly homogeneous well-ordered JRFL and 16055 SOSIP.663 trimers, which generally resembled the BG505 SOSIP.664 trimers. BG505 SOSIP.664 do not require this negative-selection purification step since, following initial 2G12 positive selection, they form well-ordered trimers that can be isolated by SEC alone (Sanders R W, et al. (2013) PLoS Pathog 9(9):e1003618). Why most HIV-1 Env sequences do not form SOSIP trimers with this degree of homogeneity is not yet clear but seems to be a relatively infrequent feature associated with the BG505 Env, perhaps by specific structural interaction focused around the I559P change that alters gp41 conformational flexibility to inhibit efficient six-helix bundle formation, the post-fusiogenic form of gp41.

The negatively selected JRFL and 16055 SOSIP.663 trimers displayed efficient recognition by bNAbs, including those recognizing quaternary epitopes, and low or undetectable reactivity to CD4bs-targeting non-bNAbs and other non-neutralizing antibodies targeting other sites than the CD4bs, such as 17b and C11. These data suggest that the CD4bs-directed negative-selection process eliminated generally disordered trimers and was not specifically restricted to the CD4bs, reflective of overall well-ordered trimers. Generally, most bNAbs that recognized the negatively selected trimers with high avidity, also neutralized the parental sequence viral strain, suggesting that these spike soluble mimetics faithfully recapitulate the quaternary packing of the native Env spike. This interpretation is consistent with the reported correlation between bNAb HIV-1 neutralizing activity and binding to the ordered BG505 SOSIP.664 trimers (Sanders R W, et al. (2013) PLoS Pathog 9(9): e1003618).

Similar to that study, and as reported here, the exception was the V3-targeting antibodies, 39F, 14e and 19b that do not neutralize the parental JRFL or 16055 viruses, but did recognize the soluble SOSIP.663 trimers. The binding of these antibodies was slightly reduced after negative selection, but not fully abrogated, suggesting that the V3 might be in a more exposed or "triggered" conformation at least in one of the protomers within some of the population of trimers. Consistent with this, EM negative stain using 19b Fab with negatively selected JRFL and 16055 SOSIP.663 detected a low percentage of Fab binding and then exclusively to one protomer. A similar level of V3 reactivity was also observed previously for BG505 SOSIP.664 and might be a slight difference between these engineered soluble trimers and the native spike that might be overcome with additional design modifications (Sanders R W, et al. (2013) PLoS Pathog 9(9):e1003618). This V3 exposure, that might be due to "breathing" of this region in the relatively well-ordered trimeric context may reflect the metastable condition of the Env spike itself since activation of the HIV-1 spike occurs by protein:protein interaction. It may be that a low energy barrier is required to trigger HIV-1 Env by this means, making conformational breathing more likely. HIV-1 Env is not triggered by pH as is, for example, 'flu HA or other endosomally triggered viral fusion units, which may allow a wider degree of trimer stability in the native Env state.

In one other exception, the N332-lacking 16055 SOSIP.663 trimers were recognized by the N332-targeting bNAbs 2G12 and PGT121. 2G12 does not neutralize the parental virus while PGT121 neutralizes the parental virus strain, which is likely related to, and consistent with, the promiscuity of "nearby" glycan usage displayed by this bNAb that does not absolutely require the presence of the 332 N-glycan (Sok D, et al. (2014) Science translational medicine 6(236):236ra263).

Both JRFL and 16055 SOSIP.663 trimers are relatively stable, displaying melting temperatures of 58.5° C. and 63.7° C., respectively. These values are substantially in excess of perhaps more relevant temperatures such as room or physiological body temperature. Since the published melting temperature of BG505 SOSIP.664 trimer is higher (68° C.) (Sanders R W, et al. (2013) PLoS Pathog 9(9): e1003618), one could postulate that the higher Tm of the SOSIP trimer will correlate with a higher degree of well-ordered trimer formation. However, the melting temperature of 16055 SOSIP.663 was almost 6° C. higher than that of JRFL SOSIP.663 and 16055 had a lower percentage of "spontaneous" trimer formation as revealed by the SEC profiling and related analysis. Other factors such as the level of glycosylation or the propensity of the V1/V2/V3 to adopt a near native arrangement even within a soluble protomer may contribute to the higher thermostability of the 16055 or BG505 SOSIP trimers. BG505 and 16055 gp120s, but not JRFL gp120, are recognized by the V2-directed, trimer-preferring antibodies PG9 and PG16. BG505 SOSIP and 16055 SOSIP display higher Tms than does JRFL SOSIP, suggesting that the propensity of the 16055 and BG505 monomers to adopt a native, trimer-like conformation may contribute to the thermostability of the SOSIP oligomers.

Antibodies PGV04 and PGT151 increased the Tm of the JRFL SOSIP.663 trimer. This could be a result of specific inter-protomer contacts established by the paratope of the antibody, simultaneously bridging two protomers and conferring structural rigidity to the architecture of the trimer. In contrast, VRC01 shows a lower level of this putative inter-protomer bridging as suggested indirectly in the recent publication of the EM structure of the BG505 SOSIP trimer bound to PGV04 (Lyumkis D, et al. (2013) Science 342

(6165):1484-1490). VRC01 did not show a significant stabilization effect on the SOSIP.663 trimers as measured by DSF, and even, destabilized the 16055 SOSIP.663 trimer as evidenced in the EM 3D reconstruction of the complex.

Obtaining soluble mimics of the HIV-1 spike representative of different subtypes/strains of HIV will be of benefit toward potential advancement of a global HIV-1 vaccine. As a critical first step, the structural characterization of the HIV-1 virion spike, for which the recently published subtype A BG505 SOSIP.664 crystal and EM structures provide fundamental insights regarding the organization of the gp120 and gp41 within the native trimer. Extending this structural information to other subtype strains of HIV is of high interest in the field. For now, SOSIP represents the best and only well-ordered soluble trimer mimetic. Frustratingly, many HIV sequences do not readily form ordered homogeneous SOSIP trimers to the extent that BG505 Env does. This trend likely explains why, in part, previous attempts to obtain high-resolution crystal structures of the JRFL and KNH144 SOSIP trimers were not fruitful until BG505 was identified. In summary, in this study, Applicants offer a new means to obtain homogenous well-ordered SOSIP trimers of subtypes B and C that potentially can be extended to more HIV-1 Env strains by the use of the non-bNAb negative-selection strategy used to rescue well-ordered trimer sub-fractions of JRFL and 16055 SOSIP oligomers.

Design of the JRFL SOSIP.663 and 16055 SOSIP.663 constructs. To generate the HIV-1 subtypes B JRFL SOSIP.663 and C 16055 SOSIP.663 expression plasmids Applicants followed established SOSIP design parameters (Sanders R W, et al. (2013) PLoS Pathog 9(9):e1003618). In brief, the JRFL and 16055 SOSIP.663 trimers were engineered with a disulfide linkage between gp120 and gp41 (residue 501 in gp120 to residue 605 in gp41) that covalently links the two subunits of the heterodimer (SOS) (Binley J M, et al. (2000) J Virol 74(2):627-643). As previously described, Applicants included the I559P mutation in the heptad repeat region 1 (HR1) of gp41 that promotes trimerization of the heterodimer, and a deletion of the most of the hydrophobic membrane proximal external region (MPER), in this case residues 664-681 of the Env ectodomain (Depetris R S, et al. (2012) J Biol Chem 287(29):24239-24254; Sanders R W, et al. (2002) J Virol 76(17):8875-8889; Klasse P J, et al. (2013) J Virol 87(17):9873-9885). The furin cleavage site between gp120 and gp41 (508REKR511) (SEQ ID NO: 3) was altered (506RRRKKR511) (SEQ ID NO: 1) to enhance cleavage (Binley J M, et al. (2002) J Virol 76(6):2606-2616). The JRFL SOSIP.663 trimer includes an additional mutation (E168K) that is associated with PG9/PG16 neutralization sensitivity in the pseudovirus neutralization assay that is naturally present in the 16055 Env (Doria-Rose N A, et al. (2012) J Virol 86(15):8319-8323; Doores K J & Burton D R (2010) J Virol 84(20):10510-10521). The CD5 leader sequence was positioned at the 5' end of the SOSIP encoding DNA to enhance secretion and expression.

Purification of soluble trimers. JRFL SOSIP.663 and 16055 SOSIP.663 expression constructs were transfected into 293F cells along with a plasmid encoding the cellular protease Furin to ensure efficient cleavage of the Env precursor gp160 using a 2:1 Env:Furin ratio (Kirschner M, et al. (2006) Protein Expr Purif 48(1):61-68). The transfected 293F cells were cultured in a CO2 humidified shaking incubator at 37° C. for 5-6 days to transiently express the soluble SOSIP trimers. Culture supernatants were collected and cells were removed by centrifugation at 3800 g for 20 minutes, filtered twice, first with a 0.45 μm pore size filter device (Nalgene) and subsequently with a 0.2 μm pore size filter. SOSIP proteins were purified by flowing the supernatant over a lectin (*Galanthus nivalis*) affinity chromatography column overnight at 4° C. Proteins were eluted from the lectin column with 3 column volumes of 0.5 M methyl-α-D-mannopyranoside and 0.5 M NaCl. The eluate was concentrated with a Millipore concentrator (MWCO 100 kDa) to 500 μL and loaded onto a Superdex 200 10/300 GL column to separate the trimer-size oligomers from aggregates and gp140 monomers. Fractions corresponding to the trimer (approximately eluate volumes 10-12 mL) were pooled and loaded into an agarose protein A column previously loaded with 10 mg of mAb F105 for JRFL trimers or GE136 for 16055 trimers. The column was rocked at 4° C. for 45 minutes, the solid phase was allowed to settle for 5 minutes and the flow-through collected by flowing one column volume of PBS through the column. The flow-through containing the well-ordered trimers was concentrated using a 100 kDa molecular weight cut off filter device from Millipore to approximately 1.5 mg/mL for analysis or cold storage.

Immunoprecipitation. To perform immunoprecipitations of supernatants containing the SOSIPs, 20 μL of protein A agarose beads were added to a 1.5 ml eppendorf tube, washed twice with PBS, resuspended in 500 μL of PBS and 5 μg of antibody were added. The protein A agarose-mAb mixture was rocked for 30 minutes at 4° C. and then washed twice with PBS containing 500 mM NaCl. 1 mL of SOSIP-containing filtered supernatant was added to the microtube containing antibody and rocked for 30 minutes at 4° C. The microtube was then centrifuged at 1000 g for 5 minutes and the supernatant discarded. The protein A-agarose pellets containing the bound antibody-Env protein were washed twice with 1 mL of PBS before resuspending them in 20 μL of SDS-PAGE loading buffer to resolve over SDS PAGE minigels for 50 minutes at 200 V.

Bio-Layer interferometry (BLI) binding analysis and kinetics. To obtain binding curves and corresponding response values by BLI, Applicants used an Octet Red instrument immobilizing IgGs on hydrated (PBS pH 7.4) anti-human IgG Fc sensors (Fortebio, Inc.). The SOSIP trimers and gp120 monomers were analyzed as analytes in solution (PBS pH 7.4). Briefly, the bio-sensors were immersed in PBS pH 7.4 containing IgGs at a concentration of 10 ug/mL for 2 minutes and with vibration at 1000 rpm prior to encounter with the analyte (SOSIP trimers or gp120 monomer, 200 nM and 600 nM respectively). The IgG-immobilized sensor was immersed in the analyte in solution for 3 minutes at 1000 rpm and then removed from the analyte solution and placed into PBS, pH 7.4 for an additional 3 minutes. The 3 minute binding intervals generated the association and dissociation binding curves reported in this study.

Electron microscopy. Negatively selected JRFL and 16055 SOSIP.663 trimeric proteins were incubated with a ten molar excess of selected Fabs at RT for 1 hour. The following complexes were analyzed 1. JRFL-SOSIP.663 with four-domain sCD4, 2. JRFL-SOSIP.663 with VRC01, 3. JRFL-SOSIP.663 with VRC03, 4. JRFL-SOSIP.663 with PGT151, 5. JRFL-SOSIP.663 with PGV04, 6. 16055 SOSIP.663 with four-domain sCD4, 7. 16055 SOSIP.663 with VRC01, 8. 16055 SOSIP.663 with VRC03, and 9. 16055 SOSIP.663 with PGT151. A 3 μL aliquot containing 0.05 mg/ml of the Fab+JRFL-SOSIP complex or the Fab+16055 complex was applied for 15 seconds (s) onto a carbon coated 400 Cu mesh grid that had been glow discharged at 20 mA for 30s, followed by negative staining with 2% uranyl formate for 30 s. Data were collected using a FEI Tecnai Spirit electron microscope operating at 120 keV, with an electron dose of ~36 e-/Å2 and a magnification of 52,000× that resulted in a pixel size of 2.05 Å at the specimen plane. Images were acquired with a Tietz 4 k×4 k TemCam-F416 CMOS camera using a nominal defocus of 1000 nm and the Leginon package (Subway C, et al. (2005) Automated molecular microscopy: the new Leginon system. Journal of structural biology 151(1):41-60). The tilts provided additional particle orientations to improve the image reconstructions.

Figure 41:
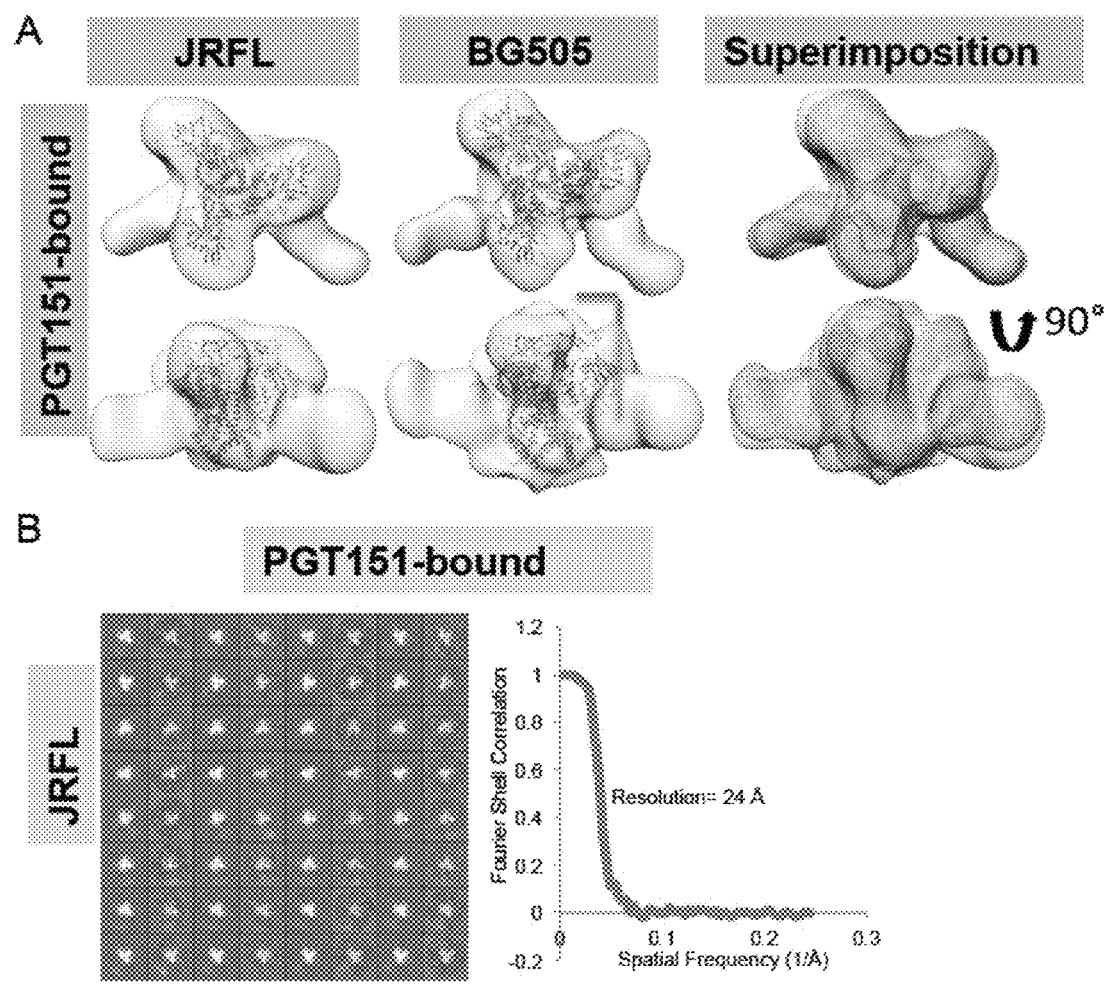
FIGS. 41A-B depict PGT151-bound JRFL SOSIP.663 EM 3D model comparison to PGT151-bound BG505 SOSIP.664 and corresponding projection matching and Fourier shell correlation graph. (A) PGT151-bound JRFL SOSIP.663 and BG505-SOSIP.664 (EMD 5921). (B) PGT151-bound JRFL SOSIP.663 projection matching and Fourier Shell correlation graph.
Figure 43:
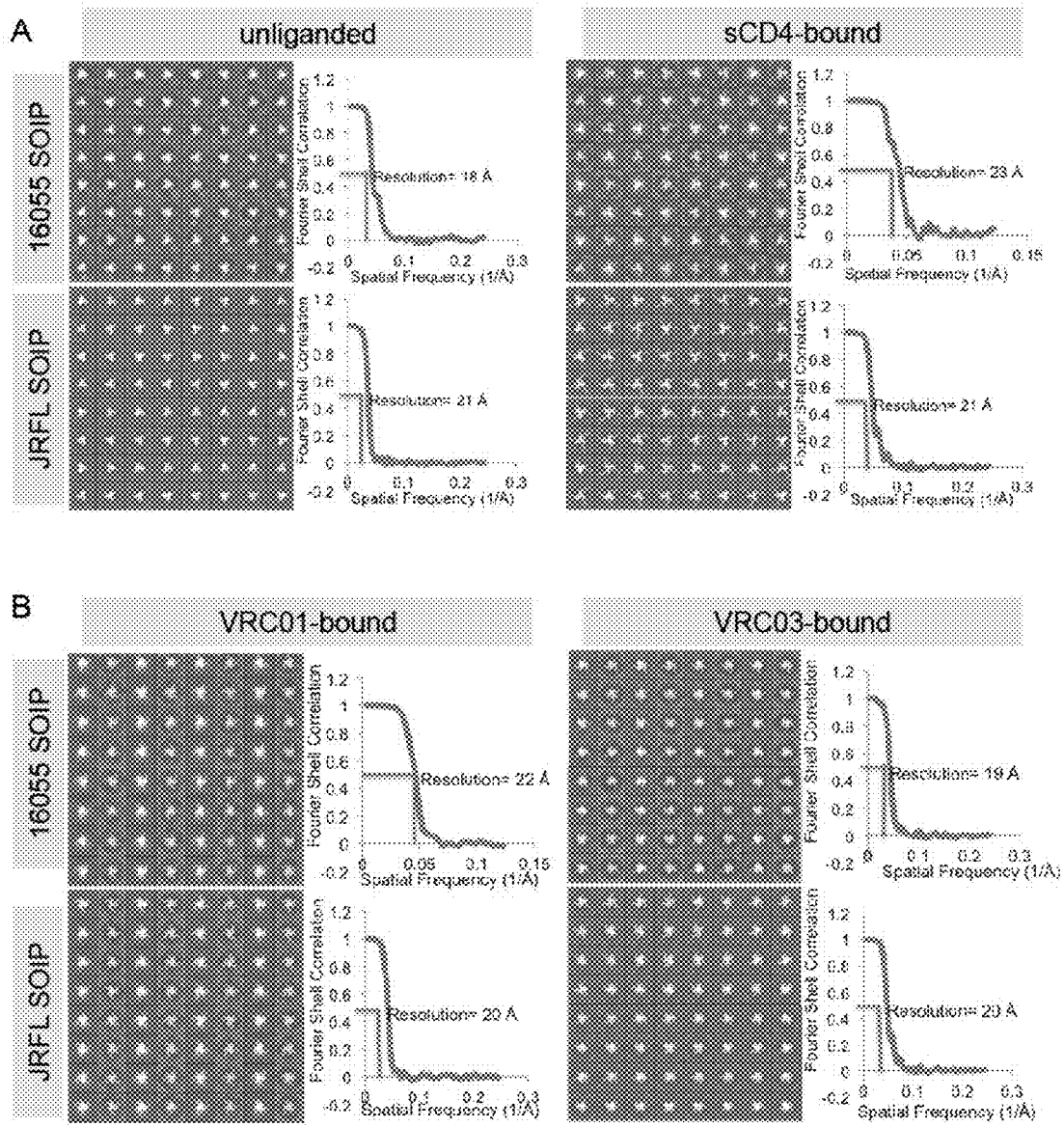
FIGS. 43A-B depict projection matching and Fourier Shell Correlation graphs. (A) Unliganded 16055 and JRFL SOSIP.663 (left) and sCD4-bound 16055 and JRFL SOSIP.663 (right) (B) VRC01-bound 16055 and JRFL SOSIP.663. (left) and VRC03-bound 16055 and JRFL SOSIP.663 (right).

Data processing and image reconstruction. Particles were picked automatically using DoG Picker and put into a particle stack using the Appion software package (Voss N R et al. (2009) Journal of structural biology 166(2):205-213; Lander G C, et al. (2009) Journal of structural biology 166(1):95-102). Initial, reference-free, two-dimensional (2D) class averages were calculated using particles binned by two via Xmipp Clustering 2D Alignment (Sorzano C O, et al. (2010) Journal of structural biology 171(2):197-206) and sorted into classes. Particles corresponding to complexes were selected into a substack and binned by two before another round of reference-free alignment was carried out using the Xmipp Clustering and 2D alignment and IMAGIC programs (van Heel M et al. (1996) Journal of structural biology 116(1):17-24). Fabs and sCD4 were clearly visualized in the 2D class averages if they are bound to the trimer, allowing the percentage of bound trimers relative to unbound trimers to be tabulated (Table 51) (Lyumkis D, et al. (2013) Science 342(6165):1484-1490). ab initio common lines models were calculated from reference-free 2D class averages in EMAN2 (Tang G, et al. (2007) Journal of structural biology 157(1):38-46) without imposing symmetry. All ab initio common lines models were the same. One of those models was then refined against raw particles for an additional 89 cycles. EMAN (Ludtke S J et al. (1999) Journal of structural biology 128(1):82-97) was used for all 3D reconstructions. The resolutions of the final models were determined using a Fourier Shell Correlation (FSC) cut-off of 0.5 (FIG. 41B, FIG. 43).

Model fitting into the EM reconstructions. The Cryo-EM structure of PGV04-liganded BG505 SOSIP.664 (3J5M), and gp120 with sCD4 (1RZK) were manually fitted into the EM densities and refined by using the UCSF Chimera (Pettersen E F, et al. (2004) Journal of computational chemistry 25(13):1605-1612) 'Fit in map' function.

Differential Scanning calorimetry (DSC). Thermal denaturation was analyzed with a N-DSC II differential scanning calorimeter from calorimetry Sciences Corp. (Prov, Utah), at a scanning rate of 1K/min under 3.0 atmospheres of pressure. Samples were dialyzed in PBS pH 7.4 and protein concentration was adjusted to 0.5 mg/mL prior to measurement. Data collected were analyzed after buffer correction, normalization and baseline subtraction.

Differential Scanning Fluorimetry (DSF). Fluorescence measurements were performed using a CFX96 RT-PCR detection System (BIO-RAD, Hercules, Calif.). SYPRO Orange dye was diluted 1:5000 in PBS pH 7.4 and added to 30 μg of protein in clear PCR tubes to a final volume of 25 μL. For samples containing trimer and Fab complexes, 30 ug of trimer protein were mixed with bug of Fab and incubated at 4° C. for 1 hr prior to adding the dye. The fluorescence emission was collected using a fluorescence resonance energy transfer filter (560-580 nm) an excitation wavelength of 450-490 nm. During the DSF experiment, the temperature was increased from 20 to 95° C. at an increment of 0.5° C. with an equilibration time of 5 s at each temperature prior to measurement. The data were exported into CFX Manager version 1.6 for analysis. The melting temperature (Tm) is defined as the temperature corresponding to the minimum value of the negative first derivative of the first fluorescence transition. Applicants note that the high initial fluorescence is likely due to exposure of hydrophobic pockets on the surface of the trimer.

Example 5: Proline Screening Data on BG505 gp140 NFL2P

Stabilization of the native Env trimer in the"NFL" platform involves a HR1 destabilization screen with proline substitutions.

FIG. 44 depicts a HR1 destabilization screen suggesting that BG505 NFL2-L556P and S649D are involved in stabilzation of the trimers. In particular, L556P and S649D make well-ordered trimers.

FIG. 45 depicts that immunoprecipitation (IP) results indicate that L555P and A558P are making well-ordered trimers. In particular, L555P and A558P looks similar to I559P.

FIG. 46 depicts that octet binding data suggest that there is no appreciable difference in the antigenicity of L555P, L556P, and A558P after negative selection. L555P, L556P, A558P bind strongly with PGT145 and show almost no binding with F105 and the pattern is very similar to I559P suggesting that they are making well-ordered, native-like BG505-NFL2 trimers.

FIG. 47 depicts a summary of the HR1 proline screen in BG505NFL2 backbone. L555P, L556P and L566P almost behave like I559P in terms of antigenic profile and trimer formation.

In the initial 15 residues of the HR1 proline screen, Applicants have got 6 positive hits, which are behaving similar to BG505 gp140-NFL2P.

Example 6: Mutations to Increase Trimer Stability

Figure 48:
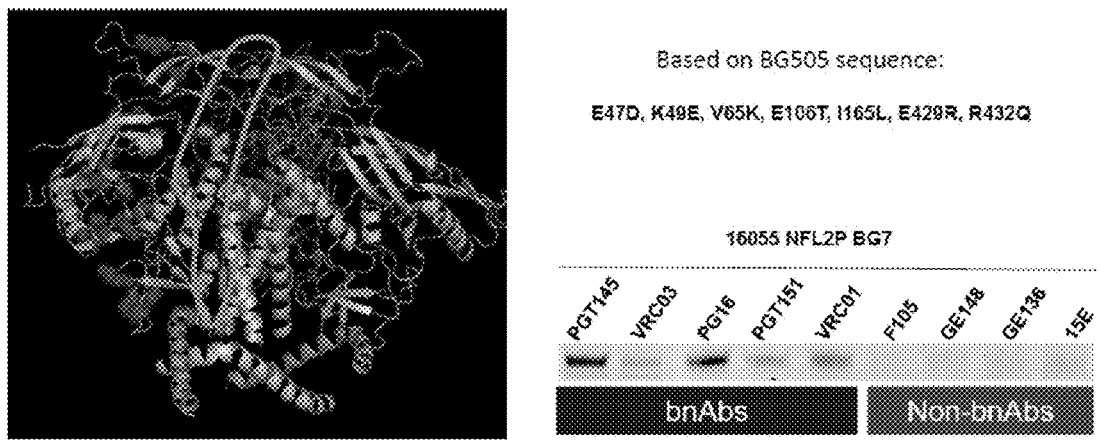
FIG. 48 depicts trimer-axis proximal mutations E47D, K49E, V65K, E106T, I165L, E429R, R432Q (residues based on BG505 sequence and numbering) increase trimer generating propensity of 16055 NFL2P. Immuno precipitation (IP) of 16055 soluble trimers from supernatants indicates that well-ordered trimers are the preponderant species.

FIG. 48 depicts trimer-axis proximal mutations E47D, K49E, V65K, E106T, I165L, E429R, R432Q (residues based on BG505 sequence and numbering) increase trimer generating propensity of 16055 NFL2P. Immuno precipitation (IP) of 16055 soluble trimers from supernatants indicates that well-ordered trimers are the preponderant species.

Example 7: Liposomal Particulate Display of HIV-1 Trimers

Liposomal preparation involves dissolving lipids in chloroform (DGPC:cholesterol:DGS-NTA-Nickle) in a (60:39:1) ratio, mixing the lipids, evaporating the chloroform under nitrogen, desiccation overnight, dissolving lipid film in PBS at 37 degrees C. in a shaker, sonicating for 10 to 15 seconds, extruding with 1 micrometer diameter to 0.1 micrometer, conjugation with Env Trimer-His$_6$ ("His$_6$" disclosed as SEQ ID NO: 4) and SEC to remove excess free Env protein.

Figure 49:
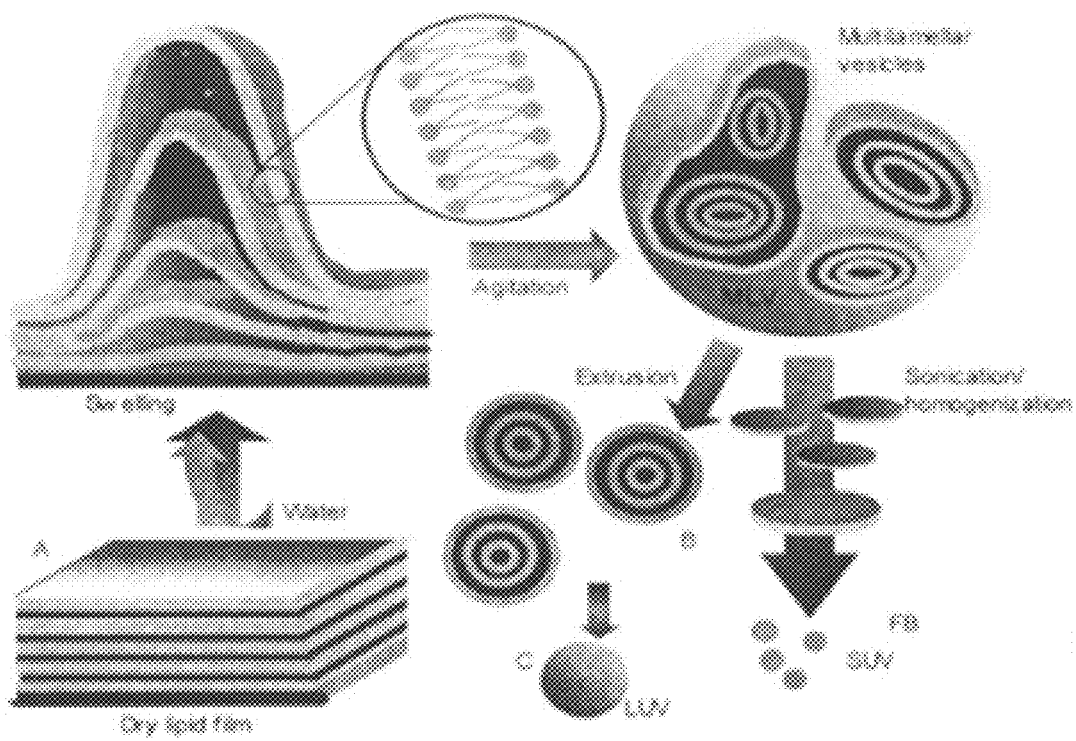
FIG. 49 depicts a schematic of liposome preparation.

FIG. 49 depicts a schematic of liposome preparation.

FIG. 50 depicts an estimation of protein molecules per liposome.

Figure 51:
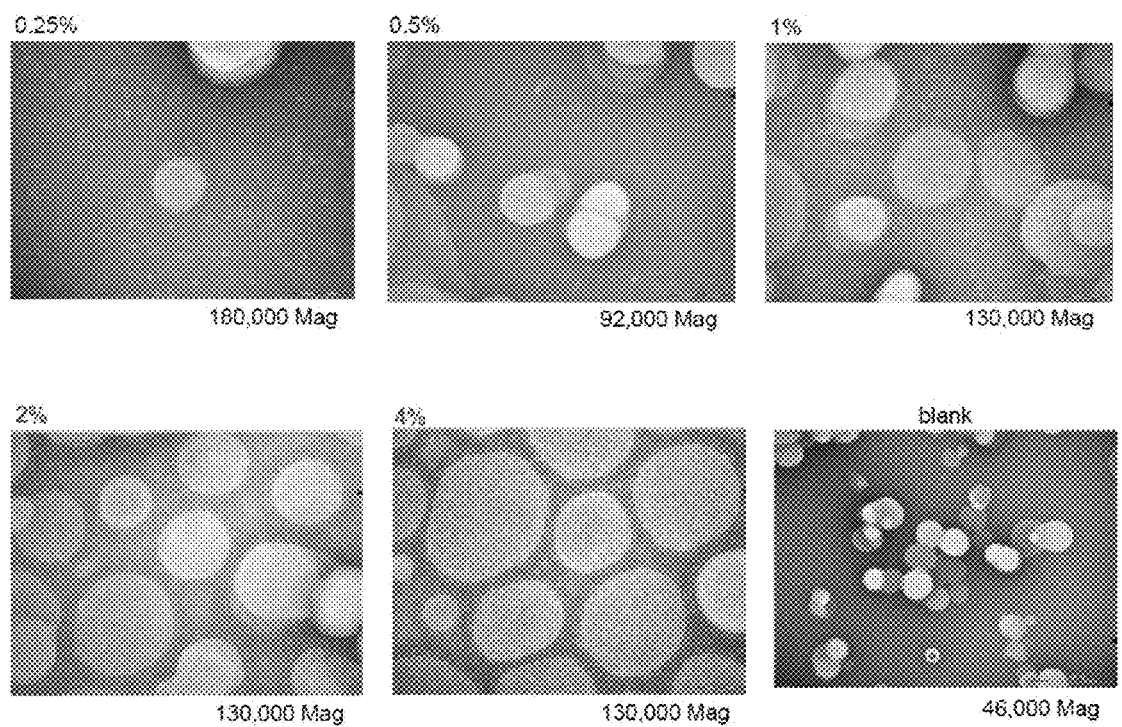
FIG. 51 depicts an EM of 0.25 to 4% Ni-lipid liposomes confirm increased loading of Env.

FIG. 51 depicts an EM of 0.25 to 4% Ni-lipid liposomes confirm increased loading of Env.

Figure 52A:
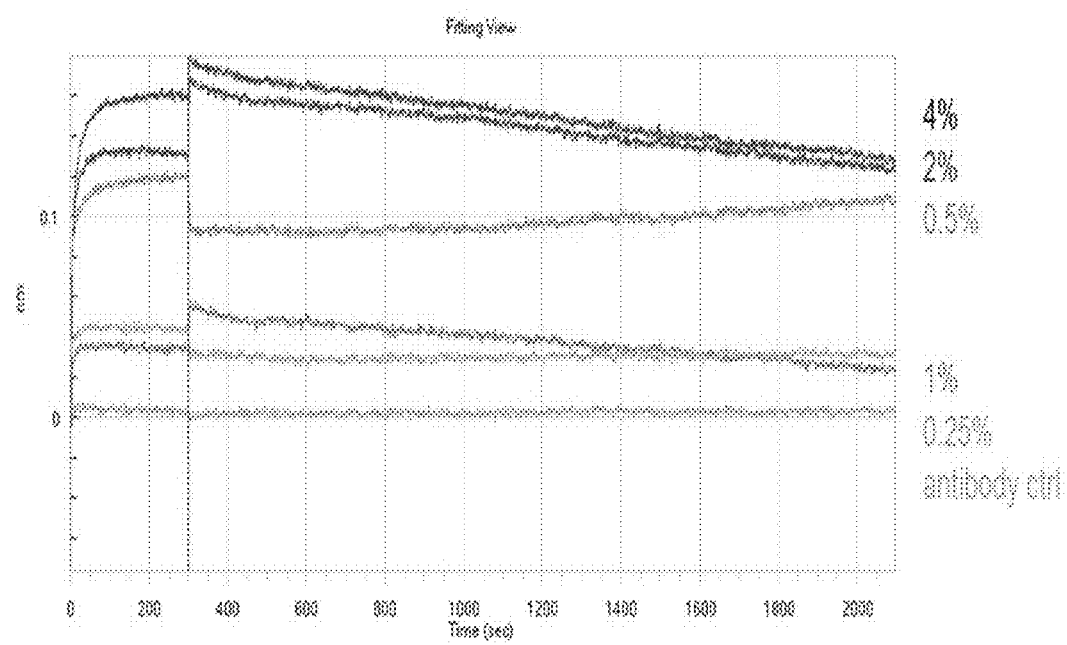
FIGS. 52A-C depicts bNAb Binding and SDS gels confirm differential loading of protein on liposomes.
Figure 52B:
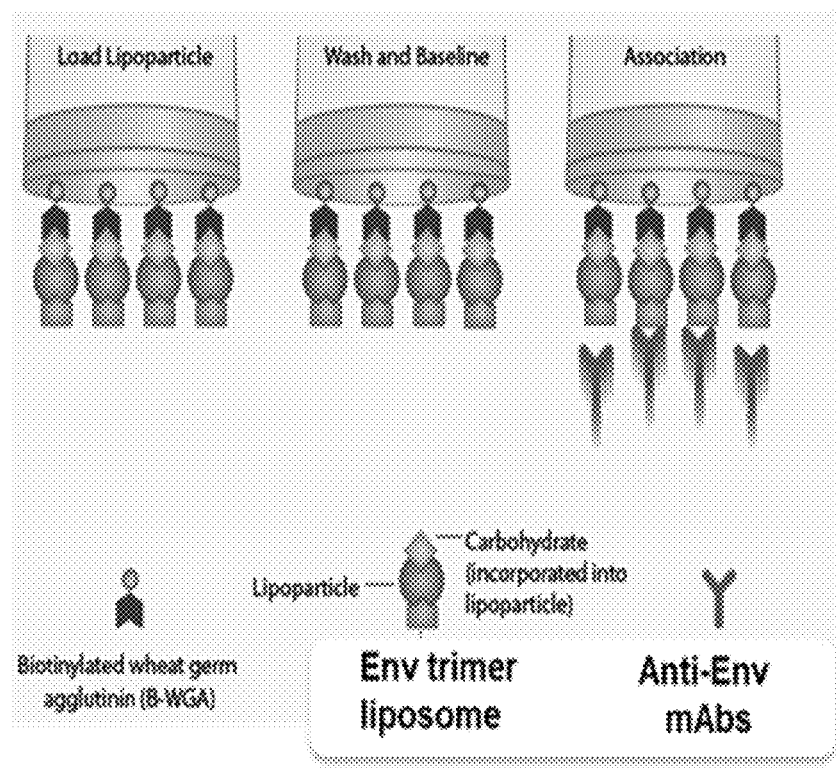
Figure 52C:
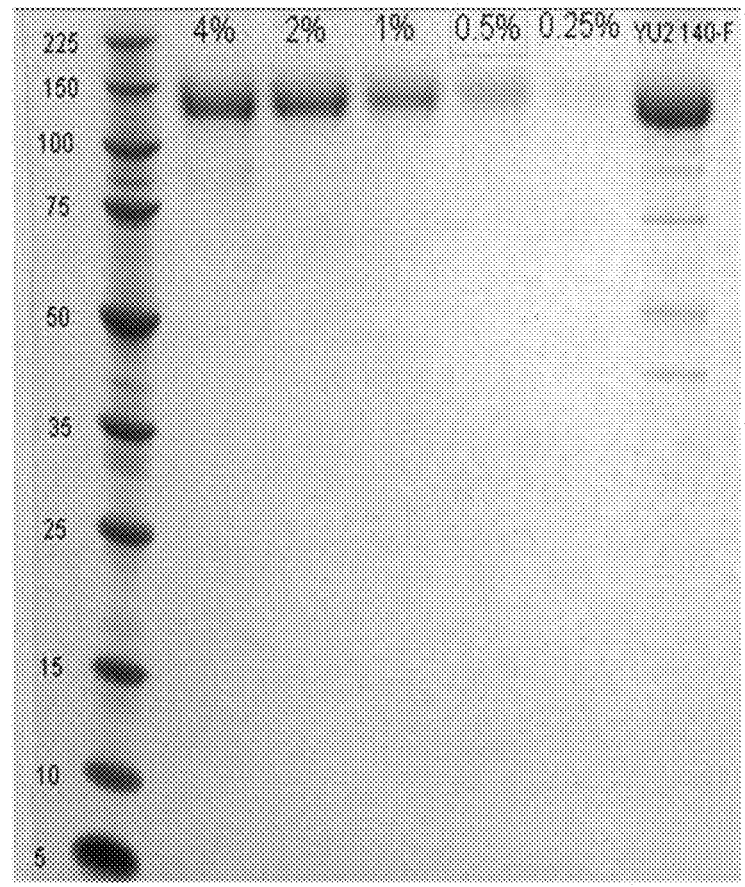

FIG. 52 depicts bNAb Binding and SDS gels confirm differential loading of protein on liposomes.

Figure 53:
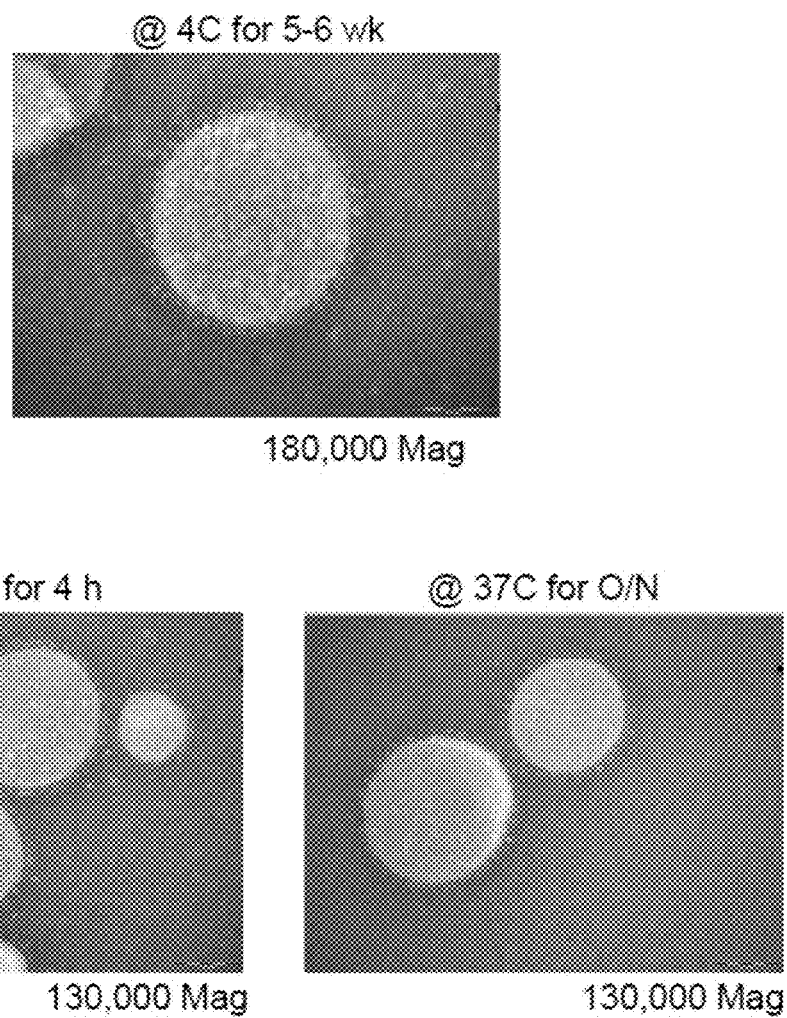
FIG. 53 depicts that JRFL gp140-Foldon liposomes are stable at 37° C.

FIG. 53 depicts that JRFL gp140-Foldon liposomes are stable at 37° C.

Figure 54:
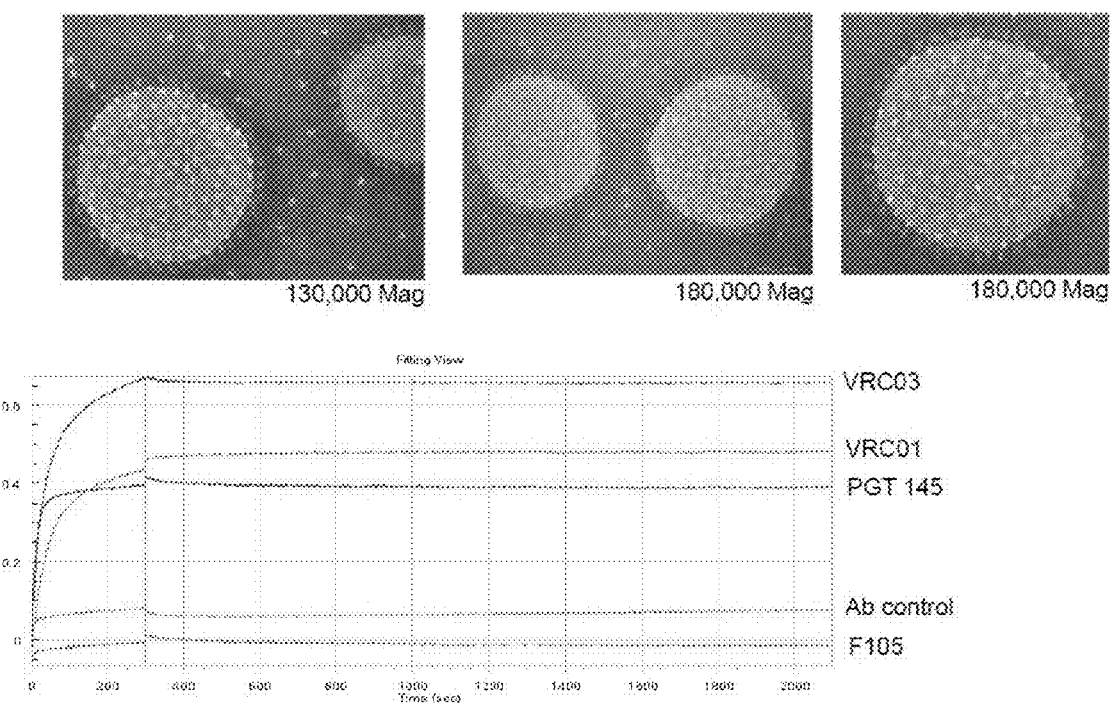
FIG. 54 depicts that JRFL NFL2P well-ordered trimers array evenly on 2% liposomes.

FIG. 54 depicts that JRFL NFL2P well-ordered trimers array evenly on 2% liposomes.

FIG. 55 depicts that well-ordered NFL trimers densely arrayed on liposomes by EM.

A schematic of nanotechnology-based drug delivery platforms and nanocarrier-based drugs on the market are presented in Nanomedicine, 2012, 7 (8), 1253-1271.

FIG. 56 depicts DLS profiles estimate size and reveals no free protein.

FIG. 57 depicts conjugation of Cys-protein to maleimide-PEG-lipid.

Example 8: gp41 Screen in NFL for Substitutions for Transfer to Other Envs

FIG. 58 depicts a gp41 screen in NFL for substitutions for transfer to other Envs. These are the proline substitutions screened in the BG505 NFL context.

The present invention also encompasses the I559P change in the BG505 NFL trimers.

Example 9: Negatively Selected JRFL SOSIP Trimers Elicit Homologous JRFL Neutralization FIG. 59 depicts negatively selected JRFL SOSIP trimers elicit homologous JRFL neutralization.

Example 10: Stability of Ordered Trimers in Selected Conditions

FIG. 60 depicts a stability assay.

FIG. 61 depicts that trimers are stable at 4° C. and 37° C.'

FIG. 62 depicts that trimers are relative stable in ISCO-MATRIX at 37° C.

FIG. 63 depicts Fixation of well-ordered trimers. The fixation protocol involves: 1. 5 mM of GLA (Glutaraldehyde, homobifunctional crosslinker) at RT for 5 min; 2. 50 mM of Glycine to quench the reaction and 3. Negative selection and Gel filtration.

FIG. 64 depicts that fixation improves trimer stability at 37° C.

FIG. 65 depicts that fixation improves trimer stability in ISCOMATRIX at 37° C.

Well-ordered trimers are stable at 4° C., most trimers are stable at 37° C., trimers are more stable in ISCOMATRIX than in Adjuplex at 37° C. and fixation improves stability of the trimers while maintaining bNAb recognition.

FIG. 66 depicts that fixation improves trimer stability in Adjuplex at 37° C.

Example 11: BG505 NFL2P Trimers with Free Cysteines

FIG. 67A depicts immunoprecipitation with BG505+cysteine trimers.

FIG. 67B depicts a blue native gel with BG505+cysteine trimers.

FIG. 68 depicts BG505 NFL2+C quality control anti human Fc sensor.

FIG. 69 depicts a sequence of BL505NFL2P with a free cysteine.

Example 12: Clade C NFL2

FIG. 70 depicts a sequence of Clade C NFLs for CMVR derived from clade C Envs with high homology to BG505 to make NFL trimers.

Example 13: Proline Screening Data on 16055 gp140-NFL2

The goals of this Example are to stabilize the clade C 16055 Env trimers in their native-like conformation in the NFL platform and to find out a common proline mutation that can be easily translated to stabilize majority of the ENV trimers spanning different clades.

In the native spike, the gp41 subunit exists in a metastable conformation and it favorably forms a stable post-fusion six-helix bundle (6HB), which is composed of trimers of HR1 (N-heptad repeat) and HR2 C-heptad repeat) heterodimers facilitating the fusion of HIV with the host CD4 T cells. The formation the 6HB is a irreversible process destabilizing the native trimer resulting in exposure of immunodominant and non-neutralizing epitopes to the immune system. Ideally, any mutation in the HR1 or HR2 that can destabilize the 6HB formation will stabilize the ENV trimers in native-like conformation.

In the initial screen 30 residues from HR1 and 3 residues from HR2 were selected. The HR1 residues were mutated individually to proline. The HR2 residues were mutated to proline and other charged residues (Aspartic acid, Glutamic acid and Arginines).

A summary of the ongoing HR1 proline screen in the 16055 gp140-NFL2 construct: based on the initial immunoprecipitation and initial octet binding data is presented in FIG. 71. FIG. 71A depicts single mutations involving only HR1 residues and FIG. 71B depicts double mutations involving both, the HR1 and HR2 residues. Green indicates a positive result, red indicates a negative result and blue indicates an experiment in progress.

So far, five single proline mutants (L555P, Q652P, Q653P, L565P and L566P) stabilize the clade C 16055-NFL2 Env trimers in the native-like conformations. So far, five double mutants stabilize and induce native-like trimer formation in 16055-NFL2 Env.

FIG. 72 depicts immunoprecipitation with selected trimer sensitive bNAbs (VRCO6 and PGT145) which suggest that L555P, Q652P, A558P-S649D, A558P-S649E and I559P-S649E are making well ordered trimers in solution.

FIG. 73 depicts immunoprecipitation with selected trimer sensitive bNAbs clearly indicate that Q653P, L565P and L566P are destabilizing the formation of 6 HB bundle resulting in the formation of well-ordered native-like 16055 gp140-NFL2 Env trimers.

FIG. 74 depicts a sequence of Clade C 16055 gp140-NFL2 Env. The region of HR1 studied in the proline screen to stabilize the trimer is highlighted in green and underlined. The residues of HR2 involved in this study are highlighted in red and underlined.

Example 14: Clade C Sequences Homologous to BG505

FIG. 75 depicts clade C sequences homologous to BG505.

Example 14: JRFL SOSIP Stabilized by Disulfide Linkages

FIG. 76 depicts binding data on two versions of the JRFL SOSIP stabilized by disulfide linkages at residues 201-433 (1st disulfide) and at 163-309 (2nd disulfide).

FIG. 76A depicts JRFL SOSIP WT octet data with an anti-human Fc sensor, IgG immobilized 5 ug/mL and trimer in solution at 400 nM.

FIG. 76B depicts JRFL SOSIP I201C A433C octet data with an anti-human Fc sensor, IgG immobilized 5 ug/mL and trimer in solution at 400 nM.

FIG. 76C depicts JRFL SOSIP T163C I309C octet data with an anti-human Fc sensor, IgG immobilized 5 ug/mL and trimer in solution at 200 nM.

FIG. 76D depicts a 4-12% SDS PAGE of JRFL SOSIP disulfide stabilizations.

The invention is further described by the following numbered paragraphs:

1. An engineered or non-naturally occurring JRFL SOSIP trimer.
2. The trimer of paragraph 1, wherein the trimer comprises
   (a) the amino acid sequence 5, or
   (b) the amino acid sequence 6 and cysteine mutations thereof, or
   (c) the amino acid sequence 7 and modifications thereof, or
   (d) amino acid sequence of FIG. 8 and modifications thereof.
3. The trimer of paragraph 1, wherein the JRFL SOSIP trimer is truncated at residue 663 (JRFL SOSIP.663 trimer) or the JRFL SOSIP is stabilized by disulfide linkages, preferably at residues 201-433 (1st disulfide) and/or at 163-309 (2nd disulfide).
4. An engineered or non-naturally occurring 16055 SOSIP trimer.
5. The trimer of paragraph 4, wherein the 16055 SOSIP trimer is truncated at residue 663 (16055 SOSIP.663 trimer).
6. An engineered or non-naturally occurring native flexible linker (NFL) gp140 trimer, wherein a linker covalently joins gp120 with gp41.
7. The trimer of paragraph 6, wherein the trimer comprises the schematic of FIG. 9.
8. The trimer of paragraph 6, wherein the trimer comprises
   (a) the amino acid sequence 10 or modifications thereof, or
   (b) the amino acid sequence 11 or modifications thereof, or
   (c) the amino acid sequence 12 or modifications thereof, or
   (d) the amino acid sequence 13 or modifications thereof, or
   (e) the amino acid sequence 14 or modifications thereof.
9. The trimer of paragraph 6, wherein the trimer is truncated following residue 664.
10. The trimer of any one of paragraphs 6 to 9, wherein the trimer comprises a His tag.
11. The trimer of any one of paragraphs 6 to 10, wherein the trimer is mutated.
12. The trimer of paragraph 11, wherein the mutation is a proline substitution.
13. The trimer of paragraph 11, wherein the mutation is selected from the group consisting of S649D, S649E, L555P, L556P, A558P and I559P, wherein the residues based on BG505 sequence and numbering, preferably wherein the mutation is I559P.
14. The trimer of paragraph 11, wherein the mutation is a double mutant containing combinations of 649D or E with the other HR1 P mutations.
15. The trimer of paragraph 11 wherein the mutation is selected from the group consisting of E47D, K49E, V65K, E106T, I165L, E429R, R432Q, wherein the residues based on BG505 sequence and numbering, or a subset thereof.
16. The trimer of paragraph 12, wherein the mutation is selected from the group consisting of L555P, Q652P, Q653P, L565P and L566P or any combination thereof, wherein the residues based on 16055 sequence and numbering.
17. The trimer of paragraph 12, wherein the mutation is a double mutant selected from the group consisting of 558P-S649D, A558P-S649E and I559P-S649E, wherein the residues based on 16055 sequence and numbering.
18. The trimer of any one of paragraphs 6 to 10 wherein the trimer is a BG505 trimer or is a trimer homologous to BG505 from HIV subtypes A, B or C, wherein the trimer comprises any one of the sequences of FIG. 70 or 75 or a sequence having 95% identity thereof.
19. The trimer of any one of paragraphs 6 to 10 comprising a free cysteine.
20. The trimer of paragraph 19, wherein the trimer is encoded by the sequence of FIG. 69.
21. A method of eliciting an immune response in a mammal comprising administering the trimer of any one of paragraphs 1 to 20.
22. The method of paragraph 21, wherein the trimer is administered with an adjuvant.
23. The method of paragraph 22, wherein the adjuvant comprises a lecithin, preferably, wherein the adjuvant is a lecithin is combined with an acrylic polymer, a lecithin coated oil droplet in an oil-in-water emulsion or a lecithin and an acrylic polymer in an oilin-water emulsion.
24. The method of paragraph 23, wherein the adjuvant is ISCOMATRIX or Adjuplex.
25. The method of paragraph 22, wherein the adjuvant comprises alum.
26. The method of any of paragraphs 21 to 25, wherein the trimer is administered in a liposome or in a nanoparticle.
27. The method of any of paragraphs 21 to 26, wherein the trimer is fixed, preferably wherein the trimer is fixed in glutaraldehyde.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An engineered or non-naturally occurring JRFL SOSIP trimer that mimics the native HIV spike conformation and is stable at 55° C. to 63° C., wherein the trimer comprises
   (a) the amino acid sequence of SEQ ID NO: 8, or
   (b) the amino acid sequence of SEQ ID NO: 9 or SEQ ID NO: 9 further comprising cysteine mutations V135C, N136C, A137C, T138C, F159C, N160C, I161C, T162C, T163C, S164C, I165C, S306C, I307C, H308C, R315C, A316C, F317C, Y318C, T319C, or T320C thereof, or
   (c) the amino acid sequence of SEQ ID NO: 10 or
   (d) the amino acid sequence of SEQ ID NO: 11, SEQ ID NO: 12, or SEQ ID NO: 13, or wherein VQSEKS in any of the three sequences is replaced with SEQ ID NO: 1.

2. The trimer of claim 1, wherein the JRFL SOSIP trimer is truncated at residue 663 when aligned with SEQ ID NO: 14 based on BG505 numbering system and/or the JRFL SOSIP is stabilized by disulfide linkages, preferably by a first disulfide between residues 201 and 433 and/or a second disulfide between residues 163 and 309.

3. An engineered or non-naturally occurring 16055 SOSIP trimer that mimics the native HIV spike conformation and is stable at 55° C. to 63° C., wherein the 16055 SOSIP trimer is truncated at residue 663 when aligned with SEQ ID NO: 14 based on BG505 numbering system.

4. An engineered or non-naturally occurring native flexible linker (NFL) gp140 trimer comprising the amino acid sequence of SEQ ID NO: 2, wherein a linker covalently joins the C terminus of gp120 with the N terminus of gp41.

5. The trimer of claim 4, wherein the linker comprises SEQ ID NO: 2, SEQ ID NO: 6, or SEQ ID NO: 7, wherein SEQ ID NO: 3 residues are deleted from the C-terminus of gp 120 and wherein the C terminus of gp41 comprises a His tag.

6. The trimer of claim 4, wherein the trimer comprises
   (a) the amino acid sequence of SEQ ID NO: 14, or
   (b) the amino acid sequence of SEQ ID NO: 15, or
   (c) the amino acid sequence of SEQ ID NO: 16, or
   (d) the amino acid sequence of SEQ ID NO: 17, or
   (e) the amino acid sequence of SEQ ID NO: 18.

7. The trimer of claim 4, wherein the trimer is truncated following residue 664 when aligned with SEQ ID NO: 14 based on BG505 numbering system.

8. The trimer of claim 4, wherein the trimer comprises a His tag.

9. The trimer of claim 4, wherein the trimer is mutated.

10. The trimer of claim 9, wherein the mutation is a proline substitution.

11. The trimer of claim 9, wherein the mutation is selected from the group consisting of S649D, S649E, L555P, L556P, A558P and I559P, wherein the residue numbers are based on BG505 numbering system when aligned with SEQ ID NO: 14, preferably wherein the mutation is I559P.

12. The trimer of claim 9, wherein the mutation is a double mutant containing combinations of 649D or E with the other HR1 P mutations.

13. The trimer of claim 9 wherein the mutation is selected from the group consisting of E47D, K49E, V65K, E106T, I165L, E429R, R432Q, wherein the residue numbers are based on BG505 numbering system when aligned with SEQ ID NO: 14, or a subset thereof.

14. The trimer of claim 10, wherein the mutation is selected from the group consisting of L555P, Q652P, Q653P, L565P and L566P or any combination thereof, wherein the residues based on 16055 SEQ ID NO: 17 numbering.

15. The trimer of claim 10, wherein the mutation is a double mutant selected from the group consisting of A558P-S649D, A558P-S649E and I559P-S649E, wherein the residues based on 16055 SEQ ID NO: 17 numbering.

16. The trimer of claim 4 wherein the trimer is a BG505 trimer or is a trimer homologous to BG505 from HIV subtypes A, B or C, wherein the trimer comprises any one of the sequences of SEQ ID NOS 21-24 or SEQ ID NOS 26-29 or a sequence having 95% identity thereof.

17. The trimer of claim 4 comprising a free cysteine.

* * * * *